US007709621B2

(12) United States Patent
Kinoh et al.

(10) Patent No.: US 7,709,621 B2
(45) Date of Patent: May 4, 2010

(54) VECTORS WITH MODIFIED PROTEASE-DEPENDENT TROPISM

(75) Inventors: Hiroaki Kinoh, Ibaraki (JP); Makoto Inoue, Ibaraki (JP); Yasuji Ueda, Ibaraki (JP); Akihiro Iida, Ibaraki (JP); Mamoru Hasegawa, Ibaraki (JP); Masanori Kobayashi, Shiga (JP)

(73) Assignee: DNAVEC Research Inc., Ibaraki (JP)

( * ) Notice: Subject to any disclaimer, the term of this patent is extended or adjusted under 35 U.S.C. 154(b) by 136 days.

(21) Appl. No.: 12/140,715

(22) Filed: Jun. 17, 2008

(65) Prior Publication Data

US 2008/0299642 A1 Dec. 4, 2008

Related U.S. Application Data

(62) Division of application No. 10/513,094, filed as application No. PCT/JP03/05528 on Apr. 30, 2003, now Pat. No. 7,402,427.

(30) Foreign Application Priority Data

Apr. 30, 2002 (JP) .............................. 2002-129351

(51) Int. Cl.
*C07H 21/04* (2006.01)
*C12N 15/45* (2006.01)
*C12N 7/00* (2006.01)
*A61K 48/00* (2006.01)

(52) U.S. Cl. ................ 536/23.4; 536/23.72; 435/320.1; 435/235.1; 424/93.2

(58) Field of Classification Search ........................ None
See application file for complete search history.

(56) References Cited

U.S. PATENT DOCUMENTS

| | | | | |
|---|---|---|---|---|
| 5,998,169 | A | * | 12/1999 | Klein et al. ................ 435/69.3 |
| 6,017,539 | A | * | 1/2000 | Klein et al. ............... 424/192.1 |
| 6,896,881 | B1 | | 5/2005 | Russell et al. |
| 2002/0100066 | A1 | | 7/2002 | Nagai et al. |
| 2002/0169306 | A1 | | 11/2002 | Kitazato et al. |
| 2003/0170266 | A1 | | 9/2003 | Kitazato et al. |
| 2005/0221292 | A1 | | 10/2005 | Kinoh et al. |
| 2007/0141705 | A1 | | 6/2007 | Inoue et al. |
| 2007/0161110 | A1 | | 7/2007 | Iida et al. |
| 2008/0199438 | A1 | | 8/2008 | Sueishi |

FOREIGN PATENT DOCUMENTS

| | | |
|---|---|---|
| EP | 0 864 645 A1 | 9/1998 |
| EP | 1 106 692 A1 | 6/2001 |
| EP | 1 186 667 A1 | 3/2002 |
| WO | WO 00/70070 | 11/2000 |
| WO | WO 01/20989 A1 | 3/2001 |
| WO | WO 03/025570 A1 | 3/2003 |

OTHER PUBLICATIONS

Cox et al., "The plasmin cascade and matrix metalloproteinases in non-small cell lung cancer," *Thorax* 54: 169-179 (1999).

de Groot et al., "Design, synthesis, and biological evaluation of a dual tumor-specific motive containing integrin-targeted plasmin-cleavable doxorubicin prodrug," *Mol. Cancer Ther.* 1: 901-911 (2002).

Zeydel et al., "Collagenase and elastase production by mouse mammary adenocarcinoma primary cultures and cloned cells," *Cancer Res.* 46: 6438-6445 (1986).

Caravokyri and Pringle, "Defective Synthesis of Envelope Proteins by Temperature-Sensitive Mutants Representing Complementation Groups B and D of Respiratory Syncytial Virus," *Journal of General Virology* 72(Pt 10):2501-2508 (1991).

Cathomen et al., "A Matrix-Less Measles Virus Is Infectious and Elicits Extensive Cell Fusion: Consequences for Propagation in the Brain," *EMBO J.* 17(14):3899-3908 (1998).

Chen et al., "A Unique Substrate Recognition Profile for Matrix Metalloproteinase-2," *J. Biol. Chem.* 277(6):4485-4491 (2002).

Hatanaka, M., ed., *Uirusugaku, Asakura Shoten*, pp. 247-248 (1997) (with English language translation).

Hsu et al., "Protease Activation Mutants of Sendai Virus: Sequence Analysis of the mRNA of the Fusion Protein (F) Gene and Direct Identification of the Cleavage-Activation Site," *Virology* 156(1):84-90 (1987).

Johnson et al., "Metalloproteinase Cleavable Linkers Can Target the Cytotoxicity of Fusogenic Membrane Glycoproteins in Gliomas," *Abstracts from the Fourth Annual Meeting of the American Society of Gene Therapy: Molecular Therapy* 3(5):S25(63) (2001).

(Continued)

*Primary Examiner*—Michael Burkhart
(74) *Attorney, Agent, or Firm*—Clark & Elbing LLP

(57) ABSTRACT

The present invention provides cell fusogenic vectors having replicative ability, whose protease-dependent tropism has been modified. M gene-deficient viral vectors encoding modified F proteins, in which the cleavage site of the F protein of paramyxovirus is modified to be cleaved by different proteases, were produced. In cells transfected with these vectors, the genomic RNA present in the vectors is replicated, and cell fusogenic infection spreads to neighboring cells depending on the presence of other proteases; however, no viral particles are released. The vectors of this invention, encoding the F proteins which are cleaved by proteases whose activity is enhanced in cancer, show cancer growth suppressive effect in vivo.

3 Claims, 49 Drawing Sheets

OTHER PUBLICATIONS

Kridel et al., "Substrate Hydrolysis by Matrix Metalloproteinase-9," *J. Biol. Chem.* 276(23):20572-20578 (2001).

Li et al., "Effect of Cleavage Mutants on Syncytium Formation Directed by the Wild-Type Fusion Protein of Newcastle Disease Virus," *Journal of Virology* 72(5):3789-3795 (1998).

Martin et al., "Retrovirus Targeting by Tropism Restriction to Melanoma Cells," *J. Virol.* 73(8):6923-6929 (1999).

Nieuwenhuizen et al., "Fluorogenic Peptide Amide Substrates for the Estimation of Plasminogen Activators and Plasmin," *Analytical Biochemistry* 83(1):143-148 (1977).

Peng et al., "A Gene Delivery System Activatable by Disease-Associated Matrix Metalloproteinases," *Human Gene Therapy* 8(6):729-739 (1997).

Peng et al., "Selective Transduction of Protease-Rich Tumors by Matrix-Metalloproteinase-Targeted Retroviral Vectors," *Gene Therapy* 6(9):1552-1557(1999).

Spiegel et al., "Pseudotype Formation of Moloney Murine Leukemia Virus with Sendai Virus Glycoprotein F," *J. Virol.* 72(6):5296-5302 (1998).

Stone-Hulslander and Morrison, "Detection of an Interaction Between the HN and F Proteins in Newcastle Disease Virus-Infected Cells," *Journal of Virology* 71(9):6287-6295 (1997).

Taira et al., "Transfection of Sendai Virus F Gene cDNA with Mutations at its Cleavage Site and HN Gene cDNA into COS Cells Induces Cell Fusion," *Archives of Virology* 140(1):187-194 (1995).

Tanabayashi, et al., "Effect on Fusion Induction of Point Mutations Introduced into the F Proteins of Mumps Virus" *Virology* 204(2):851-853 (1994).

Tashiro et al., "Changes in Specific Cleavability of the Sendai Virus Fusion Protein: Implications for Pathogenicity in Mice," *J. Gen. Virol.* 73(Pt. 6):1575-1579 (1992).

Turk et al., "Determination of Protease Cleavage Site Motifs Using Mixture-Based Oriented Peptide Libraries," *Nat. Biotechnol.* 19(7):661-667 (2001).

Yao and Compans, "Differences in the Role of the Cytoplasmic Domain of Human Parainfluenza Virus Fusion Proteins," *Journal of Virology* 69(11):7045-7053 (1995).

Yoshida et al, "Studies on the Role of M Protein in Virus Assembly Using a ts Mutant of HVJ (Sendai Virus)" *Virology* 92(1):139-154 (1979).

Supplemental Search Report for European patent application No. EP 03728016.1, dated Jul. 18, 2006.

* cited by examiner

TEMPERATURE SENSITIVITY (PLAQUE ASSAY)

SeV18+/MtsHNtsΔF-GFP          SeV18+/ΔF-GFP

*SeV18+SEAP/*
*MtsHNtsΔF-GFP*

1uM COLCHICINE

1uM COLCEMID

A-10

ANTI-M (RED)
ANTI-HN (GREEN)

m.o.i. 1
10% SERUM
INCUBATION AT 32°C
TWO DAYS AFTER INFECTION

RT-PCR

WESTERN BLOTTING

LLC-MK2
m.o.i. 3
THREE DAYS
AFTER INFECTION

ANTI-M

ANTI-F

ANTI-SeV
(DN-1)

CYTOTOXICITY OF SeV18+/ΔM-GFP

FIVE DAYS AFTER INFECTION OF LLC-MK2

SeV18+/ΔM-GFP

SeV18+/ΔF-GFP

DOSPER TRANSFECTION

TWO DAYS AFTER
TRANSFECTION OF LLC-MK2

SeV18+/ΔM-GFP

SeV18+/ΔF-GFP

SeV/F(MMP#2)ΔM-GFP

-hFB  +hFB

SW480

WiDr

SW620

SeV        3' | NP | P | M | F | HN | L | 5'

SeV/ΔM-GFP    3' | NP | P | GFP | F | HN | L | 5'

SeV/F(MMP#2)  3' | NP | P | GFP |█| F | HN | L | 5'
ΔM-GFP
              - A - P - L - G    M - T - S - F - F - G - A - V

SeV/F(MMP#6)  3' | NP | P | GFP |█| F | HN | L | 5'
ΔM-GFP
              - A - P - Q - G    M - T - S - F - F - G - A - V

SeV(TDK)/Fct14(MMP  3' | NP | P | GFP | Fct14 | HN | L | 5'
6)ΔM-GFP
              - A - P - Q - G    M - T - S - F - F - G - A - V

SeV(TDK)/Fct14(MMP  3' | NP | P | ███████ | GFP | HN | L | 5'
6)/Linker/HN ΔM-GFP
                          Fct14(MMP#6)/Linker/HN

FIG. 46

```
                         SEQUENCE LISTING

<160> NUMBER OF SEQ ID NOS: 101

<210> SEQ ID NO 1
<211> LENGTH: 3
<212> TYPE: PRT
<213> ORGANISM: Artificial Sequence
<220> FEATURE:
<223> OTHER INFORMATION: artificially synthesized sequence proteolytic
      cleavage

<400> SEQUENCE: 1

Met Thr Ser
 1

<210> SEQ ID NO 2
<211> LENGTH: 3
<212> TYPE: PRT
<213> ORGANISM: Artificial Sequence
<220> FEATURE:
<223> OTHER INFORMATION: artificially synthesized sequence proteolytic
      cleavage
<220> FEATURE:
<221> NAME/KEY: VARIANT
<222> LOCATION: 2
<223> OTHER INFORMATION: Xaa = Leu or Gln

<400> SEQUENCE: 2

Pro Xaa Gly
 1

<210> SEQ ID NO 3
<211> LENGTH: 6
<212> TYPE: PRT
<213> ORGANISM: Artificial Sequence
<220> FEATURE:
<223> OTHER INFORMATION: artificially synthesized sequence proteolytic
      cleavage
<220> FEATURE:
<221> NAME/KEY: VARIANT
<222> LOCATION: 2
<223> OTHER INFORMATION: Xaa = Leu or Gln

<400> SEQUENCE: 3
```

Pro Xaa Gly Met Thr Ser
1               5

<210> SEQ ID NO 4
<211> LENGTH: 5
<212> TYPE: PRT
<213> ORGANISM: Artificial Sequence
<220> FEATURE:
<223> OTHER INFORMATION: artificially synthesized sequence proteolytic
      cleavage
<220> FEATURE:
<221> NAME/KEY: VARIANT
<222> LOCATION: 2
<223> OTHER INFORMATION: Xaa = Leu or Gln

<400> SEQUENCE: 4

Pro Xaa Gly Met Thr
1               5

<210> SEQ ID NO 5
<211> LENGTH: 4
<212> TYPE: PRT
<213> ORGANISM: Artificial Sequence
<220> FEATURE:
<223> OTHER INFORMATION: artificially synthesized sequence derived from
      Sendai virus

<400> SEQUENCE: 5

Pro Gln Ser Arg
1

<210> SEQ ID NO 6
<211> LENGTH: 3
<212> TYPE: PRT
<213> ORGANISM: Artificial Sequence
<220> FEATURE:
<223> OTHER INFORMATION: artificially synthesized sequence proteolytic
      cleavage

<400> SEQUENCE: 6

Val Gly Arg
1

<210> SEQ ID NO 7
<211> LENGTH: 3
<212> TYPE: PRT
<213> ORGANISM: Artificial Sequence
<220> FEATURE:
<223> OTHER INFORMATION: artificially synthesized sequence derived from
      Sendai virus

<400> SEQUENCE: 7

Gln Ser Arg
1

<210> SEQ ID NO 8
<211> LENGTH: 10
<212> TYPE: DNA
<213> ORGANISM: Artificial Sequence
<220> FEATURE:
<223> OTHER INFORMATION: artificially synthesized sequence derived from
      Sendai virus

<400> SEQUENCE: 8
ctttcaccct                                                          10

<210> SEQ ID NO 9
<211> LENGTH: 15

```
<212> TYPE: DNA
<213> ORGANISM: Artificial Sequence
<220> FEATURE:
<223> OTHER INFORMATION: artificially synthesized sequence derived from
      Sendai virus

<400> SEQUENCE: 9
tttttcttac tacgg                                                      15

<210> SEQ ID NO 10
<211> LENGTH: 18
<212> TYPE: DNA
<213> ORGANISM: Artificial Sequence
<220> FEATURE:
<223> OTHER INFORMATION: artificially synthesized sequence containing
      Not I site

<400> SEQUENCE: 10
cggccgcaga tcttcacg                                                   18

<210> SEQ ID NO 11
<211> LENGTH: 39
<212> TYPE: DNA
<213> ORGANISM: Artificial Sequence
<220> FEATURE:
<223> OTHER INFORMATION: artificially synthesized sequence used in site
      directed mutagenesis of the Sendai virus

<400> SEQUENCE: 11
gaaacaaaca accaatctag agagcgtatc tgacttgac                            39

<210> SEQ ID NO 12
<211> LENGTH: 39
<212> TYPE: DNA
<213> ORGANISM: Artificial Sequence
<220> FEATURE:
<223> OTHER INFORMATION: artificially synthesized sequence used in site
      directed mutagenesis of the Sendai virus

<400> SEQUENCE: 12
gtcaagtcag atacgctctc tagattggtt gtttgtttc                            39

<210> SEQ ID NO 13
<211> LENGTH: 31
<212> TYPE: DNA
<213> ORGANISM: Artificial Sequence
<220> FEATURE:
<223> OTHER INFORMATION: artificially synthesized sequence used in site
      directed mutagenesis of the Sendai virus

<400> SEQUENCE: 13
attacggtga ggagggctgt tcgagcagga g                                    31

<210> SEQ ID NO 14
<211> LENGTH: 31
<212> TYPE: DNA
<213> ORGANISM: Artificial Sequence
<220> FEATURE:
<223> OTHER INFORMATION: artificially synthesized sequence used in site
      directed mutagenesis of the Sendai virus

<400> SEQUENCE: 14
ctcctgctcg aacagccctc ctcaccgtaa t                                    31

<210> SEQ ID NO 15
<211> LENGTH: 33
<212> TYPE: DNA
```

<213> ORGANISM: Artificial Sequence
<220> FEATURE:
<223> OTHER INFORMATION: artificially synthesized sequence used in site
directed mutagenesis of the Sendai virus

<400> SEQUENCE: 15
ggggcaatca ccatatccaa gatcccaaag acc                        33

<210> SEQ ID NO 16
<211> LENGTH: 33
<212> TYPE: DNA
<213> ORGANISM: Artificial Sequence
<220> FEATURE:
<223> OTHER INFORMATION: artificially synthesized sequence used in site
directed mutagenesis of the Sendai virus

<400> SEQUENCE: 16
ggtctttggg atcttggata tggtgattgc ccc                        33

<210> SEQ ID NO 17
<211> LENGTH: 37
<212> TYPE: DNA
<213> ORGANISM: Artificial Sequence
<220> FEATURE:
<223> OTHER INFORMATION: artificially synthesized sequence used in site
directed mutagenesis of the Sendai virus

<400> SEQUENCE: 17
catgctctgt ggtgacaacc cggactaggg gttatca                    37

<210> SEQ ID NO 18
<211> LENGTH: 37
<212> TYPE: DNA
<213> ORGANISM: Artificial Sequence
<220> FEATURE:
<223> OTHER INFORMATION: artificially synthesized sequence used in site
directed mutagenesis of the Sendai virus

<400> SEQUENCE: 18
tgataacccc tagtccgggt tgtcaccaca gagcatg                    37

<210> SEQ ID NO 19
<211> LENGTH: 41
<212> TYPE: DNA
<213> ORGANISM: Artificial Sequence
<220> FEATURE:
<223> OTHER INFORMATION: artificially synthesized sequence used in site
directed mutagenesis of the Sendai virus

<400> SEQUENCE: 19
cttgtctaga ccaggaaatg aagagtgcaa ttggtacaat a               41

<210> SEQ ID NO 20
<211> LENGTH: 41
<212> TYPE: DNA
<213> ORGANISM: Artificial Sequence
<220> FEATURE:
<223> OTHER INFORMATION: artificially synthesized sequence used in site
directed mutagenesis of the Sendai virus

<400> SEQUENCE: 20
tattgtacca attgcactct tcatttcctg gtctagacaa g               41

<210> SEQ ID NO 21
<211> LENGTH: 14
<212> TYPE: PRT
<213> ORGANISM: Artificial Sequence
<220> FEATURE:
<223> OTHER INFORMATION: artificially synthesized sequence for
      immunization

<400> SEQUENCE: 21

Met Ala Asp Ile Tyr Arg Phe Pro Lys Phe Ser Tyr Glu Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: artificially synthesized sequence for
      immunization

<400> SEQUENCE: 22

Leu Arg Thr Gly Pro Asp Lys Lys Ala Ile Pro His Cys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: artificially synthesized sequence for
      immunization

<400> SEQUENCE: 23

Cys Asn Val Val Ala Lys Asn Ile Gly Arg Ile Arg Lys Leu
1               5                   10

<210> SEQ ID NO 24
<211> LENGTH: 48
<212> TYPE: DNA
<213> ORGANISM: Artificial Sequence
<220> FEATURE:
<223> OTHER INFORMATION: artificially synthesized sequence used in site
      directed mutagenesis of the Sendai virus

<400> SEQUENCE: 24
agagtcactg accaactaga tcgtgcacga ggcatcctac catcctca                    48

<210> SEQ ID NO 25
<211> LENGTH: 48
<212> TYPE: DNA
<213> ORGANISM: Artificial Sequence
<220> FEATURE:
<223> OTHER INFORMATION: artificially synthesized sequence used in site
directed mutagenesis of the Sendai virus

<400> SEQUENCE: 25
tgaggatggt aggatgcctc gtgcacgatc tagttggtca gtgactct 48

<210> SEQ ID NO 26
<211> LENGTH: 55
<212> TYPE: DNA
<213> ORGANISM: Artificial Sequence
<220> FEATURE:
<223> OTHER INFORMATION: artificially synthesized sequence for
amplifying hygromycin resistant gene

<400> SEQUENCE: 26
tctcgagtcg ctcggtacga tgaaaaagcc tgaactcacc gcgacgtctg tcgag 55

<210> SEQ ID NO 27
<211> LENGTH: 83

```
<212> TYPE: DNA
<213> ORGANISM: Artificial Sequence
<220> FEATURE:
<223> OTHER INFORMATION: artificially synthesized sequence for
      amplifying hygromycin resistant gene

<400> SEQUENCE: 27
aatgcatgat cagtaaatta caatgaacat cgaacccag agtcccgcct attcctttgc    60
cctcggacga gtgctggggc gtc                                           83

<210> SEQ ID NO 28
<211> LENGTH: 22
<212> TYPE: DNA
<213> ORGANISM: Artificial Sequence
<220> FEATURE:
<223> OTHER INFORMATION: artificially synthesized sequence derived from
      Sendai virus

<400> SEQUENCE: 28
ccaatctacc atcagcatca gc                                            22

<210> SEQ ID NO 29
<211> LENGTH: 21
<212> TYPE: DNA
<213> ORGANISM: Artificial Sequence
<220> FEATURE:
<223> OTHER INFORMATION: artificially synthesized sequence derived from
      Sendai virus

<400> SEQUENCE: 29
ttcccttcat cgactatgac c                                             21

<210> SEQ ID NO 30
<211> LENGTH: 22
<212> TYPE: DNA
<213> ORGANISM: Artificial Sequence
<220> FEATURE:
<223> OTHER INFORMATION: artificially synthesized sequence derived from
      Sendai virus

<400> SEQUENCE: 30
agagaacaag actaaggcta cc                                            22

<210> SEQ ID NO 31
<211> LENGTH: 6
<212> TYPE: PRT
<213> ORGANISM: Artificial Sequence
<220> FEATURE:
<223> OTHER INFORMATION: artificially synthesized sequence proteolytic
      cleavage

<400> SEQUENCE: 31

Pro Leu Gly Leu Gly Leu
 1               5

<210> SEQ ID NO 32
<211> LENGTH: 74
<212> TYPE: DNA
<213> ORGANISM: Artificial Sequence
<220> FEATURE:
<223> OTHER INFORMATION: artificially synthesized sequence used in site
      directed mutagenesis of the Sendai virus

<400> SEQUENCE: 32
ctgtcaccaa tgatacgaca caaaatgccc ctcttggcat gacgagtttc ttcggtgctg    60
tgattggtac tatc                                                     74
```

<210> SEQ ID NO 33
<211> LENGTH: 74
<212> TYPE: DNA
<213> ORGANISM: Artificial Sequence
<220> FEATURE:
<223> OTHER INFORMATION: artificially synthesized sequence used in site
      directed mutagenesis of the Sendai virus

<400> SEQUENCE: 33
gatagtacca atcacagcac cgaagaaact cgtcatgcca agaggggcat tttgtgtcgt 60
atcattggtg acag 74

<210> SEQ ID NO 34
<211> LENGTH: 75
<212> TYPE: DNA
<213> ORGANISM: Artificial Sequence
<220> FEATURE:
<223> OTHER INFORMATION: artificially synthesized sequence used in site directed mutagenesis of the Sendai virus

<400> SEQUENCE: 34
ctgtcaccaa tgatacgaca caaaatgccc ctcttggcct ggggttattc ttcggtgctg 60
tgattggtac tatcg 75

<210> SEQ ID NO 35
<211> LENGTH: 75
<212> TYPE: DNA
<213> ORGANISM: Artificial Sequence
<220> FEATURE:
<223> OTHER INFORMATION: artificially synthesized sequence used in site directed mutagenesis of the Sendai virus

<400> SEQUENCE: 35
cgatagtacc aatcacagca ccgaagaata accccaggcc aagaggggca ttttgtgtcg 60
tatcattggt gacag 75

<210> SEQ ID NO 36
<211> LENGTH: 45
<212> TYPE: DNA
<213> ORGANISM: Artificial Sequence
<220> FEATURE:
<223> OTHER INFORMATION: artificially synthesized sequence used in site directed mutagenesis of the Sendai virus

<400> SEQUENCE: 36
caaaatgccg gtgctccccc gttgggattc ttcggtgctg tgatt 45

<210> SEQ ID NO 37
<211> LENGTH: 45
<212> TYPE: DNA
<213> ORGANISM: Artificial Sequence
<220> FEATURE:
<223> OTHER INFORMATION: artificially synthesized sequence used in site directed mutagenesis of the Sendai virus

<400> SEQUENCE: 37
aatcacagca ccgaagaatc ccaacggggg agcaccggca ttttg 45

<210> SEQ ID NO 38
<211> LENGTH: 50
<212> TYPE: DNA
<213> ORGANISM: Artificial Sequence
<220> FEATURE:
<223> OTHER INFORMATION: artificially synthesized sequence used in site -continued directed mutagenesis of the Sendai virus

<400> SEQUENCE: 38
gacacaaaat gccggtgctc ccgtggggag attcttcggt gctgtgattg                50

<210> SEQ ID NO 39
<211> LENGTH: 50
<212> TYPE: DNA
<213> ORGANISM: Artificial Sequence
<220> FEATURE:
<223> OTHER INFORMATION: artificially synthesized sequence used in site
      directed mutagenesis of the Sendai virus

<400> SEQUENCE: 39
caatcacagc accgaagaat ctccccacgg gagcaccggc attttgtgtc                50

<210> SEQ ID NO 40
<211> LENGTH: 11
<212> TYPE: PRT
<213> ORGANISM: Artificial Sequence
<220> FEATURE:
<223> OTHER INFORMATION: artificially synthesized sequence derived from
      F protein of Sendai virus

<400> SEQUENCE: 40

Gly Val Pro Gln Ser Arg Phe Phe Gly Ala Val
 1               5                  10

<210> SEQ ID NO 41
<211> LENGTH: 13
<212> TYPE: PRT
<213> ORGANISM: Artificial Sequence
<220> FEATURE:
<223> OTHER INFORMATION: artificially synthesized sequence derived from
      mutagenized F protein of Sendai virus

<400> SEQUENCE: 41

Gly Val Pro Leu Gly Met Thr Ser Phe Phe Gly Ala Val
 1               5                  10

<210> SEQ ID NO 42
<211> LENGTH: 13
<212> TYPE: PRT
<213> ORGANISM: Artificial Sequence
<220> FEATURE:
<223> OTHER INFORMATION: artificially synthesized sequence derived from
      mutagenized F protein of Sendai virus

<400> SEQUENCE: 42

Gly Val Pro Leu Gly Leu Gly Leu Phe Phe Gly Ala Val
 1               5                  10

<210> SEQ ID NO 43
<211> LENGTH: 10
<212> TYPE: PRT
<213> ORGANISM: Artificial Sequence
<220> FEATURE:
<223> OTHER INFORMATION: artificially synthesized sequence derived from
      mutagenized F protein of Sendai virus

<400> SEQUENCE: 43

Gly Val Pro Leu Gly Phe Phe Gly Ala Val
 1               5                  10

<210> SEQ ID NO 44
<211> LENGTH: 11
<212> TYPE: PRT

<213> ORGANISM: Artificial Sequence
<220> FEATURE:
<223> OTHER INFORMATION: artificially synthesized sequence derived from
     mutagenized F protein of Sendai virus

<400> SEQUENCE: 44

Gly Val Pro Val Gly Arg Phe Phe Gly Ala Val
1               5                   10

<210> SEQ ID NO 45
<211> LENGTH: 16
<212> TYPE: PRT
<213> ORGANISM: Artificial Sequence
<220> FEATURE:
<223> OTHER INFORMATION: amphiphilic alpha-helix domain of Sendai virus

<400> SEQUENCE: 45

Lys Ala Cys Thr Asp Leu Arg Ile Thr Val Arg Arg Thr Val Arg Ala
1               5                   10                  15

<210> SEQ ID NO 46
<211> LENGTH: 8
<212> TYPE: PRT
<213> ORGANISM: Artificial Sequence
<220> FEATURE:
<223> OTHER INFORMATION: a synthetic polypeptide

<400> SEQUENCE: 46

Phe Phe Gly Ala Val Ile Gly Thr
1               5

<210> SEQ ID NO 47
<211> LENGTH: 13
<212> TYPE: PRT
<213> ORGANISM: Artificial Sequence
<220> FEATURE:
<223> OTHER INFORMATION: a synthetic polypeptide

<400> SEQUENCE: 47

Glu Ala Arg Glu Ala Lys Arg Asp Ile Ala Leu Ile Lys
1               5                   10

<210> SEQ ID NO 48
<211> LENGTH: 13
<212> TYPE: PRT
<213> ORGANISM: Artificial Sequence
<220> FEATURE:
<223> OTHER INFORMATION: a synthetic polypeptide

<400> SEQUENCE: 48

Cys Gly Thr Gly Arg Arg Pro Ile Ser Gln Asp Arg Ser
1               5                   10

<210> SEQ ID NO 49
<211> LENGTH: 31
<212> TYPE: DNA
<213> ORGANISM: Artificial Sequence
<220> FEATURE:
<223> OTHER INFORMATION: a synthetic primer

<400> SEQUENCE: 49
ccgctcgagc atgacagcat atatccagag a                                     31

<210> SEQ ID NO 50
<211> LENGTH: 40
<212> TYPE: DNA
<213> ORGANISM: Artificial Sequence

```
<220> FEATURE:
<223> OTHER INFORMATION: a synthetic primer

<400> SEQUENCE: 50
atagtttagc ggccgctcat ctgatcttcg gctctaatgt                              40

<210> SEQ ID NO 51
<211> LENGTH: 31
<212> TYPE: DNA
<213> ORGANISM: Artificial Sequence
<220> FEATURE:
<223> OTHER INFORMATION: a synthetic primer

<400> SEQUENCE: 51
ccgctcgagc atgacagcat atatccagag a                                       31

<210> SEQ ID NO 52
<211> LENGTH: 40
<212> TYPE: DNA
<213> ORGANISM: Artificial Sequence
<220> FEATURE:
<223> OTHER INFORMATION: a synthetic primer

<400> SEQUENCE: 52
atagtttagc ggccgctcac cttctgagtc tataaagcac                              40

<210> SEQ ID NO 53
<211> LENGTH: 31
<212> TYPE: DNA
<213> ORGANISM: Artificial Sequence
<220> FEATURE:
<223> OTHER INFORMATION: a synthetic polypeptide

<400> SEQUENCE: 53
ccgctcgagc atgacagcat atatccagag a                                       31

<210> SEQ ID NO 54
<211> LENGTH: 40
<212> TYPE: DNA
<213> ORGANISM: Artificial Sequence
<220> FEATURE:
<223> OTHER INFORMATION: a synthetic primer

<400> SEQUENCE: 54
atagtttagc ggccgctcac cttctgagtc tataaagcac                              40

<210> SEQ ID NO 55
<211> LENGTH: 36
<212> TYPE: DNA
<213> ORGANISM: Artificial Sequence
<220> FEATURE:
<223> OTHER INFORMATION: a synthetic primer, F-F

<400> SEQUENCE: 55
atccgaattc agttcaatga cagcatatat ccagag                                  36

<210> SEQ ID NO 56
<211> LENGTH: 36
<212> TYPE: DNA
<213> ORGANISM: Artificial Sequence
<220> FEATURE:
<223> OTHER INFORMATION: Fct14-a synthetic primer, Fct14-R

<400> SEQUENCE: 56
atccgcggcc gccggtcatc tggattaccc attagc                                  36
```

```
<210> SEQ ID NO 57
<211> LENGTH: 152
<212> TYPE: DNA
<213> ORGANISM: Artificial Sequence
<220> FEATURE:
<223> OTHER INFORMATION: a synthetic primer, Linker-HN-F

<400> SEQUENCE: 57
atccgcggcc gcaatcgagg gaaggtggtc tgagttaaaa atcaggagca acgacggagg      60
tgaaggacca gaggacgcca acgacccacg gggaaagggg tgaacacatc catatccagc    120
catctctacc tgtttatgga cagagggtta gg                                  152

<210> SEQ ID NO 58
<211> LENGTH: 33
<212> TYPE: DNA
<213> ORGANISM: Artificial Sequence
<220> FEATURE:
<223> OTHER INFORMATION: a synthetic primer, HN-R

<400> SEQUENCE: 58
atccgcggcc gcttaagact cggccttgca taa                                  33

<210> SEQ ID NO 59
<211> LENGTH: 32
<212> TYPE: DNA
<213> ORGANISM: Artificial Sequence
<220> FEATURE:
<223> OTHER INFORMATION: a synthetic primer

<400> SEQUENCE: 59
atccgcggcc gcaatggatg gtgatagggg ca                                   32

<210> SEQ ID NO 60
<211> LENGTH: 30
<212> TYPE: DNA
<213> ORGANISM: Artificial Sequence
<220> FEATURE:
<223> OTHER INFORMATION: a synthetic primer

<400> SEQUENCE: 60
atccgcggcc gcttaagact cggccttgca                                      30

<210> SEQ ID NO 61
<211> LENGTH: 6
<212> TYPE: PRT
<213> ORGANISM: Artificial Sequence
<220> FEATURE:
<223> OTHER INFORMATION: MMP cleavage sequence

<400> SEQUENCE: 61

Pro Leu Gly Met Thr Ser
 1               5

<210> SEQ ID NO 62
<211> LENGTH: 6
<212> TYPE: PRT
<213> ORGANISM: Artificial Sequence
<220> FEATURE:
<223> OTHER INFORMATION: MMP cleavage sequence

<400> SEQUENCE: 62

Pro Gln Gly Met Thr Ser
 1               5
```

<210> SEQ ID NO 63
<211> LENGTH: 6
<212> TYPE: PRT
<213> ORGANISM: Artificial Sequence
<220> FEATURE:
<223> OTHER INFORMATION: MMP cleavage sequence

<400> SEQUENCE: 63

Pro Gln Gly Leu Tyr Ala
 1               5

<210> SEQ ID NO 64
<211> LENGTH: 75
<212> TYPE: DNA
<213> ORGANISM: Artificial Sequence
<220> FEATURE:
<223> OTHER INFORMATION: a synthetic oligonucleotide used for
     mutagenesis

<400> SEQUENCE: 64
ctgtcaccaa tgatacgaca caaaatgccc ctcttggcct ggggttattc ttcggtgctg      60
tgattggtac tatcg                                                      75

<210> SEQ ID NO 65
<211> LENGTH: 75
<212> TYPE: DNA
<213> ORGANISM: Artificial Sequence
<220> FEATURE:
<223> OTHER INFORMATION: a synthetic oligonucleotide used for
     mutagenesis

<400> SEQUENCE: 65
cgatagtacc aatcacagca ccgaagaata accccaggcc aagaggggca ttttgtgtcg      60
tatcattggt gacag                                                      75

<210> SEQ ID NO 66
<211> LENGTH: 74
<212> TYPE: DNA
<213> ORGANISM: Artificial Sequence
<220> FEATURE:
<223> OTHER INFORMATION: a synthetic oligonucleotide used for
     mutagenesis

<400> SEQUENCE: 66
ctgtcaccaa tgatacgaca caaaatgccc ctcagggctt gtatgctttc ttcggtgctg      60
tgattggtac tatc                                                       74

<210> SEQ ID NO 67
<211> LENGTH: 74
<212> TYPE: DNA
<213> ORGANISM: Artificial Sequence
<220> FEATURE:
<223> OTHER INFORMATION: a synthetic oligonucleotide used for
     mutagenesis

<400> SEQUENCE: 67
gatagtacca atcacagcac cgaagaaagc atacaagccc tgaggggcat tttgtgtcgt      60
atcattggtg acag                                                       74

<210> SEQ ID NO 68
<211> LENGTH: 74
<212> TYPE: DNA
<213> ORGANISM: Artificial Sequence
<220> FEATURE:
<223> OTHER INFORMATION: a synthetic oligonucleotide used for mutagenesis

<400> SEQUENCE: 68
ctgtcaccaa tgatacgaca caaaatgccc ctcaaggcat gacgagtttc ttcggtgctg     60
tgattggtac tatc     74

<210> SEQ ID NO 69
<211> LENGTH: 74
<212> TYPE: DNA
<213> ORGANISM: Artificial Sequence
<220> FEATURE:
<223> OTHER INFORMATION: a synthetic oligonucleotide used for
      mutagenesis

<400> SEQUENCE: 69
gatagtacca atcacagcac cgaagaaact cgtcatgcct tgagggcat tttgtgtcgt     60 atcattggtg acag     74

<210> SEQ ID NO 70
<211> LENGTH: 74
<212> TYPE: DNA
<213> ORGANISM: Artificial Sequence
<220> FEATURE:
<223> OTHER INFORMATION: a synthetic oligonucleotide used for
      mutagenesis

<400> SEQUENCE: 70
ctgtcaccaa tgatacgaca caaaatgccc ttgcttacta tacggctttc ttcggtgctg     60
tgattggtac tatc     74

<210> SEQ ID NO 71
<211> LENGTH: 74
<212> TYPE: DNA
<213> ORGANISM: Artificial Sequence
<220> FEATURE:
<223> OTHER INFORMATION: a synthetic oligonucleotide used for
      mutagenesis

<400> SEQUENCE: 71
gatagtacca atcacagcac cgaagaaagc cgtatagtaa gcaagggcat tttgtgtcgt     60
atcattggtg acag     74

<210> SEQ ID NO 72
<211> LENGTH: 74
<212> TYPE: DNA
<213> ORGANISM: Artificial Sequence
<220> FEATURE:
<223> OTHER INFORMATION: a synthetic oligonucleotide used for
      mutagenesis

<400> SEQUENCE: 72
ctgtcaccaa tgatacgaca caaaatgccc ctcttggctt ggcgagattc ttcggtgctg     60
tgattggtac tatc     74

<210> SEQ ID NO 73
<211> LENGTH: 74
<212> TYPE: DNA
<213> ORGANISM: Artificial Sequence
<220> FEATURE:
<223> OTHER INFORMATION: a synthetic oligonucleotide used for
      mutagenesis

<400> SEQUENCE: 73

```
gatagtacca atcacagcac cgaagaatct cgccaagcca agagggcat tttgtgtcgt    60 atcattggtg acag                                                    74
```

<210> SEQ ID NO 74
<211> LENGTH: 50
<212> TYPE: DNA
<213> ORGANISM: Artificial Sequence
<220> FEATURE:
<223> OTHER INFORMATION: a synthetic oligonucleotide used for
      mutagenesis

<400> SEQUENCE: 74

```
cttcggtgct gtgattgcta ctatcgcact tgcagtggcg acatcagcac              50
```

<210> SEQ ID NO 75
<211> LENGTH: 50
<212> TYPE: DNA
<213> ORGANISM: Artificial Sequence
<220> FEATURE:
<223> OTHER INFORMATION: a synthetic oligonucleotide used for
      mutagenesis

<400> SEQUENCE: 75

```
gtgctgatgt cgccactgca agtgcgatag tagcaatcac agcaccgaag              50
```

<210> SEQ ID NO 76
<211> LENGTH: 49
<212> TYPE: PRT
<213> ORGANISM: Artificial Sequence
<220> FEATURE:
<223> OTHER INFORMATION: a partial sequence of Sendai virus F protein

<400> SEQUENCE: 76

Val Ile Val Ile Val Leu Tyr Arg Leu Lys Arg Ser

-continued

```
Val Ile Val Ile Val Leu Tyr Arg Leu Lys Arg Ser Met Leu Met Gly
1               5                   10                  15

Asn Pro Asp Asp Arg
            20
```

<210> SEQ ID NO 79
<211> LENGTH: 11
<212> TYPE: PRT
<213> ORGANISM: Artificial Sequence
<220> FEATURE:
<223> OTHER INFORMATION: a partial sequence of Sendai virus F protein

<400> SEQUENCE: 79

```
Val Ile Val Ile Val Leu Tyr Arg Leu Lys Arg
1               5                   10
```

<210> SEQ ID NO 80
<211> LENGTH: 50
<212> TYPE: PRT
<213> ORGANISM: Artificial Sequence
<220> FEATURE:
<223> OTHER INFORMATION: a linker sequence

<400> SEQUENCE: 80

```
Ala Ala Ala Ile Glu Gly Arg Trp Ser Glu Leu Lys Ile Arg Ser Asn
1               5                   10                  15

Asp Gly Gly Glu Gly Pro Glu Asp Ala Asn Asp Pro Arg Gly Lys Gly
            20                  25                  30

Val Gln His Ile His Ile Gln Pro Ser Leu Pro Val Tyr Gly Gln Arg
        35                  40                  45

Val Arg
    50
```

<210> SEQ ID NO 81
<211> LENGTH: 12
<212> TYPE: PRT
<213> ORGANISM: Artificial Sequence
<220> FEATURE:
<223> OTHER INFORMATION: F protein cleavage site

<400> SEQUENCE: 81

```
Ala Gly Val Pro Gln Ser Arg Phe Phe Gly Ala Val
1               5                   10
```

<210> SEQ ID NO 82
<211> LENGTH: 12
<212> TYPE: PRT
<213> ORGANISM: Artificial Sequence
<220> FEATURE:
<223> OTHER INFORMATION: F protein cleavage site

<400> SEQUENCE: 82

```
Ala Pro Leu Gly Leu Trp Ala Phe Phe Gly Ala Val
1               5                   10
```

<210> SEQ ID NO 83
<211> LENGTH: 12
<212> TYPE: PRT
<213> ORGANISM: Artificial Sequence
<220> FEATURE:
<223> OTHER INFORMATION: F protein cleavage site

<400> SEQUENCE: 83

```
Ala Pro Leu Gly Met Thr Ser Phe Phe Gly Ala Val
1               5                   10
```

-continued

```
<210> SEQ ID NO 84
<211> LENGTH: 12
<212> TYPE: PRT
<213> ORGANISM: Artificial Sequence
<220> FEATURE:
<223> OTHER INFORMATION: F protein cleavage site

<400> SEQUENCE: 84

Ala Pro Leu Gly Leu Gly Leu Phe Phe Gly Ala Val
 1               5                  10

<210> SEQ ID NO 85
<211> LENGTH: 12
<212> TYPE: PRT
<213> ORGANISM: Artificial Sequence
<220> FEATURE:
<223> OTHER INFORMATION: F protein cleavage site

<400> SEQUENCE: 85

Ala Gly Val Pro Pro Leu Gly Phe Phe Gly Ala Val
 1               5                  10

<210> SEQ ID NO 86
<211> LENGTH: 12
<212> TYPE: PRT
<213> ORGANISM: Artificial Sequence
<220> FEATURE:
<223> OTHER INFORMATION: F protein cleavage site

<400> SEQUENCE: 86

Ala Pro Gln Gly Leu Tyr Ala Phe Phe Gly Ala Val
 1               5                  10

<210> SEQ ID NO 87
<211> LENGTH: 12
<212> TYPE: PRT
<213> ORGANISM: Artificial Sequence
<220> FEATURE:
<223> OTHER INFORMATION: F protein cleavage site

<400> SEQUENCE: 87

Ala Pro Gln Gly Met Thr Ser Phe Phe Gly Ala Val
 1               5                  10

<210> SEQ ID NO 88
<211> LENGTH: 12
<212> TYPE: PRT
<213> ORGANISM: Artificial Sequence
<220> FEATURE:
<223> OTHER INFORMATION: F protein cleavage site

<400> SEQUENCE: 88

Ala Leu Ala Tyr Tyr Thr Arg Phe Phe Gly Ala Val
 1               5                  10

<210> SEQ ID NO 89
<211> LENGTH: 12
<212> TYPE: PRT
<213> ORGANISM: Artificial Sequence
<220> FEATURE:
<223> OTHER INFORMATION: F protein cleavage site

<400> SEQUENCE: 89

Ala Pro Leu Gly Leu Ala Arg Phe Phe Gly Ala Val
 1               5                  10
```

<210> SEQ ID NO 90
<211> LENGTH: 23
<212> TYPE: PRT
<213> ORGANISM: Artificial Sequence
<220> FEATURE:
<223> OTHER INFORMATION: F protein cleavage site

<400> SEQUENCE: 90

Gln Ser Arg Phe Phe Gly Ala Val Ile Gly Thr Ile Ala Leu Gly Val
1               5                   10                  15

Ala Thr Ser Ala Gln Ile Thr
            20

<210> SEQ ID NO 91
<211> LENGTH: 26
<212> TYPE: PRT
<213> ORGANISM: Artificial Sequence
<220> FEATURE:
<223> OTHER INFORMATION: F protein cleavage site

<400> SEQUENCE: 91

Pro Leu Gly Met Thr Ser Phe Phe Gly Ala Val Ile Gly Thr Ile Ala
1               5                   10                  15

Leu Gly Val Ala Thr Ser Ala Gln Ile Thr
            20                  25

<210> SEQ ID NO 92
<211> LENGTH: 26
<212> TYPE: PRT
<213> ORGANISM: Artificial Sequence
<220> FEATURE:
<223> OTHER INFORMATION: F protein cleavage site

<400> SEQUENCE: 92

Pro Gln Gly Met Thr Ser Phe Phe Gly Ala Val Ile Gly Thr Ile Ala
1               5                   10                  15

Leu Gly Val Ala Thr Ser Ala Gln Ile Thr
            20                  25

<210> SEQ ID NO 93
<211> LENGTH: 26
<212> TYPE: PRT
<213> ORGANISM: Artificial Sequence
<220> FEATURE:
<223> OTHER INFORMATION: F protein cleavage site

<400> SEQUENCE: 93

Pro Gln Gly Met Thr Ser Phe Phe Gly Ala Val Ile Ala Thr Ile Ala
1               5                   10                  15

Leu Ala Val Ala Thr Ser Ala

```
<212> TYPE: DNA
<213> ORGANISM: Artificial Sequence
<220> FEATURE:
<223> OTHER INFORMATION: an artificially synthesized oligonucleotide

<400> SEQUENCE: 95
atccgcgcgc ccgtacgatg aactttcacc ctaagttttt cttactacgg agctttactt    60
gtacagctcg tc                                                        72

<210> SEQ ID NO 96
<211> LENGTH: 31
<212> TYPE: DNA
<213> ORGANISM: Artificial Sequence
<220> FEATURE:
<223> OTHER INFORMATION: an artificially synthesized oligonucleotide

<400> SEQUENCE: 96
atccacgcgt catgacagca tatatccaga g                                   31

<210> SEQ ID NO 97
<211> LENGTH: 66
<212> TYPE: DNA
<213> ORGANISM: Artificial Sequence
<220> FEATURE:
<223> OTHER INFORMATION: an artificially synthesized oligonucleotide

<400> SEQUENCE: 97
atccgtcgac acgatgaact ttcaccctaa gttttcttac tactttaac ggtcatctgg     60 attacc                                                               66

<210> SEQ ID NO 98
<211> LENGTH: 32
<212> TYPE: DNA
<213> ORGANISM: Artificial Sequence
<220> FEATURE:
<223> OTHER INFORMATION: an artificially synthesized oligonucleotide

<400> SEQUENCE: 98
atccgctagc ccgtacggcc atggtgagca ag                                  32

<210> SEQ ID NO 99
<211> LENGTH: 72
<212> TYPE: DNA
<213> ORGANISM: Artificial Sequence
<220> FEATURE:
<223> OTHER INFORMATION: an artificially synthesized oligonucleotide

<400> SEQUENCE: 99
atccgctagc ccgtacgatg aactttcacc ctaagttttt cttactacgg agctttactt    60
gtacagctcg tc                                                        72

<210> SEQ ID NO 100
<211> LENGTH: 36
<212> TYPE: DNA
<213> ORGANISM: Artificial Sequence
<220> FEATURE:
<223> OTHER INFORMATION: an artificially synthesized oligonucleotide

<400> SEQUENCE: 100
atccgctagc agttcaatga cagcatatat ccagag                              36

<210> SEQ ID NO 101
<211> LENGTH: 67
<212> TYPE: DNA
```

```
-continued
<213> ORGANISM: Artificial Sequence
<220> FEATURE:
<223> OTHER INFORMATION: an artificially synthesized oligonucleotide

<400> SEQUENCE: 101
atccgctagc acgatgaact ttcaccctaa gttttcttta ctactttaa gactcggcct    60 tgcataa                                                             67
```

VECTORS WITH MODIFIED PROTEASE-DEPENDENT TROPISM

CROSS-REFERENCE TO RELATED APPLICATIONS

This application is a divisional of U.S. patent application Ser. No. 10/513,094, filed May 3, 2005, now U.S. Pat. No. 7,402,427, which is the U.S. National Stage of PCT/JP2003/005528, filed Apr. 30, 2003, which, in turn, claims the benefit of Japanese application JP 2002-129351, filed Apr. 30, 2002.

TECHNICAL FIELD

The present invention relates to cell fusion vectors with modified protease-dependent tropism, and methods for producing the same. The vectors of this invention are useful as gene therapy vectors that show cancer-specific infection.

BACKGROUND ART

Development of gene therapy for cancer has been advancing in recent years. Hitherto, the present inventors have developed gene therapy vectors using the Sendai virus (SeV). SeV is a virus of the paramyxovirus family and belongs to a group of viruses comprising nonsegmented negative strand RNA as its genome. Paramyxoviral vectors enable high transfection rate and overexpression of foreign genes, and are expected to serve as gene therapy vectors for cancer. To date, a number of cancer therapies using paramyxovirus have been performed. For example, BHK21 cells infected with Mumps virus were observed to show anti-tumor effects in tumor-bearing nude mice (Minato, N. et al., J. Exp. Med. 149, 1117-1133, 1979). Similarly, antitumor effects have been reported in other paramyxoviruses. Recently, the antitumor effects of fusogenic proteins are attracting attention. Galanis et al. reported that cancer cells infected with an adenoviral vector that carries the F and HN proteins of measles virus form syncytia, resulting in antitumor effects in vivo (Galanis, E. et al., Hum. Gene Ther. 12, 811-821, 2001).

Needless to say, cancer that does not metastasize can be treated by surgically removing that portion, and metastatic cancer and malignant cancer are considered synonymous. Infiltrating metastatic cancers are known to overexpress matrix metalloprotease (MMP) and/or plasminogen activators (uPA, tPA) (Cox, G., and O'Byrne, K. J., Anticancer Res. 21, 4207-4219, 2001; Andreasen, P. A. et al., Cell Mol. Life. Sci. 57, 25-40, 2000). This overexpression is believed to occur due to the fact that infiltration and metastasis become possible only after the surrounding extracellular matrix (ECM), which is an obstacle preventing cell transposition during metastasis and infiltration of cancer cells, is degraded through the expression of enzymes (MMP, uPA, tPA) that degrade the ECM by cancer.

On the other hand, three problems have been raised regarding gene therapies for cancer. Firstly, since the gene transfer efficiency into cancer cells is low and gene transfer to the core of a solid cancer cannot be easily accomplished, genes cannot be transfected to the entire cancer. Accordingly, remaining cancer cells start to proliferate again, which leads to recurrence. Secondly, genes are transfected not only to cancer cells but also to normal cells. Toxic genes injure the normal cells, thereby resulting in increased side-effects. Thirdly, the occurrence of infiltration and metastasis as the cancer becomes malignant is a problem in all kinds of cancer therapy. To date, a vectors that solves these problems has not yet been developed.

DISCLOSURE OF THE INVENTION

The present invention provides novel cell fusion vectors with modified protease-dependent tropism which infiltrate into surrounding cells only in the presence of a particular protease; and methods for producing the same.

The paramyxovirus family of viruses, which includes Sendai virus, comprise two proteins in their envelope. The fusion (F) protein achieves membrane fusion between the virus and its host cell which results in release of nucleocapsids into the cytoplasm. The hemagglutinin-neuraminidase (HN) protein has hemagglutinating ability and neuraminidase activity, and plays the role of binding to a host receptor. The F and HN proteins are also called spike proteins, as they are displayed on the surface of the viral envelope. The matrix (M) protein lines the envelope and gives rigidity to the viral particle. The characteristics of the present vectors are such that they allow highly efficient gene transfer to a wide variety of cells and animal tissues, and accomplish high level of expression as compared to existing vectors.

The F protein (F0) does not show cell fusion activity. Its fusion activity is displayed only upon cleavage by a host-derived protease, which results in degradation into F1 and F2. Therefore, the proliferation of viruses carrying the wild-type F protein is limited to those types of tissues that express a trypsin-like protease which allows for cleavage of this protein, such as respiratory mucosal epithelium. Various studies have been carried out on paramyxoviruses regarding modification of the tropism of infection or fusogenicity due to modifications of F. In the interest of SeV, a variant comprising F that is cleaved only by α-chymotripsin has been shown to lose trypsin sensitivity, which, in turn, changes its tropism specific to the cleavage sequence of F (Tashiro, M. et al., J. Gen. Virol. 73(Pt 6), 1575-1579, 1992). Furthermore, in Newcastle disease virus and in Measles virus, it has been shown that the syncytium-forming ability changes in a trypsin-dependent manner due to the modification of the cleavage sequence of F (Li, Z. et al., J. Virol. 72, 3789-3795, 1998; Maisner, A. et al., J. Gen. Virol. 81, 441-449, 2000).

By modifying the cleavage sequence of the F protein as described above, vectors may be infected to and proliferated in specific tissues and such which express a certain protease. However, one of the problems with paramyxoviral vectors is the secondary release of viruses from cells, which occurs after the vector is introduced into a target cell. In a cell infected with replicative viruses, a virion is formed and daughter viruses are released. Therefore, viral particles also spread to sites other than the target tissue. Although viral particles comprising wild-type F proteins as described above do not show infectivity in the absence of trypsin-like enzymes, viral particles themselves are released from cells. For in vivo administration, the concern is that a viruses that has spread into the blood will spread to the entire body. Furthermore, release of virus-like particles (VLPs) has been observed from cells transfected with F gene-deficient SeV (Li, H. O. et al., J. Virol. 74, 6564-6569, 2000; WO 00/70055; WO 00/70070) which lacks the replication ability. Infection to tissues other than the target tissue and induction of immune response are of concern with such secondary released particles.

Accordingly, the present inventors discovered that paramyxovirus lacking the M gene among the viral envelope genes does not show particle formation, but does allows for cell fusogenic infection through the formation of a syncytium through the fusion of infected cells and cells contacting these infected cells (WO 00/09700). These M-deficient viruses are replicated in transfected cells, and are delivered to adjacent cells in the presence of trypsin. However, this is a phenomenon that occurs only under conditions where F is cleaved and activated. In viruses comprising the wild-type F protein, transfer of viruses will not occur under conditions without trypsin-like proteases. Thus, the present inventors postulated that a novel vector which does not produce secondary released particles, and which can spread the infection only in a specific tissue, can be developed by modifying the tropism of the F protein in this M-deficient virus. In particular, many infiltrating metastatic cancers are known to have enhanced activity of proteases, such as MMP, uPA, and tPA, which degrade ECM. Accordingly, the present inventors utilized the protease-dependent cell fusogenic infection of this M-deficient SeV and the phenomena of overexpression of MMP, uPA, and tPA in cancers in combination to prepare SeV vectors that specifically infect and spread to invasive metastatic cancers.

An M-deficient virus lacks the M gene needed for particle formation. Therefore, viral particles are either not released or are extremely suppressed in such a virus. When conventional reconstitution methods are used to produce a recombinant virus having the ability to replicate (Kato, A. et al., Genes Cells 1, 569-579, 1996), RNPs of the M-deficient virus can be prepared but infectious viral particles are not (WO 00/09700). When using the M-deficient vector as a cancer therapeutic agent, it is extremely useful to prepare the M-deficient virus as an infectious viral particle. Therefore, the present inventors developed novel production methods for preparing M-deficient-viruses as viral particles.

To achieve the objective—to construct vectors with suppressed VLP release, the present inventors considered the use of temperature-sensitive mutations in the viral gene. Mutant viral strains that can be grown at low but not high temperatures have been reported. The present inventors conceived that a mutant protein, particularly a mutant M protein, which suppresses virion formation at high temperature, could be used to suppress VLP formation in such a way that virus production could be carried out at a low temperature (for example, at 32° C.), but practical application of the virus, such as for gene therapy, could be carried out at a higher temperature (for example, at 37° C.). For this purpose, the present inventors constructed a recombinant F gene-deficient Sendai viral vector, which encodes mutant M and mutant HN proteins that have in total six temperature-sensitive mutations reported in M and HN proteins (three for M protein, and three for HN protein). VLP release for this virus was tested, and the level was determined to be about $\frac{1}{10}$ or less of that of the wild-type virus. Further, immunostaining with an anti-M antibody was used to analyze M protein subcellular localization in cells in which the Sendai virus vector with suppressed VLP release had been introduced. The results showed that introduction of virus with suppressed VLP release significantly reduced M protein aggregation on cell surfaces as compared to cells containing the introduced wild-type virus. In particular, M protein condensation patterns were extremely reduced at a high temperature (38° C.). The subcellular localization of M and HN proteins in cells infected with SeV containing a temperature-sensitive mutant M gene was closely examined using a confocal laser microscope. M protein localization on cell surfaces was significantly reduced, even at a low temperature (32° C.), and was observed to have morphology similar to that of a microtubule. At a high temperature (37° C.), the M protein was localized on the microtubules near the centrosome, that is, near the Golgi body. The addition of a microtubule-depolymerizing agent resulted in the disruption of the M protein localization structure. This occurred both in SeV comprising the temperature-sensitive M gene and in SeV comprising the wild-type M gene. This raised the possibility that M protein actually functions by localizing along microtubules. These findings confirm that the reduced level of secondary particle release in the case of viruses having temperature-sensitive mutations was due to insufficient intracellular localization of the M protein, a step believed to play a central role in particle formation. Thus, VLP formation can be effectively suppressed by preventing the normal intracellular localization of M protein. Furthermore, interaction with microtubules may be important for M protein function. For example, secondary particle release can be reduced through disruption of M protein subcellular localization, a step achieved using a gene mutation or pharmaceutical agent developed to inhibit M protein transport along microtubules from Golgi bodies into the cell. In particular, the present inventors found that recombinant viral vectors whose particle formation ability had been reduced or eliminated could be provided by preparing viral vectors comprising a mutation leading to defective M protein localization.

By deleting the M gene from the virus, the present inventors constructed a virus in which aggregation of M protein on the cell surface is completely suppressed in cells transfected with the virus. For this purpose, the present inventors constructed helper cells that can inducibly express the wild-type M protein that may be used to produce M gene-deficient viruses. By using these cells, collection of viral particles, in which the RNP of F-modified M gene-deficient viruses are enclosed in an envelope comprising the wild-type M protein, was accomplished for the first time. The methods of the present invention enable the production of viral particles at a concentration of $1\times10^8$ PFU/mL or more, and therefore, recombinant viruses sufficient for practical use, particularly clinical use, are provided for the first time. Furthermore, the virus production system of this invention avoids the possibility of contamination by other viruses and enables the production of highly safe, high-titer vectors for gene therapy. A practical F-modified M-deficient paramyxovirus was provided for the first time by using the M-deficient SeV production system of this invention, which supplies the M protein in trans by utilizing M-expressing cells.

The present inventors used infectious viral particles constructed as described above and verified the actual antitumor effect in vivo. M-deficient virus activated by matrix metalloprotease (MMP), which shows enhanced activity in cancer, was administered to mice transplanted with cancer cells, and the virus was confirmed to spread throughout the cancer tissues via cell fusogenic infection. In cancers to which wild-type virus was administered, the virus was limited to the injected site even after several days. In contrast, the vector of this invention showed high permeability towards cancer tissues, and the vector spread throughout the entire cancer. The suppressive effect of the present vectors against proliferation of cancer was apparent when compared to the controls without virus administration or administration of the wild-type virus. Vectors targeting MMP-expressing cells have also been produced to date using retroviruses (Peng, K.-W. et al., Human Gene Therapy 8, 729-738, 1997; Peng, K.-W. et al., Gene Therapy 6, 1552-1557, 1999; Martin, F. et al., J. Virol. 73, 6923-6929, 1999). However, they utilize a completely different design for the recognition sequence from that of the present invention. Furthermore, the objectives of these reports are specific infection of cancer tissues—that is, only targeting. Thus, vectors that specifically (intracellularly) spread infection through cancer tissues are provided for the first time by this invention.

Furthermore, the present inventors succeeded in preparing viral particles with uncleaved F protein on the viral surface (F-uncleaved virus) by controlling the addition of protease during viral particle production. As is, these viruses do not have infectivity; however, they display specific infectivity upon treatment with a protease that cleaves the F protein on the viral surface, or upon addition of the viruses to cells in the presence of such protease. Such inducibly infectious viral vectors enable infection of vectors specifically into cancer cells producing a particular protease.

Moreover, the present inventors successfully employed the wild-type F protein in the preparation of a vector comprising a modified F gene to develop a method for producing viral particles utilizing a protease that cleaves the wild-type F protein during vector preparation. According to this method, virus amplification can be performed using helper cells expressing the wild-type F protein and an enzyme, such as trypsin, that cleaves the wild-type F protein. The obtained viral particles comprise the cleaved wild-type F protein in their envelope and have infectivity. However, due to the modified F gene, wherein the cleavage site of the F protein is modified encoded by the viral genome, the infection spreads only in the presence of a particular protease. This method of preparing viruses using the wild-type F protein is advantageous since it allows production of viral particles without depending on the modified F gene to be integrated into the vector genome.

As described above, the present invention provides vectors whose infection spreads only in the presence of a protease expressed in a specific tissue, such as a cancer tissue. The vectors of this invention do not produce significant quantities of viral particles but instead transfer vectors to surrounding cells by cell fusion. The vectors of this invention that acquire infectivity by proteases whose activity is particularly enhanced in cancers have strong suppressive effects toward tumor growth. Thus, gene therapy of cancers using these vectors is considered to be extremely effective.

Therefore, the present invention relates to cell fusion vectors whose protease-dependent tropism has been modified, and methods for producing the same, and such. Specifically, the present invention relates to:

[1] a complex comprising a genomic RNA of paramyxovirus wherein (a) a nucleic acid encoding an M protein is mutated or deleted, and (b) a modified F protein, whose cleavage site sequence is substituted with a sequence that can be cleaved by a protease that does not cleave the wild-type F protein, is encoded, the complex further comprising the following properties:

(1) the ability to replicate the genomic RNA in a cell to which the complex has been introduced;

(2) a significant decrease in or lack of production of viral particles in the intrahost environment; and (3) the ability to introduce the RNA into a cell that contacts the cell transfected with the complex in the presence of the protease;

[2] the complex of [1], which is a viral particle;

[3] the complex of [2], further comprising the wild-type F protein;

[4] the complex of any one of [1] to [3], wherein the paramyxovirus is Sendai virus;

[5] the complex of any one of [1] to [4], wherein the protease is a protease whose activity is enhanced in cancer;

[6] the complex of any one of [1] to [5], wherein the protease is a matrix metalloproteinase or plasminogen activator;

[7] the complex of any one of [1] to [6], wherein the sequence cleaved by the protease comprises Pro-Leu-Gly, Pro-Gln-Gly, or Val-Gly-Arg;

[8] the complex of any one of [1] to [7], wherein a cytoplasmic domain of the wild-type F protein is partially deleted in the modified F protein;

[9] the complex of any one of [1] to [8], wherein the modified F protein is fused with an HN protein;

[10] a method for producing a viral particle which comprises a genomic RNA of paramyxovirus wherein (a) a nucleic acid encoding an M protein is mutated or deleted, and (b) a modified F protein, whose cleavage site sequence is substituted with a sequence that can be cleaved by a protease that does not cleave the wild-type F protein, is encoded; wherein the viral particle: (1) has the ability to replicate the genomic RNA in a cell to which the viral particle has been introduced; (2) shows a significant decrease in or lack of production of viral particles in the intrahost environment; and (3) has the ability to introduce the genomic RNA into a cell that contacts with the cell transfected with the viral particle comprising the genomic RNA in the presence of the protease; wherein the method comprises the steps of:

(i) amplifying RNP, which comprises the N, P, and L proteins of the paramyxovirus and the genomic RNA, in a cell expressing wild-type M protein of paramyxovirus; and (ii) collecting viral particles released into the cell culture supernatant;

[11] a method for producing a viral particle which comprises a genomic RNA of paramyxovirus wherein (a) a conditionally mutated M protein is encoded, and (b) a modified F protein, whose cleavage site sequence is substituted with a sequence that can be cleaved by a protease that does not cleave the wild-type F protein, is encoded; wherein the viral particle: (1) has the ability to replicate the genomic RNA in a cell to which the viral particle has been introduced; (2) shows a significant decrease in or lack of production of viral particles in the intrahost environment; and (3) has the ability to introduce the genomic RNA into a cell that contacts with the cell transfected with the viral particle comprising the genomic RNA in the presence of the protease; wherein the method comprises the steps of:

(i) amplifying RNP, which comprises the N, P, and L proteins of the paramyxovirus and the genomic RNA, in cells under permissive conditions for the mutant M protein; and (ii) collecting viral particles released into the cell culture supernatant;

[12] the method of [10] or [11], wherein step (i) is performed at 35° C. or below;

[13] the method of [10] or [1], further comprising the step of presenting the protease that cleaves the modified F protein during at least either of steps (i) or (ii); or the step of treating the viral particle collected in step (ii) with the protease;

[14] the method of [10] or [11], which further comprises the steps of expressing the wild-type F protein of paramyxovirus in the cell during step (i); and presenting the protease that cleaves the wild-type F protein during at least either of steps (i) or (ii); or the step of treating the viral particle collected in step (ii) with the protease;

[15] a therapeutic composition for cancer comprising the complex of [5] and a pharmaceutically acceptable carrier;

[16] a recombinant modified paramyxoviral F protein comprising Pro-Leu-Gly, Pro-Gln-Gly, or Val-Gly-Arg at the cleavage site, and showing cell fusogenicity in the presence of matrix metalloproteinase or plasminogen activator;

[17] a nucleic acid encoding the protein of [16];

[18] a viral particle comprising the protein of [16] or a nucleic acid encoding the protein;

[19] a fusion protein having cell fusogenic activity and comprising the transmembrane regions of the paramyxoviral F protein and HN protein, wherein the proteins are bound to each other on the cytoplasmic side;

[20] the fusion protein of [19], wherein the sequence of the cleavage site of the protein is substituted with a sequence that is cleaved by a protease that does not cleave the wild-type F protein;

[21] a nucleic acid encoding the protein of [19];

[22] a vector which comprising the nucleic acid of [21]; and

[23] a viral particle comprising the protein of [19] or a nucleic acid encoding the protein.

In the present invention, the term "paramyxovirus" refers to viruses that belong to the family Paramyxoviridae, and to viruses derived from them. Paramyxovirus is a virus group characterized by a non-segmented negative strand RNA genome, and including the subfamily Paramyxovirinae (comprising the genus *Paramyxovirus* (also called the genus *Respirovirus*, the genus *Rubulavirus* and the genus *Morbillivirus*), and the subfamily Pneumovirinae (comprising the genus *Pneumovirus* and the genus *Metapneumovirus*). Specifically, paramyxoviruses to which the present invention can be applied include the Sendai virus, Newcastle disease virus, mumps virus, measles virus, RS virus (Respiratory syncytial virus), rinderpest virus, distemper virus, simian parainfluenza virus (SV5), and human parainfluenza virus type 1, 2, and 3, etc. More specifically, for example, the Sendai virus (SeV), human parainfluenza virus-1 (HPIV-1), human parainfluenzavirus-3 (HPIV-3), phocinedistempervirus (PDV), canine distemper virus (CDV), dolphin molbillivirus (DMV), peste-des-petits-ruminants virus (PDPR), measles virus (MV), rinderpest virus (RPV), Hendra virus (Hendra), Nipah virus (Nipah), human parainfluenza virus-2 (HPIV-2), simian parainfluenza virus 5 (SV5), human parainfluenza virus-4a (HPIV-4a), human parainfluenza virus-4b (HPIV-4b), mumps virus (Mumps), and Newcastle disease virus (NDV) are included. More preferably, examples include viruses selected from the group consisting of Sendai virus (SeV), human parainfluenzavirus-1 (HPIV-1), human parainfluenza-virus-3 (HPIV-3), phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), and Nipah virus (Nipah). The viruses of the present invention preferably belong to the subfamily Paramyxovirinae (comprising the genus *Respirovirus*, the genus *Rubulavirus* and the genus *Morbillivirus*), and more preferably to the genus *Respirovirus* also called the genus *Paramyxovirus*). Examples of viruses of the genus *Respirovirus* to which the present invention can be applied include human parainfluenza virus type 1 (HPIV-1), human parainfluenza virus type 3 (HPIV-3), bovine parainfluenza virus type 3 (BPIV-3), Sendai virus (also called murine parainfluenza virus type 1), simian parainfluenza virus type 10 (SPIV-10), etc. The paramyxovirus of the present invention is most preferably the Sendai virus. These viruses may be derived from natural strains, wild-type strains, mutant strains, laboratory-passaged strains, artificially constructed strains, etc.

The phrases "recombinant protein" and "recombinant virus" refer to proteins and viruses produced via recombinant polynucleotides, respectively. The phrase "recombinant polynucleotide" refers to a polynucleotide that is not bonded as in nature. Specifically, recombinant polynucleotides comprise polynucleotides whose polynucleotide strand has been recombined artificially, and synthetic polynucleotides. Recombinant polynucleotides can be produced using conventional gene recombination methods by combining the processes of polynucleotide synthesis, nuclease treatment, ligase treatment, and such. Recombinant proteins can be produced by expressing recombinant polynucleotides encoding the proteins. Recombinant viruses can be produced by the steps of: expressing a polynucleotide encoding the viral genome, which is constructed by genetic engineering; and then reconstituting the virus.

The term "gene" used herein refers to a genetic substance, which includes nucleic acids such as RNA, DNA, etc. In the present invention, a nucleic acid encoding a protein is called a protein gene. However, a gene need not necessarily encode a protein; for example, it may encode a functional RNA such as a ribozyme, antisense RNA, etc. A gene may have a naturally derived or artificially designed sequence. Herein, the term "DNA" encompasses both single-stranded DNA and double-stranded DNA. The phrase "encoding a protein" indicates that a polynucleotide comprises an antisense or sense ORF, which encodes a protein amino acid sequence, such that the polynucleotide can be expressed under suitable conditions.

The present invention provides cell fusion vectors having replicative ability whose protease-dependent tropism has been modified. In an intrahost environment, such vectors do not release significant quantities of virus-like particles after transfection into cells, and infiltrate into surrounding cells only in the presence of a certain protease. Specifically, the vectors of the present invention include:

a complex which comprises a genomic RNA of paramyxovirus wherein (a) a nucleic acid encoding an M protein is mutated or deleted, and wherein (b) a modified F protein, whose cleavage site sequence is substituted with a sequence that can be cleaved by a protease that does not cleave the wild-type F protein, is encoded, and which comprises the following properties:

(1) the ability to replicate the genomic RNA in a cell to which the complex has been introduced;

(2) a significant decrease in or lack of production of viral particles in the intrahost environment; and (3) the ability to introduce the RNA into a cell that contacts with the cell transfected with the complex only in the presence of the protease. Since such a complex has the function of replicating the genomic RNA and transferring it to neighboring cells, it is also called a vector in the present invention. The term "vector" refers to carriers that transfer nucleic acids into cells.

More specifically, the above complex comprises the genomic RNA of paramyxovirus and viral proteins that bind to this RNA. The complexes of the present invention can consist of, for example, the genomic RNA of paramyxoviruses, and the viral proteins, i.e., the ribonucleoprotein (RNP). RNPs can be introduced into target cells, for example, in combination with a desired transfection reagent. Such RNPs are, more specifically, complexes comprising the genomic RNAs of paramyxoviruses, N proteins, P proteins, and L proteins. When RNPs are introduced into cells, the viral proteins work to transcribe cistrons encoding viral proteins from the genomic RNA; in addition, the genome itself is replicated and daughter RNPs are produced. Replication of the genomic RNA can be confirmed by detecting an increase in RNA copy number using RT-PCR, Northern hybridization, or such.

More preferably, the above-described complex is a virus particle of a paramyxovirus. The phrase "virus particle" refers to a nucleic-acid-containing minute particle that is released from a cell by the action of viral proteins. Virus particles can take various forms, e.g., that of spheres or rods, depending on the viral species. They are significantly smaller than cells, generally in the range of about 10 nm to about 800 nm. Paramyxovirus viral particles are structured such that the above-mentioned RNP comprises the genomic RNA and viral proteins, and is enclosed by a lipid membrane (or envelope) derived from the cell membrane. The viral particles may or may not show infectivity (infra). For example, some viral particles do not show infectivity as they are, but acquire infectivity upon specific treatment.

The phrase "genomic RNA of paramyxovirus" refers to RNA that has the ability to form RNP with proteins of paramyxovirus and express genes from the genome using these proteins to replicate the nucleic acids and form daughter RNPs. The paramyxovirus has as its genome a negative single-stranded RNA, a kind of RNA that encodes genes in the antisense mode. In general, paramyxovirus genomes comprise viral genes in antisense series between the 3'-leader region and the 5'-trailer region. Between the open reading frames (ORFs) for each gene, a series of sequences is present: a transcription termination sequence (E sequence), an intervening sequence (I sequence), and a transcription initiation sequence (S sequence). Thus, the RNA encoding each gene's ORF is transcribed as a separate cistron. Genomic RNAs included in the vectors of this invention encode (in antisensemode) nucleocapsid (N), phosphor (P), and large (L) proteins. These proteins are necessary for the expression of genes encoded by the RNAs, and for autonomous replication of the RNA themselves. Furthermore, the RNAs encode the fusion (F) protein, which induces cell membrane fusion necessary for spreading the RNA to neighboring cells, in an antisense orientation. Preferably, the genomic RNAs further encode the hemagglutinin-neuraminidase (HN or H) protein in an antisense orientation. However, in certain cells, the HN protein is not necessary for infection (Markwell, M. A. et al., Proc. Natl. Acad. Sci. USA 82(4), 978-982, 1985) and infection is accomplished with the F protein alone. Furthermore, vectors can be infected to cells by using proteins other than HN that binds to cells, combined with the F protein. Therefore, the vectors of this invention can be constructed using genomic RNAs that do not encode the HN gene.

Genes of viruses belonging to the subfamily Paramyxovirinae are represented in general as below: The N gene is also generally described as the "NP".

| Genus *Respirovirus* | NP | P/C/V | M | F | HN | — | L |
| Genus *Rubulavirus* | NP | P/V | M | F | HN | (SH) | L |
| Genus *Morbillivirus* | NP | P/C/V | M | F | H | — | L |

For example, database accession numbers for nucleotide sequences of Sendai virus genes classified as Respiroviruses within the Paramyxoviridae family are: M29343, M30202, M30203, M30204, M51331, M55565, M69046 and X17218 for the NP gene; M30202, M30203, M30204, M55565, M69046, X00583, X17007 and X17008 for the P gene; D11446, K02742, M30202, M30203, M30204, M69046, U31956, X00584 and X53056 for the M gene; D00152, D11446, D17334, D17335, M30202, M30203, M30204, M69046, X00152 and X02131 for the F gene; D26475, M12397, M30202, M30203, M30204, M69046, X00586, X02808 and X56131 for the HN gene; and D00053, M30202, M30203, M30204, M69040, X00587 and X58886 for the L gene. Accession numbers for virus genes encoded by additional viruses are exemplified below: AF014953 (CDV), X75961 (DMV), D01070 (HPIV-1), M55320 (HPIV-2), D10025 (HPIV-3), X85128 (Mapuera), D86172 (Mumps), K01711 (MV), AF064091 (NDV), X74443 (PDPR), X75717 (PDV), X68311 (RPV), X00087 (SeV), M81442 (SV5), and AF079780 (Tupaia) for N gene; X51869 (CDV), Z47758 (DMV), M74081 (HPIV-1), X04721 (HPIV-3), M5597-5 (HPIV-4a), M55976 (HPIV-4b), D86173 (Mumps), M89920 (MV), M20302 (NDV), X75960 (PDV), X68311 (RPV), M30202 (SeV), AF052755 (SV5), and AF079780 (Tupaia) for P gene; AF014953 (CDV), Z47758 (DMV), M74081 (HPIV-1), D00047 (HPIV-3), AB016162 (MV), X68311 (RPV), AB005796 (SeV), and AF079780 (Tupaia) for C gene; M12669 (CDV), Z30087 (DMV), S38067 (HPIV-1), M62734 (HPIV-2), D00130 (HPIV-3), D10241 (HPIV-4a), D10242 (HPIV-4b), D86171 (Mumps), AB012948 (MV), AF089819 (NDV), Z47977 (PDPR), X75717 (PDV), M34018 (RPV), U31956 (SeV), and M32248 (SV5) for M gene; M21849 (CDV), AJ224704 (DMV), M22347 (HPN-1), M60182 (HPIV-2), X05303 (HPIV-3), D49821 (HPIV-4a), D49822 (HPIV-4b), D86169 (Mumps), AB003178 (MV), AF048763 (NDV), Z37017 (PDPR), AJ224706 (PDV), M21514 (RPV), D17334 (SeV), and AB021962 (SV5) for F gene; AF112189 (CDV), AJ224705 (DMV), U709498 (HPIV-1), D000865 (HPIV-2), AB012132 (HPIV-3), M34033 (HPIV-4A), AB006954 (HPIV-4B), X99040 (Mumps), K01711 (MV), AF204872 (NDV), Z81358 (PDPR), Z36979 (PDV), AF132934 (RPV), U06433 (SeV), and S76876 (SV-5) for HN(H or G) gene. More than one strain is known for each of the viral species, and genes comprising sequences other than those shown above may exist depending on different strains.

The ORFs of these viral proteins are positioned in an antisense orientation via the above-described E-I-S sequence on the genomic RNA. On the genomic RNA, the ORF closest to the 3'-end requires only the S sequence between the 3'-leader region and the ORF, and not the E and I sequences. On the other hand, the ORF closest to the 5'-end on the genomic RNA requires only the E sequence between the 5'-trailer region and the ORF, and not the I and S sequences. Two ORFs can be transcribed as the same cistron using sequences such as IRES. In such cases, the E-I-S sequence is not necessary between these two ORFs. In the wild-type paramyxovirus, a typical RNA genome has a 3'-leader region followed by a sequence of six ORFs encoding the N, P, M, F, HN, and L proteins in this order in antisense orientation, followed by a 5'-trailer region at the other end. On the genomic RNAs of this invention, the configuration of the viral gene is not limited thereto; however, it is preferred to localize behind the 3' leader region the ORFs encoding the N, P, (M,) F, HN, and L proteins in this order followed by a 5'-trailer region similar to the wild-type virus. In a certain type of paramyxovirus, the number of viral genes is not six. However, even in such cases, each viral gene can be positioned similarly to the wild-type as described above, or they can be appropriately changed. The ORF of the M protein will be described later. However, according to one embodiment of the vectors of this invention, the ORF may be excluded or may encode a mutant M protein. Furthermore, in another embodiment of the vector of this invention, the cleavage site of the F protein encoded by the genome is modified to a sequence that is cleaved by a protease that does not cleave the wild-type F protein (infra). The genomic RNA of this invention may also encode one or more foreign genes. Any objective gene desired to be expressed in a target cell can be used as the foreign gene. The foreign gene is preferably inserted at sites in the noncoding region of the genome. For example, it may be inserted between the 3'-leader region and viral protein ORF closest to the 3'-end, between each of the viral protein ORFs, and/or between the viral protein ORF closest to the 5'-end and the 5'-trailer region. In an M gene-deficient genome, insertion can be made in the deficient region. When transferring a foreign gene to a paramyxovirus, preferably, the polynucleotide of the insertion fragment placed into the genome has a chain length that is a multiple of 6 (Journal of Virology 67(8), 4822-4830, 1993). The E-I-S sequence is placed between the inserted foreign gene and the viral ORF. Alternatively, the foreign gene may be inserted via IRES.

The expression level of the foreign gene can be adjusted by the type of transcription initiation sequence added upstream of the gene (the 3'-side of the negative strand) (WO 01/18223). Furthermore, the expression level can be regulated depending on the insertion position of the foreign gene in the genome. The closer the foreign gene is to the 3'-end of the negative strand, the higher the expression level of the foreign gene will be; similarly, the closer the foreign gene is to the 5'-end, the lower the expression level becomes. Therefore, the insertion site of the foreign gene can be adjusted appropriately to obtain a desired expression level of the foreign gene and an optimized combination with the upstream and downstream genes encoding viral proteins. Generally, high expression levels are considered advantageous for foreign genes. Therefore, the foreign gene is preferably linked to a highly efficient transcription initiation sequence, and inserted near the 3'-end of the negative strand genome. More specifically, it is preferably inserted between the 3'-leader region and the viral protein ORF closest to the 3'-end. Alternatively, the foreign gene may be inserted between the viral gene ORF closest to the 3'-end and the ORF of the secondly closest gene. Conversely, when high expression level of the transferred gene is not preferred, the expression level from the viral vector can be reduced by, for example, designing the insertion position of the gene in the vector to be as close as possible to the 5'-side of the negative strand genome, or using a transcription initiation sequence with a low efficiency, for an appropriate effect to arise.

Any viral genes included in the vector of this invention may be modified from wild-type genes in order to, for example, reduce the immunogenicity of the viral proteins, or to enhance RNA transcription and replication efficiency. Specifically, in paramyxoviral vectors, for example, transcription or replication functions can be enhanced by modifying at least one of the replication factors: N, P, and L genes. The structural protein HN comprises both hemagglutinin and neuraminidase activities. If, for example, the activity of the former can be reduced, the stability of the virus in blood can be enhanced. On the other hand, if, for example, the activity of the latter can be modified, infectivity can be regulated. In addition, membrane fusion and/or particle formation ability can be regulated by modifying the F protein and its domains, apart from the cleavage site. For example, by using analysis of the antigen-presenting epitopes and such of possible cell surface antigenic molecules, such as the F and HN proteins, a viral vector with weakened antigen-presenting ability against these proteins can be created.

Vectors with deficient accessory genes can be used as the vectors of the present invention. For example, by knocking out the V gene, an SeV accessory gene, SeV pathogenicity to hosts such as mice can be markedly decreased without damaging gene expression and replication in cultured cells (Kato, A. et al., J. Virol. 71, 7266-7272, 1997; Kato, A. et al. EMBO J. 16, 578-587, 1997; Curran, J. et al., WO 01/04272, EP 1067179). Such attenuated vectors are preferred as viral vectors for in vivo or ex vivo nontoxic gene transfer.

In a preferred embodiment, the complexes of the present invention are substantially homogeneous. The phrase "substantially homogeneous" complex refers to complexes that are isolated from a paramyxoviral RNP or viral particle which is not a complex of this invention. That is, the substantially homogeneous complexes of this invention do not comprise other paramyxovirus RNP or viral particles that possess particle-forming ability. Herein, the phrase "particle-forming ability" refers to the ability of a vector to release infectious and/or noninfectious viral particles (called virus-like particles) in cells infected with the viral vector, a process referred to as "secondary release". Furthermore, the complexes of this invention with modified cleavage site of the F protein do not comprise viral RNPs comprising genes that encode the wild-type F protein or an F protein having a similar fusion activity thereto in the genome, nor viral particles comprising this genome.

According to an embodiment of this invention, the cleavage site sequence of the F protein encoded by the above-mentioned genomic RNA is substituted by a sequence that is cleaved by another protease. The F protein of paramyxovirus (F0) itself does not show cell membrane fusion activity in its original form. However, upon cleavage of the extracellular domain of the F0 fragment (or the outer domain of the viral particle), it exhibits its fusion activity. The two F protein fragments, N-terminal side and C-terminal side fragments, resulting from the cleavage are called F1 and F2, respectively, and are bonded together via a disulfide bond. Cleaving the F protein involves cleaving the F protein on the membrane at a domain outside the membrane, thereby resulting in the generation of fragments with cell fusogenicity. The phrase "cleavage site sequence" refers to an amino acid sequence required for the cleavage by a protease or essential residues therein. The cleavage sites of the paramyxovirus F protein are known in the art, and may be cleaved by trypsin-like intracellular proteases, such as furin.

Furins generally exist in the Golgi body of most cells. The recognition motif of furin is Arg-X-Lys/Arg-Arg (RXK/RR) (separation of two amino acids by "/" means either one of the amino acids). Highly pathogenic Human PIV3 (RTKR), SV5 (RRRR), Mumps virus (RHKR), NDV (virulent strain) highly virulent strain (RQR/KR), Measles virus (RHKR), RS virus (RKRR), and such comprise the sequences of these motifs at their cleavage sites. The F protein of highly virulent strains is sensitive to proteases present in all cells, and viruses of this strain undergo multi-step proliferation upon cleavage of the F protein in all organs. Thus, the infection of these viruses is fatal. On the other hand, Sendai virus (PQSR), Human PIV1 (PQSR), and NDV (avirulent strain) weakly virulent strain (K/RQG/SR) with low virulence do not comprise this motif, but only Arg, which is the serine protease recognition sequence. The sequences of the F protein cleavage sites of paramyxovirus are well analyzed, and those skilled in the art can recognize them by appropriately referring to the literature (see, for example, "Uirusu-gaku (Virology)", Hatanaka, M. ed., Tokyo, Asakura Shoten, 247-248, 1997).

Furthermore, a cleavage site can be confirmed by identifying the cleavage site of an F protein of a virus grown in cells, tissues, individuals, or such where the paramyxovirus can proliferate, or the F protein collected by expressing them in these cells, individuals, or such. Alternatively, the F protein can be cleaved artificially and identified by treating the F protein expressed on the cell surface with a protease such as trypsin, which cleaves the cleavage site of the protein. According to an embodiment of this invention, the F protein comprises modified F protein cleavage site that may be cleaved by another protease. To accomplish this, the native cleavage sequence of the F protein is modified by replacing, deleting, and/or inserting one or more amino acids to reconstitute a sequence that is cleaved by another protease. Modification of the amino acid sequence can be performed by conventional site-directed mutagenesis methods. In addition, the modified F protein may maintain the property of being cleaved by proteases (such as trypsin) which cleave the wild-type F protein (see Examples). Vectors encoding such modified F proteins show enhanced protease-dependent tropism as compared to the wild-type F protein.

Sequences cleaved by another protease may be those cleaved by a preferable proteases. For example, sequences that are cleaved by a protease selectively expressed in tissues or cells which serve as the preferred target for vector introduction may be used (WO 01/20989). By designing a vector using an F protein gene comprising a sequence cleaved by a protease that is active in the target tissues as described above, the excellent property for proliferating and transferring the vector specifically to surrounding cells under conditions where this protease activity exists can be realized. For example, by employing a cleavage sequence of a protease specifically expressed or activated in particular tissues, vectors that specifically infiltrate only within those tissues may be constructed. Furthermore, by utilizing the cleavage sequence of a protease that is specifically expressed or activated under certain conditions, such as a disease, vectors that specifically infiltrate under such conditions (for example, only within the lesion of a specific disease) can be constructed. Both intracellular and extracellular proteases may be utilized. For example, proteases secreted to the cell exterior, and membrane proteases expressed on the membrane surface are preferred. Alternatively, the selected protease may be any desired protease that exists within the transport pathway of the F protein, starting from intracellular translation to secretion on the cell surface.

A large number of disorders are caused by aberrant expression of protease genes, including, for example, disorders belonging to all categories of general pathology, such as metabolic disorders, circulatory disorders, inflammation and immunologic disorders, infections, and malignant tumors. Specific examples include calpain in muscular dystrophy, destruction of the ubiquitin-proteasome system in autoimmune diseases and neural disorders, decreased expression of neprilysin in Alzheimer's disease, enhanced expression of MMP in infiltration andmetastasis of cancer, pathogen-derived protease from pathogenic microorganisms, serine protease in hemostatic mechanism, and aminopeptidase in the placenta.

Calpain, a calcium-dependent cysteine protease, has been studied as an enzyme involved in muscle proteolysis of muscular dystrophy. Calpain undergoes a specific activation mechanism in which activation occurs due to binding with calcium, and is considered to trigger muscle proteolysis by limited intracellular degradation of proteins important for structural maintenance of skeletal muscles, such as $\alpha$-actinin, troponin, and connectin. Regarding the cleavage sequence for calpain (Karlsson, J. O. et al., Cell Biol. Int. 24, 235-243, 2000), Leu-Leu-Val-Tyr and such are used as the degradation substrate.

The ubiquitin-proteasome system is a selective and active intracellular proteolysis mechanism, and an important cell function regulatory system for signal transduction, cell cycle, and such. Ubiquitin consists of 76 amino acids, and is covalently bonded to a protein by continuous catalytic action via the ubiquitin activating enzyme (E1), ubiquitin binding enzyme (E2), and ubiquitin ligase (E3). The ubiquitinated protein is degraded by the 26S proteasome. Several hundred types of E3 enzymes are known to exist and are categorized roughly into HECT type and RING finger type. Abnormal activities of these enzymes have been implicated in a large number of diseases. For example, Leu-Leu-Val-Tyr is used as the degradation substrate of the 26S proteasome (Reinheckel, T. et al., Arch. Biochem. Biophys. 377, 65-68, 2000).

Articular disorders, such as chronic rheumatoid arthritis, cause dyskinesia by the destruction of articular cartilage tissues. The regeneration ability of articular cartilage is extremely low, and destruction of the cartilage conformation by extracellular matrix degradation leads to progressive articular destruction. The relationship between MMP and "a disintegrin and metalloproteinase" (ADAM) molecule of related gene family is of interest in such destruction of the extracellular matrix of the cartilage. In particular, ADAMTS (ADAM with thrombospondin motif) molecule is considered to be an enzyme necessary for degrading cartilage proteoglycan (aggrecan) (Tortorella, M. D. et al., Science 284, 1664-1666, 1999). The sequence leading to aggrecan degradation by ADAMTS has been identified (Tortorella, M. D. et al., J. Biol. Chem. 275, 18566-18573, 2000).

Using the recognition sequences of these proteases, vectors specific to tissues that express these proteases can be prepared.

Particularly preferred protease cleavage sequences of this invention include those of proteases whose activity is enhanced in cancer. By constructing vectors using such sequences, vectors that specifically infect cancer tissues can be constructed. Such vectors are extremely useful as gene transfer vectors for cancer therapy. Proteases with "enhanced activity" in cancer are those that show enhanced activity in certain cancer tissues or cancer cells as compared to the activity in the corresponding normal tissues or normal cells. Herein, the phrase "enhanced activity" includes enhancement of the protease expression level and/or activity itself. The protease expression level can be measured by, for example, Northern hybridization using gene fragments of the protease as the probe, RT-PCR using a primer that specifically amplifies the protease gene, or Western blotting, ELISA, and immunoprecipitation using antibodies against the protease. The activity of the protease can be determined by degradation assay using substrates of the protease. Many in vivo proteases whose activity is regulated by various inhibitory factors are known in the art. The activity level of proteases can also be determined by measuring the expression level of these inhibitory factors.

For example, the extracellular matrix (ECM) degradation enzyme activity is particularly enhanced in metastatic cancer (Nakajima, M. and Chop, A. M., Semin. Cancer Biol. 2, 115-127, 1991; Duffy, M. J., Clin. Exp. Metastasis 10, 145-155, 1992; Nakajima, M. "Extracellular matrix degradation enzyme (Japanese)", Seiki, M. ed., "Malignant transformation and metastasis of cancer", Chugai Igaku, 124-136, 1993). In animals, matrices comprising proteins such as collagen and proteoglycan are formed in the space between cells. Specifically known components of the extracellular matrix include collagen, fibronectin, laminin, tenascin, elastin, proteoglycan, and such. These ECMs have the function of regulating adhesion, development, transfer, and such of cells, as well as regulating the distribution and activity of soluble factors via binding thereto. Infiltration of ECM by ECM degradation enzymes is deeply involved in cancer metastasis, and many reports have demonstrated that inhibitors of ECM degradation enzymes can inhibit metastasis or infiltration to the basal membrane. Vectors that specifically infect and infiltrate cancer tissues can be constructed by encoding a modified F protein having a recognition sequence for cleavage by ECM degradation enzyme at its cleavage site.

ECM degradation enzymes are categorized into aspartic acid proteases, cysteineproteases, serineprotease, and metalloproteases, depending on the kind of catalytic residues at their active center. In particular, for ECM degradation in vivo, serine proteases and metalloproteases, which are neutral proteases, play a central role. Serine proteases are widely distributed in microorganisms, animals, plants, and such. In higher animals, they are involved in many biological reactions, including, for example, food digestion, blood coagulation, fibrinolysis, immune complement reaction, cell proliferation, ontogeny, differentiation, senescence, cancer metastasis, and such. Furthermore, the activity of serine protease is generally regulated by a serine protease inhibitor (serpin) which generally exists within plasma and tissues, and quantitative or qualitative abnormalities of the inhibitor are known to cause inflammation and such.

ECM-degrading serine proteases include cathepsin G, elastase, plasmin, plasminogen activator, tumor trypsin, chymotrypsin-like neutral proteinase, thrombin, etc. Plasmin is produced by limited degradation of plasminogen existing in vivo in the inactive form. This limited degradation is regulated by plasminogen activator (PA) and its inhibitor, plasminogen activator inhibitor (PAI). PAs comprise tissue PA (tPA), which is involved in blood coagulation, and urokinase PA (uPA), which is related to ECM degradation (Blasi, F. and Verde, P., Semin. Cancer Bio. 1, 117-126, 1990). The function of these two PAs are inhibited through the binding of PAI (Cajot, J. F. et al., Proc. Natl. Acad. Sci. USA 87, 6939-6943, 1990; Baker, M. S. et al., Cancer Res. 50, 4676-4684, 1990). uPA can function while being bound to a uPA receptor (uPAR) on the cell surface. Plasmin degrades fibronectin, tenascin, laminin, and such, but fails to directly degrade collagen. However, it indirectly degrades collagen by activating the collagen degradation enzyme via cleavage of a portion of the precursor of the enzyme. These often show enhanced activity in cancer cells, and correlate well with metastatic ability (Tanaka, N. et al., Int. J. Cancer 48, 481-484, 1991; Boyd, D. et al., Cancer Res. 48, 3112-3116, 1988; Hollas, W. et al., Cancer Res. 51, 3690-3695, 1991; Correc, P. et al., Int. J. Cancer 50, 767-771, 1992; Ohkoshi, M. et al., J. Natl. Cancer Inst. 71, 1053-1057, 1983; Sakaki, Y. et al., New Horizon for Medicine (Japanese) 17, 1815-1821, 1985).

Many studies have been carried out on the cleavage sequences of uPA and tPA (Rijken, D. C. et al., J. Biol. Chem. 257, 2920-2925, 1982; Wallen, P. et al., Biochim. Biophys. Acta 719, 318-328, 1982; Tate, K. M. et al., Biochemistry 26, 338-343, 1987). The commonly used substrate sequences include VGR (Dooijewaard, G., and KLUFT, C., Adv. Exp. Med. Biol. 156, 115-120, 1983) and Substrate S-2288 (Ile-Pro-Arg) (Matsuo, O. et al., Jpn. J. Physiol. 33, 1031-1037, 1983). Butenas et al. used 54 kinds of fluorescent substrates to identify sequences highly specific to tPA (Butenas, S. et al., Biochemistry 36, 2123-2131, 1997), and demonstrated that two sequences, FPR and VPR, show high degradation activity against tPA. Therefore, these sequences are particularly preferred in the present invention.

Other ECM degradation enzymes are categorized as cysteine protease or aspartic protease. They are also involved in the metastasis and infiltration of cancer. Specific examples include: cathepsin B (Sloane, B. F., Semin. Cancer Biol. 1, 137-152, 1990) using laminin, proteoglycan, fibronectin, collagen, procollagenase (activated by degradation), and such as substrates; cathepsin L (Kane, S. E. and Gottesman, M. M., Semin. Cancer Biol. 1, 127-136, 1990) using elastin, proteoglycan, fibronectin, laminin, elastase (activated), and such as substrates; and cathepsin D (Rochefort, H., Semin. Cancer Biol. 1, 153-160, 1990) using laminin, fibronectin, proteoglycan, and cathepsin B and L (activated) as substrates. Cathepsin B and L in particular are highly expressed in breast cancer tissues (Spyratos, F. et al., Lancet ii, 1115-1118, 1989; Lah, T. T. et al., Int. J. Cancer 50, 36-44, 1992), and colon cancer carcinoma (Shuja, S. et al., Int. J. Cancer 49, 341-346, 1991). The disruption of balance between them and their inhibitory factors has been suggested to be involved in malignant transformation of cancer (Sloane, B. F., Semin. Cancer Biol. 1, 137-152, 1990; Kane, S. E. and Gottesman, M. M., Semin. Cancer Biol. 1, 127-136, 1990).

Metalloproteinase is a metalloenzyme comprising a metallic element such as Zn at its active center. Reported metalloproteinases include caspase, amino peptidase, angiotensin I converting enzyme, and collagenase. Regarding metalloproteinases that degrade ECM, 16 kinds or more of matrix metalloproteinases (MMP) have been reported. Representative MMPs include collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). In general, MMP has $Zn^{2+}$ at its active center, and $Ca^{2+}$ is required for its enzyme activity. Furthermore, MMP is secreted as a latent enzyme (referred to as latent MMP or ProMMP), is activated outside the cell, and degrades various ECMs existing in vivo. Moreover, the activity of MMPs is inhibited by a common inhibitor, namely, tissue inhibitor of metalloproteinase (TIMP). Other examples of ECM degradative metalloproteinases include amino peptidase, such as amino peptidase N/CD13 and aminopeptidase B that degrade ECM component proteins. According to experiments using inhibitors, all of these proteinases have been reported to be deeply involved in cancer.

Among these proteinases, collagenases (e.g., MMP-1, -8, and -13) cleave fibrous collagens—type I, II, and III collagen molecules—at specific sites. Two types of gelatinase, gelatinase A (MMP-2) and gelatinase B (MMP-9), are known. Gelatinase is also called type IV collagenase, and degrades type V collagen and elastin in addition to type IV collagen, the major component of basal membranes. Furthermore, MMP-2 is known to cleave type I collagen at the same site as MMP-1. MMP-9 does not degrade laminin and fibronectin; however, MMP-2 degrades them. Stromelysins (MMP-3 and -10) accept and degrade a broad range of substrates and degrade proteoglycan; type III, IV, and IX collagen; laminin; and fibronectin. Matrilysin (MMP-7) is a molecule that lacks the hemopexin domain, has a substrate specificity identical to that of MMP-3, and particularly high degradation activity for proteoglycan and elastin. Membrane-type metalloproteinases (MT-MMPs) (MT1-MMP, MT2-MMP, MT3-MMP, MT4-MMP, MT5-MMP, and MT6-MMP) comprise a transmembrane structure. MT-MMPs have an insertion sequence (approximately ten amino acids) between the propeptide domain and the active site. This insertion sequence comprises Arg-Xaa-Lys-Arg (Xaa is any amino acid), and, during the transportation process to the cell membrane, is activated through cleavage by furin, an intracellular processing enzyme. Known MT-MPPs include MT1-MMP (MMP-14), MT2-MMP (MMP-15), MT3-MMP (MMP-16), MT4-MMP (MMP-17), MT5-MMP (MMP-23), and MT-6-MMP (MMP-25). For example, MT1-MMP degrades type I, II, and III collagens, and MT3-MMP degrades type III collagen.

Overexpression of MMP is known to widely occur in cancer cells. They are categorized into those caused by the cancer itself and by cancer interstitial cells. For example, interstitial collagen degrading collagenase (MMP-1) is involved with infiltration of cancer cells, and its activity level correlates with metastaticity in colon cancer and such (Wooley, D. E., Cancer Metastasis Rev. 3, 361-372, 1984; Tarin, D. et al., Br. J. Cancer 46, 266-278, 1982). Furthermore, activities of type IV collagenases (MMP-2 and MMP-9) are highly correlated with metastatic ability of various epithelial cancers (Liotta, L. A. and Stetler-Stevenson, W. G., Semin. Cancer Biol. 1, 99-106, 1990; Nakajima, M. Experimental Medicine 10, 246-255, 1992). Moreover, stromelysin (MMP-3) is also known to be correlated with malignant alteration of dermal epithelial tumor (Matrisian, L. M. and Bowden, G. T., Semi. Cancer Biol. 1, 107-115, 1990). Stromelysin-3 (MMP-11) has been observed to be highly expressed in breast cancer and colon cancer (Basset, T. et al., Nature 348, 699-704, 1990; Porte, H. et al., Clin. Exp. Metastasis 10 (Suppl. 1), 114, 1992).

Many cleavage substrates for MMP are known. Examples of substrate sequences that are degraded by all MMPs include PLGLWAR (Bickett, D. M. et al., Anal. Biochem. 212, 58-64, 1993), GPLGMRGL (Deng, S. J. et al., J. Biol. Chem. 275, 31422-31427, 2000), PQGLEAK (Beekman, B. et al., FEBS Lett. 390, 221-225, 1996), RPKPVEWREAK (Beekman, B. et al., FEBS Lett. 418, 305-309, 1997), and PLALWAR (Jacobsen, E. J. et al., J. Med. Chem. 42, 1525-1536, 1999). Cleavage substrates of MMP-2 and -9 include PLGMWS (Netzel-Arnett, S. et al., Anal. Biochem. 195, 86-92, 1991) and PLGLG (Weingarten, H. et al., Biochemistry 24, 6730-6734, 1985).

Recently, phage-displayed peptide library screening has elucidated the degradation substrate sequences for MMP-9 (Kridel, S. J. et al., J. Biol. Chem. 276, 20572-20578, 2001), MMP-2 (Chen, E. I. et al., J. Biol. Chem. 277, 4485-4491, 2002), and MT1-MMP (Kridel, S. J. et al., J. Biol. Chem. In JBC Papers in Press, Apr. 16, 2002, Manuscript M111574200). In these articles, identified amino acid sequences are categorized into four groups depending on the presence or absence of degradation ability by three MMPs. Group IV includes sequences that are specifically degraded by MT1-MMP, and regarding sequences lacking Arg, VFSIPL and IKYHS sequences are mentioned as substrates that are not degraded by MMP-9 and MMP-2, but are degraded by MT-MMP alone.

For example, the cleavage sequence of MMP-9 is Pro-X-X-Hy (wherein, X represents an arbitrary residue; Hy, a hydrophobic residue), with Pro-X-X-Hy-(Ser/Thr) being particularly preferred. A more specific example includes Pro-Arg-(Ser/Thr)-Hy-(Ser/Thr) (cleavage occurs between X and Hy residues). Examples of Hy (hydrophobic residues) include Leu, Val, Tyr, Ile, Phe, Trp, and Met, but are not limited thereto. Other cleavage sequences have been also identified (for example, see Group I, II, IIIA, and IIIB in the following literature; Kridel, S. J. et al., J. Biol. Chem. 276, 20572-20578, 2001), and any desired sequence may be used. The above-mentioned Pro-X-X-Hy may be used for MMP-2, and in addition, (Ile/Leu)-X-X-Hy, Hy-Ser-X-Leu, and His-X-X-Hy (see, for example, Group I, II, III, and IV in the following literature; Chen, E. I. et al., J. Biol. Chem. 277, 4485-4491, 2002) may also be used. The cleavage sequence for the MMP family comprising MMP-7, MMP-1, MMP-2, MMP-9, MMP-3, and MT1-MMP (MMP-14) can be appropriately selected, for example, by referring to the sequences of natural substrate proteins or by screening a peptide library (Turk, B. E. et al., Nature Biotech. 19, 661-667, 2001; Woessner, J. F. and Nagase, H., Matrix metalloproteinases and TIMPs. (Oxford University Press, Oxford, UK, 2000); Fernandez-Patron, C. et al., Circ. Res. 85, 906-911, 1999; Nakamura, H. et al., J. Biol. Chem. 275, 38885-38890, 2000; McQuibban, G. A. et al., Science 289, 1202-1206, 2000; Sasaki, T. et al., J. Biol. Chem. 272, 9237-9243, 1997). Examples of the eight amino acid sequences P4-P3-P2-P1-P1'-P2'-P3'-P4' (cleavage occurs between P1 and P1') of the cleavage site include VPMS-MRGG for MMP-1, RPFS-MIMG for MMP-3, VPLS-LTMG for MMP-7, and IPES-LRAG for MT1-MMP, but are not limited thereto. PLAY-WAR (Nezel-Amett, S. et al., Anal. Biochem. 195, 86, 1991) is an example for MMP-8. Various synthetic substrates of MMP are available, and can be compared to each other (see, for example, each of the MMP substrates in the Calbiochem® catalog, Merck).

Generally, MMP activity in tissues is regulated through the process of: latent enzyme production, latent enzyme activation, and active enzyme inhibition by inhibitors. MMP activity is involved in various physiological phenomena, such as development and ovulation, fertilization, implantation to the endometrium, and wound healing. Disorder in the regulation of MMP activity contributes to various pathologies including, for example, infiltration and metastasis of cancer cells, arthritis, gingivitis, arteriosclerosis, tumor, and fibrosis. For example, gellatinases (MMP-2 and -9) that degrade the basal membrane components are known to be important for metastasis of cancer. MMP-2 is activated by cleavage of pro-MMP-2 by MT1-MMP. On the other hand, a pathway for the activation of MMP-9 exists wherein first plasmin is produced from plasminogen by uPA to activate proMMP-3, and then the active MMP-3 activates proMMP-9. This pathway is involved in metastasis of cancer. In order to develop the vectors of this invention as cancer-targeting vectors, it is particularly useful to introduce a sequence cleaved by those proteases involved with metastasis of cancer as the cleavage site of the F protein. Examples of such proteases include MMP-2, MMP-9, uPA, MMP-3, and MT1-MMP, more specifically, MMP-2, MMP-9, and uPA.

When incorporating a protease cleavage sequence into the F protein, the protease cleavage sequence of interest is inserted into the cleavage site of the F protein and the originally existing trypsin-like protease cleavage site is preferably degenerated. To accomplish this purpose, the amino acid sequence around the original cleavage site for the trypsin-like protease can be substituted with the protease cleavage sequence (recognition sequence) of interest. The modified F protein is cleaved by the protease of interest when expressed in cells, and maintains the cell membrane fusion activity of the F protein. The amino acids close to the N-terminus of the F1 fragment produced by cleavage of the F protein are considered to play an important role in cell membrane fusion. Therefore, unless cleavage is inhibited, the cleavage sequence is preferably designed so that the N-terminal sequence of the F1 fragment after cleavage is identical to that of the F1 fragment of the wild-type F protein. Furthermore, to insert a linker into the cleavage site to induce efficient cleavage reaction, it is preferred that the smallest number of amino acids needed is added to the N-terminus of the cleaved F1 fragment in comparison to that of the wild-type F1. For example, five amino acids or less, preferably four amino acids or less, or more preferably three amino acids or less (for example, one, two, or three amino acids) are added to the N-terminus after cleavage in comparison to the wild-type F1. For example, the present invention elucidated that the addition of Met-Thr-Ser (SEQ ID NO: 1) added to the N-terminus of the F1 fragment of the modified F protein did not impair either the cleavage reaction by MMP or the cell membrane fusion reaction after the cleavage. Therefore, the cleavage sequence is preferably designed so that Met-Thr-Ser, or conservative substitution sequences thereof or amino acids comprising a partial sequence thereof, is added to the N-terminus of F1 after cleavage. The phrase "conservative substitution" refers to a substitution between amino acids whose amino acid side chains have similar chemical characteristics. Specifically, Met can be substituted with Ile or Val, Thr can be substituted with Ser or Ala, and Ser can be substituted with Ala, Asn, or Thr. Substitution of amino acids at each position can be performed independently.

More specific examples of the preferred cleavage sequence for MMP-2 and -9 include those comprising Pro-Leu/Gln-Gly (SEQ ID NO: 2). This sequence is a common sequence among synthetic substrates (Netzel-Arnett, S. et al., Anal. Biochem. 195, 86-92, 1991) used as substrates, and the F protein is designed so that this sequence is positioned at the C-terminus of the F2 fragment after cleavage of the modified F protein. To accomplish this, the sequence comprising the C-terminal amino acids of the F2 fragment after cleavage of the wild-type F protein is replaced with a sequence comprising Pro-Leu/Gln-Gly. The original sequence corresponding to one or several amino acids of the C-terminus of the F2 fragment of the F protein is appropriately deleted, and then, Pro-Leu/Gln-Gly is inserted (i.e., perform substitution). The number of amino acids to be deleted may be equal to the number of amino acids to be inserted (for example, three amino acids), or can be selected in the range of zero to ten amino acids or such. As long as the steps of cleavage by a protease and membrane fusion are not impaired, the F protein can be prepared so that the N-terminus of F1 is directly linked downstream of Pro-Leu/Gln-Gly. However, in the F protein of Sendai virus or such, the cleavage sequence and the F1 fragment are preferably linked via an appropriate spacer. Particularly preferred examples of such spacer-comprising cleavage sequences include those sequences comprising Pro-Leu/Gln-Gly-Met-Thr-Ser (SEQ ID NO: 3) or Pro-Leu/Gln-Gly-Met-Thr (SEQ ID NO: 4). Met, Thr, and Ser can be conservatively substituted with other amino acids. More preferred examples of proteins include modified F proteins in which one to ten residues, such as one, two, three, four, five, or six residues, sequentially linked from the C-terminal amino acid in F2 after cleavage towards the N-terminus, are replaced with a sequence comprising Pro-Leu/Gln-Gly-Met-Thr-Ser or Pro-Leu/Gln-Gly-Met-Thr. For example, in the case of the Sendai virus F protein, an F protein in which the sequence (although it depends on the strain, it is typically $^{113}$Pro-Gln-Ser-Arg$^{116}$↓) corresponding to the four C-terminal amino acids of the F2 fragment in the wild-type F protein (SEQ ID NO: 5) is replaced with Pro-Leu/Gln-Gly-Met-Thr-Ser and such.

Any other desired sequence described in the present invention may be used as the cleavage sequence of MMP. In the interest of substrate specificity of the various MMPs, analyses have been performed using peptide libraries (Turk, B. E. et al., Nature Biotech. 19, 661-667, 2001). Detailed analyses have been performed for MMP-2 (Chen, E. I. et al., J. Biol. Chem. 277(6), 4485-4491, 2002) and MMP-9 (Kridel, S. J. et al., J. Biol. Chem. 276(8), 20572-20578, 2001) of interest. Regarding MMP-9 in particular, the consensus sequence from P3 to P2' (P3-P2-P1-P1'-P2'; cleavage takes place between P1-P1') is proposed as Pro-X-X-Hy-(Ser/Thr) (X=any residues; Hy=hydrophobic residue). This consensus sequence also matches one of those proposed for MMP-2 (Pro-X-X-Hy), and thus, is considered to be a good design to accomplish specificity for MMP-2 and MMP-9. Therefore, from such aspects as well, the sequences shown above (Pro-Leu/Gln-Gly-Met-Thr-Ser or Pro-Leu/Gln-Gly-Met-Thr) have been supported as preferable examples. Specifically, the sequence of the F protein cleavage site preferably comprises Pro-X-X-Hy-Thr/Ser, and more preferably Pro-X-X-Hy-Thr/Ser-Thr/Ser ("Thr/Ser" means either Thr or Ser). For example, Pro-Leu-Gly-Leu-Trp-Ala and Pro-Gln-Gly-Leu-Tyr-Ala that do not match with Pro-X-X-Hy-Thr/Ser are not preferred (FIG. 44). By inserting into the F protein cleavage site a peptide that matches with the Pro-X-X-Hy-Thr/Ser sequence, a vector showing high infiltration ability in the presence of MMP can be constructed.

Other examples of preferable cleavage sequences include those cleaved by a plasminogen activator. Specific examples of cleavage sequences of uPA and tPA include sequences comprising Val-Gly-Arg. The F protein is designed so that this sequence is positioned at the C-terminus of the F2 fragment of the modified F protein after cleavage. To accomplish this, the sequence comprising C-terminal amino acids of the F2 fragment after cleaving the wild-type F protein can be replaced with a sequence comprising Val-Gly-Arg (SEQ ID NO: 6). More preferable examples of preferred proteins include a modified F protein in which one to ten residues, for example, one, two, three, four, five, or six residues, sequentially positioned from the C-terminal amino acid of F2 after cleavage towards the N-terminus are replaced with Val-Gly-Arg or a sequence comprising this sequence. For instance, in the Sendai viral F protein, examples include the F protein whose sequence corresponding to the three C-terminal amino acids of the F2 fragment in the wild-type F protein (typically $^{114}$Gln-Ser-Arg$^{116}$↓ (SEQ ID NO: 7), although it depends on the strain) is substituted with Val-Gly-Arg.

To efficiently identify a modified F protein that exerts fusogenicity in the presence of a specific protease, an assay system using a plasmid vector can be utilized (Example 31). Specifically, a plasmid vector expressing the modified F protein is transfected to cells, and the resulting cell is cultured in the presence of a protease to detect syncytium formation. The modified F protein encoded by the plasmid that causes syncytium formation is cleaved by protease to determine if it shows fusogenicity. For example, to assay the F protein that is cleaved by MMP, HT1080 cells that express MMP may be used. Alternatively, MMP may be added to the culture system. Using the assay system developed in this invention, a modified F protein having fusogenicity can be readily obtained.

A vector encoding a modified F protein can introduce the genomic RNA contained in the vector into cells contacting the cells transfected with the vector, depending on the presence of a protease that cleaves the modified F protein. The action of the cleaved F protein causes cell fusion between cells in contact, and the RNP spreads to the fused cells. That is, the vector of the present invention does not form viral particles; however, it can transfer the vector to a localized region due to the infiltration of vectors into contacting cells such as described above. The protease may be expressed intracellularly or extracellularly, or may be added exogenously.

The modified F proteins provided by the present invention show cell fusogenicity depending on a specific protease. By utilizing this protein, viral vectors, drugs and gene delivery vectors, such as liposomes, that causes cell fusion or specific infection only in the presence of the protease can be constructed. For example, by equipping the F gene of an adenoviral vector comprising F and HN genes (Galanis, E. et al., Hum. Gene Ther. 12, 811-821, 2001) with the gene of the modified F protein which is cleaved by a protease specifically expressed in cancer cells, vectors that cause cell fusion in the presence of the specific protease can be developed. In addition, for example, when pseudotyping a retrovirus with F and HN proteins (Spiegel, M. et al., J Virol. 72(6), 5296-5302, 1998), a cancer cell-targeting vector that specifically infects cancers may be developed using the modified F protein during construction process, which protein is cleaved by a protease expressed in cancers. As described above, in addition to the vectors of this invention, the modified F proteins provided by the present invention and nucleic acids encoding them may be utilized to develop various vectors that depend on proteases.

Furthermore, the present invention provides paramyxoviral vectors comprising a modified F protein in which the cell fusogenicity is increased by deletion of the cytoplasmic domain. A portion of the amino acids of the cytoplasmic domain is deleted such that 0 to 28, preferably 1 to 27, and more preferably 4 to 27 amino acids exist in the cytoplasmic domain of this modified F protein. The phrase "cytoplasmic domain" refers to the cytoplasmic side of the membrane protein, and in the F protein, it corresponds to the C-terminal region of the transmembrane (TM) region (see FIG. 42). For example, the F protein comprising 6 to 20, preferably 10 to 16, and more preferably 13 to 15 amino acids as the cytoplasmic domain shows significantly high levels of cell fusogenicity as compared to the wild-type F protein. Therefore, preparation of a paramyxoviral vector that comprises an F protein modified such that its cytoplasmic domain comprises approximately 14 amino acids enables the acquisition of vectors having higher cell fusogenicity as compared to those obtained with a wild-type F protein. Preferably, this deletion F protein lacks 10 or more, preferably 15 or more, more preferably 20 or more, still more preferably 25 or more, and furthermore preferably 28 or more of the C-terminal amino acids of the wild-type F protein. According to the most preferred aspect, the cytoplasmic domain-deleted F protein lacks approximately 28 amino acids from the C-terminus of the wild-type F protein. The paramyxoviral vectors which comprise genes encoding these cytoplasmic domain-deleted F proteins on the genome have higher cell fusogenicity as compared to conventional vectors, and thus, more strongly infiltrate into the surrounding cells. Modification of the cleavage site of this F protein as described herein yields a vector that exhibits a high infiltration ability only in the presence of a specific protease.

The present invention further relates to a fusion protein consisting of two kinds of spike proteins carried by the paramyxovirus. The paramamyxovirus has a protein considered to function in cell fusion (called the "F" protein) and a protein considered to function in adhesion to cells (called the "HN" or "H" protein). Herein, the former is generally called the F protein, and the latter the HN protein. These two proteins expressed as a fusion protein exert extremely strong fusogenicity as compared to separate expression of the proteins. In this fusion protein, the proteins are bonded through a portion of their cytoplasmic domains. Specifically, the fusion protein comprises the F protein at its N-terminus and the HN (or H) protein at its C-terminus. When fusing these proteins, the whole proteins may be fused to each other, or alternatively, the F protein which lacks a portion or the whole cytoplasmic domain may be fused to the HN (or H) protein. In the latter case, the number of amino acid residues from downstream of the TM region of the F protein to the HN (or H) protein is five or more, preferably ten or more, more preferably 14 or more, and still more preferably 20 or more. For example, when fusing an F protein that lacks the cytoplasmic domain to the HN (or H) protein, it is preferable to adjust the length by adding a linker peptide of appropriate length to the C-terminus of the F protein portion. Specifically, a cytoplasmic domain-deleted F protein comprising 14 residues of cytoplasmic domain fused to the HN (or H) protein via any linker peptide is preferably used. The linker peptide may be, for example, approximately 50 residues. The amino acid sequence of the linker peptide is not particularly limited; however, it is preferable to adopt a polypeptide which does not have significant physiological activity, and suitable examples include the polypeptide shown in FIG. 43 (SEQ ID NO: 80).

The present invention further relates to nucleic acids encoding these fusion proteins, and expression vectors comprising these nucleic acids. Cells transfected with these expression vectors show strong fusogenicity, and form syncytia through fusion with the surrounding cells. Expression vectors are not particularly limited, and include, for example, plasmid vectors and viral vectors. In the case of a DNA vector, use in combination with a strong promoter such as the CAG promoter (a chimeric promoter comprising chicken β-actin promoter and CMV enhancer) (Niwa, H. et al., Gene 108, 193-199, 1991) is preferred. A viral vector expressing a protein of the present invention yields strong fusion in transfected cells. Examples of suitable viral vectors include retroviral vectors, lentiviral vectors, adenoviral vectors, adeno-associated viral vectors, minus strand RNA viral vectors, simple herpes viral vectors, retroviral vectors, lentiviral vectors, Semliki forest viral vectors, sindbis viral vectors, vaccinia viral vectors, fowlpox viral vectors, and other preferable viral vectors. The paramyxovirus vectors that express the present protein(s) exhibit high infiltration ability towards various tissues. In particular, the use of an M gene-deleted paramyxoviral vector encoding a fusion protein of the present invention with a modified F protein cleavage site leads to the production of a vector that induces strong cell fusion in specific tissues.

These recombinant viral vectors can be prepared according to methods well known to those skilled in the art. For example, an adenoviral vector that is most commonly used for gene therapy and such can be constructed by the method of Saito et al. and other methods (Miyake et al., Proc. Natl. Acad. Sci. USA, 93, 1320-24, 1996; Kanegae et al., Acta Paediatr. Jpn., 38, 182-188, 1996; Kanegae et al., "Baiomanyuaru shiriizu 4-Idenshi-donyu to Hatsugen•Kaisekiho (Biomanual Series 4: Methods for gene transfection, expression, and analysis)", Yodosha, 43-58, 1994; Kanegae et al., Cell Engineering, 13(8), 757-763, 1994). In addition, for example, retroviral vectors (Wakimoto et al., Protein Nucleic acid and Enzyme (Japanese) 40, 2508-2513, 1995), adeno-associated viral vectors (Tamaki et al., Protein Nucleic acid and Enzyme (Japanese) 40, 2532-2538, 1995) and such can be prepared by conventional methods. As specific methods for producing other viral vectors capable of transferring genes to mammals, methods for producing recombinant vaccinia virus are known and described in Published Japanese Translation of International Publication No. Hei 6-502069, Examined Published Japanese Patent Application No. (JP-B) Hei 6-95937, and JP-B Hei 6-71429. Known methods for producing recombinant papilloma viruses include those described in JP-B Hei 6-34727, and Published Japanese Translation of International Publication No. Hei 6-505626. Furthermore, known methods for producing recombinant adeno-associated viruses and recombinant adenoviruses include those described in Unexamined Published Japanese Patent Application No. (JP-A) Hei 5-308975 And Published Japanese Translation of International Publication No. Hei 6-508039, respectively.

In the RNA genome, which is comprised in the vector provided as an aspect of this invention, the gene encoding the matrix (M) protein (i.e., the M gene) is mutated or deleted. According to the present invention, the cleavage site of the F protein is modified to a sequence that is cleaved by another protease, and furthermore, the M gene is mutated or deleted to suppress particle forming ability. Thereby, a vector with a completely new property that does not release viral particles, and infiltrates into only a group of cells expressing a particular protease has been successfully developed. The mutation of the M gene eliminates or significantly lowers the particle forming activity in the intrahost environment. Such mutations in cells that express this M protein can be identified by detecting a decrease in the cell surface aggregation of this protein (see Examples).

According to the present invention, the most effective modification for suppressing secondary release of particles, i.e., release of VLP, was confirmed to be the deletion of the M protein. This fact is also supported by studies reporting on the role of the M proteins in virion formation in Sendai virus (SeV) and other minus (−) strand RNA viruses. For example, it has been found that strong expression of the M protein in vesicular stomatitis virus (VSV) causes the budding of VLPs (Justice, P. A. et al., J. Virol. 69, 3156-3160, 1995); likewise, parainfluenza virus VLP formation is also reported to occur on mere overexpression of M protein (Coronel, E. C. et al., J. Virol. 73, 7035-7038, 1999). While this kind of VLP formation, caused by M protein alone, is not observed in all (−) strand RNA viruses, M proteins are recognized to serve as virion formation cores in (−)strand RNA viruses (Garoff, H. et al., Microbiol. Mol. Biol. Rev. 62, 1171-1190, 1998).

The specific role of the M protein in virion formation is summarized as follows: Virions are formed in so-called lipid rafts on the cell membrane (Simons, K. and Ikonen, E., Nature 387, 569-572, 1997). These were originally identified as lipid fractions that were insoluble with non-ionic detergents, such as Triton X-100 (Brown, D. A. and Rose, J. K., Cell 68, 533-544, 1992). Virion formation in lipid rafts has been demonstrated for the influenza virus (Ali, A. et al., J. Virol. 74, 8709-8719, 2000), measles virus (MeV; Manie, S. N. et al., J. Virol. 74, 305-311, 2000), SeV (Ali, A. and Nayak, D. P., Virology 276, 289-303, 2000), and others. At these lipid raft sites, the M protein enhances virion formation, concentrating envelope proteins (also referred to as spike proteins) and ribonucleoprotein (RNP). In other words, the M protein may function as a driving force for virus assembly and budding (Cathomen, T. et al., EMBO J. 17, 3899-3908, 1998; Mebatsion, T. et al., J. Virol. 73, 242-250, 1999). In fact, the M protein has been revealed to bind to the cytoplasmic tail of influenza virus spike proteins and such (Zhang, J. et al., J. Virol. 74, 4634-4644, 2000), SeV (Sanderson, C. M. et al., J. Virol. 67, 651-663, 1993). It also binds with the RNP of the influenza virus (Ruigrok, R. W. et al., Virology 173, 311-316, 1989), parainfluenza virus, SeV (Coronel, E. C. et al., J. Virol. 75, 1117-1123, 2001), etc. Further, in the case of SeV (Heggeness, M. H. et al., Proc. Natl. Acad. Sci. USA 79, 6232-6236, 1982) and vesicular stomatitis virus, etc (VSV; Gaudin, Y. et al., Virology 206, 28-37, 1995; Gaudin, Y. et al., J. Mol. Biol. 274, 816-825, 1997), M proteins have been reported to form oligomers with themselves. Thus, due to the capacity of the M protein to function in association with many virus components and lipids, the protein is considered to function as the driving force for virus assembly and budding.

In addition, some reports suggest that envelope protein (spike protein) modification may also suppress VLP release. The following experimental examples are specific reports in which virion formation was actually suppressed: a G protein deficiency in rabies virus (RV) resulted in a 1/30 reduction of VLP formation (Mebatsion, T. et al., Cell 84, 941-951, 1996). When the M protein was deficient, this level dropped to 1/500,000 or less (Mebatsion, T. et al., J. Virol. 73, 242-250, 1999). Further, in the case of the measles virus (MeV), cell-to-cell fusion was enhanced when the M protein was deficient (Cathomen, T. et al., EMBO J. 17, 3899-3908, 1998). This is presumed to result from the suppression of virion formation (Li, Z. et al., J. Virol. 72, 3789-3795, 1998). In addition, similar fusion enhancement arose with mutations in the cytoplasmic tail of F or H protein (the tail on the cytoplasmic side) (Cathomen, T. et al., J. Virol. 72, 1224-1234, 1998). Therefore, introducing a mutation which causes the deletion of only the cytoplasmic tail of the F and/or HN proteins may suppress particle formation. However, since many VLPs have been reported to exist in the F-deficient form (WO 00/70070) or the HN-deficient form (Stricker, R. and Roux, L., J. Gen. Virol. 72, 1703-1707, 1991), particularly in SeV, the effect of modifying these spike proteins may be limited. Furthermore, the following has also been clarified with regards to SeV: When the SeV proteins F and HN are on secretory pathways (specifically, when they are located in Golgi bodies, etc.), the cytoplasmic tails (of the F and HN proteins) bind with the M protein (Sanderson, C. M. et al., J. Virol. 67, 651-663, 1993; Sanderson, C. M. et al., J. Virol. 68, 69-76, 1994). Thus, it is presumed that this binding is important for the efficient transfer of the M protein to cell membrane lipid rafts, where virions are formed. The M protein was thought to bind to the F and HN proteins in the cytoplasm, and as a result to be transferred to the cell membrane via F and HN protein secretory pathways. As described above, the M protein plays an essential role in viral particle formation. The use of a modified M protein gene that eliminates M protein aggregation on the cell surface enables production of vectors without particle forming ability.

The subcellular localization of the M protein can be determined by cell fractionation, or by directly detecting M protein localization using immunostaining, or such. In immunostaining, for example, M protein stained by a fluorescently labeled antibody can be observed under a confocal laser microscope. Alternatively, after the cells have been lysed, a cell fraction can be prepared using a known cell fractionation method, and localization can then be determined by identifying the M protein-containing fraction using a method such as immunoprecipitation or Western blotting using an antibody against the M protein. Virions are formed in so-called cell membrane lipid rafts, lipid fractions that are insoluble with non-ionic detergents such as Triton X-100. The M protein is believed to participate in the aggregation of viral components in the lipid rafts due to its ability to bind to spike proteins, RNP, and to M protein itself, and further to lipids. Accordingly, the M protein, detected by electrophoresis or such with the lipid raft fraction, is presumed to reflect aggregated M protein. Namely, when the amount of detectable M protein is reduced, cell-surface M protein aggregation is determined to be reduced. M protein aggregation on cell membranes can be directly observed using the immunocytological staining methods used by the present inventors for detecting subcellular localization. This utilizes an anti-M antibody available for immunocytological staining. On investigation using this method, an intensely condensed image is observed near the cell membrane when the M protein is aggregated. When the M protein is not aggregated, there is neither a detectable condensation pattern nor a clear outline of the cell membrane. In addition, only a slight stain is observed in the cytoplasm. Thus, when little or no condensation pattern is detected, the cell membrane outline is indistinct, and slight staining is observed throughout the cytoplasm, cell-surface M protein aggregation is judged to be reduced.

Mutant M proteins having significantly reduced cell-surface aggregation activity are judged to have significantly lower particle formation ability as compared to that of wild-type M proteins. The reduction of particle formation ability in the virus is statistically significant (for example, at a significant level of 5% or less). Statistical verification can be carried out using, for example, the Student t-test or the Mann-Whitney U-test. Particle formation ability of the virus vectors, comprising mutant M gene, in intrahost environment is reduced to a level of preferably 1/5 or less, more preferably 1/10 or less, more preferably 1/30 or less, more preferably 1/50 or less, more preferably 1/100 or less, more preferably 1/300 or less, and more preferably 1/500 or less. Most preferably, the vectors of this invention substantially lack viral particle-producing ability in the intrahost environment. The phrase "substantially lack" means that no viral particle production is detected in the intrahost environment. In such cases, there exist $10^3$ or less, preferably $10^2$ or less, and more preferably $10^1$ or less per ml of the viral particles.

The presence of viral particles can be directly confirmed by observation under an electron microscope, etc. Alternatively, they can be detected and quantified using viral nucleic acids or proteins as indicators. For example, genomic nucleic acids in the viral particles may be detected and quantified using general methods of nucleic acid detection such as the polymerase chain reaction (PCR). Alternatively, viral particles comprising a foreign gene can be quantified by infecting them into cells and detecting expression of that gene. Non-infective viral particles can be quantified by detecting gene expression after introducing the particles into cells in combination with a transfection reagent. The viral particles of the present invention comprise particles without infectivity, such as VLP.

Furthermore, potency of the virus can be determined, for example, by measuring Cell-Infected Units (CIU) or hemagglutination activity (HA) (WO 00/70070; Kato, A. et al., Genes Cells 1, 569-579, 1996; Yonemitsu, Y. and Kaneda, Y., "Hemaggulutinating virus of Japan-liposome-mediated gene delivery to vascular cells.", Ed. by Baker, A. H., Molecular Biology of Vascular Diseases. Methods in Molecular Medicine., Humana Press., 295-306, 1999). In the case of vectors labeled with marker genes, such as the GFP gene, virus titer is quantified by directly counting infected cells using the marker as an indicator (e.g., as GFP-CIU) as described in the Examples. Titers thus determined can be considered equivalent to CIU (WO 00/70070). For example, the loss of viral particle production ability can be confirmed by the lack of detectable infectivity titer when cells are transfected with a sample which may comprise viral particles. Detection of viral particles (VLP and such) without infectivity can be performed by transfection using a lipofection reagent. Specifically, for example, DOSPER Liposomal Transfection Reagent (Roche, Basel, Switzerland; Cat. No. 1811169) can be used. One hundred microliters of a solution with or without viral particles is mixed with 12.5 μl DOSPER, and allowed to stand for ten minutes at room temperature. The mixture is shaken every 15 minutes and transfected to cells confluently cultured on 6-well plates. VLPs can be detected by the presence or absence of infected cells from the second day after transfection.

The phrase "intrahost environment" refers to an environment within the host wherein the wild-type paramyxovirus, from which the vector of interest is derived, normally proliferates in nature, or an environment that allows equivalent virus proliferation. The intrahost environment may be, for example, the optimum growth condition for the virus. When the host of the paramyxovirus is a mammal, the intrahost environment refers to the in vivo environment of a mammal, or equivalent environment thereof. Namely, the temperature is approximately 37° C. to 38° C. (for example, 37° C.) corresponding to that in the body of the mammal. An example of an in vitro condition includes a normal cell culture condition, more specifically a moist culture environment in a media with or without serum (pH 6.5 to 7.5), at 37° C., under 5% $CO_2$.

Important differences in the activity of a modified M protein due to environmental conditions include conditional mutations of the M protein, such as temperature sensitive mutations. The phrase "conditional mutation" refers to a mutation which shows a mutated phenotype of "loss of function" in the intrahost environment, while exhibiting functional activity in another environment. For example, a gene encoding a temperature-sensitive mutated M protein, whose function is mostly or completely lost at 37° C. but is recovered at a lower temperature, can be preferably used. The phrase "temperature-sensitive mutation" refers to a mutation wherein the activity is significantly decreased at high temperature (for example, 37° C.) as compared to that at low temperature (for example, 32° C.). The present inventors successfully produced a viral particle whose particle forming ability is dramatically decreased at 37° C., a temperature corresponding to the intrahost environment, using the temperature-sensitive mutant of the M protein. This M protein mutant aggregates at the cell surface under low temperature conditions (for example, 32° C.) to form viral particles; however, at the normal body temperature (37° C.) of a host, it loses aggregability and fails to form viral particles. A vector comprising nucleic acids encoding such a temperature-sensitive M protein mutant on its genome is preferred as the vector of this invention. The M protein of such a viral vector encodes a conditionally mutated M protein that functions under M protein functioning conditions, i.e., permissive conditions, to form viral particles. When viral particles produced in this manner are infected under normal environment, the M protein cannot function and, thus, no particles are formed.

The temperature-sensitive M gene mutation is not particularly limited, however, and includes, for example, at least one of the amino acid sites selected from the group consisting of G69, T116, and A118 from the Sendai virus M protein, preferably two sites arbitrarily selected from among these, and more preferably all three sites. Other (−) strand RNA virus M proteins comprising homologous mutations can also be used as appropriate. Herein, G69 means the 69th amino acid glycine in M protein, T116 the 116th amino acid threonine in M protein, and A183 the 183rd amino acid alanine in M protein.

The gene encoding the M protein (i.e., the M gene) is widely conserved in (−)strand RNA viruses, and is known to interact with both the viral nucleocapsid and the envelope proteins (Garoff, H. et al., Microbiol. Mol. Biol. Rev. 62, 117-190, 1998). The SeV M protein amino acid sequence 104 to 119 (104-KACTDLRITVRRTVRA-119/SEQ ID NO: 45) is presumed to form an amphiphilic α-helix, and has been identified as an important region for viral particle formation (Mottet, G. et al., J. Gen. Virol. 80, 2977-2986, 1999). This region is widely conserved among (−)strand RNA viruses. M protein amino acid sequences are similar among (−)strand RNA viruses. In particular, known M proteins in viruses belonging to the subfamily Paramyxovirus are commonly proteins with 330 to 380 amino acid residues. Their structure is similar over the whole region, though the C-end halves have particularly high homology (Gould, A. R., Virus Res. 43, 17-31, 1996; Harcourt, B. H. et al., Virology 271, 334-349, 2000). Therefore, for example, amino acid residues homologous to G69, T116 and A183 of the SeV M protein can be easily identified.

Amino acid residues at sites homologous to other (−) strand RNA virus M proteins corresponding to G69, T116 and A183 of the SeV M proteins can be identified by one skilled in the art through alignment with the SeV M protein, using an amino acid sequence homology search program which includes an alignment forming function, such as BLAST, or an alignment forming program, such as CLUSTAL W.

Examples of homologous sites in M proteins that correspond to G69 in the SeV M protein include G69 in human parainfluenza virus-1 (HPIV-1); G73 in human parainfluenza virus-3 (HPIV-3); G70 in phocine distemper virus (PDV) and canine distemper virus (CDV); G71 in dolphin molbillivirus (DMV); G70 in peste-des-petits-ruminants virus (PDPR), measles virus (MV) and rinderpest virus (RPV); G81 in Hendra virus (Hendra) and Nipah virus (Nipah); G70 in human parainfluenza virus-2 (HPIV-2); E47 in human parainfluenza virus-4a (HPIV-4a) and human parainfluenza virus-4b (HPIV-4b); and E72 in mumps virus (Mumps). (Descriptions in brackets indicate the abbreviation; letters and numbers indicate amino acids and positions.) Examples of homologous sites of M proteins corresponding to T116 in the SeV M protein include T116 in human parainfluenza virus-1 (HPIV-1); T120 in human parainfluenza virus-3 (HPIV-3); T104 in phocine distemper virus (PDV) and canine distemper virus (CDV); T105 in dolphin molbillivirus (DMV); T104 in peste-des-petits-ruminants virus (PDPR), measles virus (MV), rinderpest virus (RPV); T120 in Hendra virus (Hendra) and Nipah virus (Nipah); T117 in human parainfluenza virus-2 (HPIV-2) and simian parainfluenza virus 5 (SV5); T121 in human parainfluenza virus-4a (HPIV-4a) and human parainfluenza virus-4b (HPIV-4b); T119 in mumps virus (Mumps); and S120 in Newcastle disease virus (NDV). Examples of homologous sites of M proteins corresponding to A183 of SeV M protein are A183 in human parainfluenza virus-1 (HPIV-1); F187 in human parainfluenza virus-3 (HPIV-3); Y171 in phocine distemper virus (PDV) and canine distemper virus (CDV); Y172 in dolphin molbillivirus (DMV); Y171 in peste-des-petits-ruminants virus (PDPR); measles virus (MV) and rinderpest virus (RPV); Y187 in Hendra virus (Hendra) and Nipah virus (Nipah); Y184 in human parainfluenza virus-2 (HPIV-2); F184 in simian parainfluenza virus 5 (SV5); F188 in human parainfluenza virus-4a (HPIV-4a) and human parainfluenza virus-4b (HPIV-4b); F186 in mumps virus (Mumps); and Y187 in Newcastle disease virus (NDV). Among the viruses mentioned above, viruses suitable for use in the present invention include those comprising genomes which encode an M protein mutant, where amino acid residue(s) have been substituted at any one of the above-mentioned three sites, preferably at an arbitrary two of these three sites, and more preferably at all three sites.

An amino acid mutation includes substitution with any other desirable amino acid. However, the substitution is preferably with an amino acid having different chemical characteristics in its side chain. Amino acids can be divided into groups such as basic amino acids (e.g., lysine, arginine, histidine); acidic amino acids (e.g., aspartic acid, glutamic acid); uncharged polar amino acids (e.g., glycine, asparagine, glutamine, serine, threonine, tyrosine, cysteine); nonpolar amino acids (e.g., alanine, valine, leucine, isoleucine, proline, phenylalanine, methionine, tryptophane); β-branched amino acids (e.g., threonine, valine, isoleucine); and aromatic amino acids (e.g., tyrosine, phenylalanine, tryptophane, histidine). One amino acid residue, belonging to a particular group of amino acids, may be substituted for by another amino acid, which belongs to a different group. Specific examples include but are not limited to: substitution of a basic amino acid for an acidic or neutral amino acid; substitution of a polar amino acid for a nonpolar amino acid; substitution of an amino acid of molecular weight greater than the average molecular weights of 20 naturally-occurring amino acids, for an amino acid of molecular weight less than this average; and conversely, substitution of an amino acid of molecular weight less than this average, for an amino acid of molecular weight greater than this average. For example, Sendai virus M proteins comprising mutations selected from the group consisting of G69E, T116A, and A183S or other paramyxovirus M proteins comprising mutations at homologous positions thereto can be suitably used. Herein, G69E refers to a mutation wherein the 69th M protein amino acid glycine is substituted by glutamic acid, T116A refers to a mutation wherein the 116th M protein amino acid threonine is substituted by alanine, and A183S refers to a mutation wherein the 183rd M protein amino acid alanine is substituted by serine. In other words, G69, T116 and A183 in the Sendai virus M protein or homologous M protein sites in other viruses, can be substituted by glutamic acid (E), alanine (A), and serine (S), respectively. These mutations are preferably utilized in combination, and it is particularly preferable to include all three of the above-mentioned mutations. M gene mutagenesis can be carried out according to a known mutagenizing method. For example, as described in the Examples, a mutation can be introduced by using an oligonucleotide containing a desired mutation.

In the case of measles virus for example, the M gene sequence of temperature-sensitive strain P253-505, in which the epitope sequence of an anti-M protein monoclonal antibody has been altered, can be used (Morikawa, Y. et al., Kitasato Arch. Exp. Med. 64, 15-30, 1991). In addition, the threonine at residue 104 of the measles virus M protein, or the threonine at residue 119 of the mumps virus M protein, which correspond to the threonine at residue 116 of the SeV M protein, may be substituted with any other amino acid (for example, alanine).

According to a more preferred embodiment, the vectors of the present invention comprise M gene deficiencies. The phrase "M gene deficiency" refers to a lack of the function of M protein, including cases where the vector has an M gene comprising a functionally deficient mutation, and cases where the M gene is absent from the vector. A functionally deficient M gene mutation can be produced, for example, by deleting the M gene protein-encoding sequence, or by inserting another sequence. For example, a termination codon can be inserted partway through the M protein-encoding sequence (WO 00/09700). Most preferably, the vectors of the present invention are completely devoid of M protein-encoding sequences. Unlike a vector encoding a conditional mutant M protein, a vector without an M protein open reading frame (ORF) cannot produce viral particles under any conditions.

In order to produce the vectors of the present invention, cDNAs encoding the paramyxovirus' genomic RNA are transcribed, in the presence of viral proteins necessary for the reconstitution of RNPs which comprise the paramyxovirus' genomic RNA, i.e., in the presence of N, P, and L proteins. The viral RNP may be reconstituted by forming a negative strand genome (i.e., the antisense strand that is the same as the viral genome) or a positive strand (the sense strand encoding the viral proteins). For improved reconstitution efficiency, formation of the positive strand is preferable. The 3'-leader and 5'-trailer sequence at the RNA ends preferably reflects the natural viral genome as accurately as possible. To accurately control the 5'-end of the transcription product, a T7 RNA polymerase recognition sequence may be used as a transcription initiation site to express the RNA polymerase in cells. The 3'-end of the transcription product can be controlled, for example, by encoding a self-cleaving ribozyme onto this 3'-end, ensuring it is accurately cut (Hasan, M. K. et al., J. Gen. Virol. 78, 2813-2820, 1997; Kato, A. et al., EMBO J. 16, 578-587, 1997; Yu, D. et al., Genes Cells 2, 457-466, 1997).

A cloning site for inserting foreign genes into cDNA that encodes the genomic RNA can be designed in order to facilitate insertion of a foreign gene. The site may be inserted at any preferred position of the protein non-coding region on the genome. Specifically, the site may be inserted between the 3'-leader region and the viral protein ORF closest to the 3'-terminus, between viral protein ORFs, and/or between the viral protein ORF closest to the 5'-terminus and the 5'-trailer region. In an M gene-deficient genome, the cloning site can be designed at the deleted site of the M gene. The cloning site may be, for example, a recognition sequence for a restriction enzyme. The cloning site may be the so-called multi-cloning site comprising a plurality of restriction enzyme recognition sequences. The cloning site can be divided to exist at multiple sites on the genome so that a plurality of foreign genes can be inserted into different positions of the genome.

Recombinant virus RNP lacking particle formation ability can be constructed according to, for example, the descriptions in "Hasan, M. K. et al., J. Gen. Virol. 78, 2813-2820, 1997", "Kato, A. et al., EMBO J. 16, 578-587, 1997" and "Yu, D. et al., Genes Cells 2, 457-466, 1997". This method is outlined below:

To introduce a foreign gene, a DNA sample comprising the cDNA nucleotide sequence of the desired foreign gene is first prepared. The DNA sample is preferably electrophoretically identified as a single plasmid at a concentration of 25 ng/μl or more. The following example describes the use of the NotI site in the insertion of a foreign gene into DNA encoding viral genomic RNA: If the target cDNA nucleotide sequence comprises a NotI recognition site, this site should be removed beforehand using a technique such as site-specific mutagenesis to change the nucleotide sequence, without changing the amino acid sequence it codes. The desired gene fragment is amplified and recovered from this DNA sample using PCR. By attaching NotI sites to the 5'-regions of the two primers, both ends of the amplified fragment become NotI sites. The E-I-S sequence or a part thereof is included in the primer, so that the E-I-S sequence is placed between both the ORFs on either side of the viral genes, and the ORF of the foreign gene (after it has been incorporated into the viral genome).

For example, to assure cleavage by NotI, the forward side synthetic DNA sequence is arranged as follows: Two or more nucleotides (preferably four nucleotides, excluding sequences such as GCG and GCC that are derived from the NotI recognition site; more preferably ACTT) are randomly selected on its 5'-side, and a NotI recognition site "gcggccgc" is added to its 3'-side. In addition, a spacer sequence (nine random nucleotides, or nucleotides of nine plus a multiple of six) and an ORF (a sequence equivalent to about 25 nucleotides and comprising the initiation codon ATG of the desired cDNA) are also added to the 3'-side. About 25 nucleotides are preferably selected from the desired cDNA, such that G or C is the final nucleotides on the 3'-end of the forward side synthetic oligo DNA.

The reverse side synthetic DNA sequence is arranged as follows: Two or more random nucleotides (preferably four nucleotides, excluding sequences such as GCG and GCC that originate in the NotI recognition site; more preferably ACTT) are selected from the 5'-side, a NotI recognition site "gcggccgc" is added to the 3'-side, and an oligo DNA insertion fragment is further added to the 3'-side in order to regulate length. The length of this oligo DNA is designed such that the number of nucleotides in the final PCR-amplified NotI fragment product, which comprises the E-I-S sequence, becomes a multiple of six (the so-called "rule of six"; Kolakofski, D. et al., J. Virol. 72, 891-899, 1998; Calain, P. and Roux, L., J. Virol. 67, 4822-4830, 1993; Calain, P. and Roux, L., J. Virol. 67, 4822-4830, 1993). A sequence complementary to the Sendai virus S sequence, preferably 5'-CTTTCACCCT-3' (SEQ ID NO: 8), a sequence complementary to the I sequence, preferably 5'-AAG-3', and a sequence complementary to the E sequence, preferably 5'-TTTTTCTTACTACGG-3' (SEQ ID NO: 9), are further added to the 3'-side of the inserted oligo-DNA fragment. When these primers to which E-I-S sequence is added are used, the 3'-end of the reverse side synthetic DNA is formed by the addition of a complementary sequence, equivalent to about 25 nucleotides counted in reverse from the termination codon of the desired cDNA, and whose length is selected such that G or C becomes the final nucleotide.

PCR can be carried out according to a usual method with Taq polymerase or such. Desired fragments thus amplified are digested with NotI, and then inserted into the NotI site of the plasmid vector pBluescript. The nucleotide sequences of the PCR products thus obtained are confirmed using a sequencer to select a plasmid comprising the correct sequence. The inserted fragment is excised from the plasmid using NotI, and cloned to the NotI site of the plasmid carrying the genomic cDNA. Alternatively, recombinant Sendai virus cDNA can be obtained by directly inserting the fragment into the NotI site, without the mediation of the plasmid vector.

For example, a recombinant Sendai virus genome cDNA can be constructed according to the method described in the references (Yu, D. et al., Genes Cells 2, 457-466, 1997; Hasan, M. K. et al., J. Gen. Virol. 78, 2813-2820, 1997). For example, an 18-bp spacer sequence comprising a NotI restriction site (5'-(G)-CGGCCGCAGATCTTCACG-3') (SEQ ID NO: 10) is inserted into a cloned Sendai virus genome cDNA (pSeV(+)) between the leader sequence and the ORF of N protein, and thus a plasmid pSeV18+b(+) containing a self-cleaving ribozyme site derived from the antigenomic strand of delta-hepatitis virus is obtained (Hasan, M. K. et al., J. General Virology 78, 2813-2820, 1997).

In addition, for example, in the case of M gene deletion, or introduction of a temperature-sensitive mutation, the cDNA encoding genomic RNA is digested by a restriction enzyme, and the M gene-comprising fragments are collected and cloned into an appropriate plasmid. M gene mutagenesis or construction of an M gene-deficient site is carried out using such a plasmid. The introduction of a mutation can be carried out, for example, using a QuikChange™ Site-Directed Mutagenesis Kit (Stratagene, La Jolla, Calif.) according to the method described in the kit directions. For example, M gene deficiency or deletion can be carried out using a combined PCR-ligation method, whereby deletion of all or part of the M gene ORF, and ligation with an appropriate spacer sequence, can be achieved. After obtaining an M gene-mutated or -deficient sequence, fragments comprising the sequence are recovered, and the M gene region in the original full-length cDNA is substituted by this sequence. Thus, a viral genome cDNA comprising a mutated M gene, can be prepared. Using similar methods, mutation can be introduced into, for example, F and/or HN genes.

The vectors of this invention can be reconstituted by intracellularly transcribing DNAs encoding the genomic RNAs in the presence of the viral protein. The present invention provides DNAs encoding the viral genomic RNAs of the vectors of this invention, which are used to produce the vectors of this invention. Furthermore, the present invention relates to the use of DNAs encoding the genomic RNAs of the vectors for producing the vectors of this invention. Viral reconstitution from (−)strand virus' genomic cDNAs can be carried out using known methods (WO 97/16539; WO 97/16538; Durbin, A. P. et al., Virology 235, 323-332, 1997; Whelan, S. P. et al., Proc. Natl. Acad. Sci. USA 92, 8388-8392, 1995; Schnell. M. J. et al., EMBO J. 13, 4195-4203, 1994; Radecke, F. et al., EMBO J. 14, 5773-5784, 1995; Lawson, N. D. et al., Proc. Natl. Acad. Sci. USA 92, 4477-4481, 1995; Garcin, D. et al., EMBO J. 14, 6087-6094, 1995; Kato, A. et al., Genes Cells 1, 569-579, 1996; Baron, M. D. and Barrett, T., J. Virol. 71, 1265-1271, 1997; Bridgen, A. and Elliott, R. M., Proc. Natl. Acad. Sci. USA 93, 15400-15404, 1996). Using these methods, (−) strand RNA viruses, or RNP as viral components, can be reconstituted from their DNA, including viruses such as parainfluenza virus, vesicular stomatitis virus, rabies virus, measles virus, rinderpest virus, Sendai virus, etc. The vectors of the present invention can be reconstituted according to these methods.

Specifically, the vectors of the present invention can be produced by the steps of: (a) transcribing the cDNA, which encodes the paramyxoviral genomic RNA (negative strand RNA) or its complementary strand (positive strand), in cells expressing N, P, and L proteins; and (b) collecting a complex, which comprises the genomic RNA, from the cells or their culture supernatant. The transcribed genomic RNA is replicated in the presence of N, L, and P proteins to form the RNP complex. When step (a) is performed in the presence of a protease that cleaves the modified F protein encoded by the genome, the resulting RNP is transferred to cells that are in contact with the cells, infection spreads, and the vector is amplified. According to this method, the vectors of this invention can be produced in RNP form in spite of the absence of a functional M protein.

Enzymes needed for the initial transcription of the genomic RNA from DNA, such as T7 RNA polymerase, can be provided by transfecting plasmids or viral vectors that express the enzymes. Alternatively, the enzymes can be provided by incorporating their genes into the chromosome of cells to allow expression to be induced during virus reconstitution. Furthermore, viral proteins necessary for genomic RNA and vector reconstitution are provided, for example, by introducing plasmids that express these proteins. To provide these viral proteins, helper viruses such as wild-type paramyxovirus or certain kinds of mutant paramyxovirus may be used. However, since this causes contamination by these viruses, the use of helper viruses is not preferred.

Methods for transferring DNAs which express genomic RNAs into cells include, for example, the following: 1) the method for preparing DNA precipitates that can be taken up by objective cells; 2) the method for preparing a positively charged DNA-comprising a complex which has low cytotoxicity and can be taken up by target cells; and 3) the method for using electric pulses to instantaneously open holes in target cell membranes so that DNA molecules can pass through.

In the above method 2), a variety of transfection reagents can be utilized, examples including DOTMA (Roche), Superfect (QIAGEN #301305), DOTAP, DOPE, DOSPER (Roche #1811169), etc. An example of method 1) is a transfection method using calcium phosphate, in which DNA that enters cells is incorporated into phagosomes, but is also incorporated into the nuclei at sufficient amounts (Graham, F. L. and Van Der Eb, J., Virology 52, 456, 1973; Wigler, M. and Silverstein, S., Cell 11, 223, 1977). Chen and Okayama have investigated the optimization of this transfer technique, reporting that optimal precipitates can be obtained under conditions wherein 1) cells are incubated with co-precipitates in an atmosphere of 2% to 4% $CO_2$ at 35° C. for 15 to 24 hours; 2) circular DNA having a higher activity than linear DNA is used; and 3) DNA concentration in the precipitate mixture is 20 to 30 μg/ml (Chen, C. and Okayama, H., Mol. Cell. Biol. 7, 2745, 1987). Method 2) is suitable for transient transfection. In an older known method, a DEAE-dextran (Sigma #D-9885, M.W. $5 \times 10^5$) mixture is prepared in a desired DNA concentration ratio, and transfection is performed. Since many complexes are decomposed inside endosomes, chloroquine may be added to enhance results (Calos, M. P., Proc. Natl. Acad. Sci. USA 80, 3015, 1983). Method 3) is referred to as electroporation, and is more versatile than methods 1) and 2) because it doesn't involve cell selectivity. Method 3) is said to be efficient when conditions are optimal for pulse electric current duration, pulse shape, electric field potency (the gap between electrodes, voltage), buffer conductivity, DNA concentration, and cell density.

Of the above three categories, method 2) is easily operable, and facilitates examination of many test samples using a large numbers of cells. Transfection reagents are therefore suitable for cases where DNA is introduced into cells for vector reconstitution. Preferably, Superfect Transfection Reagent (QIAGEN, Cat. No. 301305) or DOSPER Liposomal Transfection Reagent (Roche, Cat. No. 1811169) is used, but the transfection reagents are not limited thereto.

Specifically, the reconstitution of viral vectors from cDNA can be performed, for example, as follows:

Simian kidney-derived LLC-MK2 cells are cultured to approximately 100% confluency in 24-well to 6-well plastic culture plates, or 100 mm diameter culture dishes and such, using a minimum essential medium (MEM) containing 10% fetal calf serum (FCS) and antibiotics (100 units/ml penicillin G and 100 μg/ml streptomycin). These cells are then infected, for example, at 2 PFU/cell with recombinant vaccinia virus vTF7-3 expressing T7 polymerase. This virus has been inactivated by UV irradiation treatment for 20 minutes in the presence of 1 μg/ml psoralen (Fuerst, T. R. et al., Proc. Natl. Acad. Sci. USA 83, 8122-8126, 1986; Kato, A. et al., Genes Cells 1, 569-579, 1996). The amount of psoralen added and the UV irradiation time can be appropriately adjusted. One hour after infection, the lipofection method or the like is used to transfect cells with 2 μg to 60 μg, more preferably 3 μg to 20 μg, of the above-described DNA, which encodes the genomic RNA of the recombinant Sendai virus. Such methods use Superfect (QIAGEN), and plasmids which express the trans-acting viral proteins required for the production of viral RNP (0.5 μg to 24 μg of pGEM-N, 0.25 μg to 12 μg of pGEM-P and 0.5 μg to 24 μg of pGEM-L) (Kato, A. et al., Genes Cells 1, 569-579, 1996). The ratio of expression vectors encoding N, P, and L is preferably 2:1:2. The amount of plasmid is appropriately adjusted, for example, to 1 μg to 4 μg of pGEM-N, 0.5 μg to 2 μg of pGEM-P, and 1 μg to 4 μg of pGEM-L.

The transfected cells are cultured in a serum-free MEM containing 100 μg/ml each of rifampicin (Sigma) and cytosine arabinoside (AraC) if desired, more preferably containing only 40 μg/ml of cytosine arabinoside (AraC) (Sigma). Reagent concentrations are optimized for minimum vaccinia virus-caused cytotoxicity, and maximum recovery rate of the virus (Kato, A. et al., Genes Cells 1, 569-579, 1996). After transfection, cells are cultured for about 48 hours to about 72 hours, recovered, and then disrupted by three repeated freezing and thawing cycles. LLC-MK2 cells are re-transfected with the disrupted cells and then cultured. RNP may be introduced to cells as a complex formed together with, for example, lipofectamine and a polycationic liposome. Specifically, a variety of transfection reagents can be utilized. Examples of these are DOTMA (Roche), Superfect (QIAGEN #301305), DOTAP, DOPE, DOSPER (Roche #1811169), etc. Chloroquine may be added to prevent RNP decomposition in endosomes (Calos, M. P., Proc. Natl. Acad. Sci. USA 80, 3015, 1983). In cells transfected with RNP, the steps of expressing viral genes from RNP and replicating RNP proceed to amplify the vector. By diluting the obtained cell lysate and repeating amplification, vaccinia virus vTF7-3 can be completely removed. Reamplification may be repeated, for example, 3 times or more. The obtained RNP can be stored at −80° C.

Host cells used for reconstitution are not restricted so long as the viral vector can be reconstituted. For example, in the reconstitution of the Sendai virus vector and such, monkey kidney-derived LLC-MK2 cells and CV-1 cells, cultured cells such as hamster kidney-derived BHK cells, human-derived cells, and such, can be used. By expressing a suitable envelope protein in these cells, infective virions comprising this protein in the envelope can be obtained.

When the M gene in the viral genome is defective or deleted, viral particles are not formed from cells infected with such virus. Therefore, even though the vectors of this invention can be prepared as RNP or cells comprising RNP by the methods as described above, the vectors cannot be prepared as viral particles. Furthermore, after the transfection of RNPs, RNPs that proliferated in the cell are transmitted only to contacting cells. Therefore, infection spreads slowly which makes the production of large amounts of viral vector in high titers difficult. The present invention provides a method for producing the vectors of this invention as viral particles. Viral particles are more stable in solution as compared to RNPs. In addition, by letting the viral particles have infectivity, the vectors can be introduced to target cells through simple contact without a transfection reagent and such. Therefore, the viral particles are particularly useful in industrial application. As a method for producing the vectors of this invention as viral particles, the virus is reconstituted under permissive conditions using a viral genome comprising an M gene having a conditional mutation. Specifically, the M protein functions to form particles by culturing cells transfected with a complex obtained through the above-described step (a) or steps (a) and (b) under permissive conditions. A method for producing viral particles that comprise genomic RNA encoding the mutant M protein having conditional mutation comprises the steps of: (i) amplifying the RNP, which comprises N, P, and L proteins of paramyxovirus and the genomic RNA, intracellularly under conditions permissive for the mutant M protein; and (ii) collecting viral particles released into the cell culture supernatant. For example, a temperature-sensitive mutant M protein may be cultured at its permissive temperature.

Another method for producing the vectors of the present invention as viral particles uses helper cells that express the M protein. By using M helper cells, the present inventors produced a vector wherein the cleavage site of the F protein is modified to a sequence that is cleaved by another protease and the M gene is mutated or deleted as viral particles. Since the method of this invention does not require a helper virus, such as the wild-type paramyxovirus, contamination by an M gene-comprising virus having particle forming ability does not occur. Thus, the vectors of this invention can be prepared in a pure form. The present invention provides viral particles which comprises (i) a genomic RNA of paramyxovirus wherein (a) a nucleic acid encoding the M protein is mutated or deleted, and (b) a modified F protein whose cleavage site sequence is substituted with a sequence that is cleaved by a protease that does not cleave the wild-type F protein is encoded, further wherein the viral particle: (1) has the ability to replicate the genomic RNA in a cell transfected with the viral particle; (2) shows significantly decreased or eliminated production of a viral particle in the intrahost environment; and (3) has the ability to introduce the genomic RNA in a cell that contacts with the cell transfected with the viral particle comprising the genomic RNA in the presence of the protease. According to a preferred embodiment, such viral particle will not produce viral particles.

A method for producing the viral particles of this invention in cells expressing a functional M protein may comprise the steps of: (i) amplifying the RNP, comprising N, P, and L proteins of the paramyxovirus, and the genomic RNA in cells expressing wild-type M protein of paramyxovirus or equivalent proteins thereto; and (ii) collecting the viral particles released into the cell culture supernatant. So long as the wild-type M protein has activity to form viral particles, it may be derived from a paramyxovirus from which the genomic RNA is not derived. Furthermore, a tag peptide and such may be added to the protein, or alternatively, when it is expressed through an appropriate expression vector, a linker peptide derived from the vector may be added to the protein. As described above, the protein to be used does not have to be the wild-type M protein itself but may be a protein having viral particle-forming ability equivalent to the wild-type protein. A viral particle produced from M protein-expressing cells comprises the M protein expressed in these cells in its envelope; however, it does not comprise the gene encoding this protein. Therefore, the wild-type M protein is no longer expressed in cells infected with this virus. Thus, viral particles cannot be formed.

Production of helper cells expressing the M protein can be performed as described below. To prepare a vector that expresses the M protein in an inducible fashion, for example, inducible promoters or expression regulating systems using recombination (such as Cre/loxP) are used. A Cre/loxP inducible expression plasmid can be constructed using, for example, a plasmid pCALNd1w, which has been designed to inducibly express gene products using Cre DNA recombinase (Arai, T. et al., J. Virology 72, 1115-1121, 1998). As cells capable of expressing M proteins, helper cell lines capable of persistently expressing M proteins are preferably established by inducing M genes introduced into their chromosomes. For example, the monkey kidney-derived cell line LLC-MK2 or the like can be used for such cells. LLC-MK2 cells are cultured at 37° C. in MEM containing 10% heat-treated immobilized fetal bovine serum (FBS), 50 units/ml sodium penicillin G, and 50 μg/ml streptomycin, under an atmosphere of 5% $CO_2$. The above-mentioned plasmid, which has been designed to inducibly express the M gene products with Cre DNA recombinase, is introduced into LLC-MK2 cells using the calcium-phosphate method (mammalian transfection kit (Stratagene)) according to a known protocol.

For example, 10 μg of M-expression plasmid may be introduced into LLC-MK2 cells grown to be 40% confluent in a 10-cm plate. These cells are then incubated in an incubator at 37° C., in 10 ml of MEM containing 10% FBS and under 5% $CO_2$. After 24 hours of incubation, the cells are harvested and suspended in 10 ml of medium. The suspension is then plated onto five dishes of 10-cm diameter: 5 ml of the suspension are added to one dish, 2 ml to two dishes, and 0.2 ml to two dishes. The cells in each dish are cultured with 10 ml of MEM containing 10% FBS and 1200 μg/ml G418 (GIBCO-BRL) for 14 days; the medium is changed every two days. Thus, cell lines in which the gene has been stably introduced are selected. The G418-resistant cells grown in the medium are harvested using cloning rings. Cells of each clone harvested are further cultured to confluence in a 10-cm plate.

High level expression of the M protein in helper cells is important in recovering a high titer virus. For this purpose, for example, the above selection of M-expressing cells is preferably carried out twice or more. For example, an M-expressing plasmid comprising a drug-resistance marker gene is transfected, and cells comprising the M gene are selected using the drug. Following this, an M-expressing plasmid comprising a marker gene resistant to a different drug is transfected into the same cells, and cells are selected using this second drug-resistance marker. Cells selected using the second marker are likely to express M protein at a higher level than cells selected after the first transfection. Thus, M-helper cells constructed through twice-repeated transfections can be suitably applied. Since the M-helper cells can simultaneously express the F gene, production of infective viral particles deficient in both F and M genes is possible (WO 03/025570). In this case, transfection of the F-gene-expressing plasmids more than twice is also suggested to raise the level of F protein expression induction. The genes of modified F proteins as described herein can be used as F genes.

An M protein induction expression may be achieved by incubating cells to confluence in a 6-cm dish, and then, for example, infecting these cells with adenovirus AxCANCre at MOI=~3, according to the method of Saito et al. (Saito et al., Nucleic Acids Res. 23, 3816-3821, 1995; Arai, T. et al., J. Virol. 72, 1115-1121, 1998).

To produce the virus particles of the present invention using cells that express wild-type M protein or an equivalent protein (M helper cells), the above-described RNP of the present invention may be introduced into these cells and then cultured. RNP can be introduced into M helper cells, for example, by the transfection of RNP-containing cell lysate into M helper cells, or by cell fusion induced by the co-cultivation of RNP-producing cells and M helper cells. It can also be achieved by transcribing genomic RNA into M helper cells and conducting de novo RNP synthesis under the presence of N, P, and L proteins.

Above-described step (i) (the step of amplifying RNP using an M helper cell) is preferably carried out at a low temperature in the present invention. In the production of a vector using a temperature-sensitive mutant M protein, the process of producing viral particles is necessarily carried out at temperatures below the permissive temperature. However, surprisingly, the present inventors found that in the present method, efficient particle production was possible when the process of viral particle formation was carried out at low temperatures, even when using the wild-type M protein. In the context of the present invention, the term "low temperature" means 35° C. or less, preferably 34° C. or less, more preferably 33° C. or less, and most preferably 32° C. or less.

According to the present invention, viral particles can be released into the external fluid of virus-producing cells, for example, at a titer of $1\times10^5$ CIU/ml or more, preferably $1\times10^6$ CIU/ml or more, more preferably $5\times10^6$ CIU/ml or more, more preferably $1\times10^7$ CIU/ml or more, more preferably $5\times10^7$ CIU/ml or more, more preferably $1\times10^8$ CIU/ml or more, and more preferably $5\times10^8$ CIU/ml or more. The virus titer can be measured by the methods described in the specification and other literature (Kiyotani, K. et al., Virology 177(1), 65-74, 1990; WO 00/70070).

One preferred embodiment of a method for reconstituting a recombinant viral vector from the M-deficient viral genome cDNA is as follows: Namely, the method comprises the steps of (a) transcribing a DNA encoding the (negative-stranded or positive-stranded) genomic RNA in cells expressing the viral proteins necessary for the formation of infective viral particles (i.e., NP, NP, P, L, M, F, and HN proteins); (b) co-culturing these cells with cells expressing chromosomally integrated M gene (i.e., M helper cells); (c) preparing a cell extract from this culture; (d) transfecting the cells expressing the chromosomally integrated M gene (i.e., M helper cells) with the extract and culturing these cells; and (e) recovering viral particles from the culture supernatant. Step (d) is preferably carried out under the low temperature conditions described above. The obtained viral particles can be amplified by re-infection of helper cells (preferably at low temperatures). Specifically, the virus can be reconstituted according to the description in the Examples. The recovered viral particles can be diluted and then infected again to M helper cells to be amplified. This amplification step can be performed repeatedly two or three times or more. The obtained virus stock can be stored at −80° C. The virus titer can be determined by measuring the hemagglutination activity (HA). HA can be determined by the "end-point dilution method".

Specifically, first, LLC-MK2 cells are plated onto a 100-mm dish at a density of $5\times10^6$ cells/dish. When inducing the transcription of genomic RNA using T7 RNA polymerase, cells may be cultured for 24 hours and then infected at room temperature for one hour with T7 polymerase-expressing recombinant vaccinia virus (PLWUV-VacT7) at MOI=approximately 2, which has been treated with psoralen and long-wavelength ultraviolet light (365 nm) for 20 minutes (Fuerst, T. R. et al., Proc. Natl. Acad. Sci. USA 83, 8122-8126, 1986). After the cells are washed with serum-free MEM, plasmids expressing the genomic RNA and plasmids expressing the N, P, L, F, and HN proteins of paramyxoviruses, respectively, are used to transfect cells using appropriate lipofection reagents. The ratio of plasmids can be, for example, 6:2:1:2:2:2, but it is not limited thereto. After culturing for five hours, the cells are washed twice with serum-free MEM, and then cultured in MEM containing 40 μg/ml cytosine-β-D-arabinofuranoside (AraC, Sigma, St. Louis, Mo.) and 7.5 μg/ml trypsin (GIBCO-BRL, Rockville, Md.). After culturing for 24 hours, the cells are overlaid with cells that continuously express M protein (M helper cells), at a density of about $8.5\times10^6$ cells/dish, and then cultured for a further two days at 37° C. in MEM containing 40 μg/ml AraC and 7.5 μg/ml trypsin (P0). The cultured cells are collected and the precipitate is suspended in 2 ml/dish OptiMEM. After repeating the cycle of freezing and thawing for three times, the lysate is directly transfected to the M helper cells and the cells are cultured at 32° C. in serum-free MEM containing 40 μg/mL AraC and proteases that cleaves the F protein (P1). A portion of the culture supernatant is collected three to 14 days later, infected into freshly prepared M helper cells, and then cultured at 32° C. in serum-free MEM containing 40 μg/mL AraC and the protease (P2). Three to 14 days later, freshly prepared M helper cells are reinfected, and cultured in the presence (for preparing F-cleaved virus) or absence (for preparing F-uncleaved viral particle) of the protease for three to seven days at 32° C. using serum-free MEM (P3). By repeating the reamplification three times or more, the initially used vaccinia virus can be completely eliminated. BSA is added to the collected culture supernatant at a final concentration of 1%, and this is stored at −80° C.

The viral particle of this invention may be an infectious particle whose modified F protein is cleaved, or may be a potentially infectious viral particle having no infectivity in its initial form but becoming infective upon treatment with a protease that cleaves the modified F protein. The modified F protein encoded by the genome exists on the envelope of the viral particle; however, it lacks infectivity when left uncleaved. This kind of virus acquires infectivity though the treatment with a protease that cleaves the cleavage sequence of this modified F protein, or through contact with cells or tissues in the presence of the protease to cleave the F protein. In order to obtain viral particles whose modified F protein is not cleaved through the above virus production using virus producing cells, the final step of virus amplification step may be performed in the absence of proteases that cleave the modified F protein. On the other hand, preparation of the virus in the presence of the protease allows production of infective viral particles with cleaved F protein.

Furthermore, by expressing, in the cell, an envelope protein that is not encoded in the viral genome during viral particle production, a viral particle comprising this protein in its envelope can be produced. An example of such an envelope protein is the wild-type F protein. The viral particle produced in this manner encodes the modified F protein on its genomic RNA and carries the wild-type F protein in addition to this modified protein on its envelope. By providing the wild-type F protein in trans at the step of viral particle production and amplifying in the presence of trypsin that cleaves the protein, the viral particles become infective through the cleavage of the wild-type F protein on the viral particles. According to this method, even if a protease that cleaves the modified F protein is not used, infective viral particles can be prepared at high titers. Therefore, the viral particles of this invention may be viral particles comprising the wild-type F protein of a paramyxovirus. The wild-type F protein does not necessarily have to be derived from the same type of paramyxovirus as the viral genome, and may be an envelope protein from another paramyxovirus.

Moreover, viral particles comprising any desired viral envelope protein other than the wild-type F protein in the envelope can be produced. Specifically, during reconstitution of the virus, the desired envelope protein may be expressed in cells to produce viral vectors comprising this envelope protein. There are no particular limitations to these proteins. A preferred example includes the G protein (VSV-G) of vesicular stomatitis virus (VSV). The viral particles of the present invention comprise pseudotype viral vectors which comprise envelope proteins, such as the VSV-G protein, derived from viruses other than the virus from which the genomic RNA has been derived. As in the case with the wild-type F protein, this protein will not be expressed from the viral vector after infection of the viral particle into cells, since this envelope protein is not encoded on the genomic RNA of the virus.

The viral particles of this invention may comprise chimeric proteins, for example, which comprise on the extracellular region, one or more proteins that can adhere to specific cells on the surface of the envelope, such as adhesion factors, ligands, receptors, and antibodies or fragments thereof, and polypeptides derived from the viral envelope in the intracellular region. This enables the production of vectors that infect specific tissues as targets. These can be provided in trans by intracellular expression during reconstitution of the viral vectors. Specific examples include fragments comprising the receptor binding domain of soluble factors such as cytokines, or antibody fragments against cell surface proteins (WO 01/20989).

When preparing a vector having deficient viral genes, for example, two or more vector types, each of which has a different deficient viral gene in its viral genome, may be introduced into the same cells. Each deficient viral protein is then expressed and supplied by the other vector. This mutual complementation results in the formation of infective viral particles, and the viral vector can be amplified in the replication cycle. Namely, when two or more types of vector of the present invention are inoculated in combination to complement viral proteins, mixed viral gene-deficient viral vectors can be produced on a large scale and at a low cost. As these viruses lack viral genes, their genome is smaller than that of an intact virus, and they can thus comprise larger foreign genes. In addition, co-infectivity is difficult to maintain in these viruses, which are non-propagative due to viral gene deficiency and diluted outside of cells. Such vectors are thus sterile, which is advantageous from the viewpoint of controlling environmental release.

Large amounts of a viral vector may be obtained by infecting the viral vector obtained by the above-described method into embryonated chicken eggs to amplify the vector. For example, M gene-transgenic chickens can be generated and the vectors may be inoculated to the chicken eggs for amplification. The basic method for producing viral vectors using chicken eggs has already been developed ("Shinkei-kagaku Kenkyu-no Saisentan Protocol III, Bunshi Shinkei Saibou Seirigaku (Leading edge techniques protocol III in neuroscience research, Molecular, Cellular Neurophysiology)", edited by Nakanishi, et al., KOSEISHA, Osaka, pp. 153-172, 1993). Specifically, for example, fertilized eggs are moved to an incubator and the embryo is grown under culture for nine to twelve days at 37° C. to 38° C. The viral vector is then inoculated into the allantoic membrane cavity, the egg is incubated for a few days to proliferate the viral vector. The allantoic fluid containing the virus is then collected. Conditions such as culture duration change according to the recombinant virus amplified. Separation and purification of the viral vector from the allantoic fluid is done according to conventional methods ("Protocols of Virology" by Masato Tashiro, edited by Nagai and Ishihama, Medical View, pp. 68-73, 1995).

The recovered virus vectors can be purified to substantial purity. Purification can be performed by known purification and separation methods including filtration, centrifugation, column chromatographic purification, and such, or combinations thereof. The phrase "substantial purity" used herein means that the virus vectors, as components, are the main proportion of the sample in which they exist. Typically, substantially pure viral vectors can be detected by confirming that the ratio of virus-derived protein to total protein in the sample (except protein added as a carrier or stabilizer) is 10% or more, preferably 20% or more, more preferably 50% or more, more preferably 70% or more, more preferably 80% or more, and even more preferably 90% or more. Specifically, paramyxoviruses can be purified, for example, by a method in which cellulose sulfate ester or crosslinked polysaccharide sulfate ester is used (JP-B No. Sho 62-30752; JP-B Sho 62-33879; JP-B Sho 62-30753), a method in which adsorption to fucose sulfate-containing polysaccharide and/or a decomposition product thereof is used (WO 97/32010), etc.

The M gene-deficient vector whose F cleavage site is modified transmits the vector intracellularly, in the presence of a specific protease, by cell fusogenic infection alone. Therefore, the vector of this invention is useful in gene therapy targeting tissues expressing a certain protease. Normal vectors enable gene transfer into the surface layer of the target tissue; however, they are incapable of penetrating to the interior of the tissue. On the other hand, the vectors of this invention have the ability infiltrate deeply into target tissues having enhanced protease activity. For example, the vectors of this invention can be transmitted to the interior of cancer cells deeply infiltrated into normal tissues by infecting to a portion of vector-infectable cancer cells at the surface layer.

The vectors of the present invention can be applied to cancer, arteriosclerosis, articular diseases such as rheumatoid arthritis (RA), and the like. For example, in articular diseases such as RA, destruction of the higher order structure of the cartilage by extracellular matrix degradation proceeds as described above, and the joint is destroyed. By removing cells whose ECM degradation enzyme activity is enhanced through the vector of this invention, articular destruction is expected to be diminished. Furthermore, in arteriosclerosis, accumulation of macrophage-derived foam cells proceeds. The foam cells secrete a large amount of metalloproteinase and, as a result, destroy the fibrous hyperplasia to cause plaque breakdown. By killing the macrophages that express MMP using the vectors of this invention, treatment of such arteriosclerosis is achieved. Moreover, as described below, various proteases are activated in cancer. The vectors of this invention are useful as therapeutic vectors that infect and infiltrate in a cancer-specific manner.

To produce a composition comprising a vector of the present invention, the vector can be combined, as necessary, with a desired pharmaceutically acceptable carrier or solvent. A "pharmaceutically acceptable carrier or solvent" refers to a material that can be administered along with the vector and that does not significantly inhibit gene transfer of that vector. For example, vectors can be formulated into compositions by appropriately diluting with physiological saline, phosphate-buffered physiological saline (PBS), or such. When the vectors are propagated in chicken eggs or such, the composition may contain allantoic fluid. Furthermore, compositions comprising the vector may contain carriers or solvents such as deinonized water and 5% dextrose solution. In addition to these, the composition can contain vegetable oil, suspending agents, detergents, stabilizers, biocides, etc. Further, preservatives and other additives can be added to the composition. Compositions comprising the present vectors are useful as reagents and pharmaceuticals.

Vector dosage depends on the type of disease, the patient's weight, age, sex and symptoms, the purpose of administration, the dosage form of the composition to be administered, the method for administration, type of gene to be introduced, etc. However, those skilled in the art can routinely determine the proper dosage. The administration dose of a vector is preferably within about $10^5$ to $10^{11}$ CIU/ml, more preferably within about $10^7$ to $10^9$ CIU/ml, most preferably within about $1\times10^8$ to $5\times10^8$ CIU/ml. It is preferable to administer the vector mixed with pharmaceutically acceptable carriers. For administration to carcinoma tissues, vectors can be administered to multiple points in the target site so that they distribute uniformly. The preferred dose for each administration to a human individual is $2\times10^9$ to $2\times10^{10}$ CIU. Administration can be carried out one or more times within the limits of clinically acceptable side effects. The frequency of daily administration can be similarly determined. When administering the viral vector to animals other than humans, for example, the dose to be administered can be determined by converting the above dose based on the weight ratio, or the volume ratio of the administration target sites (for example, an average value) between the target animals and humans. Compositions comprising the vectors of the present invention can be administered to all mammalian species including humans, monkeys, mice, rats, rabbits, sheep, cattle, dogs, etc.

The vectors of this invention are particularly useful in treating cancer. Cells infected with the vectors of this invention form syncytia by cell fusion under the presence of a protease. Utilizing this characteristic, the vectors of this invention can be used for treating cancers with enhanced activity of a specific protease. The present invention provides therapeutic compositions for cancers which comprise pharmaceutically acceptable carriers and the vectors of this invention encoding an F protein that is cleaved by a protease showing enhanced activity in cancers. Furthermore, the present invention relates to the use of the vectors in producing therapeutic compositions for cancer. The present invention further provides methods for treating cancer which comprise the step of administering such vectors to cancer tissues. Since the activity of ECM degradation enzyme is enhanced in infiltrating and metastatic malignant cancers, a vector comprising the gene of an F protein that is cleaved by ECM degradation enzyme can be used for specific infection to malignant cancers to cause death of the cancer tissues.

A vector of the present invention can further comprise foreign genes. The foreign gene may be a marker gene for monitoring infection by the vector or a therapeutic gene for cancer. Examples of therapeutic genes include cell-inducible genes for apoptosis and such; genes encoding cytotoxic proteins; cytokines; and hormones. The administration of the vectors of this invention to cancers can be direct (in vivo) administration to cancers or indirect (ex vivo) administration, wherein the vector is introduced into patient-derived cells or other cells, and the cells are then injected to cancers.

The targeted cancer may be any cancer in which the activity of a specific protease is enhanced. Examples include most invasive and metastatic malignant tumors (lung cancer, gastric cancer, colon cancer, esophageal cancer, breast cancer, and such). However, proteases such as MMP, uPA, and tPA are expressed at low levels in some malignant cancers. Therefore, whether the cancer can be targeted is judged according to presence or absence of enhanced protease activity. The vectors of this invention are particularly useful for application to a cancer that has infiltrated to the submucosal layer in esophageal cancer, colon cancer progressed in the intrinsic sphincter to stage III and IV cancer, and invasive melanoma deeply infiltrated so that it cannot be completely removed by surgery.

BRIEF DESCRIPTION OF THE DRAWINGS

FIG. 3 provides microscopic images representing GFP expression in cells (LLC-MK2/F7/A) persistently expressing F protein, which were cultured at 32° C. and 37° C., respectively, for six days after infection with SeV18+/ΔF-GFP or SeV18+/MtsHNtsΔF-GFP.

MtsHNtsΔF-GFP at MOI=3. Each lane contained the equivalent of 1/10 of the content of one well from a 6-well plate culture.

Figure 8:
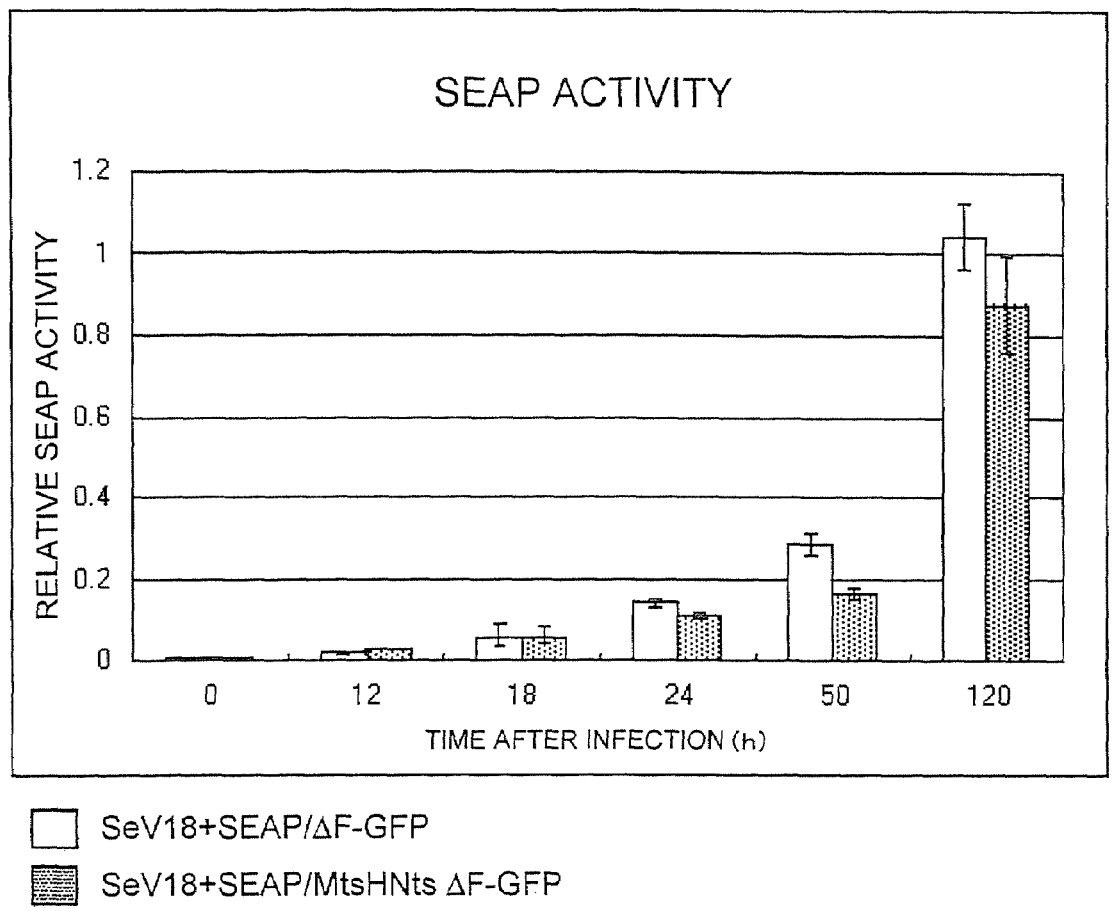

FIG. 8 depicts SEAP activity in the culture supernatant of LLC-MK2 cells cultured for 12, 18, 24, 50, or 120 hours after infection with SeV18+SEAP/ΔF-GFP or SeV18+SEAP/MtsHNtsΔF-GFP at MOI=3.

Figure 9:
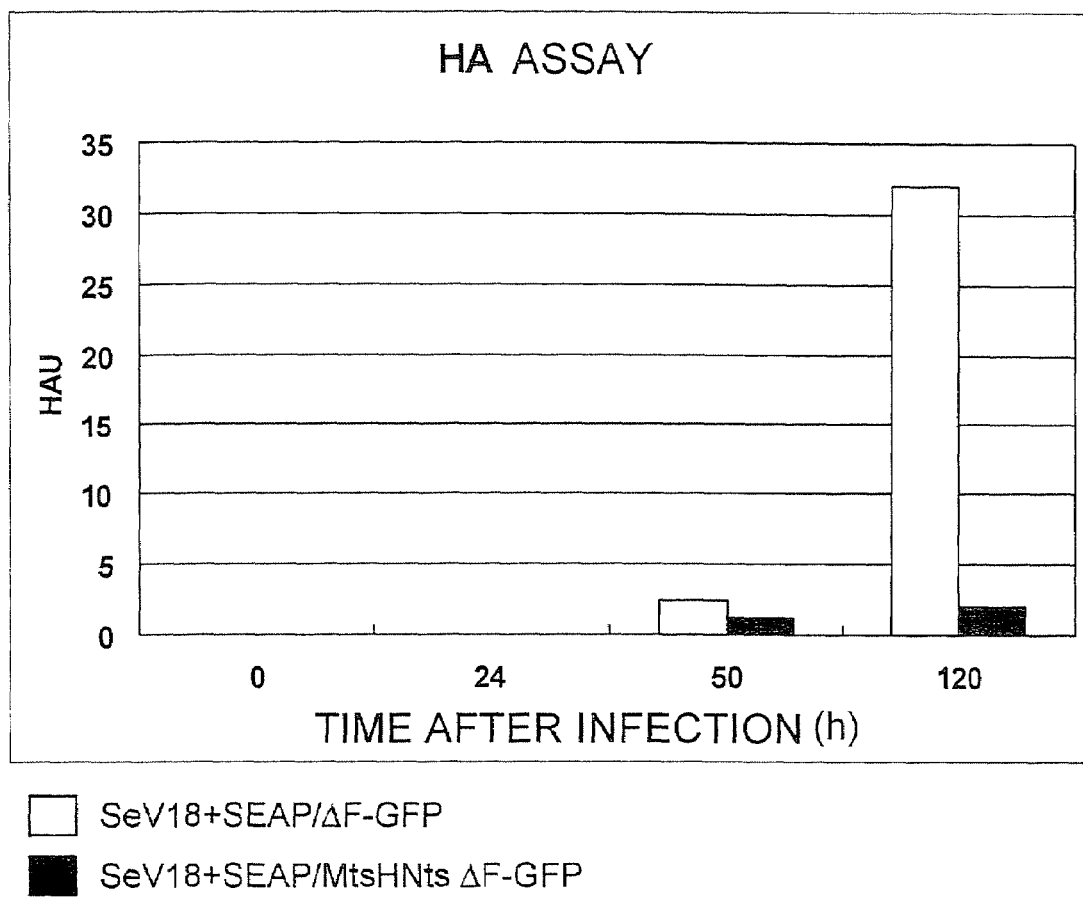

FIG. 9 depicts HA activity in the culture supernatant of LLC-MK2 cells cultured for 24, 50, or 120 hours after infection with SeV18+SEAP/ΔF-GFP or SeV18+SEAP/MtsHNtsΔF-GFP at MOI=3.

Figure 10:
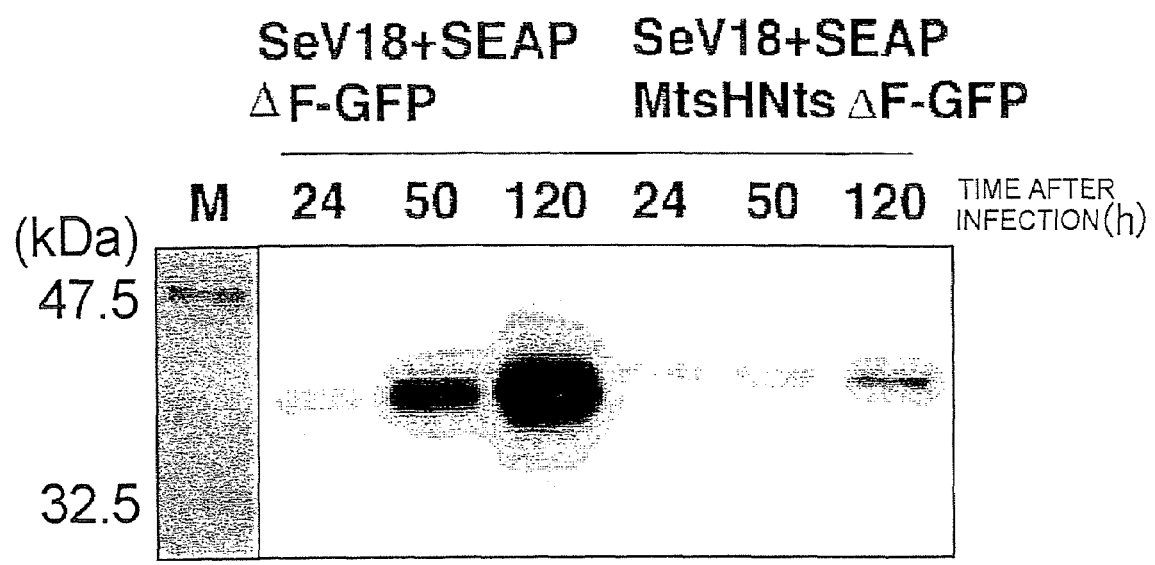

FIG. 10 is a picture representing the quantity of VLPs determined by Western blotting using an anti-M antibody. LLC-MK2 cells were cultured for five days after infection with SeV18+SEAP/ΔF-GFP or SeV18+SEAP/MtsHNtsΔF-GFP at MOI=3. The culture supernatant was centrifuged to recover the viruses. Each lane contained the equivalent of 1/10 of the content of one well from a 6-well plate culture.

Figure 11:
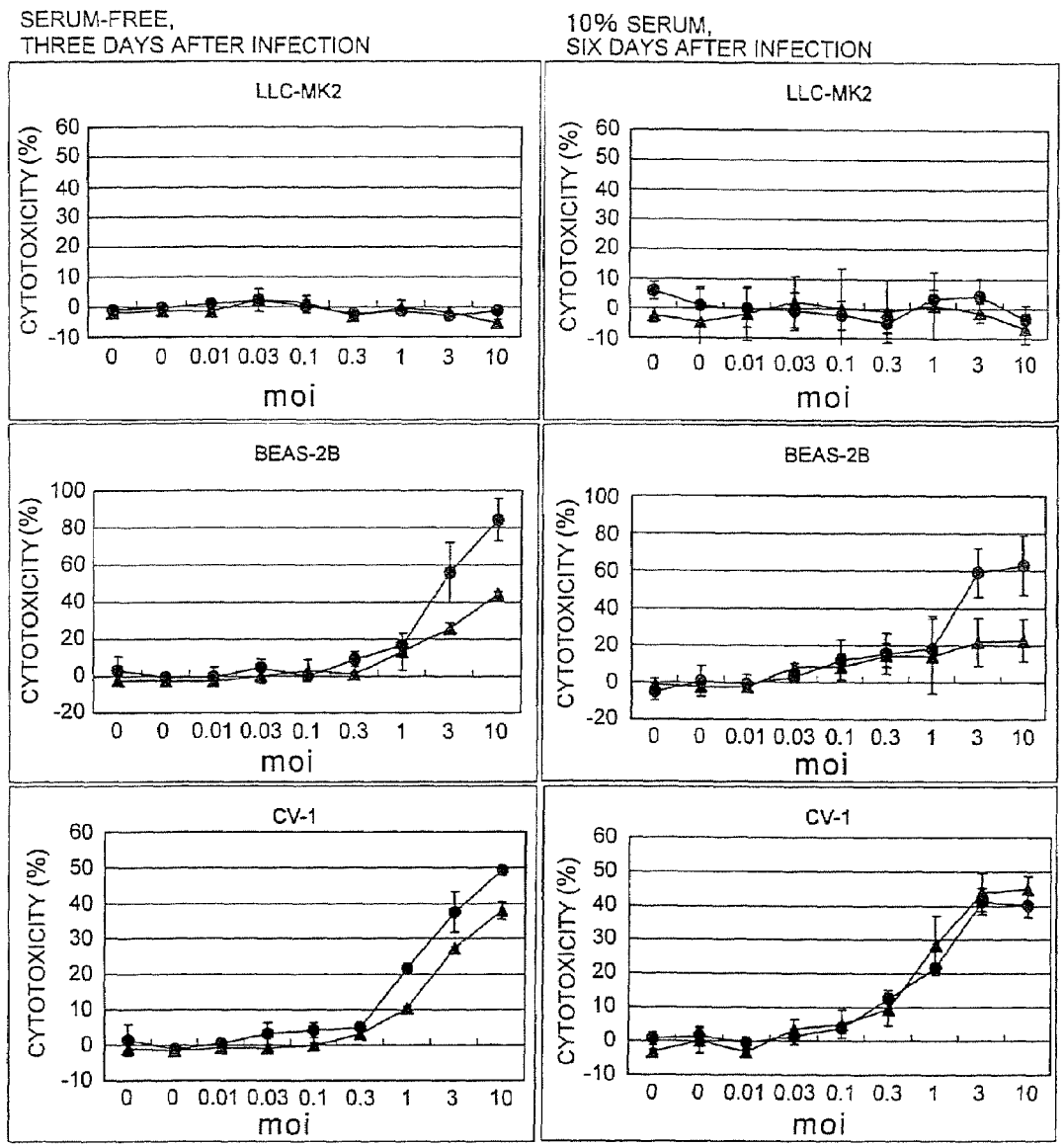

FIG. 11 depicts cytotoxicity estimates based on the quantity of LDH released into the cell culture medium. LLC-MK2, BEAS-2B or CV-1 cells were infected with SeV18+GFP, SeV18+/ΔF-GFP or SeV18+/MtsHNtsΔF-GFP at MOI=0.01, 0.03, 0.1, 0.3, 1, 3, or 10. Cells were cultured in a serum-free or 10% FBS-containing medium, and the cytotoxicity assay was carried out three or six days after infection, respectively. The relative cytotoxicity values of cells are represented, considering the cytotoxicity of equal numbers of cells, 100% of which are lysed by cell denaturant (Triton), as 100%.

Figure 12:
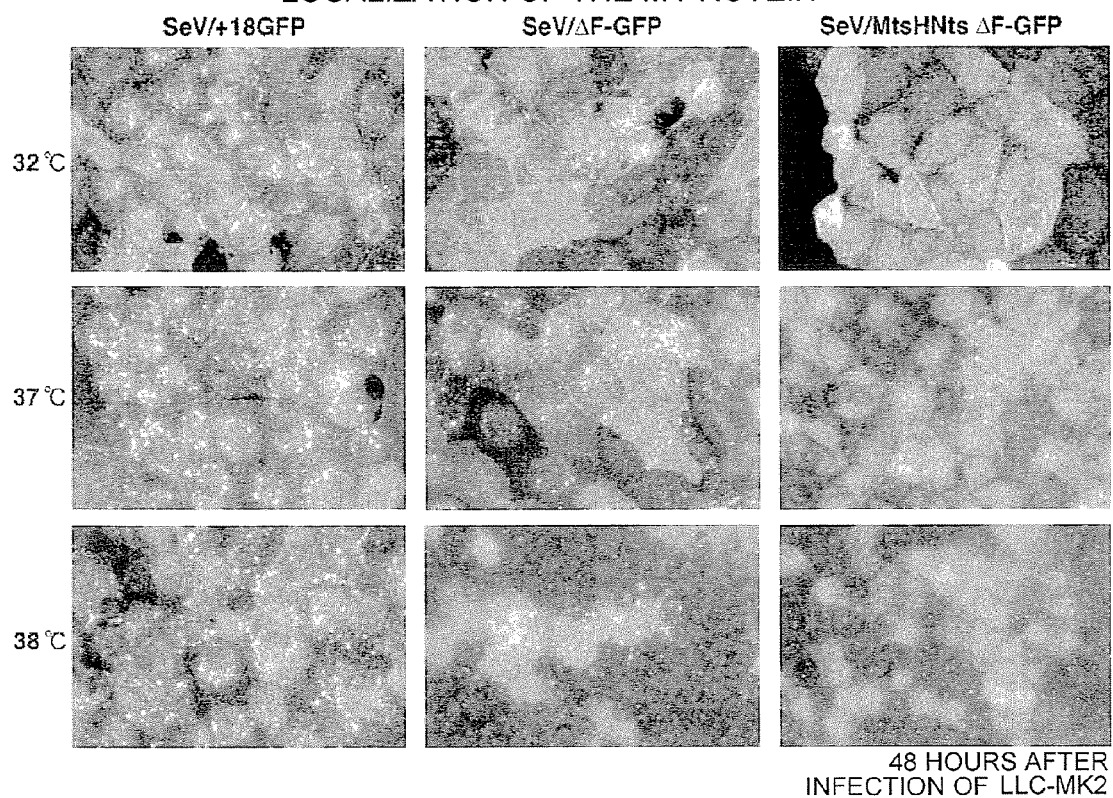

FIG. 12 provides pictures representing the subcellular localization of the M protein in LLC-MK2 cells cultured at 32° C., 37° C. or 38° C. for two days after infection with SeV18+GFP, SeV18+/ΔF-GFP or SeV18+/MtsHNtsΔ-F-GFP at MOI=1, which was observed by immunostaining using an anti-M antibody.

Figure 13:
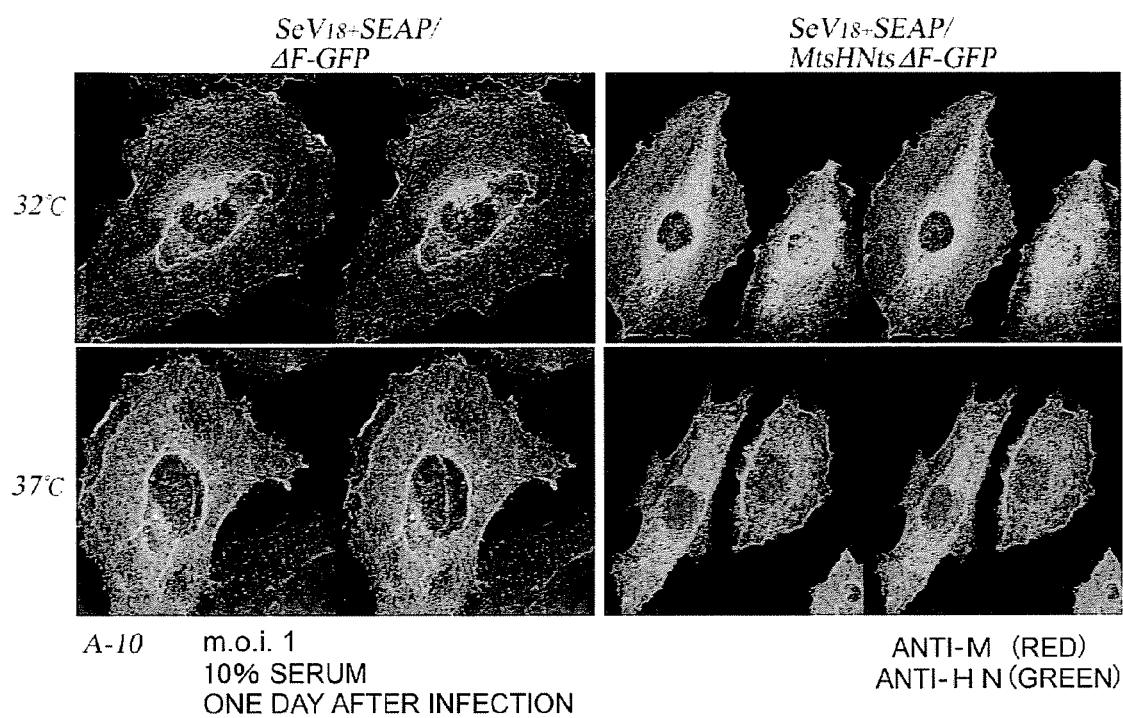

FIG. 13 provides stereo three-dimensional images for the subcellular localization of the M and HN proteins observed under a confocal laser microscope. A-10 cells were infected with SeV18+SEAP/ΔF-GFP or SeV18+SEAP/MtsHNtsΔF-GFP at MOI=1, and then cultured in medium containing 10% serum at 32° C. or 37° C. for one day. These images were obtained by immunostaining using an anti-M antibody and anti-HN antibody.

Figure 14:
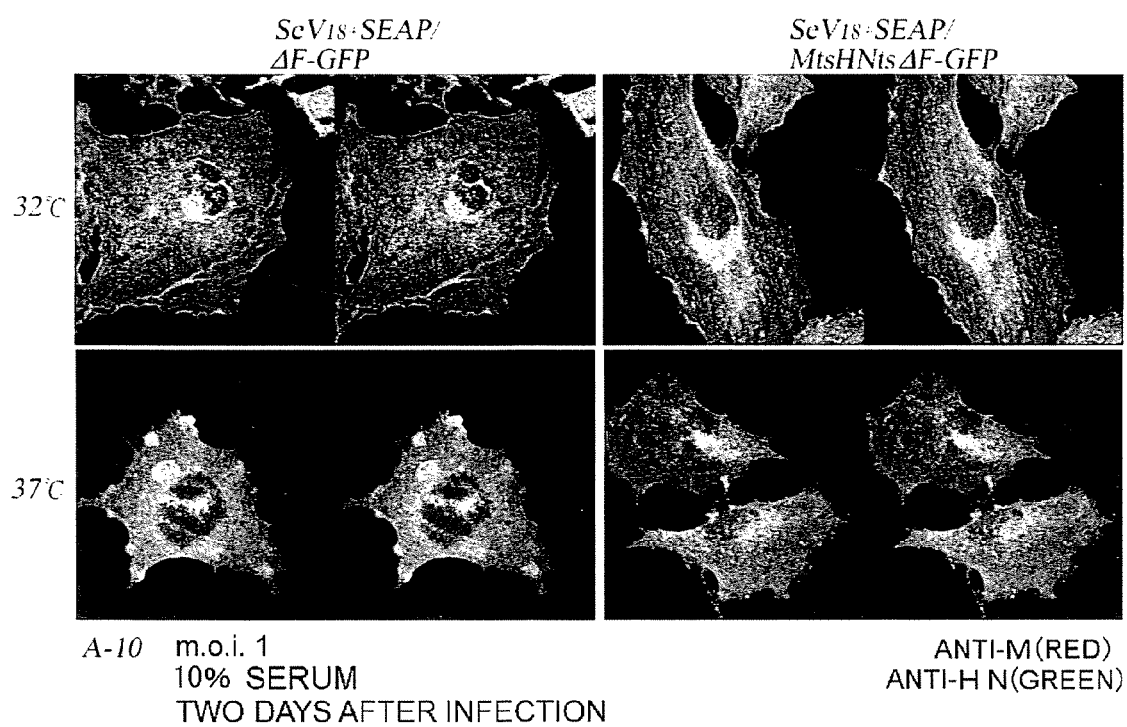

FIG. 14 provides stereo three-dimensional images for the subcellular localization of the M and HN proteins observed under a confocal laser microscope. A-10 cells were infected with SeV18+SEAP/ΔF-GFP or SeV18+SEAP/MtsHNtsΔF-GFP at MOI=1, and then cultured in medium containing 10% serum at 32° C. or 37° C. for two days. These images were obtained by immunostaining using an anti-M antibody and anti-HN antibody.

Figure 15:
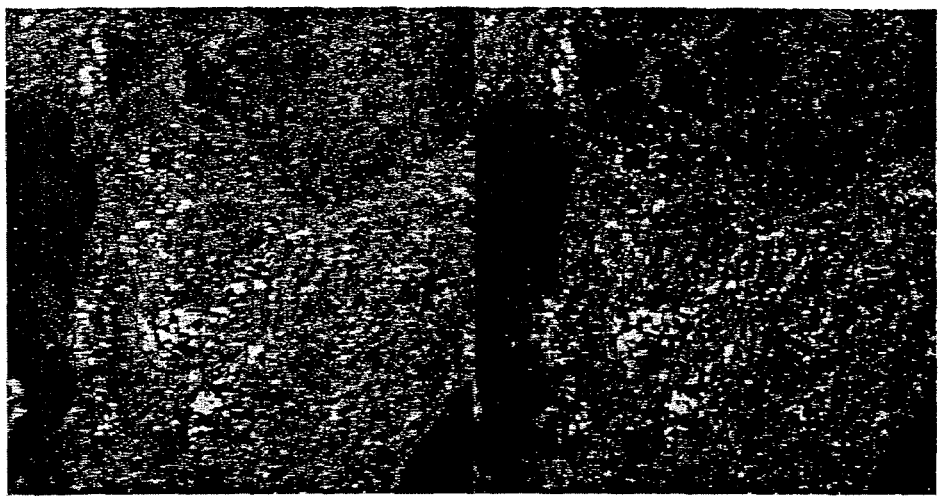
Figure 15:
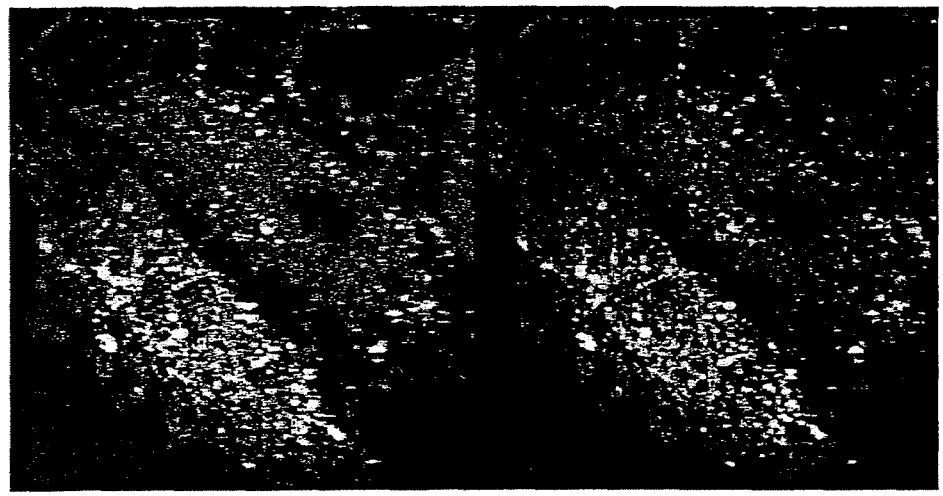

FIG. 15 provides pictures representing the effects of a microtubule depolymerization reagent on the subcellular localization of the M and HN proteins. A-10 cells were infected with SeV18+SEAP/MtsHNtsΔF-GFP at MOI=1, and a microtubule depolymerization reagent, colchicine or colcemid, was immediately added to these cells at a final concentration of 1 μM. The cells were cultured in medium containing 10% serum at 32° C. After two days, the cells were immunostained with an anti-M antibody and anti-HN antibody and then observed under a confocal laser microscope. These photographs show stereo three-dimensional images of the subcellular localization of the M and HN proteins.

Figure 16:
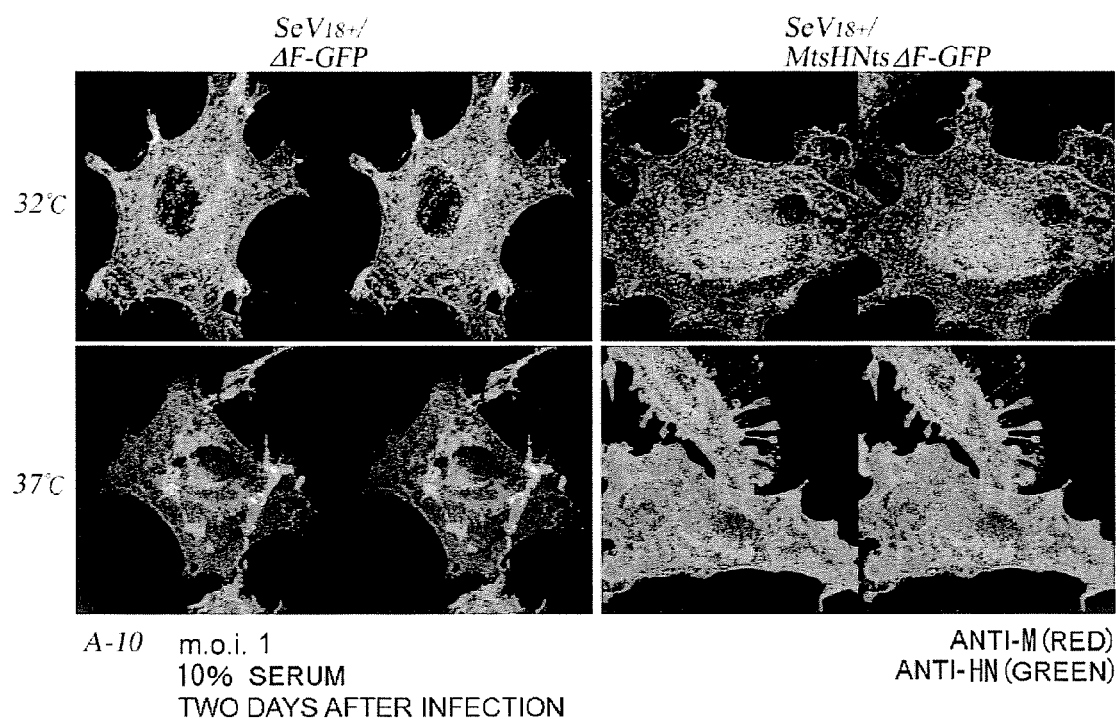

FIG. 16 provides pictures representing the effects of a microtubule depolymerization reagent on the subcellular localization of the M and HN proteins. A-10 cells were infected with SeV18+/ΔF-GFP or SeV18+/MtsHNtsΔF-GFP at MOI=1, and a microtubule depolymerization reagent, colchicine, was immediately added to the cells at a final concentration of 1 μM. The cells were cultured in medium containing 10% serum at 32° C. or 37° C. After two days, these cells were immunostained with anti-M antibody and anti-HN antibody, and then observed under a confocal laser microscope. These photographs show stereo three-dimensional images for the subcellular localization of the M and HN proteins.

Figure 17:
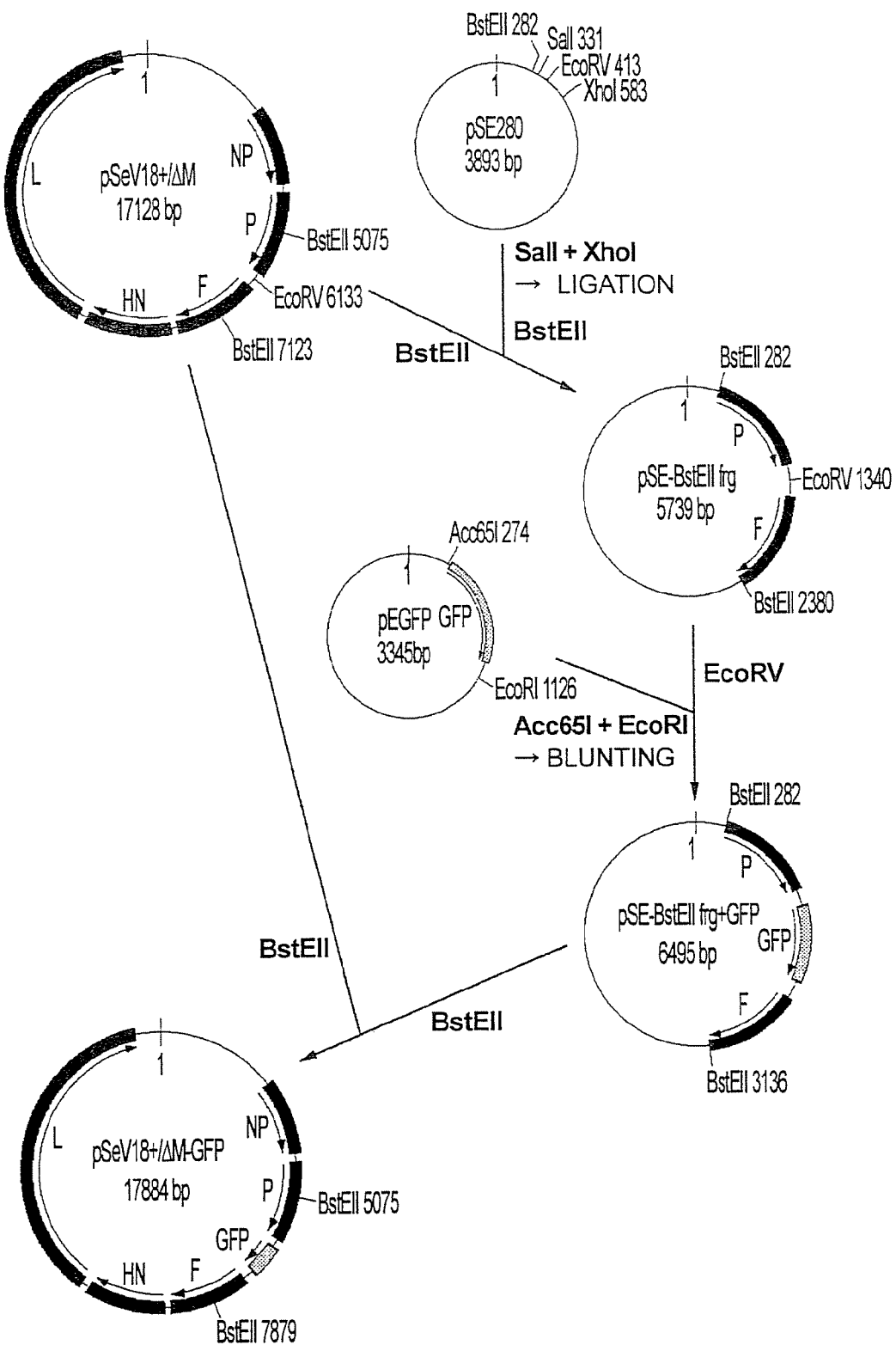

FIG. 17 is a schematic representation of the construction of an M-deficient SeV genome cDNA comprising the EGFP gene.

Figure 18:
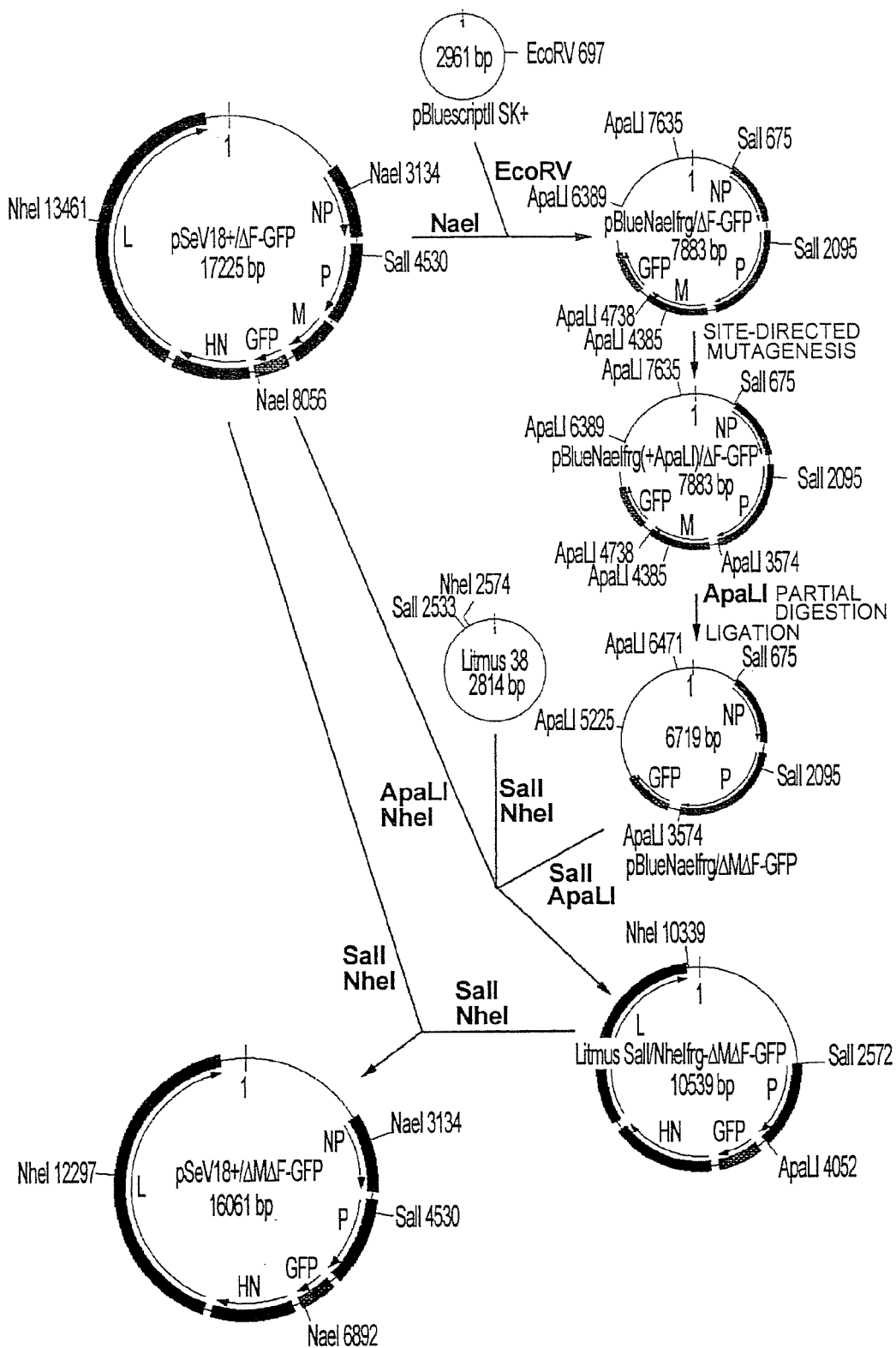

FIG. 18 is a schematic representation of the construction of an F- and M-deficient SeV genome cDNA.

Figure 19:
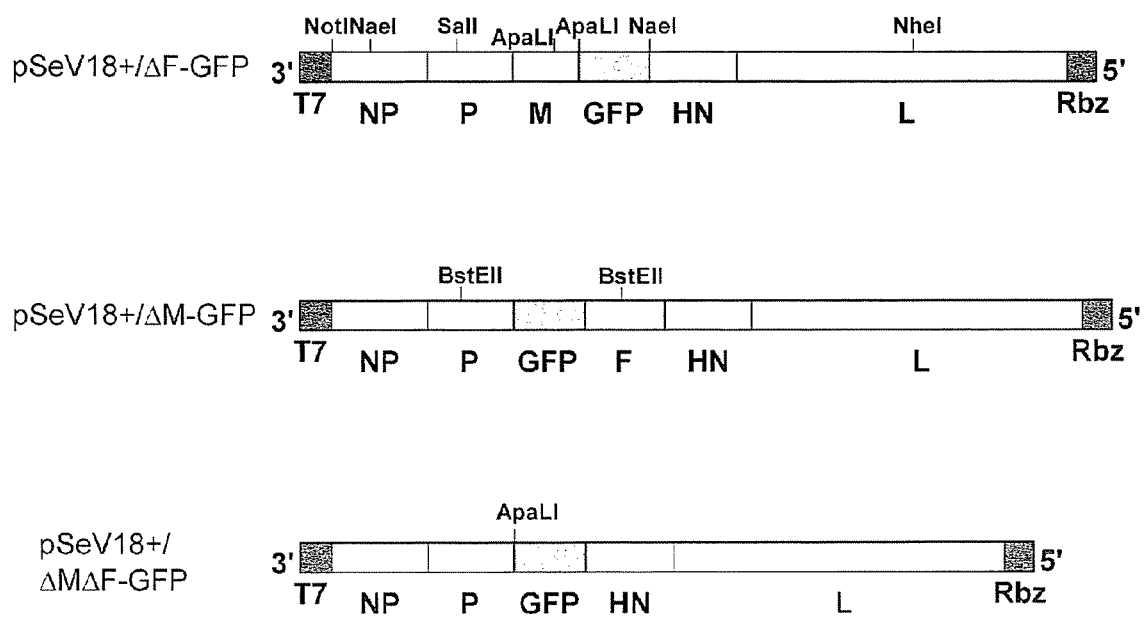

FIG. 19 depicts the structures of the constructed F- and/or M-deficient SeV genes.

Figure 20:
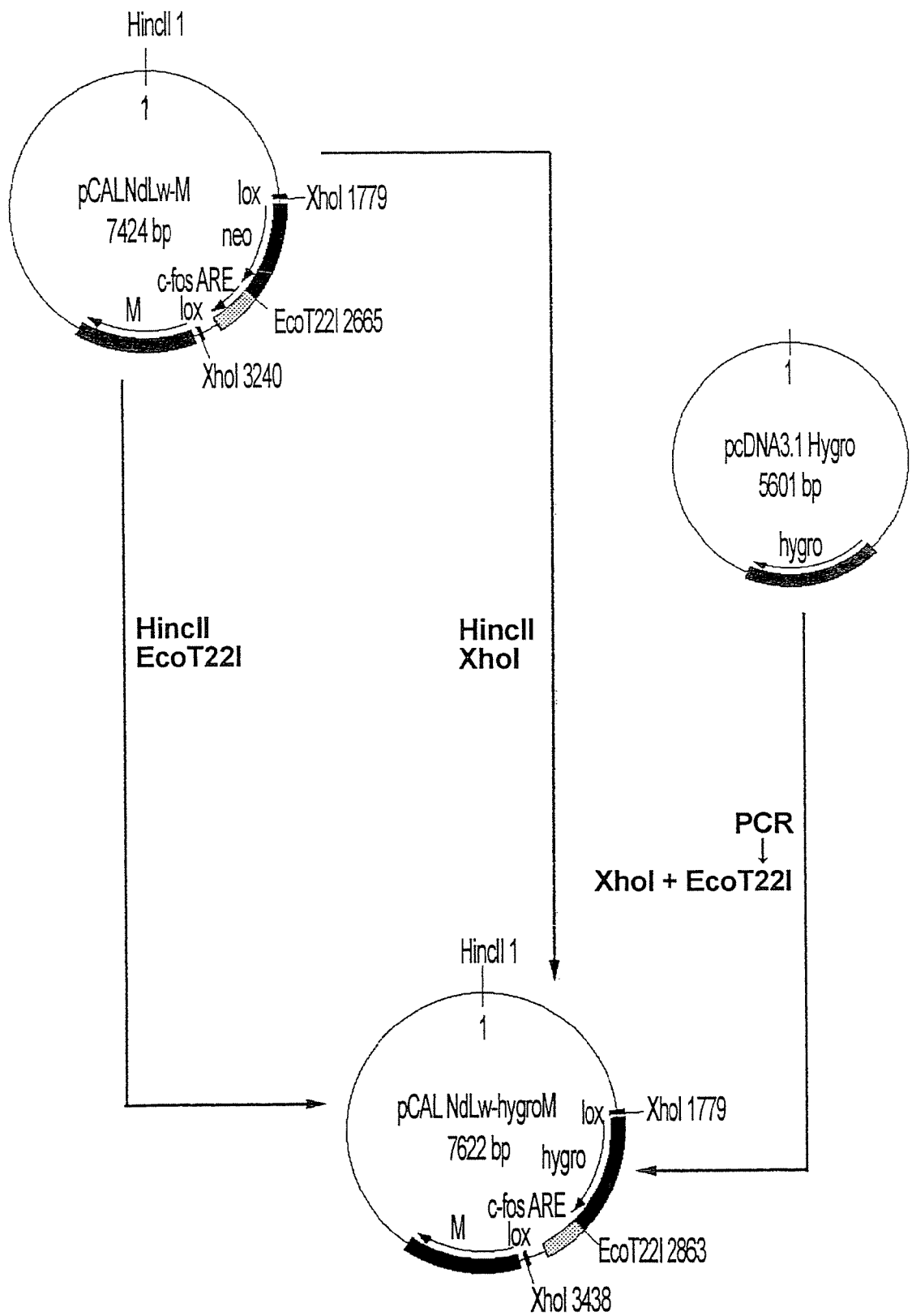

FIG. 20 is a schematic representation of the construction of an M gene-expressing plasmid comprising the hygromycin-resistance gene.

Figure 21:
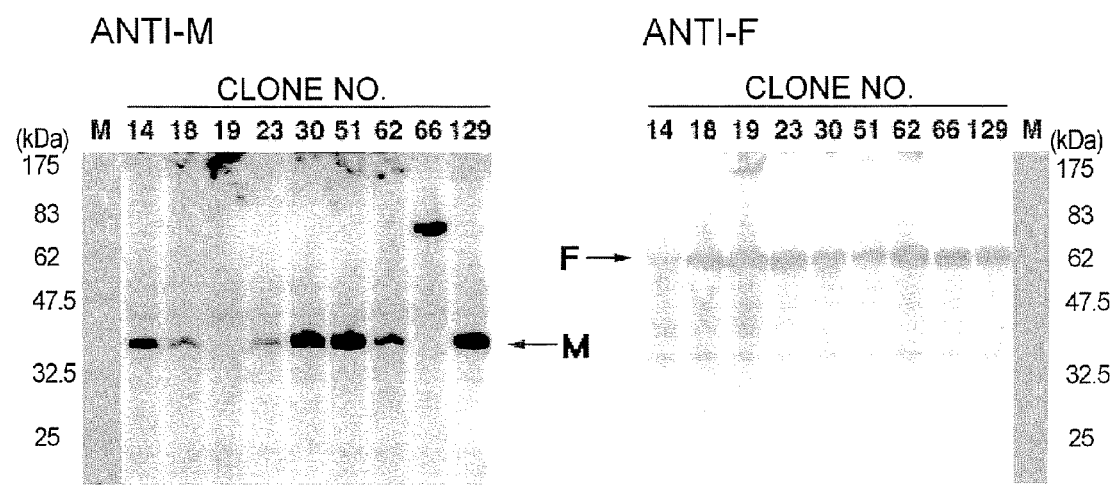

FIG. 21 provides pictures representing a semi-quantitative comparison, by Western blotting, of the expression levels of the M and F proteins in cloned cells inducibly expressing the cloned M protein (and F protein); following infection with a recombinant adenovirus (AcCANCre) that expresses Cre DNA recombinase.

Figure 22:
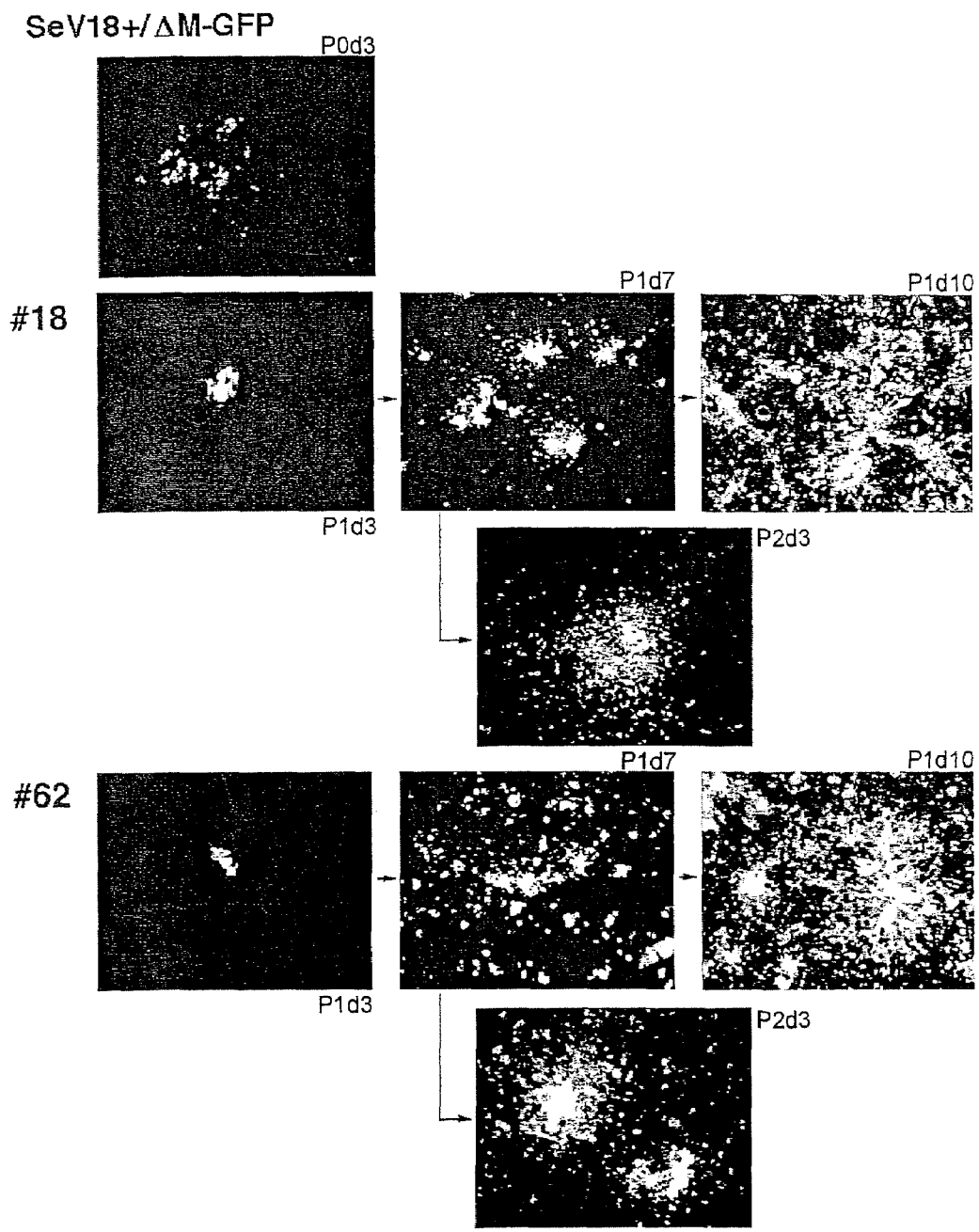

FIG. 22 provides pictures representing the viral reconstitution of an M-deficient SeV (SeV18+/ΔM-GFP) with helper cell (LLC-MK2/F7/M) clones #18 and #62.

Figure 23:
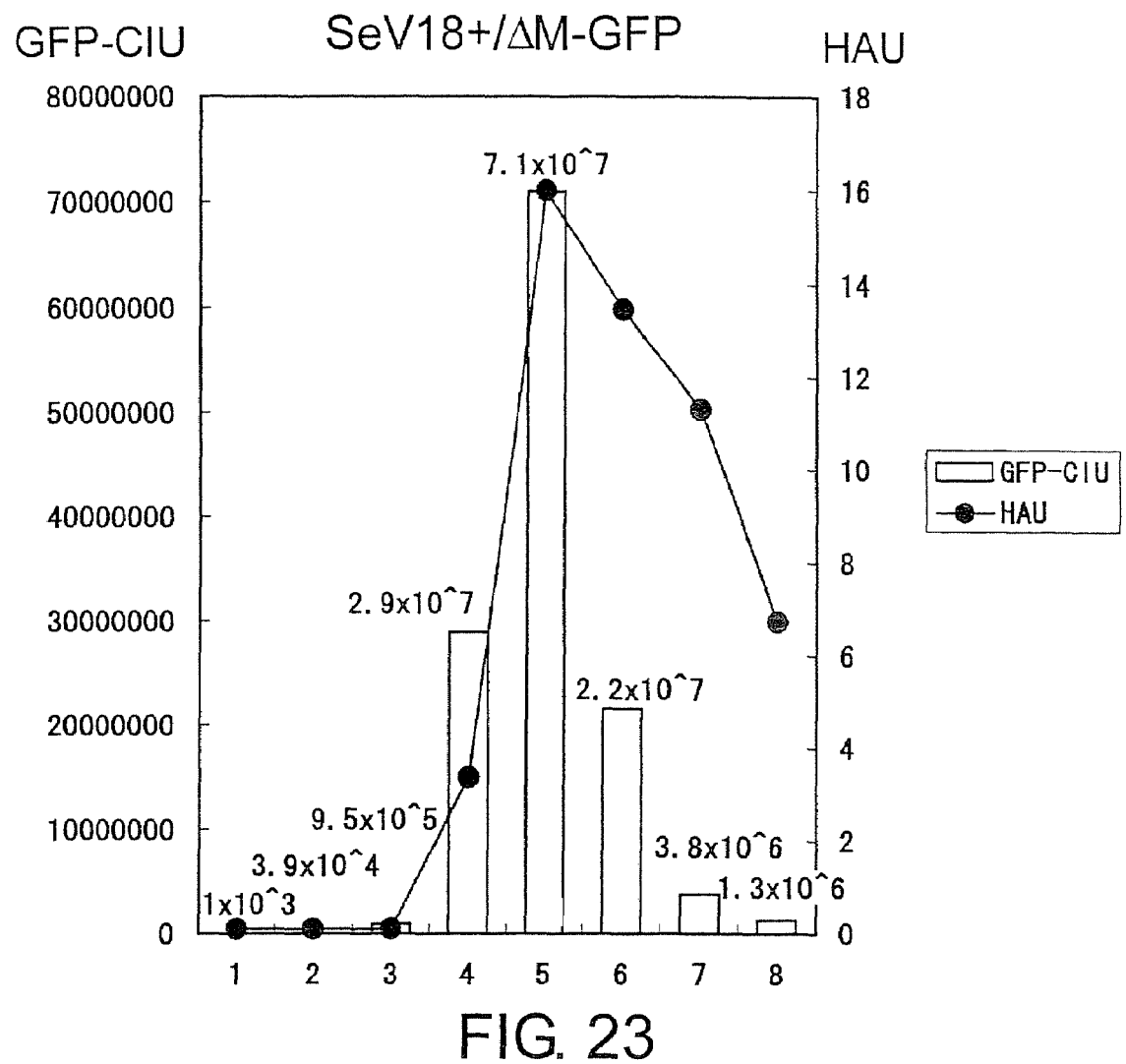

FIG. 23 depicts the viral productivity of SeV18+/ΔM-GFP (CIU and HAU time courses).

Figure 24:
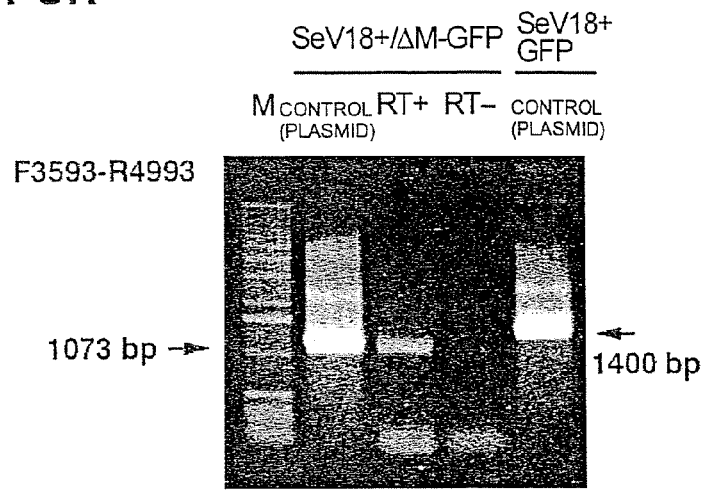
Figure 24:
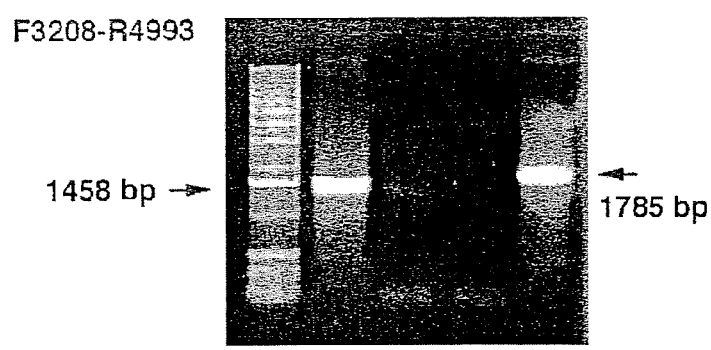
Figure 24:
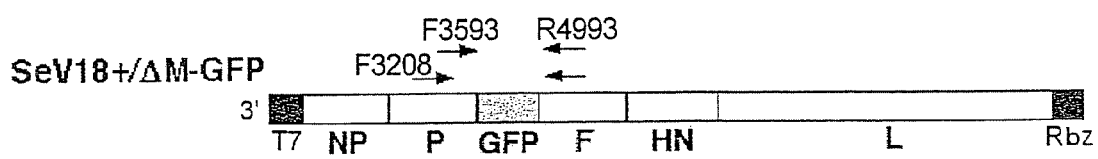

FIG. 24 provides pictures and an illustration representing the results of RT-PCR confirming gene structure in SeV18+/ΔM-GFP virions.

Figure 25:
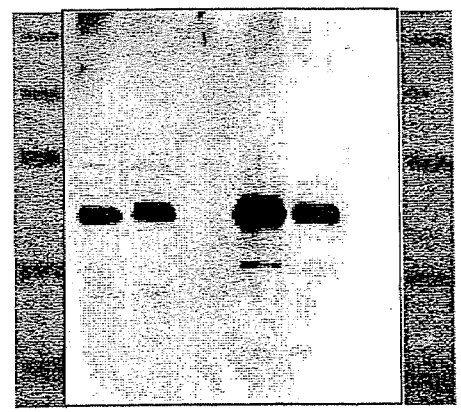
Figure 25:
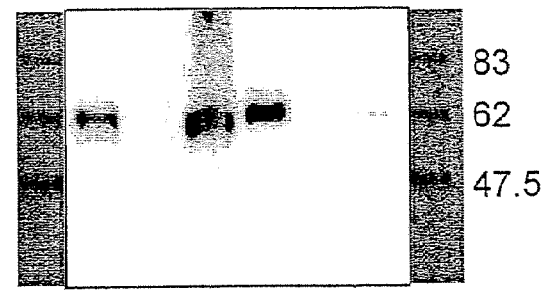
Figure 25:
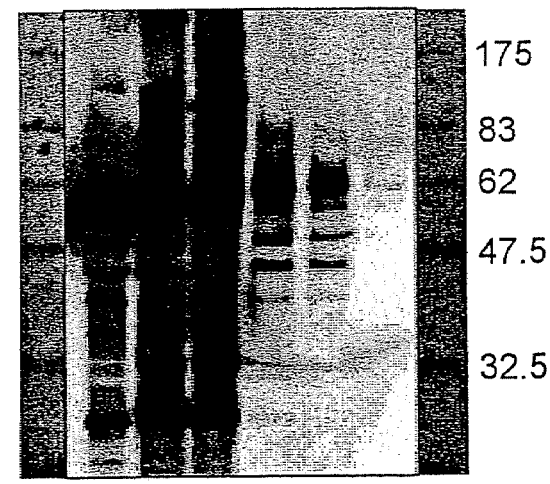

FIG. 25 provides pictures representing the result of a comparison of SeV18+/ΔM-GFP with SeV18+GFP and SeV18+/ΔF-GFP, where, after infection of LLC-MK2 cells, Western blotting was carried out on the viral proteins from these cells and cell cultures to confirm the viral structure of SeV18+/ΔM-GFP from a protein viewpoint.

Figure 26:
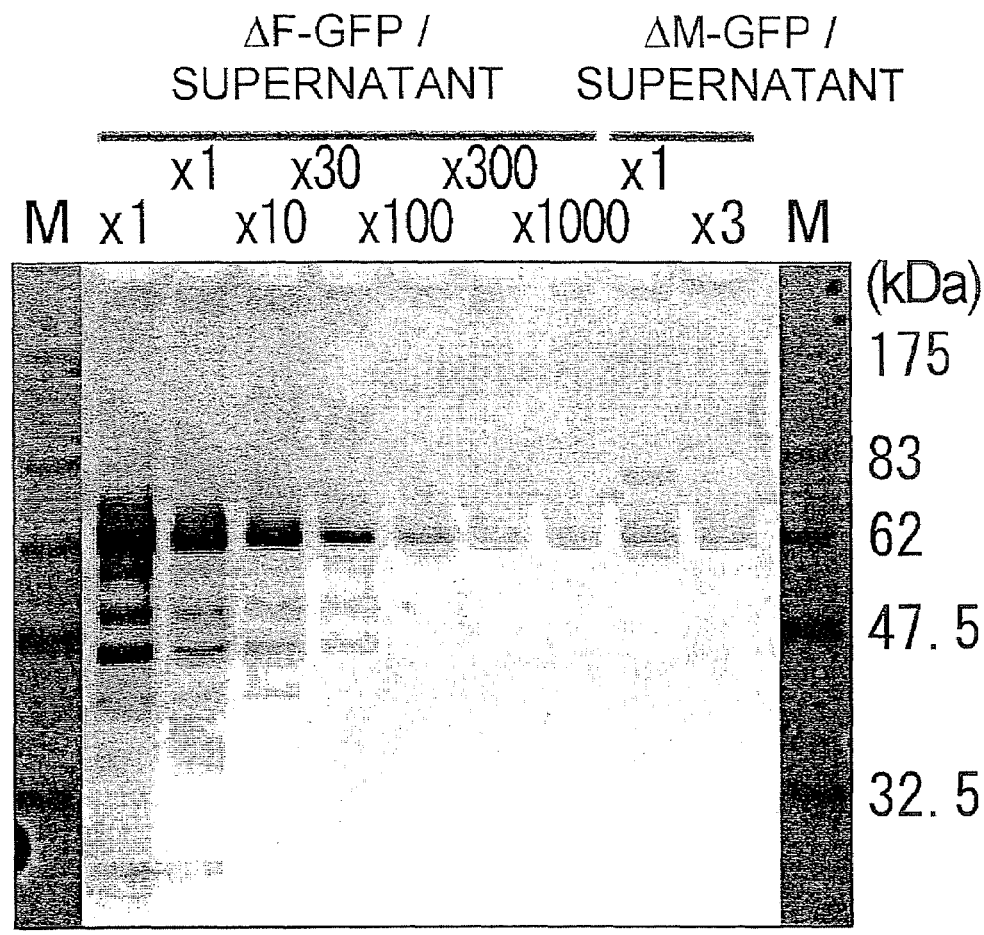

FIG. 26 provides pictures representing a quantitative comparison of virus-derived proteins in the culture supernatant of LLC-MK2 cells infected with SeV18+/ΔM-GFP and SeV18+/ΔF-GFP (a series of dilutions were prepared and assayed using Western blotting). Anti-SeV antibody was used.

Figure 27:
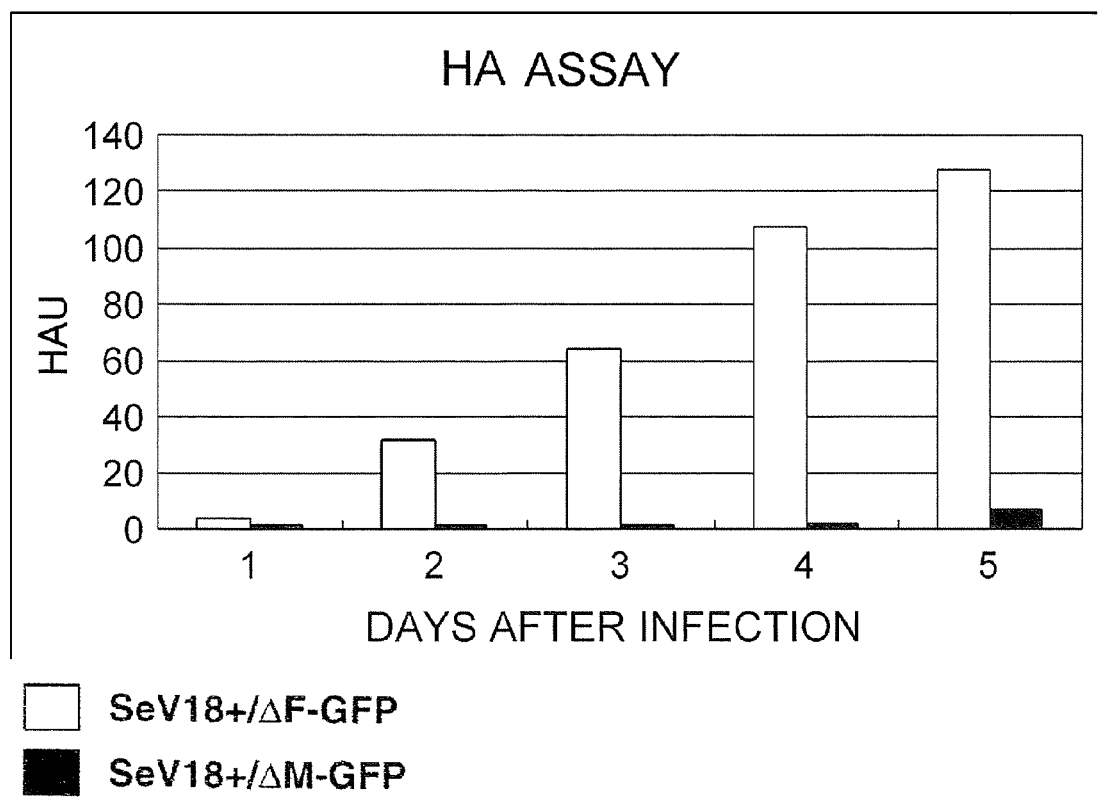

FIG. 27 depicts HA activity in the culture supernatant, collected over time, of LLC-MK2 cells infected with SeV18+/ΔM-GFP or SeV18+/ΔF-GFP at MOI=3.

Figure 28:
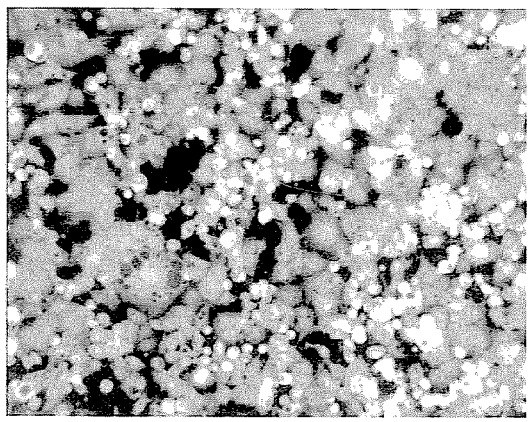
Figure 28:
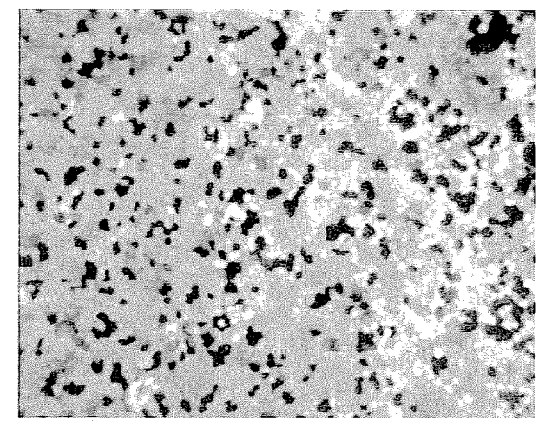

FIG. 28 provides fluorescence microscopic images obtained five days after LLC-MK2 cells were infected with SeV18+/ΔM-GFP or SeV18+/ΔF-GFP at MOI-3.

Figure 29:
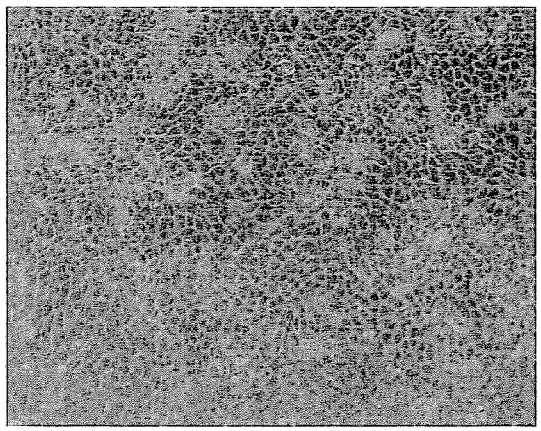
Figure 29:
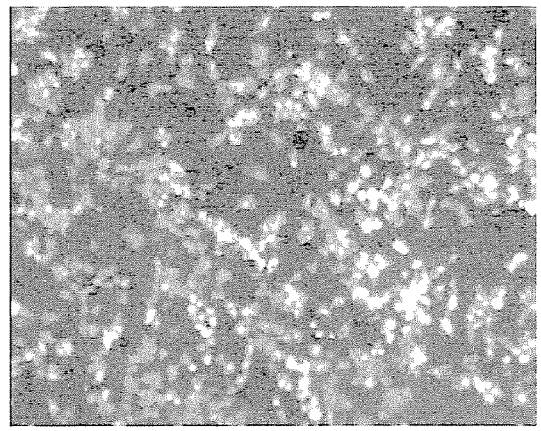

FIG. 29 provides fluorescence microscopic images of LLC-MK2 cells prepared as follows: LLC-MK2 cells were infected with SeV18+/ΔM-GFP or SeV18+/ΔF-GFP at MOI=3, and then five days after infection the culture supernatant was recovered and transfected into LLC-MK2 cells using a cationic liposome (Dosper). Microscopic observation was carried out after two days.

Figure 30:
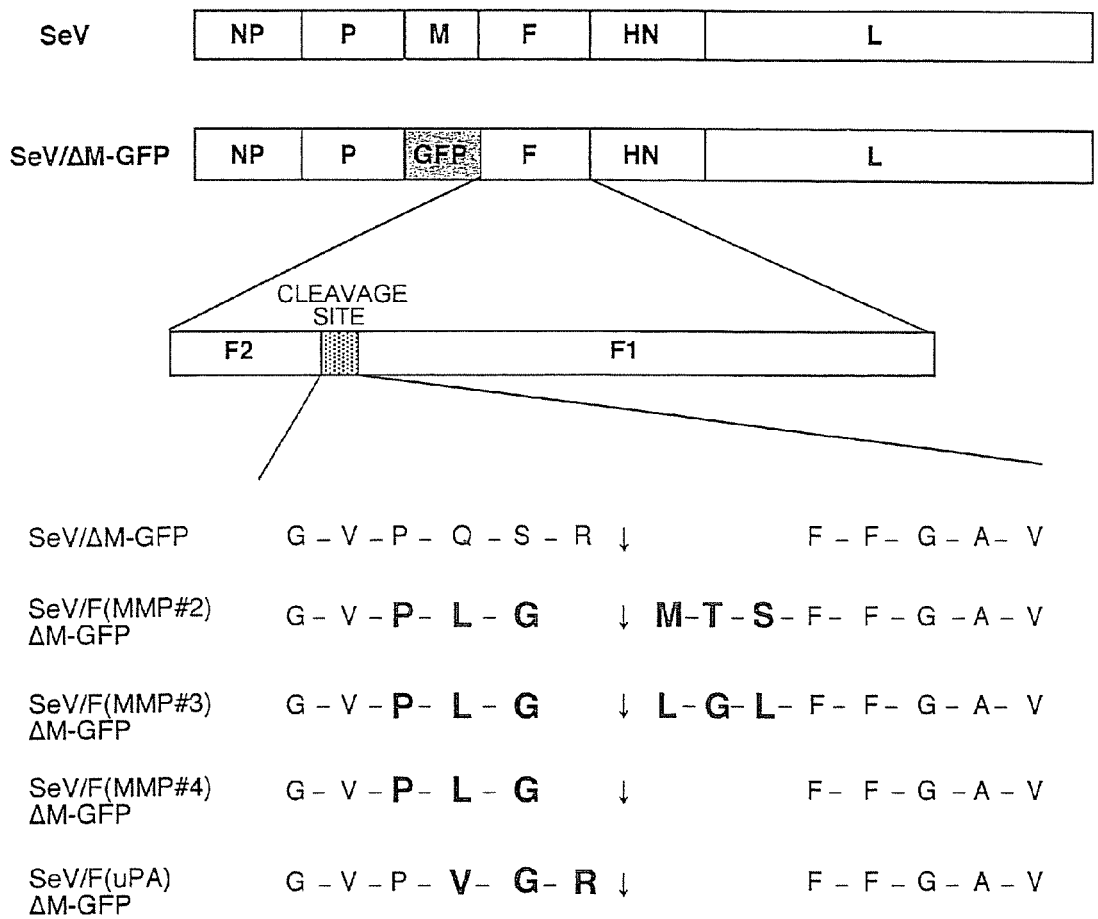

FIG. 30 depicts the design of the amino acid sequences at the F1/F2 cleavage sites (activation sites of the F protein). The recognition sequences of proteases (MMP or uPA) highly expressed in cancer cells were designed based on those of the synthetic substrates. From the top, the sequences of SEQ ID NOs: 40 to 44 are shown.

Figure 31:
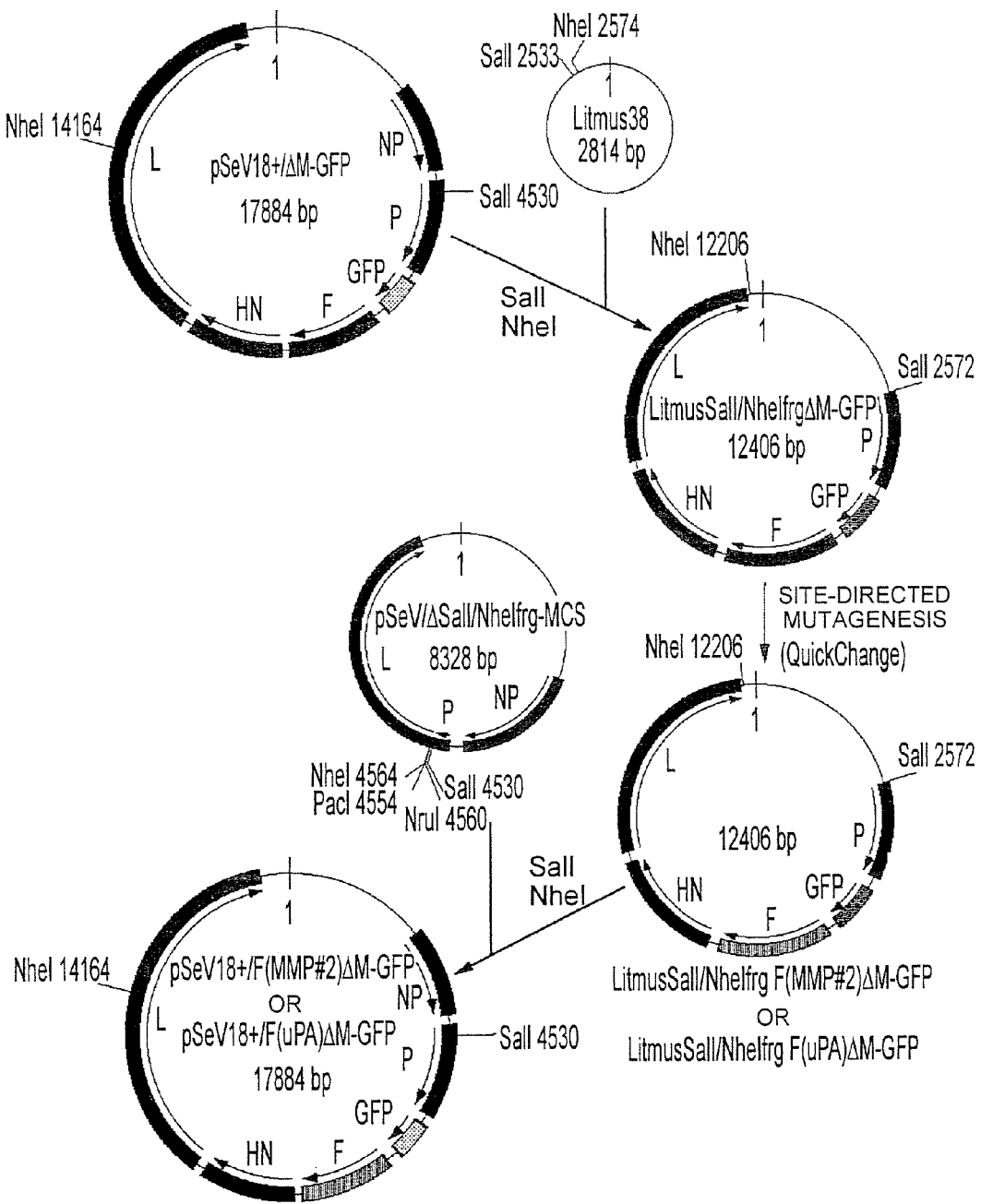

FIG. 31 is a schematic representation of the construction of an M-deficient SeV vector cDNA in which the activation site of F is modified.

Figure 32:
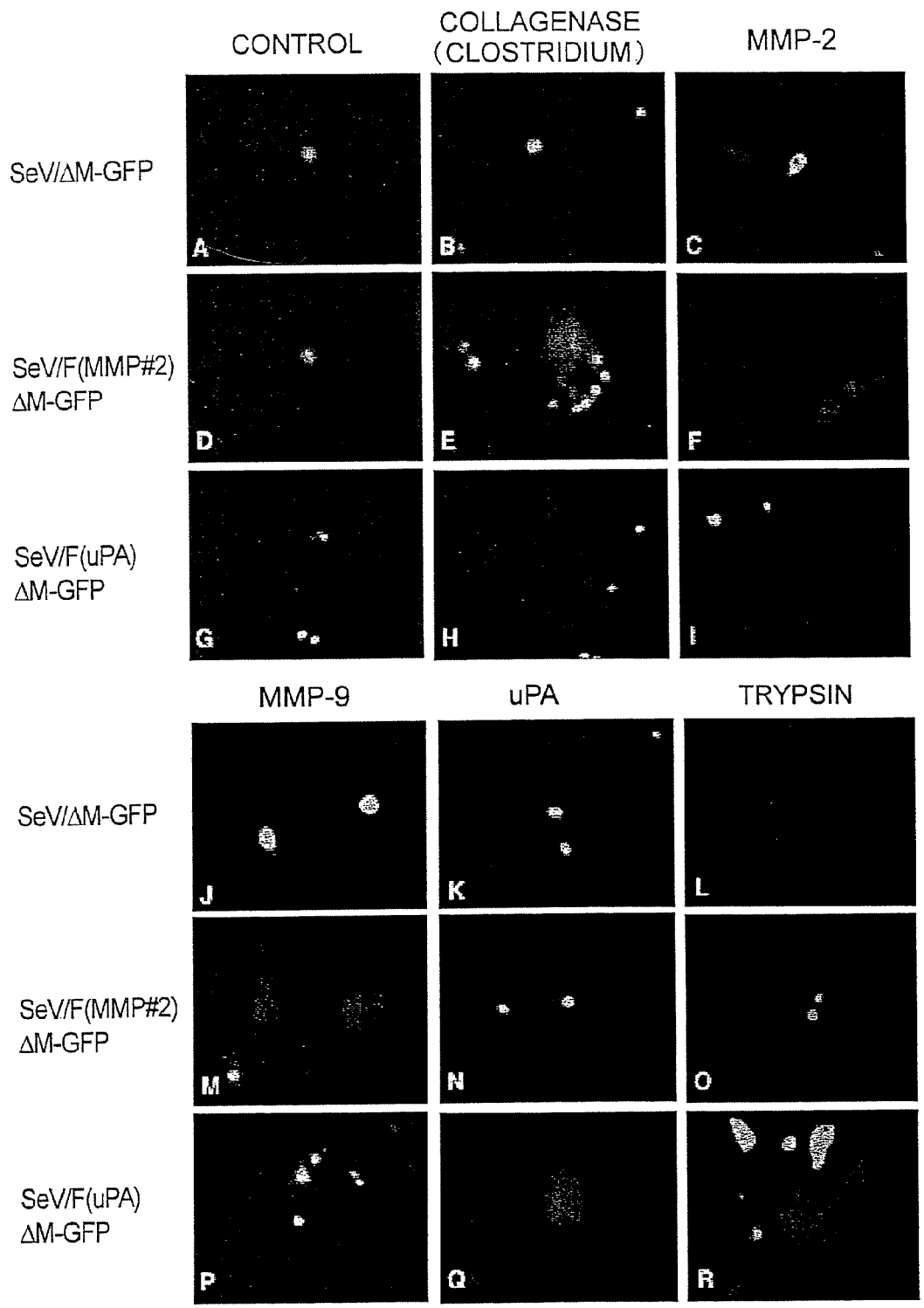

FIG. 32 provides pictures representing protease-dependent cell fusogenic infection by F-modified, M-deficient Sendai viral vectors. By using LLC-MK2, it was confirmed that modification of F causes cell fusogenic infection in a protease-dependent manner. Each of the M-deficient SeVs (SeV/ΔM-GFP (A, B, C, J, K, and L), SeV/F(MMP#2)ΔM-GFP (D, E, F, M, N, and O), and SeV/F(uPA)ΔM-GFP (G, H, I, P, O, and R)) was infected to cells with simultaneous addition of 0.1 μg/ml collagenase (Clostridium) (B, E, and H), MMP-2 (C, F, and I), MMP-9 (J, M, and P), uPA (K, N, and Q), and 7.5 μg/ml trypsin (L, Q, and R). Four days later, the cells were observed under a fluorescent microscope. Only in LLC-MK2 added with trypsin, SeV/ΔM-GFP comprising unmodified F caused cell fusion of infected cells with surrounding cells, resulting in cell fusogenic infection to form multinuclear cells, syncytia (L). In LLC-MK2 to which collagenase, MMP-2, and MMP-9 were added, SeV/F(MMP#2)ΔM-GFP comprising an MMP degradation sequence introduced in F caused cell fusogenic infection to form syncytia (E, F, and M). On the other hand, SeV/(uPA)ΔM-GFP comprising urokinase-type plasminogen activator (uPA) and tissue-type PA (tPA) degradation sequences introduced in F was observed to cause cell fusogenic infection under the presence of trypsin, and by further modification, formation of syncytia was observed under the presence of uPA (Q and R).

Figure 33:
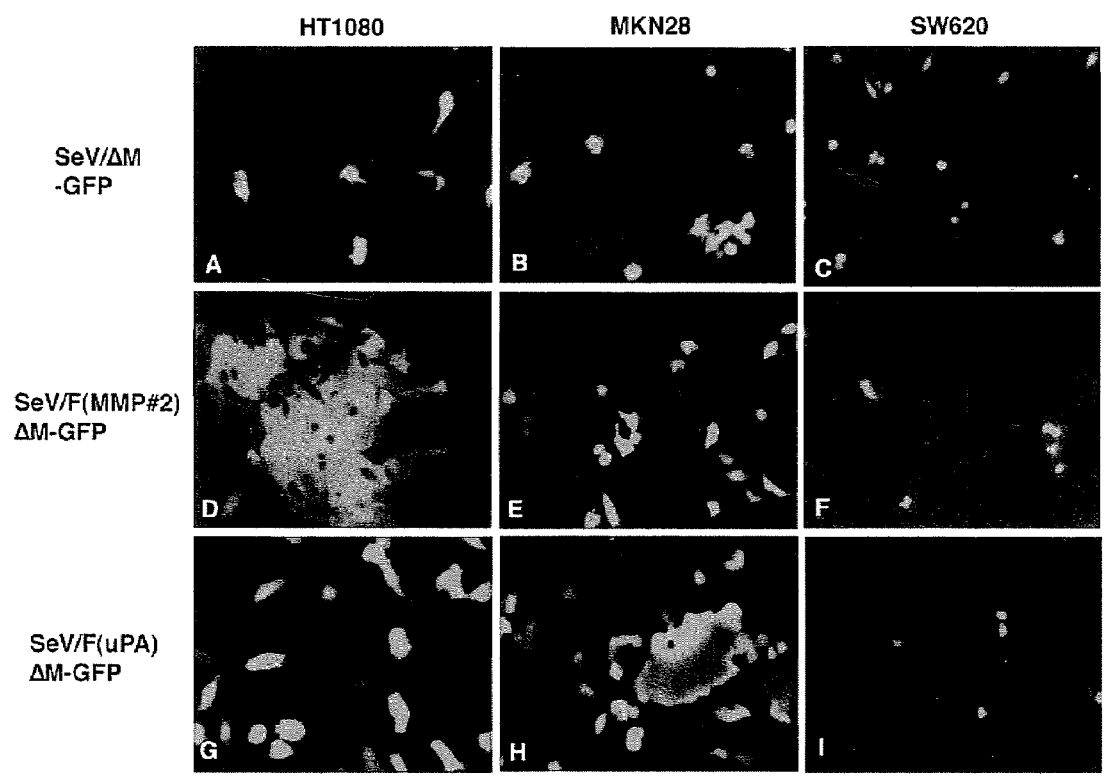

FIG. 33 provides pictures representing protease-dependent cell fusogenic infection of cancer cells by F-modified, M-deficient Sendai viral vectors. Experiments were performed to test whether endogenous protease-selective cell fusogenic infection can be observed. The following cells were used: HT1080, an MMP-expressing cancer cell strain (A, D, and G); MKN28, a tPA-expressing strain (B, E, and H); and SW620, cell strain expressing neither of these proteases (C, F, and I). In HT1080, the infection spread only with SeV/F(MMP#2)ΔM-GFP ten times or more (D). In tPA-expressing strain MKN28, cell fusogenic infection was observed to spread only with SeV/F(uPA)ΔM-GFP. In SW620 expressing neither of these proteases, no spread of infection could be observed.

Figure 34:
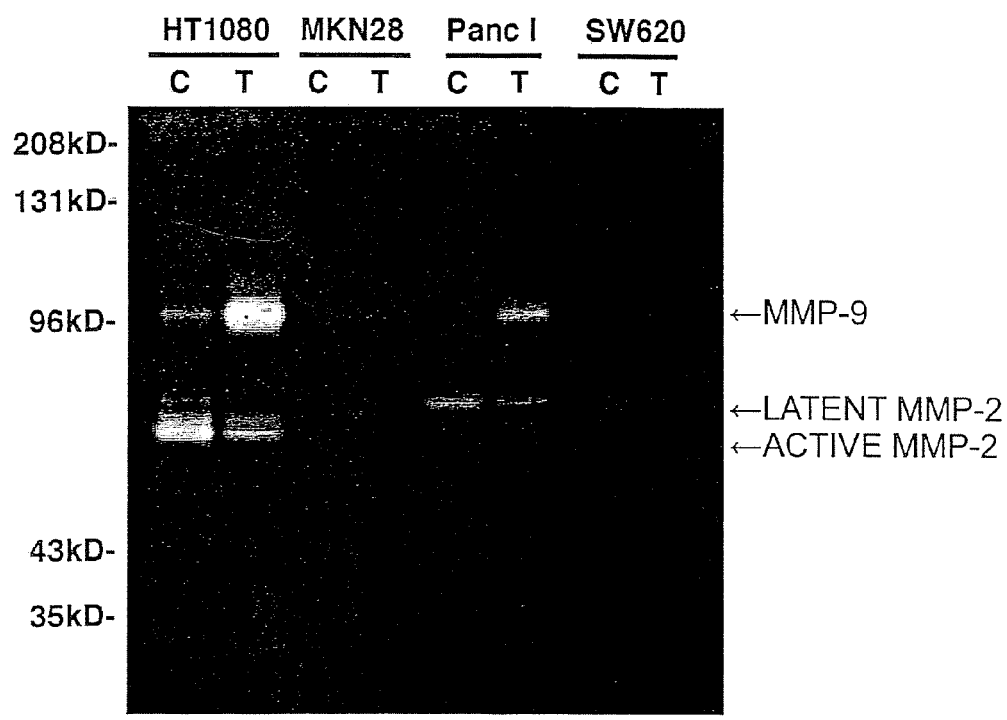
Figure 34:
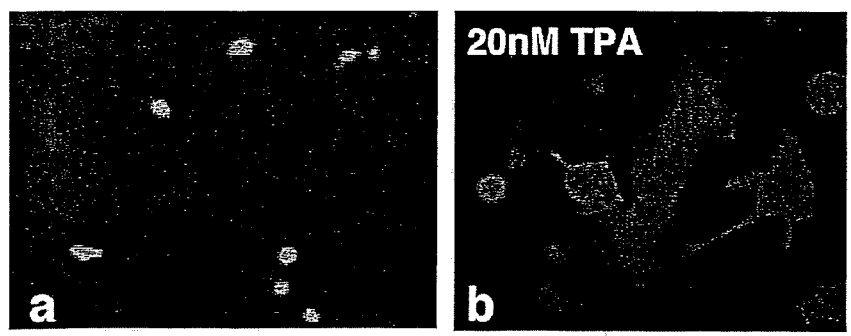

FIG. 34 provides pictures representing MMP induction by phorbol ester and induction of cell fusogenic infection by an F-modified, M-deficient Sendai viral vector. The expression of MMP-2 and MMP-9 was confirmed by gelatin zymography in which the portion where gelatinolytic activity exists becomes clear (A). Lane C represents the control. Lane T shows the result wherein the supernatant obtained after induction with 20 nM PMA was used. A band corresponding to MMP-9 was observed in HT1080 and Panc I, proving induction of MMP-9. Regarding MMP-2, latent MMP-2 having hardly any activity is detected in Panc I before induction. As indicated in FIG. 34B, SeV/F(MMP#2)ΔM-GFP displayed cell fusogenic infection due to MMP-9 induction.

Figure 35:
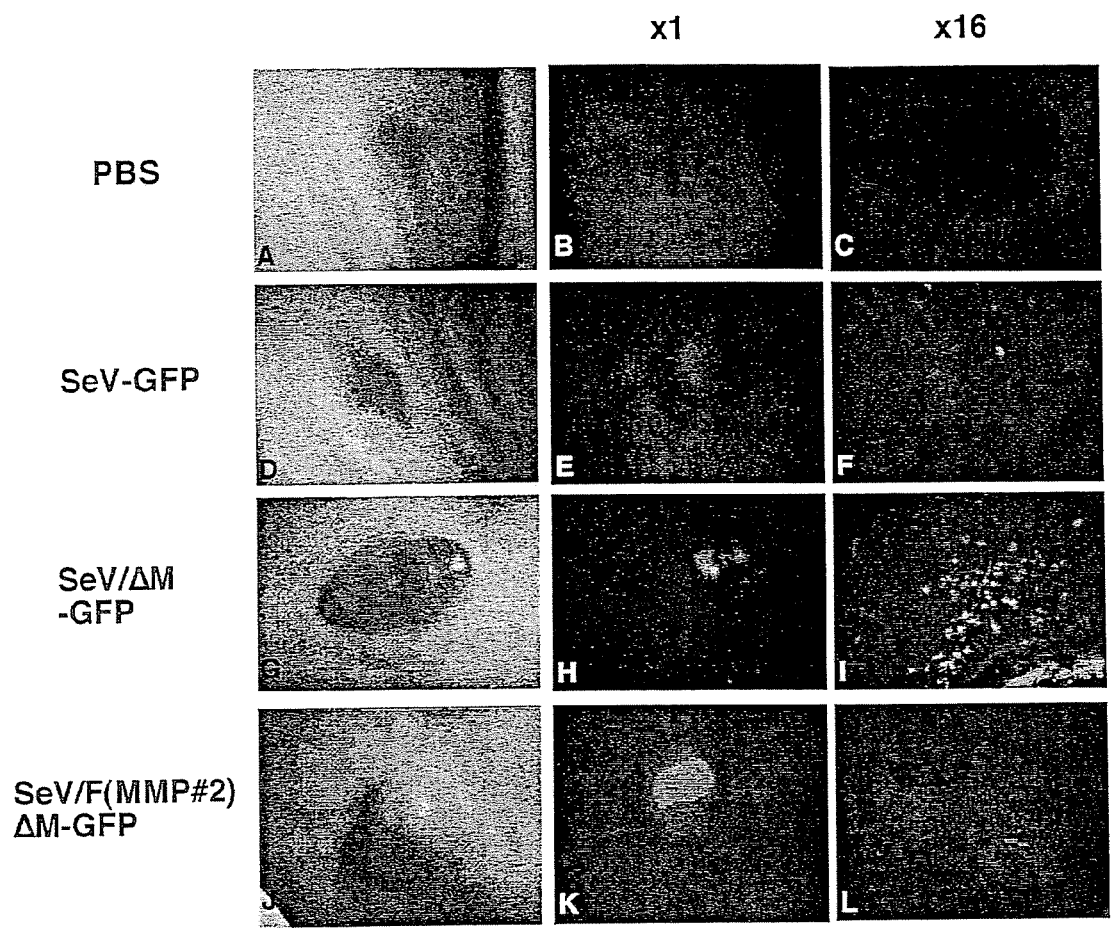

FIG. 35 provides pictures representing cell fusogenic infection of an F-modified, M-deficient Sendai viral vector in vivo. HT1080 carcinoma-bearing nude mice were prepared. Among them, animals having carcinoma with a diameter of more than 3 mm, seven to nine days after subcutaneous injection were used. A fifty μL dose of SeV was injected once into the animals. Two days later, the carcinoma was observed under a fluorescent microscope. Panels A, D, G, and J are bright field images; B, E, H, and K are the corresponding fluorescent images of GFP; and C, F, I, and L are their enlarged images. Fluorescence was observed only in the region surrounding the site to which SeV-GFP and SeV/ΔM-GFP, respectively, had been injected (panels E and H). In contrast, injection of SeV/F(MMP#2)ΔM-GFP was observed to spread the fluorescence throughout the entire cancer (panel K). In the enlarged images, fluorescence in each of the cells can be confirmed for SeV-GFP and SeV/ΔM-GFP; however, the shapes of the cells were unclear for SeV/F(MMP#2)ΔM-GFP which suggests occurrence of cell fusion.

Figure 36:
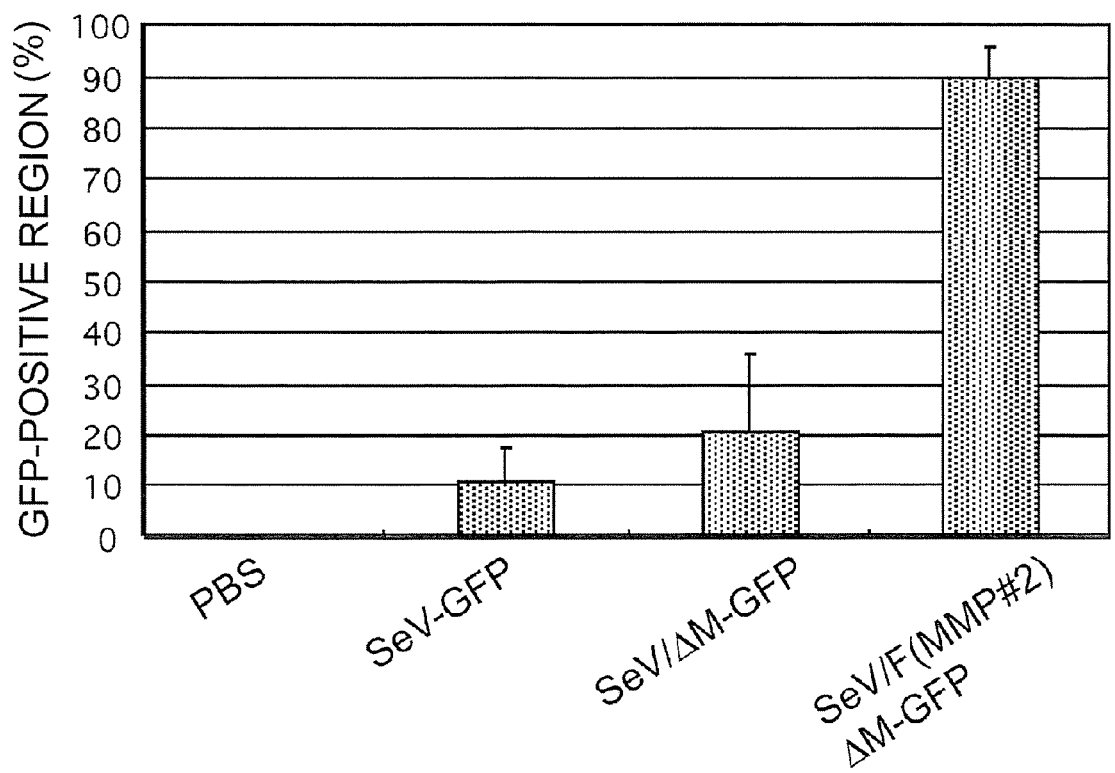

FIG. 36 depicts cell fusogenic infection of an F-modified, M-deficient Sendai viral vector in vivo. The percentages of GFP to the entire cancer in the pictures of FIG. 35 were measured from their areas using NIH image. As a result, SeV-GFP and SeV/ΔM-GFP showed 10% and 20% infections, respectively; whereas SeV/F(MMP#2)ΔM-GFP showed 90% infection, suggesting obvious spreading of infection.

Figure 37:
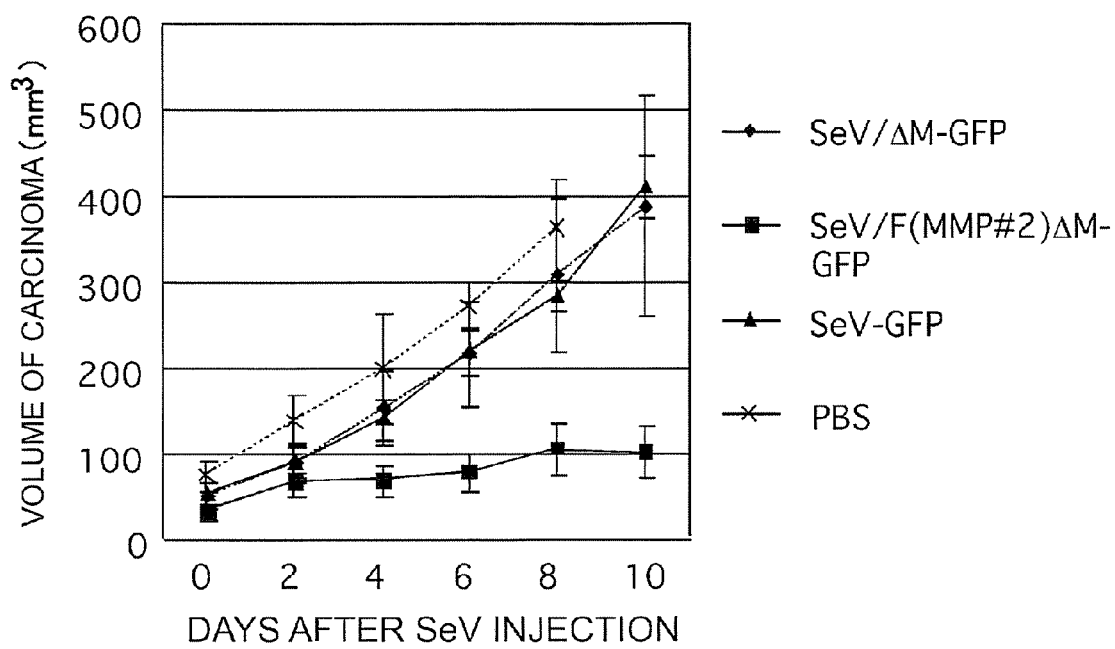

FIG. 37 depicts the antitumor effects of F-modified, M-deficient SeV vectors in carcinoma-bearing nude mice. The volume of the carcinoma of the mice assayed in FIG. 35 was measured. Four groups of SeVs were injected into carcinomas with a diameter of 3 mm or more. Reinjection was performed two days later, and the size of the carcinoma was measured. Carcinomas to which PBS, SeV-GFP, and SeV/ΔM-GFP were injected showed rapid growth. In contrast, those injected with SeV/F(MMP#2)ΔM-GFP demonstrated in the assays of FIG. 36 to spread throughout the entire carcinoma clearly did not proliferate and remained small. Significant antitumor effects as compared to the other three groups was observed at P<0.05 according to the t-test.

Figure 38:
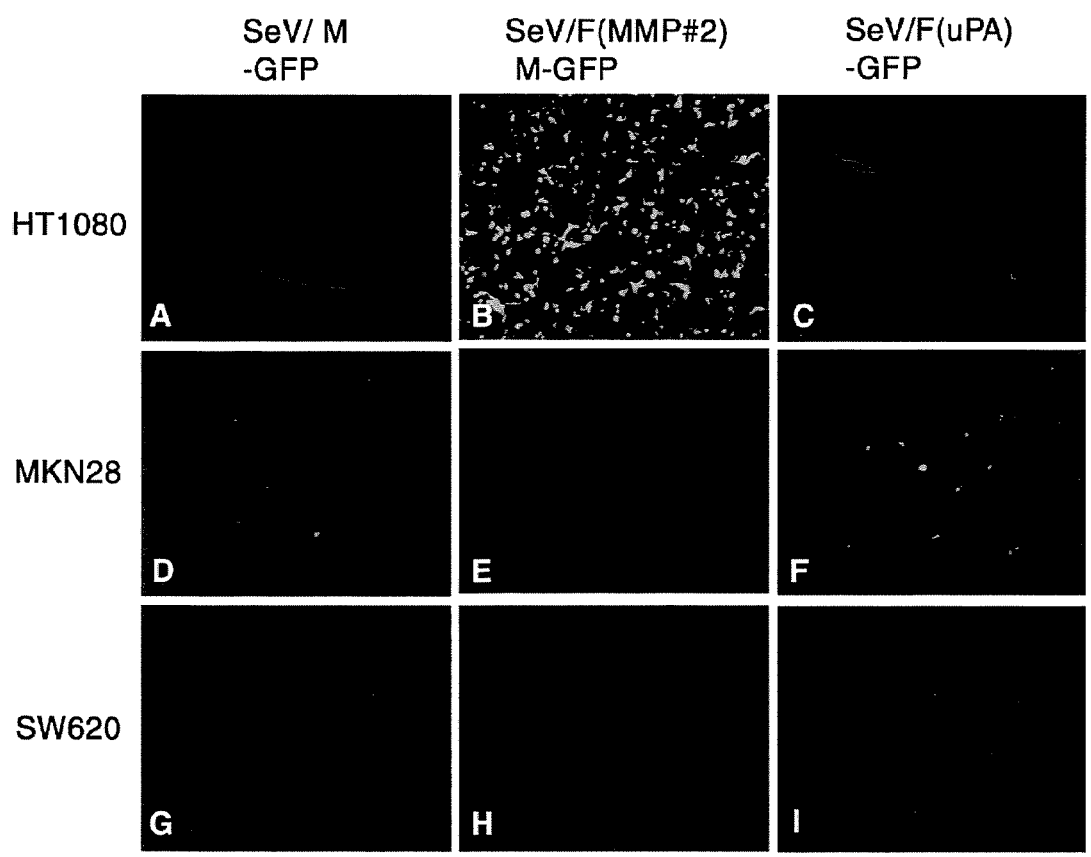

FIG. 38 provides pictures representing protease expression-selective infection of an F-uncleaved, F-modified, M-deficient SeV vector to cancer cells. The possibility of selective infection by protease expression was examined in MMP-expressing HT1080 strain, tPA-expressing MKN28 strain, and SW620 that hardly expresses proteases. Infection by SeV/F(MMP#2)ΔM-GFP was observed in MMP-expressing HT1080 strain, but not in tPA-expressing MKN28 strain. Infection by SeV/F(uPA)ΔM-GFP was observed in tPA-expressing MKN28 strain, but in MMP-expressing HT1080 strain.

Figure 39:
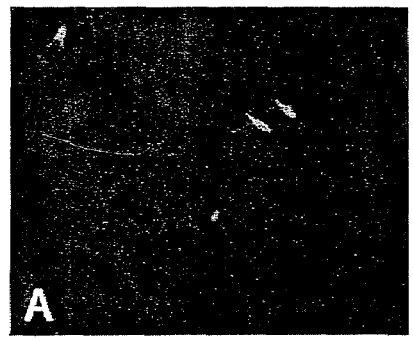
Figure 39:
Figure 39:
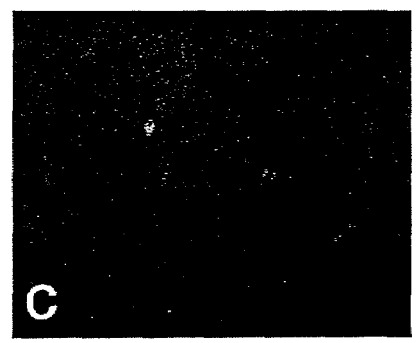
Figure 39:
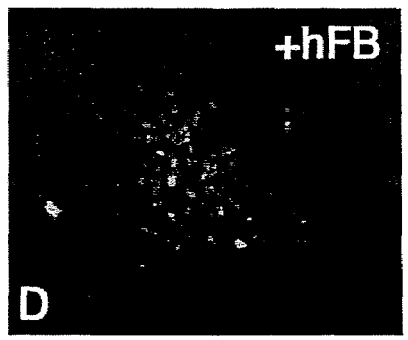
Figure 39:
Figure 39:

FIG. 39 provides pictures representing the acquisition of infection ability via the F-uncleaved, F-modified, M-deficient SeV vector due to MMP-3 and MMP-7 induction by fibroblasts. Changes in the infectivity of the F-modified, M-deficient SeV vector due to MMP induction by fibroblasts in vitro was examined using SW480 and WiDr. Co-culturing human fibroblasts (hFB) with SW480 and WiDr caused infection of SeV/F(MMP#2)ΔM-GFP (B and D). Such phenomenon was not observed in SW620 where induction did not take place (F).

Figure 40:
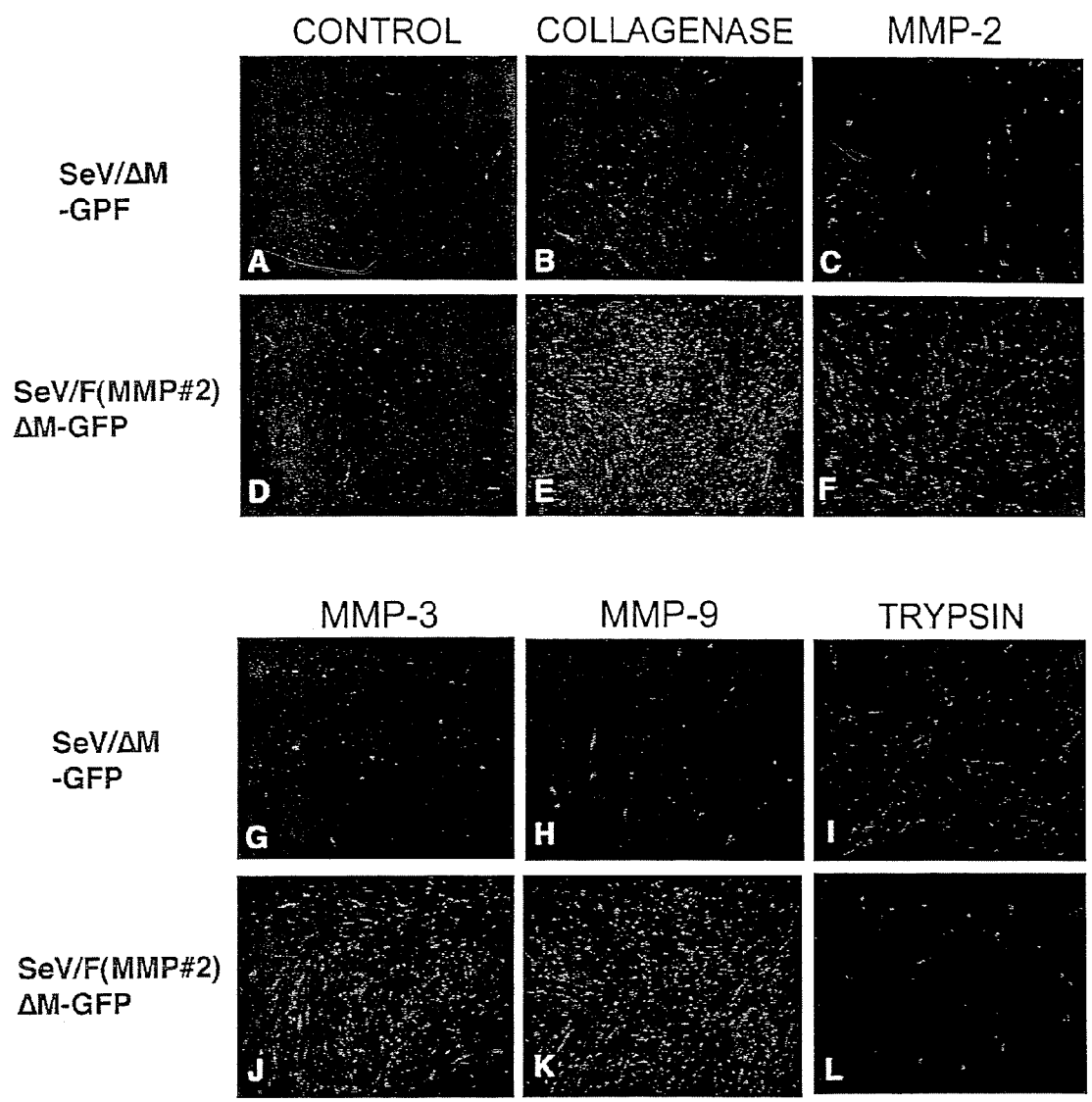

FIG. 40 provides pictures representing MMP-selective infection of an F-modified, M-deficient SeV vector to human aortic smooth muscle cells. Infection of SeV/ΔM-GFP proceeds only by the addition of trypsin. In contrast, the infection of SeV/F(MMP#2)ΔM-GFP proceeds with collagenase, MMP-2, MMP-3, and MMP-9.

Figure 41:
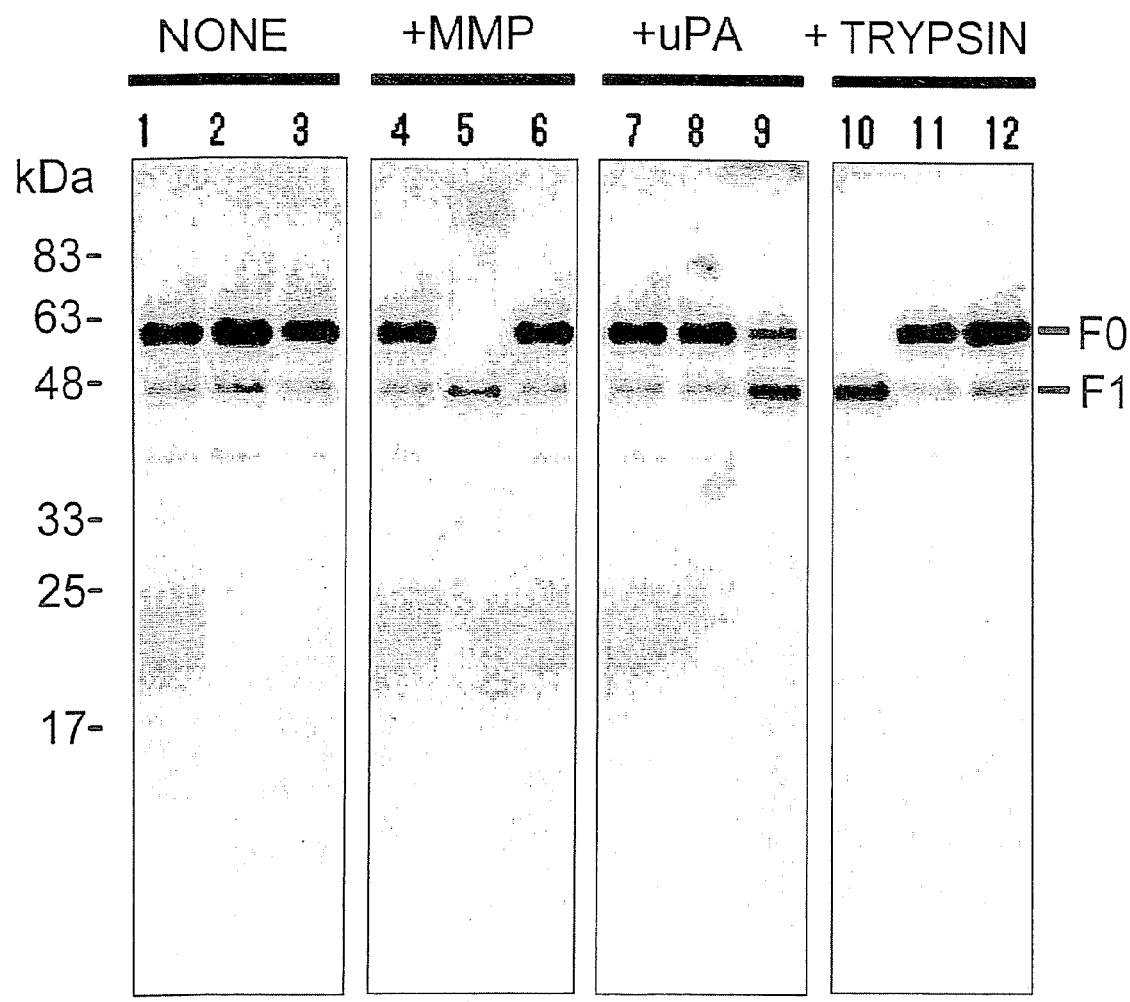

FIG. 41 provides pictures representing the cleavage of the protease-dependent F protein within the F-modified, M-deficient SeV vector. The protease-dependent cleavage of F0 of Sendai virus to F1 was confirmed by Western blotting. An M-deficient SeV vector comprising unmodified F (shown in lanes 1, 4, 7, and 10), an M-deficient SeV vector with insertion of an MMP#2 sequence into F (shown in lanes 2, 5, 8, and 11), and an M-deficient SeV vector with insertion of a uPA sequence into F (shown in lanes 3, 6, 9, and 12) were treated with above-described proteases (untreated (lanes 1, 2, and 3); 0.1 ng/mL MMP-9 (lanes 4, 5, and 6); 0.1 ng/mL uPA (lanes 7, 8, and 9); and 7.5 g/mL trypsin (lanes 10, 11, and 12)) at 37° C. for 30 minutes. As a result, F1 cleavage occurred depending on the inserted protease substrates. Namely, trypsin cleaved the F protein of the F-unmodified M-deficient SeV vector, MMP-9 cleaved that of the M-deficient SeV vector having the MMP#2 sequence inserted into the F protein, and uPA cleaved that of the M-deficient SeV vector having the uPA sequence inserted into the F protein.

Figure 42:
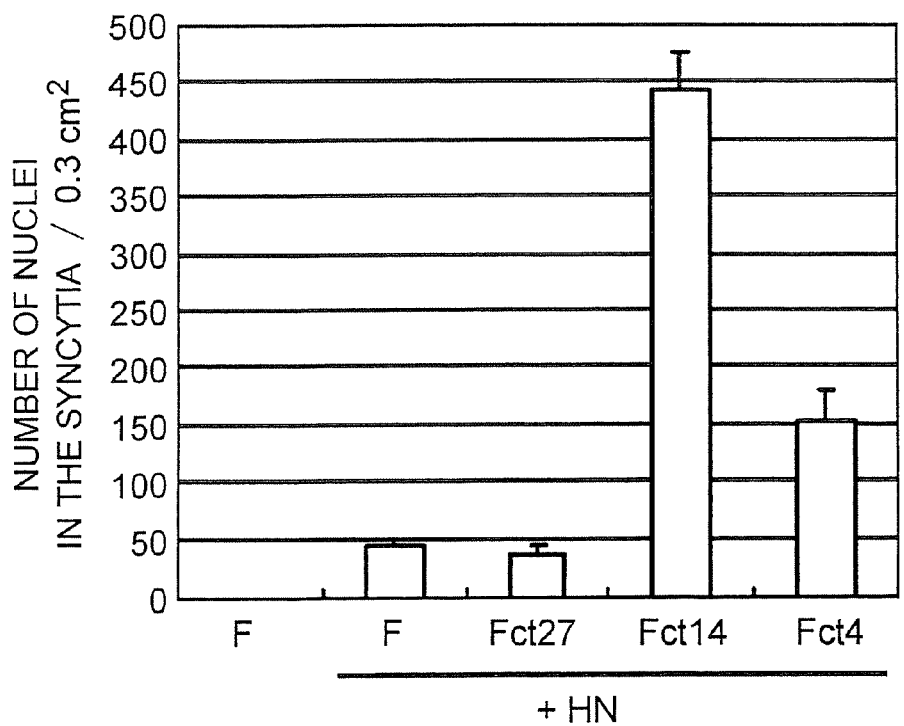

FIG. 42 depicts the production of cytoplasmic domain deletion mutants of F, and compares their fusogenicity through simultaneous expression with HN. FIG. 42A is a schematic representation of the construction of the cytoplasmic domain deletion mutants of Sendai viral F protein. From the top, SEQ ID NOs: 76 to 79. FIG. 42B depicts the production of cytoplasmic domain deletion mutants of the F protein and the comparison of fusogenicity due to simultaneous expression with HN. Each of the cytoplasmic domain deletion mutants of Sendai viral F protein and HN were expressed simultaneously in LLC-MK2 cells added with 7.5 µg/mL trypsin. Four days later, nuclear staining was performed with hematoxylin, and the number of nuclei that underwent syncytium formation was counted.

Figure 43:
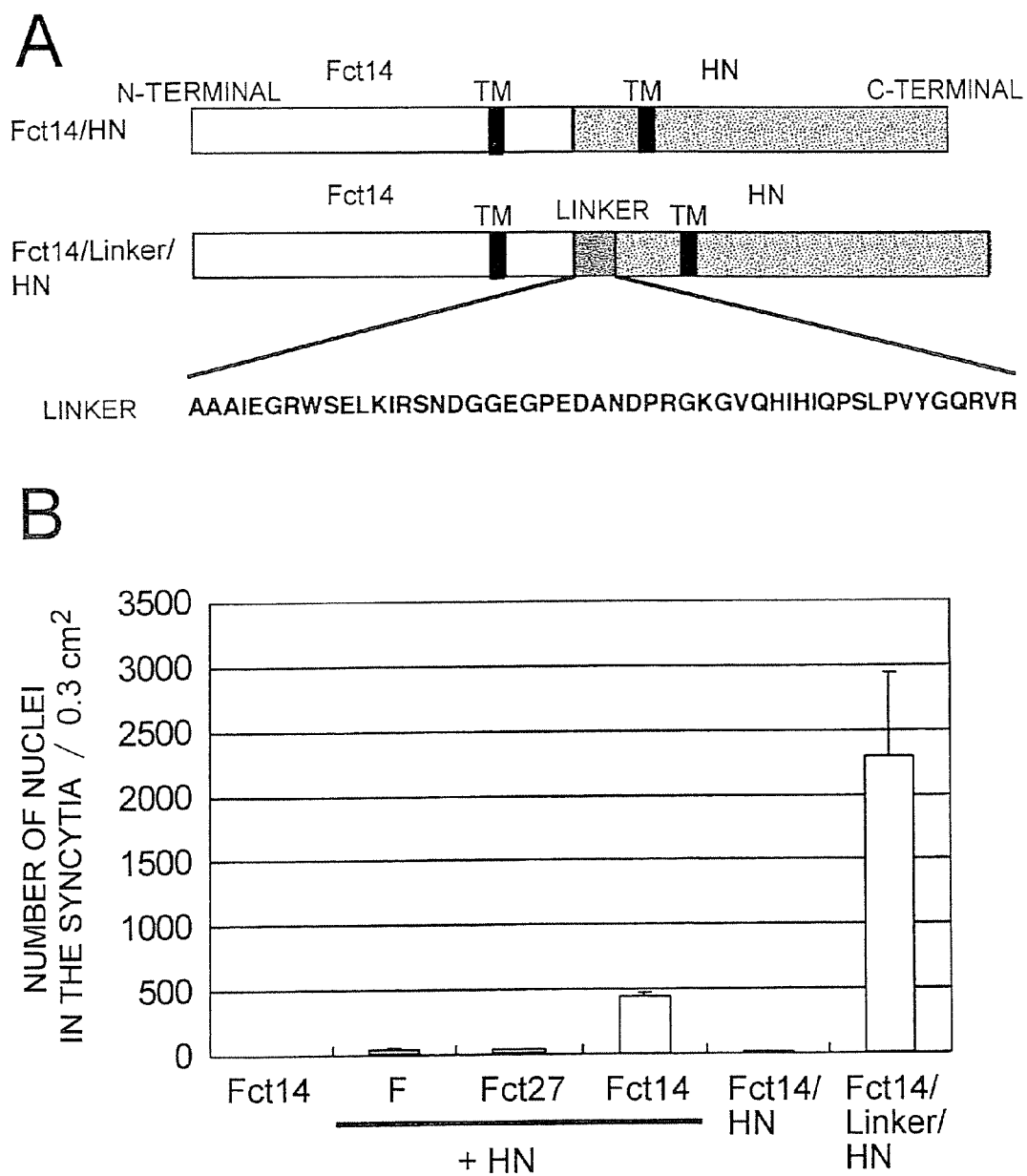

FIG. 43 depicts the drastic increase of fusogenicity resulting from the F/HN chimeric protein. FIG. 43A shows the structure of the F/HN chimeric protein. The linker sequence is described in SEQ ID NO: 80. FIG. 43B shows the increased fusogenicity of the F/HN chimeric protein by the insertion of a linker. Each of the Sendai viral F/HN chimeric proteins and HN were expressed simultaneously in LLC-MK2 cells added with 7.5 µg/mL trypsin.

Figure 44:
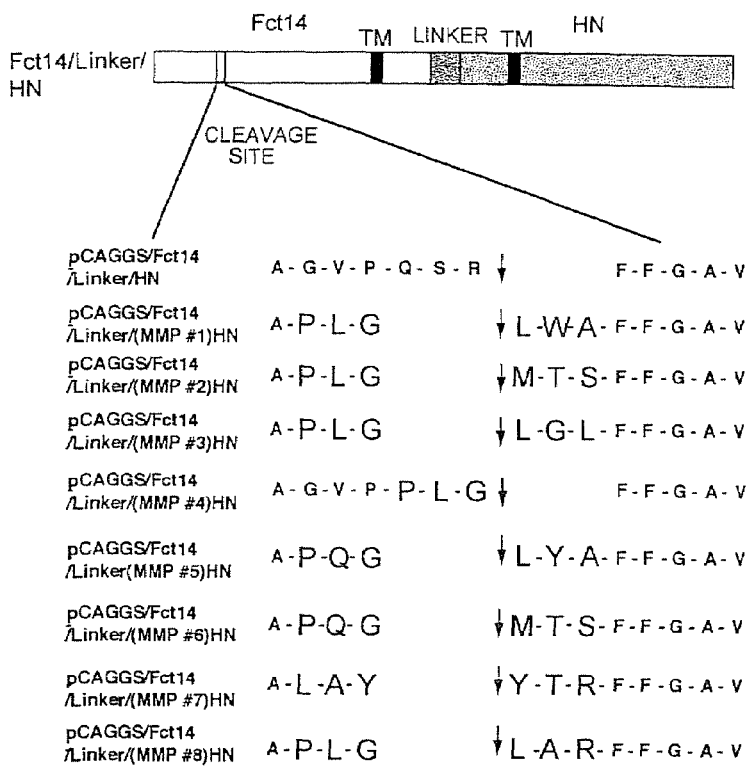
Figure 44:
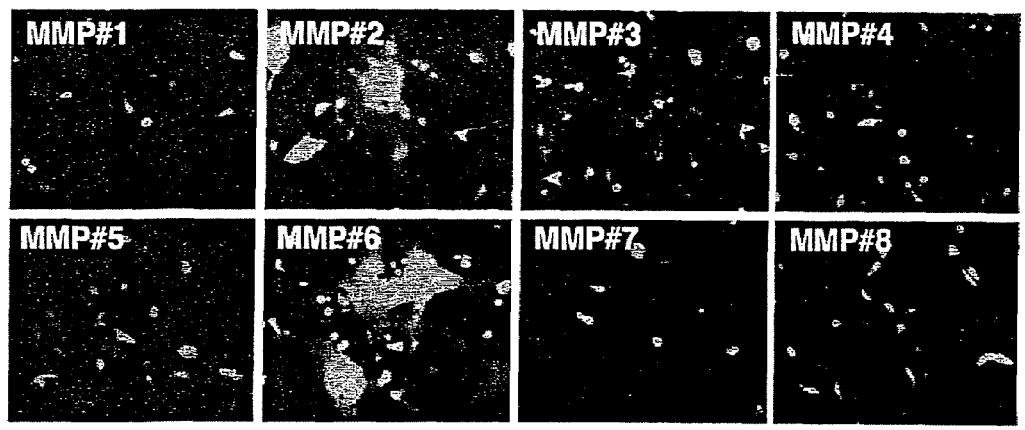

FIG. 44 provides a schematic representation and pictures depicting the outline of the MMP substrate sequence insertion into the F cleavage site of the F/HN chimeric proteins. FIG. 44A is a schematic representation of the construction of F-modified F/HN chimeric proteins inserted with MMP substrate sequences. From the top, SEQ ID NOs: 81 to 89. FIG. 44B depicts the syncytium formation due to the expression of F-modified F/HN in MMP-expressing HT1080 cells.

Figure 45:
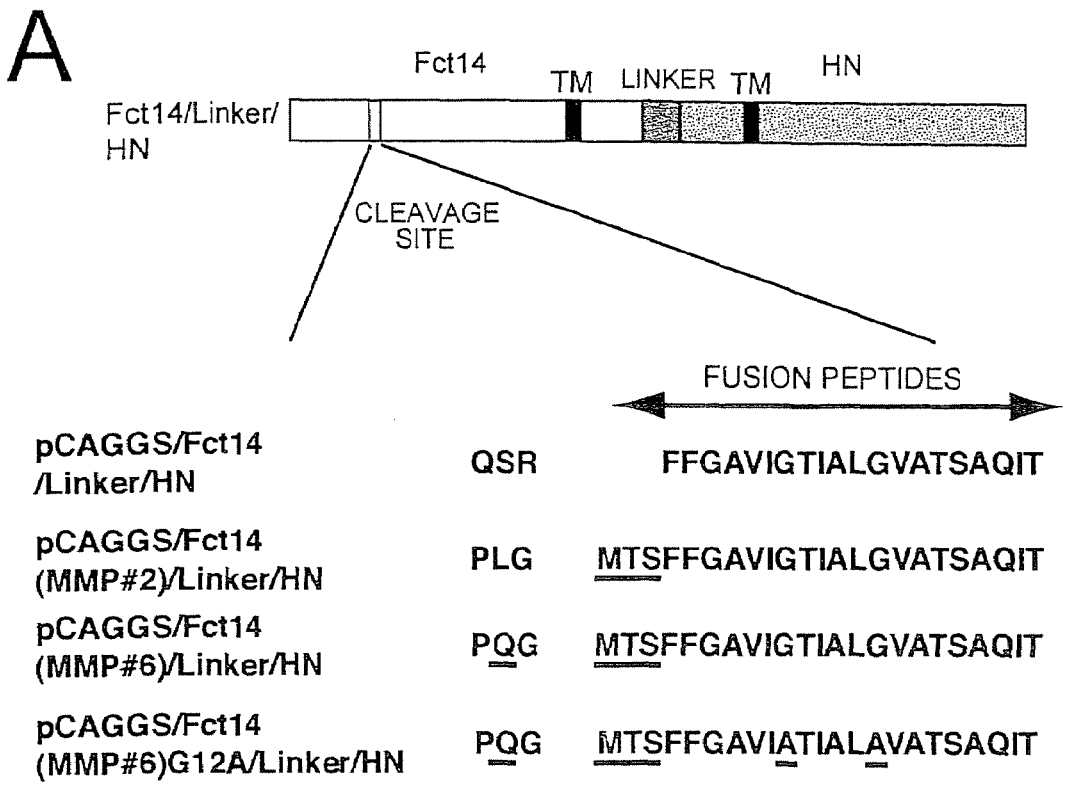
Figure 45:
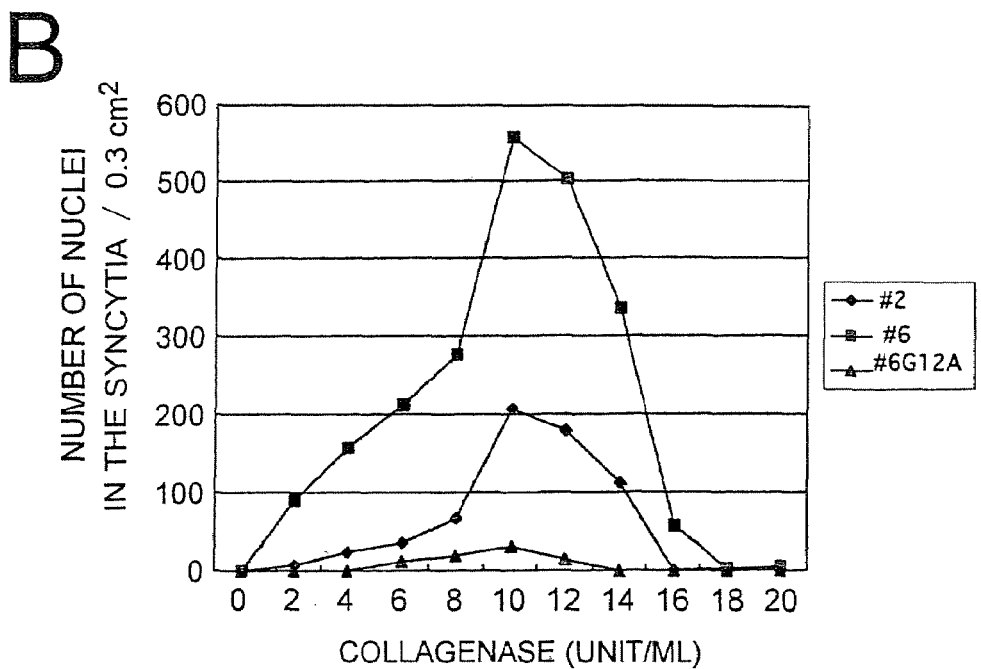

FIG. 45 depicts the modification of the F peptide (fusion peptide) and its concentration-dependent effect on syncytium formation. FIG. 45A is a schematic representation of the construction of modified fusion peptides. From the top, SEQ ID NOs: 90 to 93. FIG. 45B depicts the fusogenicity of MMP#2, MMP#6, and MMP#6G12A relative to the concentration of added collagenase (Clostridium).

FIG. 46 depicts the genomic structure of the improved F-modified M-deficient Sendai viruses.

Figure 47:
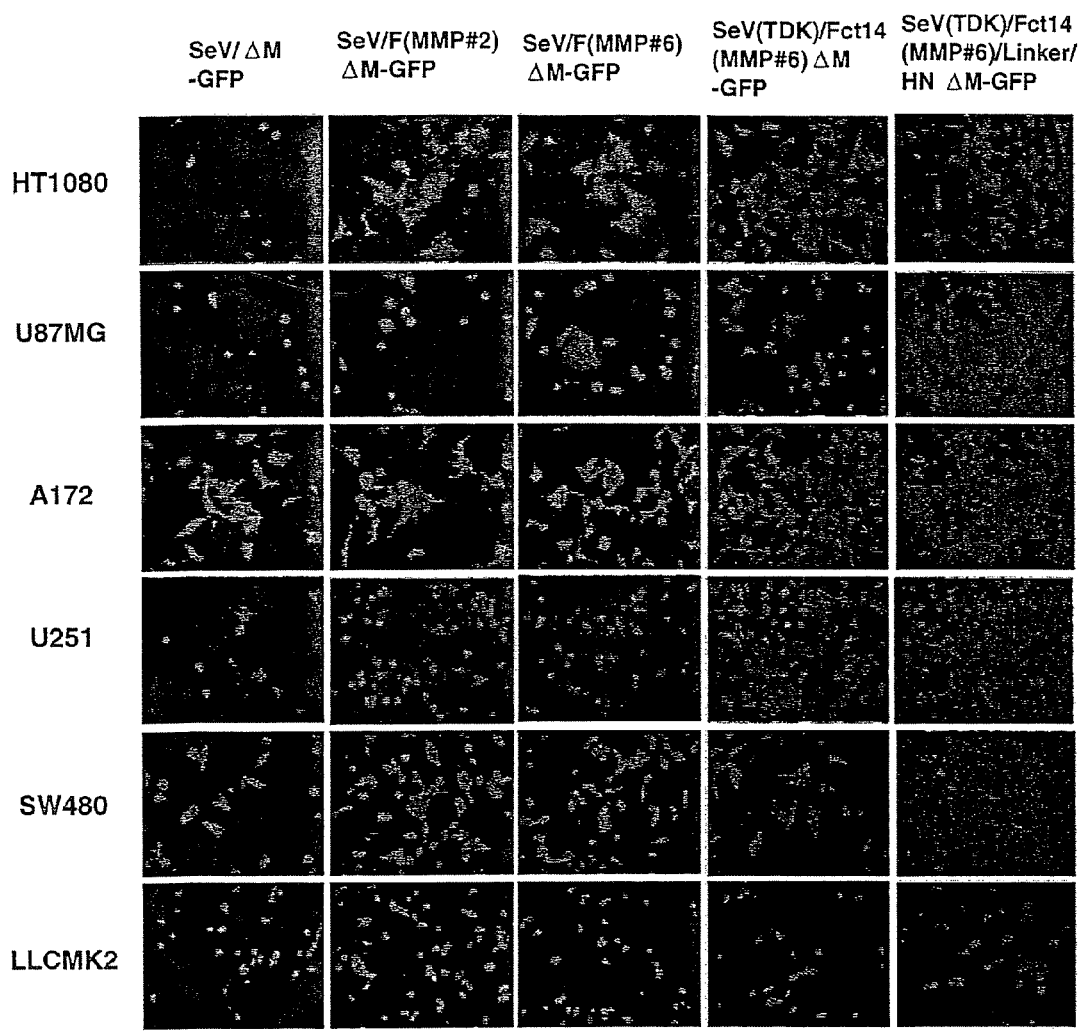

FIG. 47 provides pictures representing the spreading of the improved F-modified, M-deficient Sendai viruses in cancer with low expression levels of MMP. The spread of cell fusion 2 days after infection of the improved F-modified M-deficient Sendai viruses are shown.

Figure 48:
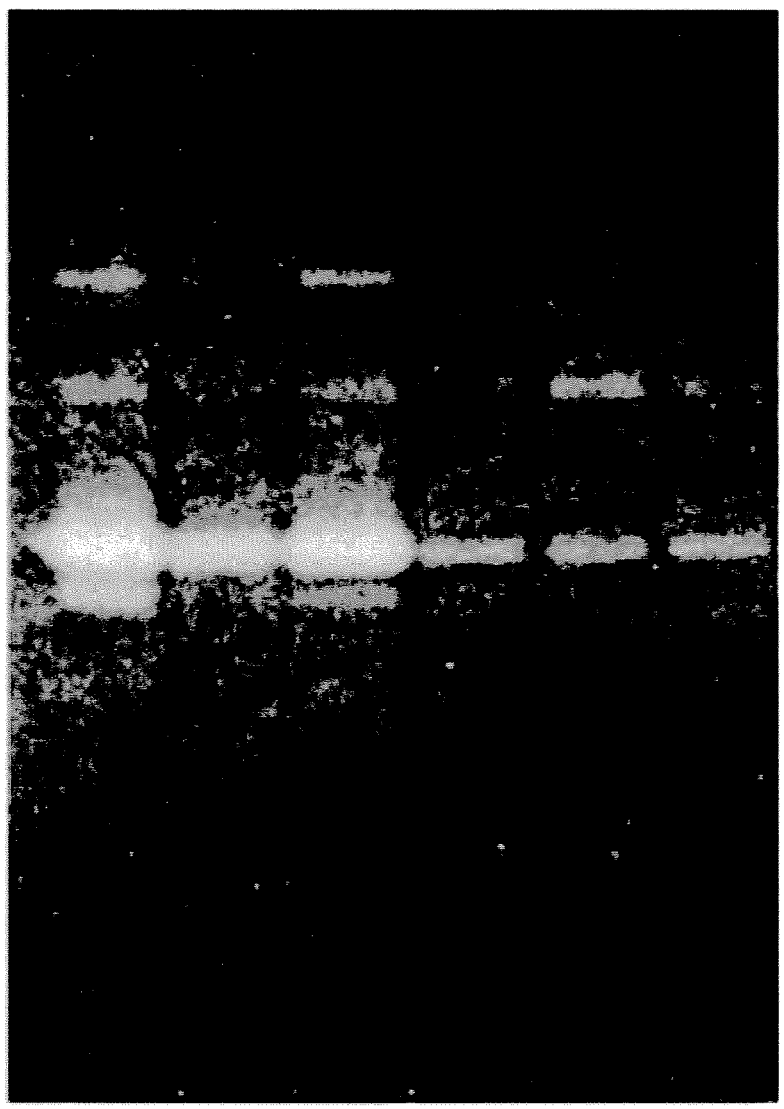

FIG. 48 is a picture representing MMP-2 and MMP-9 expression in cancer cell lines. Gelatin zymography of the supernatants of the cancer cell lines is shown.

Figure 49:
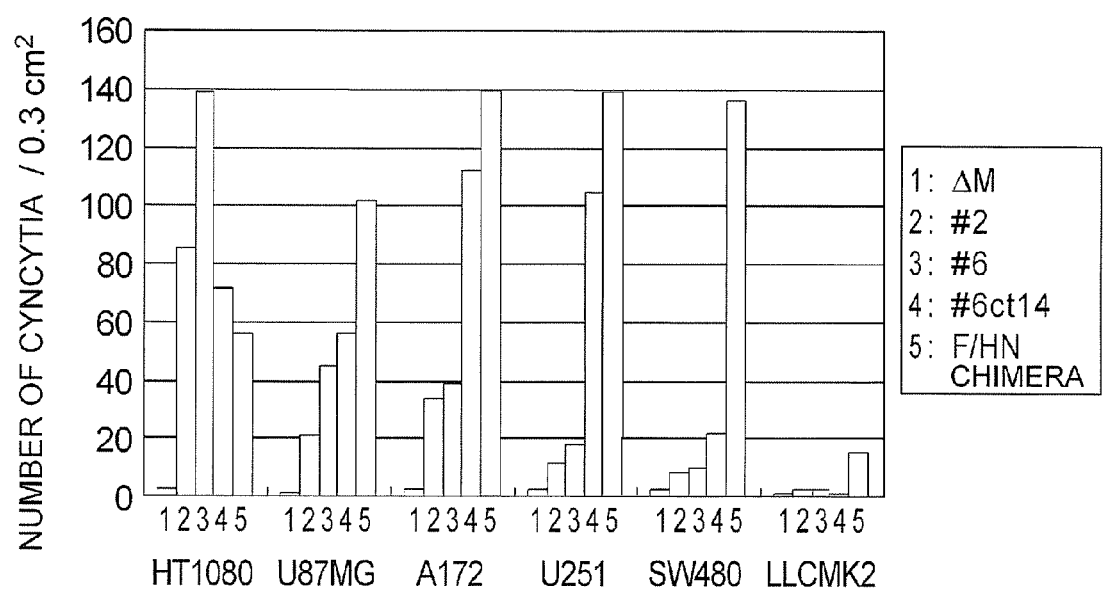

FIG. 49 depicts the spreading of the improved F-modified M-deficient Sendai viruses in tumors with low expression levels of MMP. Comparison of the number of syncytia per 0.3 $cm^2$ two days after infection is indicated. "ΔM" denotes SeV18+/ΔM-GFP, "#2" denotes SeV18+/F(MMP#2)ΔM-GFP, "#6" denotes SeV/F(MMP#6)ΔM-GFP, "#6ct14" denotes SeV(TDK)/Fct14(MMP#6)ΔM-GFP, and "F/HN chimera" denotes SeV(TDK)/Fct14(MMP#6)/Linker/HNΔM-GFP.

BEST MODE FOR CARRYING OUT THE INVENTION

Herein below, the present invention is specifically described using Examples; however, it is not to be construed as being limited thereto. All references cited herein are incorporated by reference herein as a part of this description.

1. Construction of SeV Vectors with Decreased or Defective Particle Forming Ability Example 1

Construction of a Temperature-Sensitive Mutant SeV Genome cDNA

Figure 1:
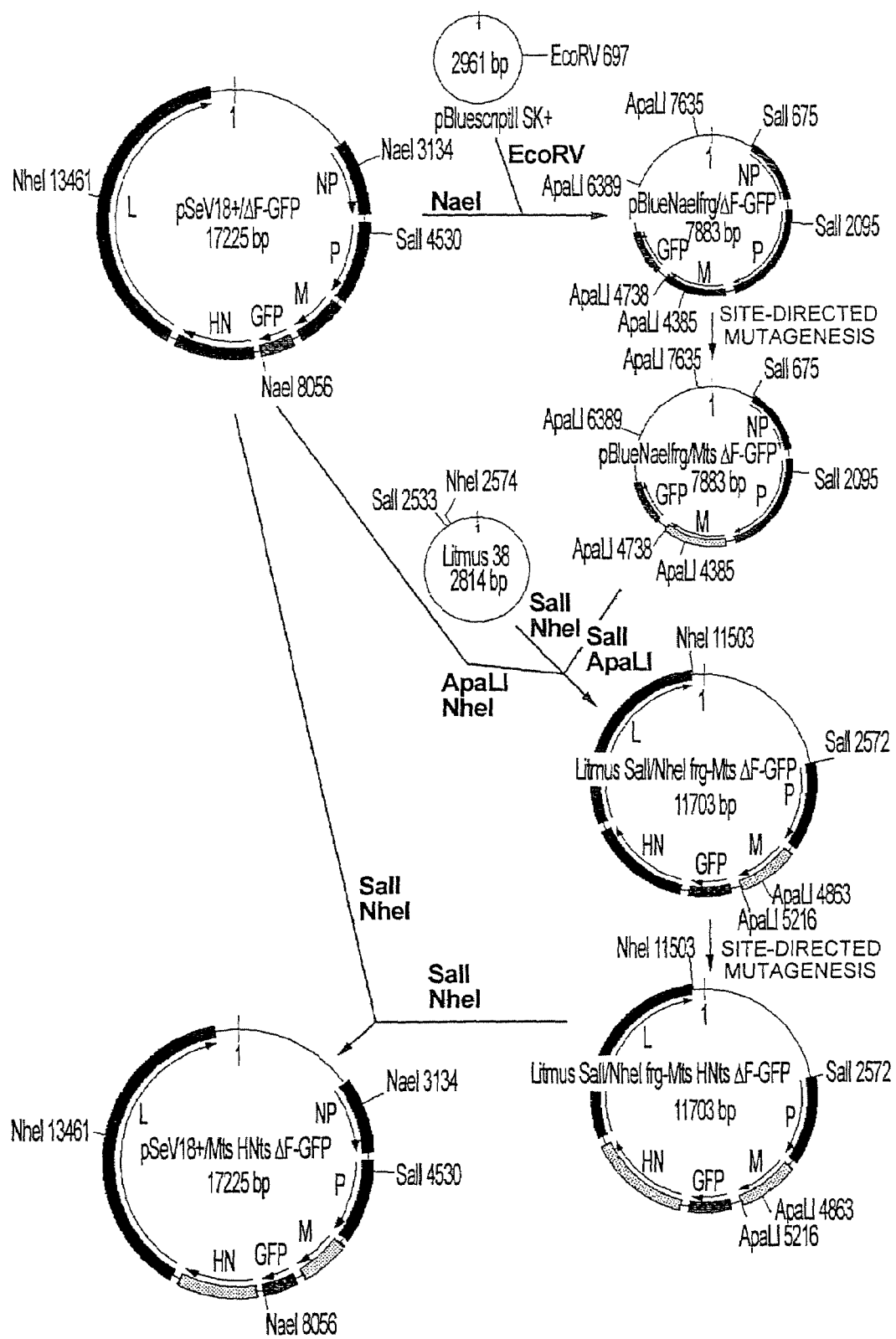
FIG. 1 is a schematic representation of the construction of an F-deficient SeV genome cDNA in which a temperature-sensitive mutation has been introduced into the M gene.

An SeV genome cDNA in which temperature-sensitive mutations were introduced in M gene was constructed. FIG. 1, which shows a scheme that represents the construction of the cDNA, is described as follows. An F-deficient full-length Sendai viral genome cDNA containing the EGFP gene at the F deletion site (pSeV18+/ΔF-GFP: Li, H.-O. et al., J. Virology 74, 6564-6569, 2000; WO 00/70070) was digested with NaeI. The M gene-containing fragment (4922 bp) was separated using agarose electrophoresis. After cutting the band of interest out, the DNA was recovered by QIAEXII Gel Extraction System (QIAGEN, Bothell, Wash.) and subcloned into pBluescript II (Stratagene, La Jolla, Calif.) at the EcoRV site (pBlueNaeIfrg-ΔFGFP construction). Introduction of temperature-sensitive mutations into the M gene of pBlueNaeIfrg-ΔFGFP was achieved using a QuikChange™ Site-Directed Mutagenesis Kit (Stratagene, La Jolla, Calif.), according to the kit method. The three types of mutation introduced into the M gene were G69E, T116A and A183S, based on the sequence of the Cl.151 strain reported by Kondo et al. (Kondo, T. et al., J. Biol. Chem. 268, 21924-21930, 1993). The sequences of the synthetic oligonucleotides used to introduce the mutations were as follows:

```
G69E
(5'-gaaacaaacaaccaatctagagagcgtatctgacttgac-3'/SEQ ID NO: 11,

5'-gtcaagtcagatacgctctctagattggttgtttgtttc-3'/SEQ ID NO: 12),

T116A
(5'-attacggtgaggagggctgttcgagcaggag-3'/SEQ ID NO: 13,

5'ctcctgctcgaacagccctcctcaccgtaat-3'/SEQ ID NO: 14)
and

A183S
(5'-ggggcaatcaccatatccaagatcccaaagacc-3'/SEQ ID NO: 15,

5'-ggtctttgggatcttggatatggtgattgcccc-3'/SEQ ID NO: 16).
```

The plasmid pBlueNaeIfrg-ΔFGFP, whose M gene contains the three mutations, was digested with SalI and then partially digested with ApaLI. The fragment containing the entire M gene was then recovered (2644 bp). pSeV18+/ΔF-GFP was digested with ApaLI/NheI, and the HN gene-containing fragment (6287 bp) was recovered. The two fragments were subcloned into Litmus38 (New England Biolabs, Beverly, Mass.) at the SalI/NheI site (LitmusSalI/NheIfrg-MtsΔ-FGFP construction). Temperature-sensitive mutations were introduced into the LitmusSalI/NheIfrg-MtsΔFGFP HN gene in the same way as for the introduction of mutations into the M gene, by using a QuikChange™ Site-Directed Mutagenesis Kit according to the kit method. The three mutations introduced into the HN gene were A262T, G264R and K461G, based on the sequence of ts271 strain reported by Thompson et al. (Thompson, S. D. et al., Virology 160, 1-8, 1987). The sequences of the synthetic oligonucleotides used to introduce the mutations were as follows:

```
A262T/G264R
(5'-catgctctgtggtgacaacccggactaggggttatca-3'/SEQ ID NO: 17,

5'-tgataacccctagtccgggttgtcaccacagagcatg-3'/SEQ ID NO: 18),
and

K461G
(5'-cttgtctagaccaggaaatgaagagtgcaattggtacaata-3'/SEQ ID NO: 19,

5'-tattgtaccaattgcactcttcatttcctggtctagacaag-3'/SEQ ID NO: 20).
```

While the mutations were introduced into the M and HN genes in separate vectors, it is also possible to introduce all of the mutations into both M and HN genes by using a plasmid (LitmusSalI/NheIfrg-ΔFGFP) obtained by subcloning, at the SalI/NheI site of Litmus38, a fragment containing the M and HN genes (8931 bp), provided by digesting pSeV18+/ΔF-GFP with SalI/NheI. Successive introduction of mutations resulted in the introduction of six temperature-sensitive mutations in total; three mutations in the M gene, and three mutations in the HN gene (LitmusSalI/NheIfrg-MtsHNtsΔFGFP construction).

Figure 2:
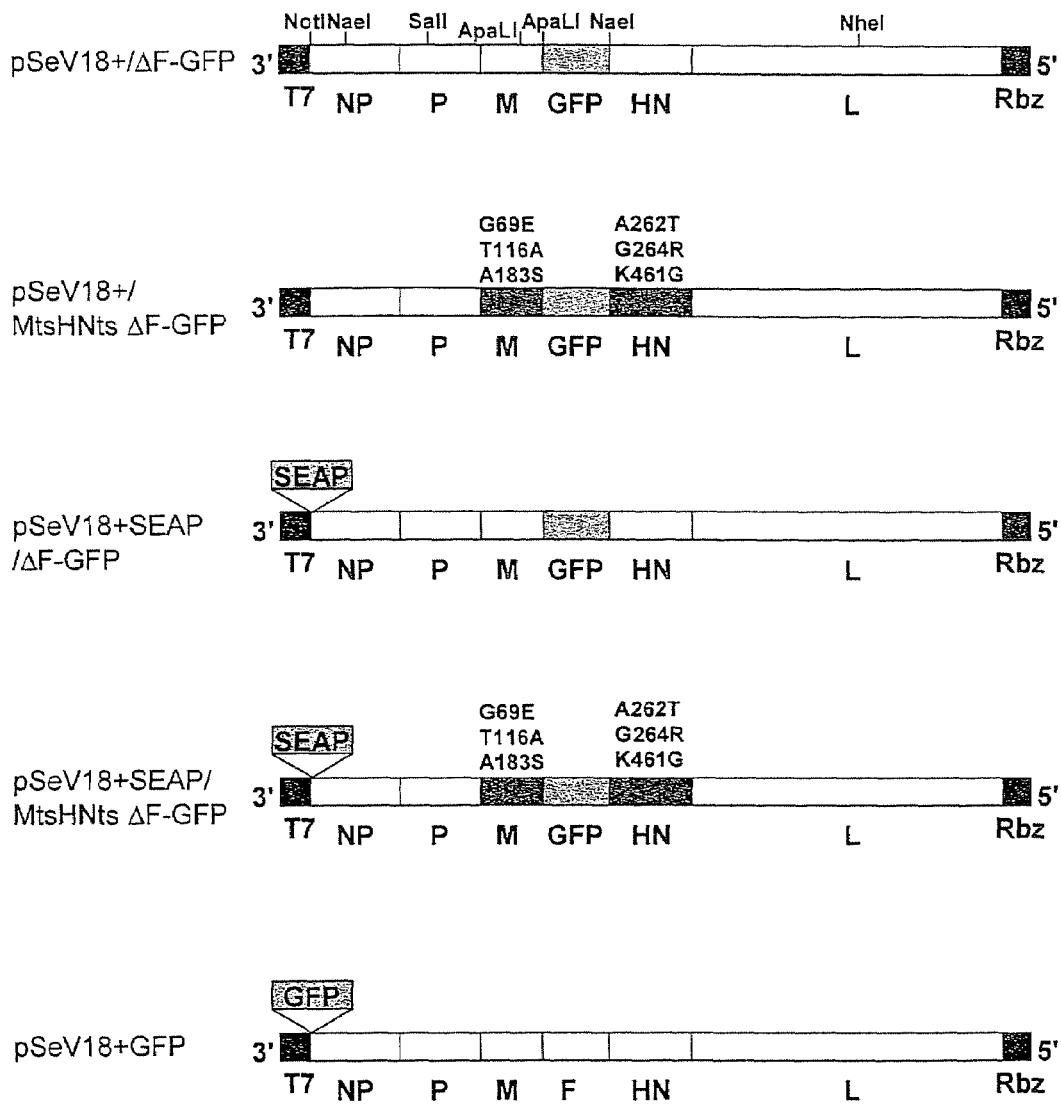
FIG. 2 depicts the structures of viral genes constructed to suppress secondary particle release based on temperature-sensitive mutations introduced into the M gene, and viral genes constructed or used to test and compare the effects of these introduced mutations.

LitmusSalI/NheIfrg-MtsHNtsΔFGFP was digested with SalI/NheI and an 8931 bp fragment was recovered. Another fragment (8294 bp), lacking the M and HN genes and such, was recovered on digestion of pSeV18+/ΔF-GFP with SalI/NheI. Both fragments were ligated together to construct the F-deficient full-length Sendai virus genome cDNA (pSeV18+/MtsHNtsΔF-GFP) comprising the six temperature-sensitive mutations in the M and HN genes, and the EGFP gene at the site of the F deletion (FIG. 2).

Further, to quantify the expression level of genes in the plasmid, a cDNA containing the secretory alkaline phosphatase (SEAP) gene was also constructed. Specifically, NotI was used to cut out an SEAP fragment (1638 bp) comprising the termination signal-intervening sequence-initiation signal downstream of the SEAP gene (WO 00/70070). This fragment was recovered and purified following electrophoresis. The fragment was then inserted into pSeV18+/ΔF-GFP and pSeV18+/MtsHNtsΔF-GFP at their respective NotI sites. The resulting plasmids were named pSeV18+SEAP/ΔF-GFP and pSeV18+SEAP/MtsHNtsΔF-GFP, respectively (FIG. 2).

Example 2

Reconstitution and Amplification of Virus Introduced with Temperature-Sensitive Mutations Viral reconstitution was performed according to the procedure reported by Li et al. (Li, H.-O. et al., J. Virology 74, 6564-6569, 2000; WO 00/70070). F protein helper cells, prepared using an inducible Cre/loxP expression system, were utilized to reconstitute F-deficient viruses. The system uses a pCALNdLw plasmid, designed for Cre DNA recombinase-mediated inducible gene product expression (Arai, T. et al., J. Virol. 72, 1115-1121, 1988). In this system, the inserted gene is expressed in a transformant carrying this plasmid using the method of Saito et al. to infect the transformant with a recombinant adenovirus (AxCANCre) expressing Cre DNA recombinase (Saito, I. et al., Nucleic Acids Res. 23, 3816-3821, 1995; Arai, T. et al., J. Virol. 72, 1115-1121, 1998). In the case of the SeV-F protein, the transformed cells comprising the F gene are herein referred to as LLC-MK2/F7, and cells persistently expressing the F protein after induction by AxCANCre are herein referred to as LLC-MK2/F7/A.

Reconstitution of the virus comprising the temperature-sensitive mutations was carried out as follows: LLC-MK2 cells were plated onto a 100-mm dish at $5 \times 10^6$ cells/dish, and then cultured for 24 hours. T7 polymerase-expressing recombinant vaccinia virus, which had been treated with psoralen and long-wavelength ultraviolet light (365 nm) for 20 minutes (PLWUV-VacT7: Fuerst, T. R. et al., Proc. Natl. Acad. Sci. USA 83, 8122-8126, 1986), was infected (MOI=2) to these cells at room temperature for one hour. The cells were washed with serum-free MEM. Plasmids, pSeV18+/MtsHNtsΔF-GFP, pGEM/NP, pGEM/P, pGEM/L and pGEM/F-HN (Kato, A. et al., Genes Cells 1, 569-579, 1996), were suspended in Opti-MEM (Gibco-BRL, Rockville, Md.) at amounts of 12 μg, 4 μg, 2 μg, 4 μg and 4 μg/dish, respectively. SuperFect transfection reagent (Qiagen, Bothell, Wash.) corresponding to 1 μg DNA/5 μl was added and mixed. The resulting mixture was allowed to stand at room temperature for 15 minutes, and then added to 3 ml of Opti-MEM containing 3% FBS. This mixture was added to the cells. After being cultured for five hours, the cells were washed twice with serum-free MEM, and cultured in MEM containing 40 μg/ml cytosine β-D-arabinofuranoside (AraC: Sigma, St. Louis, Mo.) and 7.5 μg/ml trypsin (Gibco-BRL, Rockville, Md.). After 24 hours of culture, cells persistently expressing the F protein (LLC-MK2/F7/A: Li, H.-O. et al., J. Virology 74, 6564-6569, 2000; WO 00/70070) were overlaid at $8.5 \times 10^6$ cells/dish. These cells were further cultured in MEM containing 40 μg/mL AraC and 7.5 μg/mL trypsin at 37° C. for two days (P0). The cells were harvested and the pellet was suspended in 2 ml Opti-MEM per dish. Freeze-and-thaw treatment was repeated three times, and the lysate was directly transfected into LLC-MK2/F7/A. The cells were cultured in serum-free MEM containing 40 μg/mL AraC and 7.5 μg/mL trypsin at 32° C. (P1). After five to seven days, part of the culture supernatant was infected into freshly prepared LLC-MK2/F7/A, and the cells were cultured in same serum-free MEM containing 40 μg/mL AraC and 7.5 μg/mL trypsin at 32° C. (P2). After three to five days, freshly prepared LLC-MK2/F7/A were infected again, and the cells were cultured in serum-free MEM containing only 7.5 μg/mL trypsin at 32° C. for three to five days (P3). BSA was added to the recovered culture supernatant at a final concentration of 1%, and the mixture was stored at −80° C. The viral solution stored was thawed and used in subsequent experiments.

The titers of viral solutions prepared by this method were as follows: SeV18+/ΔF-GFP, $3 \times 10^8$; SeV18+/MtsHNtsΔF-GFP, $7 \times 10^7$; SeV18+SEAP/ΔF-GFP, $1.8 \times 10^8$; SeV18+ SEAP/MtsHNtsΔF-GFP, $8.9 \times 10^7$ GFP-CIU/mL (GFP-CIU has been defined in WO 00/70070). On the other hand, for vectors comprising GFP, CIU determined by direct detection of GFP is defined as GFP-CIU. GFP-CIU values are confirmed to be substantially identical to corresponding CIU values (WO 00/70070). In determining SeV18+/ΔF-GFP and SeV18+/MtsHNtsΔF-GFP titers, the post-infection spread of plaques of cells persistently expressing F protein (LLC-MK2/F7/A) was observed at 32° C. and 37° C. FIG. 3 shows photographs of patterns observed six days after infection. SeV18+/MtsHNtsΔF-GFP plaques spread to some extent at 32° C., but were greatly reduced at 37° C. This suggests that virion formation is reduced at 37° C.

Example 3

Effect of Culture Temperature (32° C.) on Viral Reconstitution

In the experimental reconstitution of viruses in which temperature-sensitive mutations were introduced (Example 2), P1 and all subsequent cultures were carried out at 32° C. This temperature was used because the reference virus, used for assessing the introduction of temperature-sensitive mutations, grows well at 32° C. (Kondo, T. et al., J. Biol. Chem. 268, 21924-21930, 1993; Thompson, S. D. et al., Virology 160, 1-8, 1987). Close examination of the experimental conditions revealed that, for SeV reconstitution (and for other viruses in addition to those in which temperature-sensitive mutations had been introduced), reconstitution efficiency was improved by carrying out P1 and subsequent cultures at 32° C., giving a high possibility of recovering viruses that were previously difficult to obtain.

Figure 4:
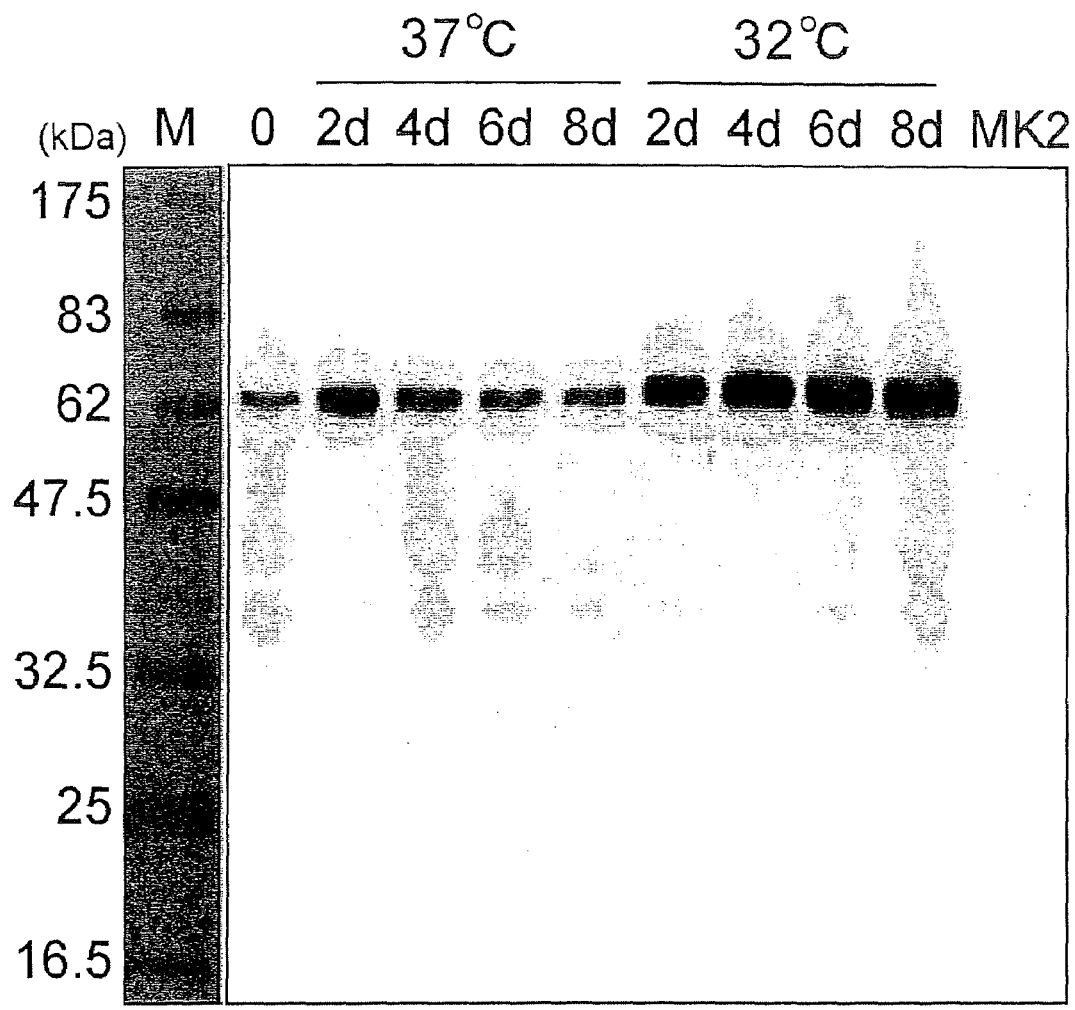
FIG. 4 is a picture representing the result of semi-quantitative determination, over time and using Western blotting, of F protein expression levels in cells (LLC-MK2/F7/A) persistently expressing SeV-F protein, which were cultured in trypsin-free, serum-free MEM at 32° C. or 37° C.

There are thought to be two reasons for enhanced reconstitution efficiency at 32° C. The first point is that, when cultured at 32° C. as opposed to 37° C., cytotoxicity due to AraC, which is supplemented to inhibit vaccinia virus amplification, is thought to be suppressed. Under conditions for viral reconstitution, culturing LLC-MK2/F7/A cells at 37° C., in serum-free MEM containing 40 μg/ml AraC and 7.5 μg/ml trypsin, caused cell damage after three to four days, including an increase in detached cells. However, cultures at 32° C. could be sufficiently continued for seven to ten days with cells still intact. When reconstituting SeV with inefficient transcription and/or replication, or with inefficient formation of infectious virions, success is thought to be a direct reflection of culture duration. The second point is that F protein expression is maintained in LLC-MK2/F7/A cells when the cells are cultured at 32° C. After culturing LLC-MK2/F7/A cells that continuously express F protein to confluency on 6-well culture plates in MEM containing 10% FBS and at 37° C., the medium was replaced with a serum-free MEM containing 7.5 μg/ml trypsin, and the cells were further cultured at 32° C. or 37° C. Cells were recovered over time using a cell scraper, and Western blotting using an anti-F protein antibody (mouse monoclonal) was used to semi-quantitatively analyze intra-cellular F protein. F protein expression was maintained for two days at 37° C., and then decreased. However, at 32° C. expression was maintained for at least eight days (FIG. 4). These results confirm the validity of viral reconstitution at 32° C. (after P1 stage).

The above-described Western blotting was carried out using the following method: Cells recovered from one well of a 6-well plate were stored at −80° C., then thawed in 100 μl of 1× diluted sample buffer for SDS-PAGE (Red Loading Buffer Pack; New England Biolabs, Beverly, Mass.). Samples were then heated at 98° C. for ten minutes, centrifuged, and a 10-μl aliquot of the supernatant was loaded on to SDS-PAGE gel (multigel 10/20; Daiichi Pure Chemicals Co., Ltd., Tokyo, Japan). After electrophoresis at 15 mA for 2.5 hours, proteins were transferred onto a PVDF membrane (Immobilon PVDF transfer membrane; Millipore, Bedford, Mass.) using semi-dry method at 100 mA for one hour. The transfer membrane was immersed in a blocking solution (Block Ace; Snow Brand Milk Products Co., Ltd., Sapporo, Japan) at 4° C. for one hour or more, soaked in a primary antibody solution containing 10% Block Ace supplemented with 1/1000 volume of the anti-F protein antibody, and then allowed to stand at 4° C. overnight. After washing three times with TBS containing 0.05% Tween 20 (TBST), and a further three times with TBS, the membrane was immersed in a secondary antibody solution containing 10% Block Ace supplemented with 1/5000 volume of the anti-mouse IgG+IgM antibody bound with HRP (Goat F(ab')2 Anti-Mouse IgG+IgM, HRP; BioSource Int., Camarillo, Calif.). Samples were then stirred at room temperature for one hour. The membrane was washed three times with TBST, and three times with TBS. The proteins on the membrane were then detected using the chemiluminescence method (ECL western blotting detection reagents; Amersham Pharmacia biotech, Uppsala, Sweden).

Example 4

Quantification of Secondarily Released Particles from Viruses Having Temperature Sensitive Mutations Introduced Therein HA Assay, Western Blotting Levels of secondarily released particles were compared, together with SeV18+/ΔF-GFP and SeV18+/MtsHNtsΔF-GFP, using the autonomously replicating type SeV that comprises all of the viral proteins and the GFP fragment (780 bp), which comprises the termination signal-intervening sequence-initiation signal downstream of the GFP gene at the NotI site (SeV18+GFP: FIG. 2).

Figure 5:
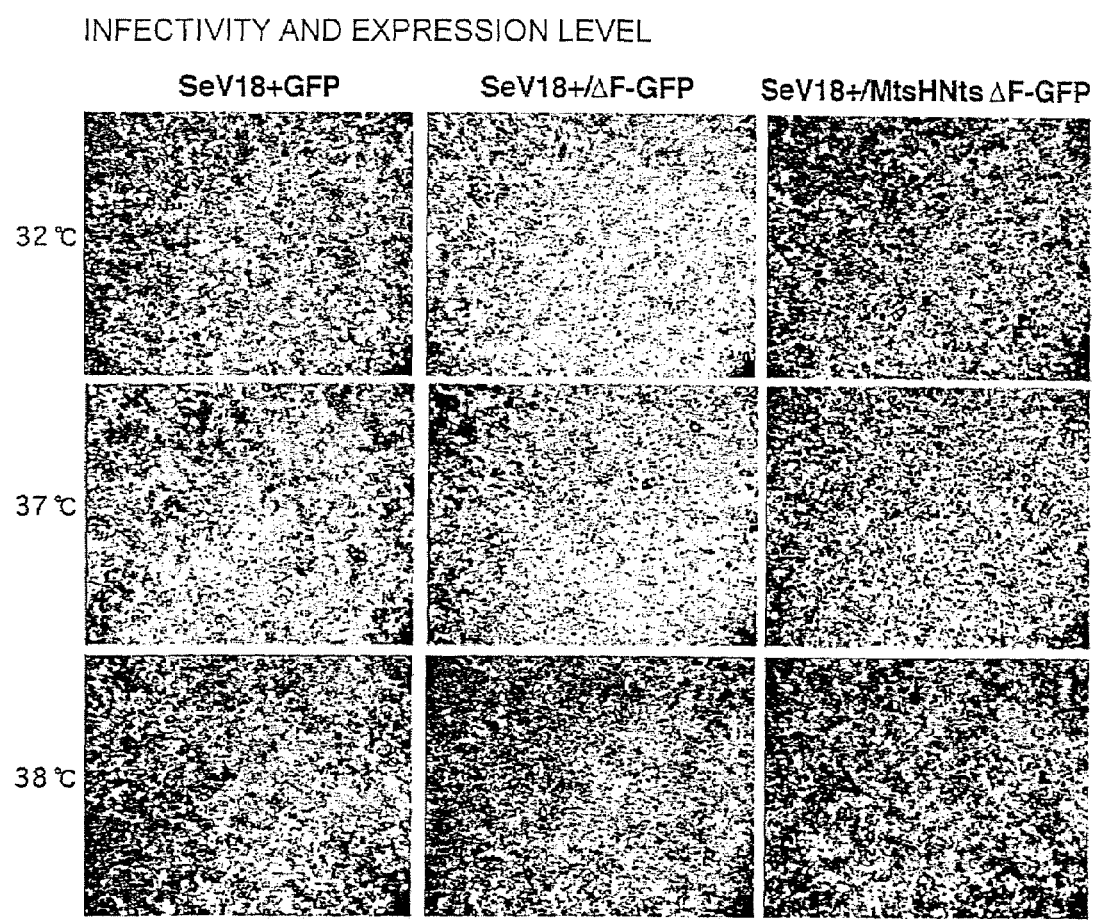
FIG. 5 provides microscopic images representing GFP expression in LLC-MK2 cells which were cultured at 32° C., 37° C. or 38° C. for three days after infection with SeV18+GFP, SeV18+/ΔF-GFP or SeV18+/MtsHNtsΔF-GFP at MOI=3.

LLC-MK2 cells were grown to confluency on 6-well plates. To these cells were added $3 \times 10^7$ CIU/ml of each virus solution at 100 μl per well (MOI=3), and the cells were infected for one hour. After washing the cells with MEM, serum-free MEM (1 ml) was added to each well, and the cells were cultured at 32° C., 37° C. and 38° C., respectively. Sampling was carried out every day, and immediately after sampling, 1 ml of fresh serum-free MEM was added to the remaining cells. Culturing and sampling were performed over time. Three days after infection, observation of GFP expression under a fluorescence microscope indicated that infection levels were almost equal for the three types of virus for all temperature conditions (32° C., 37° C. and 38° C.), and that GFP expression was similar (FIG. 5).

Secondarily released particles were quantified using an assay for hemagglutination activity (HA activity) according to the method of Kato et al. (Kato, A., et al., Genes Cell 1, 569-579, 1996). Specifically, round-bottomed 96 well-plates were used for serial dilution of the viral solution with PBS. Serial two-fold 50 μl dilutions were carried out in each well.

Figure 6:
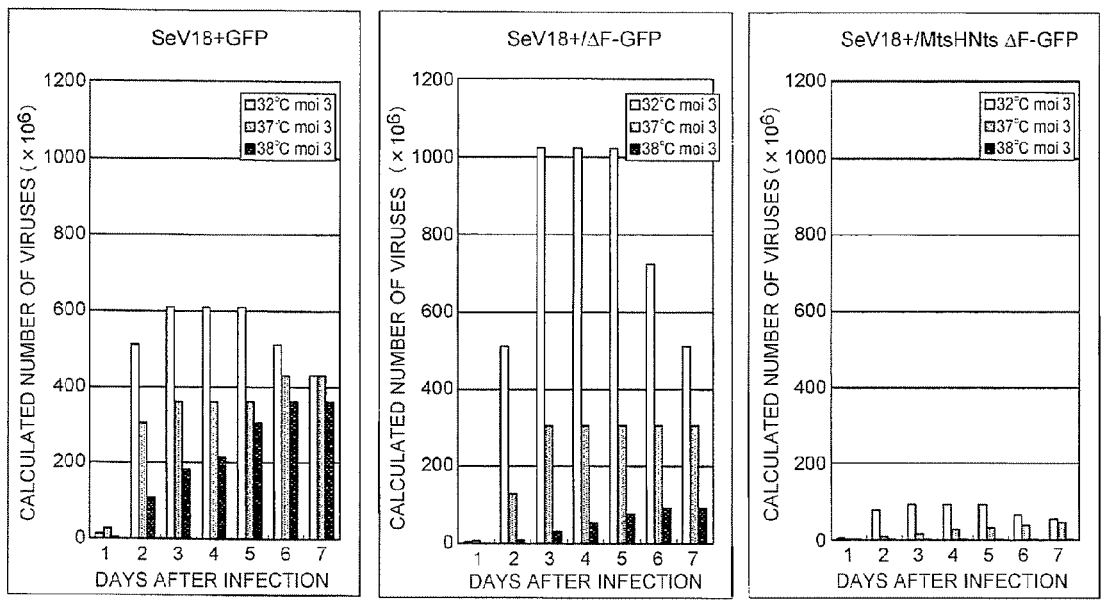
FIG. 6 depicts hemagglutination activity (HA activity) in the culture supernatant, which was sampled over time (supplemented with fresh medium at the same time), of LLC-MK2 cells cultured at 32° C., 37° C. or 38° C. after infection with SeV18+GFP, SeV18+/ΔF-GFP or SeV18+/MtsHNtsΔF-GFP at MOI=3.

50 μl of preserved chicken blood (Cosmo Bio, Tokyo, Japan), diluted to 1% with PBS, was added to 50 μl of the viral solution, and the mixture was allowed to stand at 4° C. for one hour. Erythrocyte agglutination was then examined. The highest virus dilution rate among the agglutinated samples was judged to be the HA activity. In addition, one hemagglutination unit (HAU) was calculated to be $1 \times 10^6$ viruses, and expressed as a number of viruses (FIG. 6). The secondarily released particles of SeV18+/MtsHNtsΔF-GFP remarkably decreased, and at 37° C., was judged to be about 1/10 of the level of SeV18+/ΔF-GFP. SeV18+/MtsHNtsΔF-GFP viral particle formation was also reduced at 32° C., and although only a few particles were produced, a certain degree of production was still thought possible.

Figure 7:
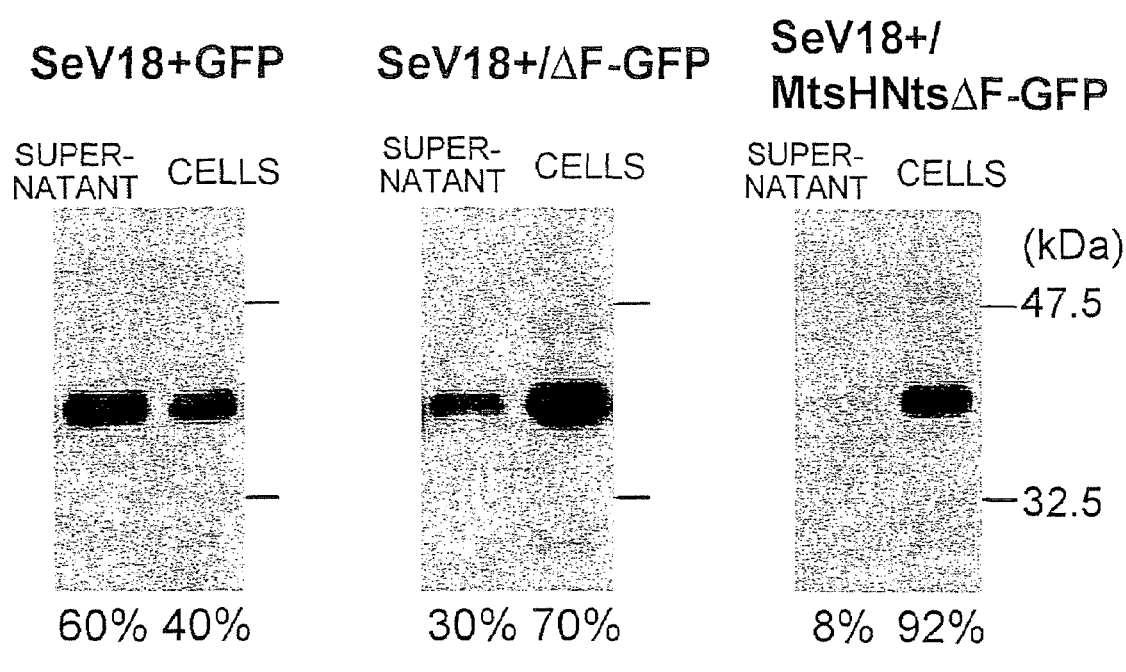
FIG. 7 provides pictures representing the ratio of M protein level in cells to that in virus-like particles (VLPs). This ratio was determined by Western blotting using an anti-M antibody. The culture supernatant and cells were recovered from a LLC-MK2 cell culture incubated at 37° C. for two days after infection with SeV18+GFP, SeV18+/ΔF-GFP or SeV18+/

Western blotting was used to quantify the secondarily released particles. In a manner similar to that described above, LLC-MK2 cells were infected at MOI=3 with the virus, and the culture supernatant and cells were recovered two days after infection. The culture supernatant was centrifuged at 48,000×g for 45 minutes to recover the viral proteins. After SDS-PAGE, Western blotting was performed to detect these proteins using an anti-M protein antibody. This anti-M protein antibody is a newly prepared polyclonal antibody, prepared from the serum of rabbits immunized with a mixture of three synthetic peptides: corresponding to amino acids 1-13 (MADIYRFPKFSYE+Cys/SEQ ID NO: 21), 23-35 (LRTGPDKKAIPH+Cys/SEQ ID NO: 22), and 336-348-(Cys+NVVAKNIGRIRKL/SEQ ID NO: 23) of the SeV M protein. Western blotting was performed according to the method described in Example 3, in which the primary antibody, anti-M protein antibody, was used at a 1/4000 dilution, and the secondary antibody, anti-rabbit IgG antibody bound with HRP (Anti-rabbit IgG (Goat) H+L conj.; ICN P., Aurola, Ohio), was used at a 1/5000 dilution. In the case of SeV18+/MtsHNtsΔF-GFP infected cells, M proteins were widely expressed to a similar degree, but expression of viral proteins was reduced (FIG. 7). Western blotting also confirmed a decrease in secondarily released viral particles.

Example 5

The Expression Level of Genes Comprised by the Virus Induced by Temperature-sensitive Mutations SEAP Assay SeV18+/MtsHNtsΔF-GFP secondary particle release was reduced. However, such a modification would be meaningless in a gene expression vector if accompanied with a simultaneous decrease in comprised gene expression. Thus, the gene expression level was evaluated. LLC-MK2 cells were infected with SeV18+SEAP/ΔF-GFP or SeV18+SEAP/MtsHNtsΔF-GFP at MOI=3, and culture supernatant was collected over time (12, 18, 24, 50 and 120 hours after infection). SEAP activity in the supernatant was assayed using a Reporter Assay Kit-SEAP (TOYOBO, Osaka, Japan) according to the kit method. SEAP activity was comparable for both types (FIG. 8). The same samples were also assayed for hemagglutination activity (HA activity). The HA activity of SeV18+SEAP/MtsHNtsΔF-GFP was reduced to about one tenth (FIG. 9). Viral proteins were harvested from viruses in the samples by centrifugation at 48,000×g for 45 minutes, and then semi-quantitatively analyzed by Western blotting using an anti-M antibody. The level of viral protein in the supernatant was also reduced (FIG. 10). These findings indicate that the introduction of temperature-sensitive mutations reduces the level of secondary particle release to about 1/10, with virtually no reduction in the expression of comprised genes.

Example 6

Cytotoxicity of Viruses Having Temperature-sensitive Mutations Introduced Therein LDH Assay SeV infection is often cytotoxic. The influence of introduced mutations was thus examined from this respect. LLC-MK2, BEAS-2B and CV-1 cells were each plated on a 96-well plate at $2.5 \times 10^4$ cells/well (100 μL/well), and then cultured. LLC-MK2 and CV-1 were cultured in MEM containing 10% FBS, and BEAS-2B was cultured in a 1:1 mixed medium of D-MEM and RPMI (Gibco-BRL, Rockville, Md.) containing 10% FBS. After 24 hours of culture, virus infection was carried out by adding 5 μL/well of a solution of SeV18+/ΔF-GFP or SeV18+/MtsHNtsΔF-GFP diluted with MEM containing 1% BSA. After six hours, the medium containing the viral solution was removed, and replaced with the corresponding fresh medium, with or without 10% FBS. The culture supernatant was sampled three days after infection when FBS-free medium was used, or six days after infection when medium containing FBS was used. Cytotoxicity was analyzed using a Cytotoxicity Detection Kit (Roche, Basel, Switzerland) according to the kit instructions. Neither of the viral vectors was cytotoxic in LLC-MK2. Further, SeV18+/MtsHNtsΔF-GFP cytotoxicity was assessed as being comparable to or lower than that of SeV18+/ΔF-GFP in CV-1 and BEAS-2B (FIG. 11). Thus, it was concluded that cytotoxicity was not induced by suppressing secondary particle release through the introduction of temperature-sensitive mutations.

Example 7

Study of the Mechanism of Secondary Particle Release Suppression

In order to elucidate the part of the mechanism underlying the suppression of secondary particle release associated with the introduction of temperature-sensitive mutations, subcellular localization of the M protein was examined. LLC-MK2 cells were infected with each type of SeV (SeV18+GFP, SeV18+/ΔF-GFP, SeV18+/MtsHNtsΔF-GFP), and cultured at 32° C., 37° C. or 38° C. for two days. The cells were immunostained by using an anti-M antibody. Immunostaining was performed as follows: The cultured cells were washed once with PBS, methanol cooled to −20° C. was added, and the cells were fixed at 4° C. for 15 minutes. After washing the cells three times with PBS, blocking was carried out at room temperature for one hour using PBS solution containing 2% goat serum and 0.1% Triton. After washing with PBS a further three times, the cells were reacted with a primary antibody solution (10 μg/mL anti-M antibody) containing 2% goat serum at 37° C. for 30 minutes. After washing three times with PBS, the cells were reacted with a secondary antibody solution (10 μg/mL Alexa Fluor 488 goat anti-rabbit IgG(H+L) conjugate: Molecular Probes, Eugene, Oreg.) containing 2% goat serum at 37° C. for 15 minutes. Finally, after a further three washes with PBS, the cells were observed under a fluorescence microscope. In the case of the self-replicating SeV18+GFP comprising both F and HN proteins, condensed M protein was detectable on cell surfaces at all of the temperatures tested (FIG. 12). Such M protein condensation has been previously reported (Yoshida, T. et al., Virology 71, 143-161, 1976), and is presumed to reflect the site of virion formation. Specifically, in the case of SeV18+GFP, cell-surface M protein localization appeared to be normal at all temperatures, suggesting that a sufficient amount of virions were formed. On the other hand, in the case of SeV18+/ΔF-GFP, M protein condensation was drastically reduced at 38° C. M protein is believed to localize on cell surfaces, binding to both F and HN protein cytoplasmic tails (Sanderson, C. M. et al., J. Virology 68, 69-76, 1994; Ali, A. et al., Virology 276, 289-303, 2000). Since one of these two proteins, namely the F protein, is deleted in SeV18+/ΔF-GFP, F protein deficiency is presumed to have an impact on M protein localization. This impact was expected to be stronger for SeV18+/MtsHNtsΔF-GFP, and it was also expected that, even at 37° C., M protein localization would be disturbed and the number of particles in the secondary release would be reduced.

Example 8

Study of the Suppression Mechanism of Secondary Particle Release (2)

In order to study the SeV protein's subcellular localization in more detail, analyses were carried out using a confocal laser microscope (MRC1024; Bio-Rad Laboratories Inc., Hercules, Calif.). A-10 cells (rat myoblasts) were infected with each of SeV18+SEAP/ΔF-GFP and SeV18+SEAP/MtsHNtsΔF-GFP (MOI=1), and then cultured in MEM containing 10% serum at 32° C. or 37° C. One or two days later, the cells were immunostained using anti-M antibody and anti-HN antibody. Immunostaining was performed as follows: The infected culture cells were washed once with PBS. Methanol cooled to −20° C. was added to the cells, and the cells were fixed at 4° C. for 15 minutes. The cells were washed three times with PBS, and blocking was then carried out for one hour at room temperature, using a PBS solution containing 2% goat serum, 1% BSA and 0.1% Triton. The cells were reacted with an M primary antibody solution (10 μg/mL anti-M antibody) containing 2% goat serum at 37° C. for 30 minutes. The cells were then reacted with an HN primary antibody solution (1 μg/mL anti-HN antibody (IL4-1)) at 37° C. for 30 minutes. After washing three times with PBS, the cells were reacted with a secondary antibody solution (10 μg/mL Alexa Fluor 568 goat anti-rabbit IgG(H+L) conjugate and 10 μg/mL Alexa Fluor 488 goat anti-mouse IgG(H+L) conjugate: Molecular Probes, Eugene, Oreg.) containing 2% goat serum at 37° C. for 15 minutes. The cells were washed three times with PBS and the nuclei were stained with TO_PRO3 (Molecular Probes, Eugene, Oreg.) diluted 4000 times. The cells were allowed to stand at room temperature for 15 minutes. Finally, to prevent quenching, a Slow Fade Antifade Kit solution (Molecular Probes, Eugene, Oreg.) was substituted for the liquid, and the cells were observed under a confocal laser microscope. FIG. 13 shows the results one day after infection. Red represents M protein localization; green, HN protein localization; and yellow, co-localization of the two. Far red has been subjected to color conversion, and thus blue represents the nucleus. In the case of SeV18+SEAP/ΔF-GFP, each protein's localization pattern did not differ largely between 32° C. and 37° C., and cell-surface localization of the M and HN proteins was observed. On the other hand, localization of each protein for SeV18+SEAP/MtsHNtsΔF-GFP was different at both temperatures from that for SeV18+SEAP/ΔF-GFP. Specifically, hardly any M protein was localized on the cell surface. In particular, at 37° C., the M and HN proteins were almost completely separated, such that the M protein was localized at sites presumed to be close to the centrosome of microtubules (i.e., near the Golgi body). A similar result was obtained for cells cultured two days after infection. Particularly in SeV18+SEAP/MtsHNtsΔF-GFP-infected cells, subcellular M protein localization did not change between one day and two days after infection (FIG. 14), and protein transport appeared to have stopped. This result also showed that the reduced secondary particle release by viruses having temperature-sensitive mutations introduced therein was caused by a deficiency in localization of the M protein, which is expected to play a central role in particle formation.

When the cells were cultured at 32° C. after infection with SeV18+SEAP/MtsHNtsΔF-GFP, the M protein stained in a morphology similar to that of a microtubule (FIG. 13). To show the involvement of microtubules, a reagent that enhances microtubule depolymerization was added, and changes in M protein (and the HN protein) localization were then studied. A-10 cells were infected with SeV18+SEAP/MtsHNtsΔF-GFP at MOI=1, and a depolymerization reagent, colchicine (Nakarai Tesque, Kyoto, Japan) or colcemid (Nakarai Tesque, Kyoto, Japan), was immediately added at a final concentration of 1 mM. The cells were then cultured at 32° C. Two days after infection, the subcellular localizations of the M and HN proteins were observed by the same method as described above. In the absence of the depolymerization reagent, M protein distribution was similar in morphology to a microtubule (FIG. 13). However, addition of the depolymerization reagent resulted in disruption of this structure, and the M protein was detected as a large fibrous structure (FIG. 15). This structure may be an aggregate of the M protein by itself, or M protein bound to the residues of depolymerized microtubules. In either case, as seen in FIG. 13, it was plausibly judged that the M protein was localized on microtubules in cells cultured at 32° C. after infection with SeV18+SEAP/MtsHNtsΔF-GFP.

In order to clarify whether or not the above-mentioned localization of the M protein in microtubules was characteristic of temperature-sensitive viruses, the post-infection influence of the microtubule depolymerization reagent (colchicine) on changes to M protein (and HN protein) localization was evaluated for both viruses SeV18+/ΔF-GFP and SeV18+/MtsHNtsΔF-GFP. A-10 cells were infected with SeV18+/ΔF-GFP or SeV18+/MtsHNtsΔF-GFP at MOI=1, and the depolymerization reagent colchicine was immediately added at a final concentration of 1 μM. The cells were cultured at 32° C. or 37° C. Two days after infection, the subcellular localization of the M protein (and the HN protein) was observed using the same method as described above. The results are shown in FIG. 16. Infected cells exhibited similar features for both viruses. Specifically, when the cells were cultured at 32° C. after infection, the M protein was observed as a large fibrous structure, similar to that in FIG. 15. The M protein's coexistence with microtubules was also suggested for SeV18+/ΔF-GFP. In particular, in cells infected with SeV18+/MtsHNtsΔF-GFP and cultured at 37° C., the M protein was observed to be localized in areas supposed to be near the Golgi body.

Based on the above results, the following can be inferred: the M protein is synthesized near the Golgi body; it is transported around the cell along microtubules (for example, bound to a motor protein such as kinesin), mainly bound to the cytoplasmic tails of the F and HN proteins (Sanderson, C. M. et al., J. Virology 68, 69-76, 1994; Ali, A. et al., Virology 276, 289-303, 2000); and the M protein is localized on the cell surface, followed by particle formation. In viruses comprising a temperature-sensitive mutation, everything up to the point of intracellular transport along microtubules may be normal at 32° C. However, translocation from microtubules to the cell surface may be hindered, resulting in localization along microtubules. At 37° C., it can be presumed that even intracellular transport along microtubules may be hindered, and thus, localization in the vicinity of the Golgi body is observed. M protein synthesis is supposed to take place near the Golgi body. However, it is possible that M protein aggregation is observed at these sites, and that the area of synthesis itself is elsewhere. However, it has been reported that tubulin, a microtubule component, activates and is involved in SeV transcription and replication (Moyer, S. A. et al., Proc. Natl. Acad. Sci. U.S.A. 83, 5405-5409, 1986; Ogino, T. et al., J. Biol. Chem. 274, 35999-36008, 1999). Moreover, as the Golgi body is located near the centrosome, where tubulin is predicted to exist in abundance, the Golgi body can be synthesized close to the microtubule central body (i.e., near the Golgi body). In addition, although the SeV mutant strain, F1-R, comprises a mutation in its M gene, it modifies microtubules after infecting cells, and this modification may enable particle formation independent of F1-R strain cell polarity (Tashiro, M. et al., J. Virol. 67, 5902-5910, 1993). In other words, the results obtained in the present Example may also be interpreted by assuming the intracellular transport of the M protein along tubulin. In this supposed mechanism, introduction of temperature-sensitive mutations to the M and HN genes may result in deficient subcellular M protein localization, resulting in a reduction in secondary particle release.

Example 9

Construction of the Genomic cDNA of an M Gene-deficient SeV Comprising the EGFP Gene Construction of cDNA used the full-length genomic cDNA of an M-deficient SeV, which is M gene-deficient (pSeV18+/ΔM: WO 00/09700). The construction scheme is shown in FIG. 17. The BstEII fragment (2098 bp) comprising the M-deficient site of pSeV18+/ΔM was subcloned to the BstEII site of pSE280 (pSE-BstEIIfrg construction). The EcoRV recognition site at this pSE280 site had been deleted by previous digestion with SalI/XhoI followed by ligation (Invitrogen, Groningen, Netherlands). pEGFP comprising the GFP gene (TOYOBO, Osaka, Japan) was digested using Acc65I and EcoRI, and the 5'-end of the digest was blunted by filling in using a DNA blunting Kit (Takara, Kyoto, Japan). The blunted fragment was then subcloned into the pSE-BstEIIfrg, which had been digested with EcoRV and treated with BAP (TOYOBO, Osaka, Japan). This BstEII fragment, comprising the EGFP gene, was returned to the original pSeV18+/ΔM to construct the M gene-deficient SeV genomic cDNA (pSeV18+/ΔM-GFP), comprising the EGFP gene at the M-deficient site.

Example 10

Construction of the Genomic cDNA of an M Gene- and Replication Ability-deficient SeV The genomic cDNA of an M- and F gene-deficient SeV was constructed. The construction scheme described below is shown in FIG. 18. The M gene was deleted using pBlueNaeIfrg-ΔFGFP, which was constructed by subcloning a NaeI fragment (4922 bp) of the F-deficient Sendai virus full-length genomic cDNA comprising the EGFP gene at the F gene-deficient site (pSeV18+/ΔF-GFP: Li, H.-O. et al., J. Virology 74, 6564-6569, 2000; WO 00/70070), to the EcoRV site of pBluescript II (Stratagene, La Jolla, Calif.). Deletion was designed so as to excise the M gene using the ApaLI site directly behind it. That is, the ApaLI recognition site was inserted right behind the P gene, so that the fragment to be excised became 6n. Mutagenesis was performed using the QuikChange™ Site-Directed Mutagenesis Kit (Stratagene, La Jolla, Calif.) according to the kit method. The synthetic oligonucleotide sequences used for the mutagenesis were as follows:

```
5'-agagtcactgaccaactagatcgtgcacgaggcatcctaccatcctca-3'/SEQ ID NO: 24
and

5'-tgaggatggtaggatgcctcgtgcacgatctagttggtcagtgactct-3'/SEQ ID NO: 25.
```

After mutagenesis, the resulting mutant cDNA was partially digested using ApaLI (at 37° C. for five minutes), recovered using a QIAquick PCR Purification Kit (QIAGEN, Bothell, Wash.), and then ligated as it was. The DNA was again recovered using the QIAquick PCR Purification Kit, digested with BsmI and StuI, and used to transform DH5α to prepare the M gene-deficient (and F gene-deficient) DNA (pBlueNaeIfrg-ΔMΔFGFP).

pBlueNaeIfrg-ΔMΔFGFP deficient in the M gene (and the F gene) was digested with SalI and ApaLI to recover the 1480 bp fragment comprising the M gene-deficient site. pSeV18+/ΔF-GFP was digested with ApaLI/NheI to recover the HN gene-comprising fragment (6287 bp), and these two fragments were subcloned into the SalI/NheI site of Litmus 38 (New England Biolabs, Beverly, Mass.) (LitmusSalI/NheIfrg-ΔMΔFGFP construction). The 7767 bp fragment recovered by digesting LitmusSalI/NheIfrg-ΔMΔFGFP with SalI/NheI was ligated to another fragment (8294 bp) obtained by digesting pSeV18+/ΔF-GFP with SalI/NheI, that did not comprise genes such as the M and HN genes. In this way an M- and F-deficient Sendai virus full-length genome cDNA comprising the EGFP gene at the deficient site (pSeV18+/ΔMΔF-GFP) was constructed. Structures of the M-deficient (and the M- and F-deficient) viruses thus constructed are shown in FIG. 19. This genomic cDNA is useful for constructing M- and F-deficient SeV comprising the desired, modified F protein.

Example 11

Preparation of Helper Cells Expressing SeV-M Proteins

To prepare helper cells expressing M proteins, the Cre/loxP expression induction system was used. For constructing this system, plasmid, pCALNdLw, which is designed to induce the expression of gene products using the Cre DNA recombinase, was used (Arai, T. et al., J. Virol. 72, 1115-1121, 1988). This system was also employed for the preparation of helper cells (LLC-MK2/F7 cells) for the F protein (Li, H.-O. et al., J. Virology 74, 6564-6569, 2000; WO 00/70070).

<1> Construction of M Gene-Expressing Plasmids:

To prepare helper cells which induce the expression of the F and M proteins, the above-described LLC-MK2/F7 cells were used to transfer the M gene to these cells using the above-mentioned system. Since the pCALNdLw/F used in the transfer of the F gene contained the neomycin resistance gene, it was essential to insert a different drug resistance gene to enable use of the same cells. Therefore, according to the scheme described in FIG. 20, the neomycin resistance gene of the M gene-comprising plasmid (pCALNdLw/M: the M gene was inserted at the SwaI site of pCALNdLw) was replaced with the hygromycin resistance gene. That is, after pCALNdLw/M was digested with HincII and EcoT22I, an M gene-comprising fragment (4737 bp) was isolated by electrophoresis on agarose and the corresponding band was excised and recovered using the QIAEXII Gel Extraction System. At the same time, pCALNdLw/M was digested with XhoI to recover a fragment that did not comprise the neomycin resistance gene (5941 bp) and then further digested with HincII to recover a 1779 bp fragment. The hygromycin resistance gene was prepared by performing PCR using pcDNA3.1hygro(+) (Invitrogen, Groningen, Netherlands) as the template and the following pair of primers:

```
hygro-5'
(5'-tctcgagtcgctcggtacgatgaaaaagcctgaactcaccgcgacgtctgtcgag-3'/SEQ ID NO: 26)
and hygro-3'
(5'-aatgcatgatcagtaaattacaatgaacatcgaacccagagtcccgcctattcctttgccctcggacgag tgctggggcgtc-3')/SEQ ID NO: 27).
```

The PCR product was recovered using the QIAquick PCR Purification Kit, and then digested using XhoI and EcoT22I. pCALNdLw-hygroM was constructed by ligating these three fragments.

<2> Cloning of Helper Cells which Induce the Expression of SeV-M and SeV-F Proteins:

Transfection was performed using the Superfect Transfection Reagent by the method described in the Reagent's protocol. Specifically, the following steps were performed: LLC-MK2/F7 cells were plated on 60 mm diameter Petri dishes at $5 \times 10^5$ cells/dish, and then cultured in D-MEM containing 10% FBS for 24 hours. pCALNdLw-hygroM (5 µg) was diluted in D-MEM containing neither FBS nor antibiotics (150 µl in total). This mixture was stirred, 30 µl of the Superfect Transfection Reagent was added, and the mixture was stirred again. After standing at room temperature for ten minutes, D-MEM containing 10% FBS (1 ml) was added. The transfection mixture thus prepared was stirred, and added to LLC-MK2/F7 cells which had been washed once with PBS. After three hours of culture in an incubator at 37° C. and in 5% $CO_2$ atmosphere, the transfection mixture was removed, and the cells were washed three times with PBS. D-MEM containing 10% FBS (5 ml) was added to the cells, which were then cultured for 24 hours. After culture, the cells were detached using trypsin, plated onto a 96-well plate at a dilution of about 5 cells/well, and cultured in D-MEM containing 10% FBS supplemented with 150 µg/ml hygromycin (Gibco-BRL, Rockville, Md.) for about two weeks. Clones propagated from a single cell were cultured to expand to a 6-well plate culture. A total of 130 clones were thus prepared, and were analyzed as detailed below.

<3> Analysis of Helper Cell Clones which Induce the Expression of SeV-M (and SeV-F) Protein(s):

Western blotting was used to semi-quantitatively analyze M protein expression in the 130 clones obtained as detailed above. Each clone was plated onto a 6-well plate, and, when in a state of near confluence, infected at MOI=5 with a recombinant adenovirus expressing Cre DNA recombinase (Ax-CANCre) diluted in MEM containing 5% FBS, according to the method of Saito et al. (Saito, I. et al., Nucleic Acids Res. 23, 3816-3821, 1995; Arai, T. et al., J. Virol. 72, 1115-1121, 1998). After culturing at 32° C. for two days, the culture supernatant was removed. The cells were washed once with PBS, and recovered by detachment using a cell scraper. SDS-PAGE was performed by applying 1/10 of the cells thus recovered per lane, and then Western blotting was carried out using anti-M protein antibody, according to the method described in Examples 3 and 4. Of the 130 clones, those showing relatively high M protein expression levels were also analyzed by Western blotting using the anti-F protein antibody (f236: Segawa, H. et al., J. Biochem. 123, 1064-1072, 1998). Both results are described in FIG. 21.

Example 12

Evaluation of Helper Cells Inducing the Expression of SeV-M Proteins

Using the helper cells inducing the expression of SeV-M proteins cloned in Example 11, virus reconstitution of M-deficient SeV (SeV18+/ΔM-GFP) was carried out to evaluate virus-producing ability of these cell clones. P0 lysate of SeV18+/ΔM-GFP was added to each clone, and whether or not GFP protein spread was observed (whether or not the trans-supply of M protein was achieved) was examined. P0 lysate was prepared as follows. LLC-MK2 cells were plated on 100-mm diameter Petri dishes at $5 \times 10^6$ cells/dish, cultured for 24 hours, and then infected at MOI=2 with PLWUV-VacT7 at room temperature for one hour. Plasmids pSeV18+/ΔM-GFP, pGEM/NP, pGEM/P, pGEM/L, pGEM/F-HN and pGEM/M were suspended in Opti-MEM at weight ratios of 12 µg, 4 µg, 2 µg, 4 µg, 4 µg and 4 µg/dish, respectively. To these suspensions, the equivalent of 1 g DNA/5 µl of Super-Fect transfection reagent was added and mixed. The mixture was allowed to stand at room temperature for 15 minutes, and finally added to 3 ml of Opti-MEM containing 3% FBS. This mixture was added to the cells, which were then cultured. After culturing for five hours, the cells were washed twice with serum-free MEM, and cultured in MEM containing 40 µg/ml AraC and 7.5 µg/ml trypsin. After 24 hours of culture, LLC-MK2/F7/A cells were layered at $8.5 \times 10^6$ cells/dish, and further cultured in MEM containing 40 µg/ml AraC and 7.5 µg/ml trypsin at 37° C. for two days (P0). These cells were recovered, the pellet was suspended in 2 ml/dish Opti-MEM, and P0 lysate was prepared by repeating three cycles of freezing and thawing. At the same time, ten different clones were plated on 24-well plates. When nearly confluent, they were infected with AxCANCre at MOI=5, and cultured at 32° C. for two days. These cells were transfected with P0 lysate of SeV18+/ΔM-GFP at 200 μl/well, and cultured using serum-free MEM containing 40 μg/ml AraC and 7.5 μg/ml trypsin at 32° C. GFP protein spread due to SeV18+/ΔM-GFP was observed in clones #18 and #62 (FIG. 36). This spread was especially rapid in clone #62, which was used in subsequent experiments. Hereafter, these cells prior to induction with AxCANCre are referred to as LLC-MK2/F7/M62. After induction, cells which continuously express F and M proteins are referred to as LLC-MK2/F7/M62/A. Preparation of SeV18+/ΔM-GFP cells was continued using LLC-MK2/F7/M62/A cells. Six days after P2 infection, $9.5 \times 10^7$ GFP-CIU viruses were prepared. Five days after P4 infection, $3.7 \times 10^7$ GFP-CIU viruses were prepared.

As indicated in Example 3, it was presumed that culturing at 32° C. or such after the P1 stage is significantly important for recovery of the SeV18+/ΔM-GFP virus. In SeV18+/ΔM-GFP, in trans supply of M protein from expression cells (LLC-MK2/F7/M62/A) is thought to be a cause; however, spread of infection was extremely slow and was finally observed seven days after P1 infection (FIG. 22). Thus, as in the viral reconstitution experiments, "culturing at 32° C. after the P1 stage" is supported as being very effective in reconstituting SeV having inefficient transcription-replication or poor ability to form infectious virions.

Example 13

Investigation of Virus Producing Conditions Using Helper Cells Inducing the Expression of SeV-M Proteins The productivity of the above-described virus was also investigated. LLC-MK2/F7/M62/A cells were plated on 6-well plates and cultured at 37° C. When the cells were nearly confluent, they were shifted to 32° C. One day later, these cells were infected at MOI=0.5 with SeV18+/ΔM-GFP. The culture supernatant was recovered over time, and replaced with fresh medium. Supernatants thus recovered were assayed for CIU and HAU. Most viruses were recovered four to six days after infection (FIG. 23). HAU was maintained for six or more days after infection, however cytotoxicity was strongly exhibited at this point, indicating the cause was not HA protein originating in viral particles, but rather the activity of HA protein free or bound to cell debris. Therefore for virus collection, the culture supernatant is preferably recovered by the fifth day after infection.

Example 14

Structural Confirmation of the M Gene-deficient SeV

SeV18+/ΔM-GFP's viral genes were confirmed by RT-PCR, and the viral proteins by Western blotting. In RT-PCR, the P2 stage virus six days after infection was used. QIAamp Viral RNA Mini Kit (QIAGEN, Bothell, Wash.) was used in the recovery of RNA from the viral solution. Thermoscript RT-PCR System (Gibco-BRL, Rockville, Md.) was used to prepare the cDNA. Both systems were performed using kit protocol methods. The random hexamer supplied with the kit was used as the primer for cDNA preparation. To confirm that the product was formed starting from RNA, RT-PCR was performed in the presence or absence of reverse transcriptase. PCR was performed with the above-prepared cDNA as the template, using two pairs of primers: one combination of F3593 (5'-ccaatctaccatcagcatcagc-3'/SEQ ID NO: 28) on the P gene and R4993 (5'-ttcccttcatcgactatgacc-3'/SEQ ID NO: 29) on the F gene, and another combination of F3208 (5'-agagaacaagactaaggctacc-3'/SEQ ID NO: 30) on the P gene and R4993. As expected from the gene structure of SeV18+/ΔM-GFP, amplifications of 1073 bp and 1458 bp DNAs were observed from the former and latter combinations respectively (FIG. 24). When reverse transcriptase was omitted (RT-), gene amplification did not occur. When the M gene was inserted instead of the GFP gene (pSeV18+GFP), 1400 bp and 1785 bp DNAs were amplified respectively. These DNAs are clearly different in size from those described above, supporting the fact that this virus is M gene-deficient in structure.

Protein confirmation was performed using Western blotting. LLC-MK2 cells were infected at MOI=3 with SeV18+/ΔM-GFP (shown as ΔM in Figures), SeV18+/ΔF-GFP (shown as ΔF in Figures), and SeV18+GFP (shown as 18+ in Figures), respectively, and the culture supernatant and cells were recovered three days after infection. The culture supernatant was centrifuged at 48,000×g for 45 minutes to recover viral proteins. After SDS-PAGE, Western blotting was performed to detect proteins using anti-M protein antibody, anti-F protein antibody, and DN-1 antibody (rabbit polyclonal) which mainly detects NP protein, according to the method described in Examples 3 and 4. In cells infected with SeV18+/ΔM-GFP, the M protein was not detected while the F and/or NP proteins were observed. Therefore, this virus was also confirmed to have the SeV18+/ΔM-GFP structure from the point of view of proteins (FIG. 25). The F protein was not observed in cells infected with SeV18+/ΔF-GFP, while all viral proteins examined were detected in cells infected with SeV18+GFP. In addition, very little NP protein was observed in the culture supernatant in the case of infection with SeV18+/ΔM-GFP, indicating that there were no or very few secondarily released particles.

Example 15

Quantitative Analysis Concerning the Presence or Absence of Secondarily Released Particles of M Gene-deficient SeV As described in Example 14, LLK-MK2 cells were infected with SeV18+/ΔM-GFP at MOI=3, the culture supernatant was recovered three days after infection, filtered through an 0.45 μm pore diameter filter, and then centrifuged at 48,000×g for 45 minutes to recover viral proteins. Western blotting was then used to semi-quantitatively detect viral proteins in the culture supernatant. Samples similarly prepared from cells infected with SeV18+/ΔF-GFP were used as the control. Serial dilutions of respective samples were prepared and subjected to Western blotting to detect proteins using the DN-1 antibody (primarily recognizing NP protein). The viral protein level in the culture supernatant of cells infected with SeV18+/ΔM-GFP was estimated to be about 1/100 that of cells infected with SeV18+/ΔF-GFP (FIG. 26). Sample HA activities were 64 HAU for SeV18+/ΔF-GFP, compared to less than 2 HAU for SeV18+/ΔM-GFP.

Time courses were examined for the same experiments. That is, LLC-MK2 cells were infected at MOI=3 with SeV18+/ΔM-GFP, and the culture supernatant was recovered over time (every day) to measure HA activity (FIG. 27). Four days or more after infection, slight HA activity was detected. However, measurements of LDH activity, an indicator of cytotoxicity, revealed clear cytotoxicity four or more days after infection in the SeV18+/ΔM-GFP-infected cells (FIG. 28). This indicated the strong possibility that elevated HA activity was not due to VLPs, but to the activity of HA protein bound to or free from cell debris. Furthermore, the culture supernatant obtained five days after infection was examined using Dosper Liposomal Transfection Reagent, a cationic liposome (Roche, Basel, Switzerland). The culture supernatant (100 μl) was mixed with Dosper (12.5 μl), allowed to stand at room temperature for ten minutes, and then transfected to LLC-MK2 cells cultured to confluency on 6-well plates. Inspection under a fluorescence microscope two days after transfection revealed that many GFP-positive cells were observed in the supernatant of cells infected with SeV18+/ΔF-GFP which contained secondarily released particles, while very few or almost no GFP-positive cells were observed in the supernatant of cells infected with SeV18+/ΔM-GFP (FIG. 29). From the above results, the secondary release of particles was concluded to be almost completely suppressed by an M protein deficiency.

2. Construction of the SeV Vector with Decreased or Defective Particle Forming Ability Due to Modified Protease-Dependent Tropism Utilizing the reconstitution system for the M-defective SeV constructed above, SeV in which the cleavage site of the F protein is modified, as shown below, was constructed.

Example 16

Construction of an M-Deficient SeV Genomic cDNA with Modified F Protein Activation Site An M-deficient SeV genomic cDNA inserted with a recognition sequence for a protease highly expressed in cancer cells at the F1/F2 cleavage site (activation site) of the F protein was constructed. Various sequences based on sequences used as synthetic substrates of MMP-2 and MMP-9, and sequences based on substrates of uPA were designed. FIG. 30 shows four kinds of sequences: two sequences designed based on the sequence of synthetic substrates utilized as substrates of MMP-2 and MMP-9 (Netzel-Arnett, S. et al., Anal. Biochem. 195, 86-92, 1991) with additional modifications [PLG↓MTS (SEQ ID NO: 3) and PLG↓LGL (SEQ ID NO: 31); hereinafter, F proteins comprising these sequences is referred to as F(MMP#2) and F(MMP#3), respectively]; another sequence designed by inserting only the three-amino acid sequence, PLG, that is common to synthetic substrates of MMP (hereinafter, the F protein having this sequence is referred to as F(MMP#4)); and the sequence designed based on a substrate of uPA, VGR (SEQ ID NO: 6), (hereinafter, the F protein comprising this sequence is referred to as F(uPA)).

For actual sequence designing to achieve a more selective action towards the MMPs of interest (MMP-2 and MMP-9), the sequences of commercially available synthetic substrates, as well as reports that made detailed examinations of substrate specificity (Turk, B. E. et al., Nature Biotech. 19(7), 661-667, 2001; Chen, E. I. et al., J. Biol. Chem. 277(6), 4485-4491, 2002) can be referenced. Particularly for MMP-9, a consensus sequence from P3 to P2', Pro-X-X-Hy-(Ser/Thr) (X=any residues; Hy=hydrophobic residues), is recommended (Kridel, S. J. et al., J. Biol. Chem. 276(23), 20572-20578, 2001). Therefore, F(MMP#2) was newly designed as the present design, PLG↓MTS, from the sequence of the original synthetic substrate, PLG↓MWS, so that it matches the consensus sequence.

The gene construction scheme is shown in FIG. 31. The full-length genomic cDNA (pSeV18+/ΔM-GFP) of M-deficient Sendai virus, in which an EGFP gene is inserted at M-deficient site, was digested with SalI and NheI. The fragment (9634 bp) comprising the F gene was separated by agarose gel electrophoresis, and then the corresponding band was cut out and collected with QIAEXII Gel Extraction System (QIAGEN, Bothell, Wash.). The obtained fragment was subcloned into the SalI/NheI site of LITMUS38 (New England Biolabs, Beverly, Mass.) (construction of Litmus-SalI/NheIfrgΔM-GFP). Mutagenesis to the F gene was performed on this LitmusSalI/NheIfrgΔM-GFP, using Quick-Change™ Site-Directed Mutagenesis Kit (Stratagene, La Jolla, Calif.) according to the method described in the kit. The sequences of the synthetic oligos used for the mutagenesis were as follows:

```
                                    (SEQ ID NO: 32)
5'-CTGTCACCAATGATACGACACAAAATGCCccTctTggCatGaCGAGt

TTCTTCGGTGCTGTGATTGGTACTATC-3'
and
                                    (SEQ ID NO: 33)
5'-GATAGTACCAATCACAGCACCGAAGAAaCTCGtCatGccAagAggGG CATTTTGTGTCGTATCATTGGTGACAG-3' for the conversion to F (MMP#2);
                                    (SEQ ID NO: 34)
5'-CTGTCACCAATGATACGACACAAAATGCCccTctTggCCtGggGttA TTCTTCGGTGCTGTGATTGGTACTATCG-3'
and
                                    (SEQ ID NO: 35)
5'-CGATAGTACCAATCACAGCACCGAAGAATaaCccCaGGccAagAggG GCATTTTGTGTCGTATCATTGGTGACAG-3' for the conversion to F (MMP#3);
                                    (SEQ ID NO: 36)
5'-CAAAATGCCGGTGCTCCCCcGTtGgGATTCTTCGGTGCTGTGAT T-3'
and
                                    (SEQ ID NO: 37)
5'-AATCACAGCACCGAAGAATCcCaACgGGGGAGCACCGGCATTTT G-3' for the conversion to F (MMP#4);
and
                                    (SEQ ID NO: 38)
5'-GACACAAAATGCCGGTGCTCCCgtGggGAGATTCTTCGGTGCTGTGA TTG-3'
and
                                    (SEQ ID NO: 39)
5'-CAATCACAGCACCGAAGAATCTCccCacGGGAGCACCGGCATTTTGT GTC-3' for the conversion to F (uPA).
```

Lower case letters indicate mutated nucleotides.

LitmusSalI/NheIfrgΔM-GFP comprising an objective mutation on the F gene was digested with SalI/NheI to collect a fragment (9634 bp) comprising the F gene. The full-length genomic cDNA of F-deficient Sendai virus comprising the EGFP gene at the F-deficient site (pSeV18+/ΔF-GFP: Li, H.-O. et al., J. Virol. 74, 6564-6569, 2000; WO 00/70070) was digested with SalI and NheI to collect an NP gene-comprising fragment (8294 bp), and a multicloning site was introduced to the fragment using synthetic oligo DNA to obtain a plasmid (pSeV/ΔSalINheIfrg-MCS: PCT/JP00/06051). The obtained plasmid was digested with SalI and NheI to collect a fragment (8294 bp). These collected fragments were ligated to each other to construct an M-deficient SeV cDNA (pSeV18+/F (MMP#2)ΔM-GFP, pSeV18+/F(MMP#3)ΔM-GFP, or pSeV18+/F(MMP#4)ΔM-GFP) comprising the F(MMP#2), F(MMP#3), or F(MMP#4) gene (an F gene designed to be activated by MMP), and M-deficient SeV cDNA (pSeV18+/F (uPA)ΔM-GFP) comprising the F(uPA) gene (an F gene designed to be activated by uPA).

Example 17

Reconstitution and Amplification of an M-deficient SeV Vector Having a Modified F Activation Site Reconstitution of the virus was performed according to the procedure reported by Li et al. (Li, H.-O. et al., J. Virol. 74, 6564-6569, 2000; WO 00/70070). Since the virus was an M-deficient form, the above-mentioned helper cells (as in Example 11) that provide the M protein in trans were used. The Cre/loxP expression induction system was used for helper cell production. The system utilized the pCALNdLw plasmid designed to induce the expression of gene products with Cre DNA recombinase (Arai, T. et al., J. Virol. 72, 1115-1121, 1988). Thus, a recombinant adenovirus (Ax-CANCre) expressing Cre DNA recombinase was infected to the transformant of this plasmid using the method of Saito et al. (Saito, I. et al., Nucleic Acids Res. 23, 3816-3821, 1995; Arai, T. et al., J. Virol. 72, 1115-1121, 1998) to express the inserted genes (see Examples 11 and 12).

The reconstitution of the M-deficient SeV in which the activation site of F was modified was performed as follows. LLC-MK2 cells were plated onto a 100-mm dish at a density of $5 \times 10^6$ cells/dish and incubated for 24 hours. Recombinant vaccinia viruses (PLWUV-VacT7: Fuerst, T. R. et al., Proc. Natl. Acad. Sci. USA 83, 8122-8126, 1986) expressing T7 polymerase was treated with psoralen under ultraviolet A irradiation (365 nm) for 20 minutes, and infected (at MOI=2) to the cells at room temperature for one hour. The cells were washed with serum-free MEM. pSeV18+/F(MMP#2)ΔM-GFP (alternatively, pSeV18+/F(MMP#3)ΔM-GFP, pSeV18+/F(MMP#4)ΔM-GFP, or pSeV18+/F (uPA)ΔM-GFP), pGEM/NP, pGEM/P, pGEM/L (Kato, A. et al., Genes Cells 1, 569-579, 1996), and pGEM/F-HN (Li, H.-O. et al., J. Virology 74, 6564-6569, 2000; WO 00/70070) plasmids were suspended in Opti-MEM (Gibco-BRL, Rockville, Md.) at densities of 12 μg, 4 μg, 2 μg, 4 μg, and 4 μg per dish, respectively. SuperFect transfection reagent (Qiagen, Bothell, Wash.) corresponding to 5 μL per 1 μg DNA was added to respective solutions, mixed, and then allowed standing at room temperature for 15 minutes. Finally, the mixture was added to 3 mL of Opti-MEM comprising FBS at a final concentration of 3%, and then added to the cells for culture. After five hours of culturing, the cells were washed twice in serum-free MEM, and were cultured in MEM containing 40 μg/mL Cytosine β-D-arabinofuranoside (AraC: Sigma, St. Louis, Mo.) and 7.5 μg/mL trypsin (Gibco-BRL, Rockville, Md.). After culturing for 24 hours, cells (LLC-MK2/F7/M62/ A) that continuously expressed the M protein were layered at a density of $8.5 \times 10^6$ cells/dish, and cultured in MEM containing 40 μg/mL AraC and 7.5 μg/mL trypsin at 37° C. for another two days (P0). These cells were collected and the pellet was suspended in 2 mL/dish of Opti-MEM. After repeating three cycles of freezing and thawing, the lysate was directly transfected to LLC-MK2/F7/M62/A, and cultured at 32° C. in serum-free MEM containing 40 μg/mL AraC, 7.5 μg/mL Trypsin, and 50 U/mL type IV collagenase (ICN, Aurola, Ohio) (P1). Three to 14 days later, a portion of the culture supernatant was sampled and infected to freshly prepared LLC-MK2/F7/A, and cultured at 32° C. in serum-free MEM containing 40 μg/mL AraC, 7.5 μg/mL trypsin, and 50 U/mL type IV collagenase (P2). Three to 14 days later, this was reinfected to freshly prepared LLC-MK2/F7/M62/A and cultured at 32° C. for 3 to 7 days in serum-free MEM containing 7.5 μg/mL trypsin and 50 U/mL type IV collagenase (P3). BSA was added to the collected culture supernatant to a final concentration of 1%, and culture was stored at −80° C. The viral stock solution was thawed for later production and in vitro experiments.

Furthermore, helper cells (LLC-MK2/F7/M62-#33) which enables production of the M-deficient SeV vector at higher titers was successfully obtained by introducing the SeV-M gene (and SeV-F gene) of the same system (pCALNdLw: Arai, T. et al., J. Virol. 72, 1115-1121, 1988) into LLC-MK2/ F7/M62 as the helper cell that provides the M protein in trans and continuing the cloning of cells. Using these cells, an M-deficient SeV vector (SeV18+/ΔM-GFP) in which the F gene has not been mutated can be produced at titers of $1 \times 10^8$ GFP-CIU/mL (GFP-CIU is defined in WO 00/70070) or more. In addition, the use of these cells accomplished also the preparation of both SeV18+/F(MMP#2)ΔM-GFP and SeV18+/F (uPA)ΔM-GFP at a titer of $1 \times 10^8$ GFP-CIU/mL or more.

When reconstitution was similarly performed for SeV18+/ F(MMP#3)ΔM-GFP and SeV18+/F(MMP#4)ΔM-GFP, no viral particles could be collected. In order to collect these viral particles, conditions for reconstitution must be further examined. Considering the fact that they could not be collected under the same conditions, there may be problems with the design of the F1/F2 cleavage sites (activation sites of F protein) in F(MMP#3) and F(MMP#4), which cause, for example, poor cleavage efficiency or weak activity of the cleaved F protein. On the other hand, since high titers of viral particles were collected with the design of F(MMP#2), this was considered to be a good design which shows good cleavage efficiency, and which does not affect the activity of the cleaved F protein.

Example 18

Preparation of In Vivo Samples of an M-Deficient SeV Vector Having a Modified F Activation Site Various M-deficient SeV vectors for in vivo examinations were prepared by simple purification, wherein the viral particles were spun down by centrifugation. LLC-MK2/F7/ M62-#33 was grown in a 6-well plate until nearly confluent, infected with AxCANCre (MOI=5), and then cultured at 32° C. for two days. These cells were infected with SeV18+/F (MMP#2)ΔM-GFP or SeV18+/ΔM-GFP at MOI=0.5. Then, the cells were cultured for three days at 32° C. in serum-free MEM (1 mL/well) containing 7.5 μg/mL trypsin and 50 U/mL type IV collagenase for SeV18+/F(MMP#2)ΔM-GFP; and in serum-free MEM (1 mL/well) containing only 7.5 μg/mL trypsin for SeV18+/ΔM-GFP. The supernatants were collected from the six wells and combined together, then centrifuged at 2,190×g for 15 minutes. The collected supernatants were passed through a filter with pores having an inside diameter of 0.45 μm, and then further centrifuged at 40,000×g for 30 minutes. The resulting pellet was suspended in 500 μL of PBS to prepare purified virus solutions. The titer of the M-deficient SeV vectors prepared as described above was $1.3 \times 10^9$ and $4.5 \times 10^9$ GFP-CIU/mL for SeV18+/F (MMP#2)ΔM-GFP and SeV18+/ΔM-GFP, respectively. The F proteins in the viruses prepared in Examples 17 and 18 are cleaved, and the viruses have infectivity. Such SeVs are called F-cleaved SeV or infective SeV. Hereinafter, SeV18+/ΔM-GFP, SeV18+/F(MMP#2)ΔM-GFP, and SeV18+/F (uPA) ΔM-GFP are also abbreviated as SeV/ΔM-GFP, SeV/F (MMP#2)ΔM-GFP, and SeV/F(uPA)ΔM-GFP, respectively.

Example 19

Method for Evaluating Protease-Dependent Infection and Cell Fusogenic Infection of F-Modified, M-Deficient SeV Vectors <1> Exogenous Experiment:
An infection procedure in which an extracellular protease is added to a cell line is called an exogenous experiment. The basic procedure of the exogenous experiment performed in the following Examples is described below. The use of different conditions is described in respective Examples. LLC-MK2 was cultured until confluence in a 96-well plate ($5 \times 10^5$ cells/well). After washing twice with MEM, 50 μL MEM containing SeV [F-cleaved form: $1 \times 10^5$ CIU/mL, or F-uncleaved form: $1 \times 10^7$ particles/mL (in HA units; see Example 25)] was added and infected to the cells. Simultaneously, 50 μL of protease-containing MEM was also added thereto, and the cells were cultured at 37° C. Four days later, the spread of the infection was observed under a fluorescent microscope. The number of cells expressing GFP per cells in 1 mm² was counted. The proteases to be used were purchased from ICN Biomedicals Inc. for collagenase (type IV collagenase), and MMP-2 (active MMP-2), MMP-3, MMP-7, MMP-9 (active MMP-9), and plasmin were purchased from COSMO BIO Co. ltd.

<2> Endogenous Experiment:
An infection procedure achieved by intracellularly expressed protease without extracellular addition of protease is called an endogenous experiment. The basic procedure of the endogenous experiment performed in the following Examples is described below. The use of different conditions is described in respective Examples. Respective cancer cells were cultured in a 96-well plate until confluence ($5 \times 10^5$ cells/well). After washing twice with MEM, 50 μL MEM containing SeV [F-cleaved form: $1 \times 10^5$ CIU/mL or F-uncleaved form: $1 \times 10^7$ HAU/mL (see Example 25)] was added and infected to the cells. Simultaneously, FBS was added to the medium at a final concentration of 1%. Four days later, the spread of the infection was observed under a fluorescent microscope. The number of cells expressing GFP per cells in 1 mm² was counted.

Example 20

Protease-Dependent Cell Fusogenic Infection by an F-Modified M-Deficient Sendai Viral Vector Exogenous Experiment Using LLC-MK2 cells that hardly express proteases, modification of F was confirmed and assayed by the above-mentioned exogenous experiment to determine whether it causes protease-dependent cell fusogenic infection (FIG. 32). Three types of M-deficient SeVs, (as in Example 17), SeV/ΔM-GFP, SeV/F(MMP#2)ΔM-GFP, and SeV/F(uPA)ΔM-GFP, were infected to cells. Simultaneously, 0.1 μg/mL each of type IV collagenase (*Clostridium histolyticum*), active MMP-2, active MMP-9, or uPA, or 7.5 μg/mL trypsin was added thereto. Four days later, cells were observed under a fluorescence microscope. Only in LLC-MK2 to which trypsin was added, SeV/ΔM-GFP with unmodified F caused cell fusion of the infected cells with their surrounding cells, resulting in cell fusogenic infection and multinuclear cell (syncytia) formation (FIG. 32L) SeV/F(MMP#2)ΔM-GFP inserted with an MMP degradation sequence into the F protein gene showed cell fusogenic infection of LLC-MK2 to which collagenase, active MMP-2, and active MMP-9 have been added, resulting in formation of syncytia (FIGS. 32E, 32F, and 32M). On the other hand, SeV/F(uPA)ΔM-GFP inserted with urokinase-type plasminogen activator (uPA) and tissue-type PA (tPA) degradation sequences into the F protein showed cell fusogenic infection in the presence of trypsin, and, upon further modification of the F protein, showed the formation of syncytia, multinuclear cells, in the presence of uPA (FIGS. 32Q and 32R). These results indicate that, due to the incorporation of each of the protease degradation substrate sequences into the F protein, an M-deficient SeV causes degradation substrate sequence-dependent cell fusogenic infection and spread to contacting cells.

Example 21

MMP Expression-Specific Cell Fusogenic Infection of Cancer Cell Lines

Endogenous Experiment

Using the SeV prepared in Example 17, an endogenous experiment was performed to determine whether or not endogenous protease selective cell fusogenic infection occurs. An MMP-expressing cancer cell line, HT1080 (human fibroblastic sarcoma) (Morodomi, T. et al., Biochem. J. 285 (Pt 2), 603-611, 1992), a tPA-expressing cell line, MKN28 (human gastric cancer cell line) (Koshikawa, N. et al., Cancer Res. 52, 5046-5053, 1992), and a cell line expressing neither protease, SW620 (human colon cancer line), were used. MKN28 was provided from Riken Institute of Physical and Chemical Research (Cell No. RCB1000), while HT1080 (ATCC No. CCL-121) and SW620 (ATCC No. CCL-227), as well as SW480 (ATCC No. CCL-228), WiDr (ATCC No. CCL-218), and Panc-1 (ATCC No. CRL-1469) that were used in the following Examples were provided from American type culture collection (ATCC). The media used at the respective institutions that handed out the cells were used in the experiment. In addition, FBS was added to all of the media at a final concentration of 1%. As shown in FIG. 33, in MMP-expressing cell line, HT1080, only the infection with SeV/F(MMP#2)ΔM-GFP spread ten times or more. Furthermore, in tPA-expressing cell line, MKN28, cell fusogenic infection spread with only SeV/F(uPA)ΔM-GFP. In SW620, which expresses neither protease, no spreading of infection was observed at all.

Example 22

Cell Fusogenic Infection Due to MMP Induction by Phorbol Ester

MMP is reported to be induced in vivo in cancer cells due to the growth factors and such existing around the cells. This phenomenon can be reproduced in vitro using a phorbol ester, phorbol 12-myristate 13-acetate (PMA). To investigate infection that occurs under reproduced conditions in which MMP expression is induced, PancI, a pancreatic cancer cell line known to activate MMP-2 and induce MMP-9 via PMA, was used to examine the presence or absence of cell fusogenic infection by F-modified M-deficient SeV vector (Zervos, E.

E. et al., J. Surg. Res. 84, 162-167, 1999). PancI and other cancer cell lines were cultured in a 96-well plate until confluence ($5\times10^5$ cells/well). The endogenous experiment was performed using SeV prepared in Example 17. After washing twice with MEM, 50 µL MEM containing $1\times10^5$ CIU/mL SeV was added for infection (at MOI=0.01). The same amount (50 µL) of MEM containing 40 nM phorbol 12-myristate 13-acetate (Sigma) was added thereto. Simultaneously, FBS was added to the medium at a final concentration of 1%.

The induced expression of MMP-2 and MMP-9 was confirmed by gelatin zymography in which the portion where gelatinolytic activity exists becomes clear (Johansson, S., and Smedsrod, B., J. Biol. Chem. 261, 4363-4366, 1986). Specifically, the supernatant of each culture was collected and dissolved in a sample buffer. This was mixed with acrylamide to a final concentration of 1 mg/mL gelatin to prepare an 8% acrylamide gel. After SDS polyacrylamide gel electrophoresis, the gel was washed with 10 mM Tris (pH 8.0) and 2.5% Triton X-100, incubated in gelatinase activation buffer (50 mM Tris, 0.5 mM $CaCl_2$, $10^{-6}$ M $ZnCl_2$) at 37° C. for one day, and stained with 1% Coomassie Blue R-250, 5% acetic acid, and 10% methanol (top panel of FIG. 34). "C" represents the control, and "T" the supernatant of a sample induced by 20 nM PMA. This panel shows that MMP-9 is induced in HT1080 and Panc I. Latent MMP-2 has been detected before induction in Panc I. However, this latent form is known to have hardly any gelatinolytic activity. As shown in FIG. 34 (lower panel), Panc I infected with SeV/F(MMP#2)ΔM-GFP indicated cell fusogenic infection by MMP induction.

Example 23

Spread of Infection with SeV/F(MMP#2)ΔM-GFP in an HT1080 Cell Line In Vivo

HT1080 carcinoma-bearing nude mice were produced. $5\times10^6$ cells of a human fibroblastoma cell line, HT1080, (50 µL of $1\times10^8$ cells/mL), were injected subcutaneously to the right dorsal skin of BALB/c nude mice (Charles River). Seven to nine days later, animals having a tumor with a diameter of more than 3 mm were used. The volume of the carcinoma, its shape presumed to be elliptical, was 30 to 100 mm³. Fifty µL of the following F-cleaved SeV was injected once to the carcinoma: MEM (control) (N=5); MEM containing SeV-GFP ($1\times10^8$ CIU/mL) (N=5); MEM containing SeV/ΔM-GFP ($1\times10^8$ CIU/mL) (N=7); and MEM containing SeV/F(MMP#2)ΔM-GFP ($1\times10^8$ CIU/mL) (N=7). Two days later, the carcinomas were observed under a fluorescence microscope (FIG. 35). Fluorescence is observed only in the area around the injected site for SeV-GFP and SeV/ΔM-GFP (FIGS. 35E and 35H). In contrast, for SeV/F(MMP#2)ΔM-GFP, fluorescence was observed to spread throughout the entire carcinoma (FIG. 35K). Enlarged images show fluorescence from individual cells for SeV-GFP and SeV/ΔM-GFP, whereas, for SeV/F(MMP#2)ΔM-GFP, the shape of the cells is unclear, suggesting fusion of the cells. Furthermore, the area of the entire carcinoma and the area of GFP expression in the above pictures were determined by NIH image. The proportions of the GFP expression region in the entire cancer were 10% for SeV-GFP and 20% for SeV/ΔM-GFP, and, in contrast, 90% for SeV/F(MMP#2)ΔM-GFP, clearly indicating the spread of infection (FIG. 36). In tissues other than cancer tissues, cell fusogenic infection was hardly observed in the fascia and subcutaneous connective tissues existing at the border to the cancer cells. Thus, under these conditions, infection was determined not to spread to normal tissues other than cancer tissues.

Example 24

Anti-Tumor Effect of an F-Modified M-Deficient SeV Vector on Carcinoma-Bearing Nude Mice HT1080 tumor-bearing mice were produced in the same manner as described in FIG. 35. Eight or nine days later, animals having a tumor with a diameter of more than 3 mm were selected, and 50 µL of the following four kinds of F-cleaved SeV were injected to the cancerous site: MEM (N=5); MEM containing SeV-GFP ($1\times10^8$ CIU/mL) (N=5); MEM containing SeV/ΔM-GFP ($1\times10^8$ CIU/mL) (N=7); and MEM containing SeV/F(MMP#2)ΔM-GFP ($1\times10^8$ CIU/mL) (N=7). Two days later, equal amounts of SeV were injected again to the cancerous site. The lengths of the long axis (a), short axis (b), and thickness (c) of the cancerous site was measured every other day. Assuming the carcinoma is an ellipsoid, the carcinoma volume V was calculated as $V=\pi/6\times abc$. The carcinoma to which PBS, SeV-GFP, and SeV/ΔM-GFP were administered, respectively, enlarged rapidly. In contrast, SeV/F(MMP#2)ΔM-GFP-administered carcinoma, in which the vector had spread throughout the carcinoma as shown in FIG. 37, clearly indicated no proliferation and remained small. Analysis of significant difference by t-test showed that it is significantly smaller compared to the other three groups at P<0.05. This indicates that the vector has anticancer effect even without therapeutic genes.

Example 25

Production and Selective Infection of an F-Uncleaved/F-Modified M-Deficient SeV Vector In the production procedure of the SeV vector used above, culture was performed in a medium containing a high concentration (7.5 µg/mL) of trypsin and 50 U/mL collagenase to induce the cleavage of F, and the F-cleaved vector was collected (see Examples 17 and 18). In the present Example, to accomplish protease-dependent selection during infection, an F-uncleaved SeV was produced by collecting SeV without adding proteases during production.

Specifically, LLC-MK2/F7/M62/A cells were cultured in a 10-cm dish until confluence. Each of the F-modified M-deficient SeVs prepared in Example 17 were infected to cells (MOI=5). One hour later, the supernatant was removed and washed twice with MEM medium. 4 mL MEM was added to the cells and then cultured at 32° C. Five days later, the supernatant was collected, and bovine serum albumin (BSA) was added to a final concentration of 1%. After measuring the HAU titer, the supernatant was stored at −70° C. until use. Each of the F-modified M-deficient SeVs were collected in the range of 27 to 210 HAU/mL (1 HAU=$1\times10^6$ viral particles/mL, and therefore this corresponds to $1\times10^8$ to $1\times10^9$ particles/mL) and were adjusted to $1\times10^8$ particles/mL by dilution.

The results of this exogenous experiment confirmed the production of vectors that infect LLC-MK2 in MMP-dependent and uPA- or tPA-dependent manners by SeV/F(MMP#2)ΔM-GFP and SeV/F(uPA)ΔM-GFP, respectively (the data of exogenous proteases are not shown). In addition, whether selective infection due to protease expression is possible in MMP-expressing HT1080 strain, tPA-expressing MKN28 strain, and SW620 which hardly expresses the proteases, was tested by endogenous experiments (FIG. 38). SeV/F (MMP#2)ΔM-GFP infects to MMP-expressing HT1080 strain, but not to tPA-expressing MKN28 strain. SeV/F(uPA) ΔM-GFP infects to tPA-expressing MKN28 strain but not to MMP-expressing HT1080 strain. As shown above, each of the SeVs showed selective infection in a protease-dependent manner.

Example 26

F-Modified M-Deficient SeV Vector Infection Due to MMP-3 and MMP-7 Induction Via Human Fibroblasts SW480 and WiDr were shown to induce MMP-3 and MMP-7, respectively, through co-culture with fibroblasts or in vivo culture (Kataoka, H. et al., Oncol. Res. 9, 101-109, 1997; Mc Donnell, S. et al., Clin. Exp. Metastasis. 17, 341-349, 1999). These cells were used to investigate whether infection of F-modified M-deficient SeV vector changes in vivo. Each cancer cell line was cultured in a 96-well plate until confluence ($5 \times 10^4$ cells/well). After washing twice with MEM, 50 μL MEM containing 1 HAU/mL (1 HAU=$1 \times 10^6$ viral particles/mL, and thus, corresponding to $1 \times 10^6$ particles/mL) of F-uncleaved SeV, was added for infection. Normal human lung fibroblasts (TAKARA) were added at a concentration of $5 \times 10^4$ cells/well to the cells and cultured for four days at 37° C. (FIG. 39). SW480 and WiDr were infected by SeV/F(MMP#2)ΔM-GFP, through co-culturing with human fibroblasts. Such a phenomenon is not observed in SW620, which is not inducible.

Example 27

MMP-Selective Infection of an F-Modified M-Deficient SeV Vector to Human Aortic Smooth Muscle Cells Aberrant expression of MMP has been reported in arteriosclerosis, rheumatoid arthritis, wound healing, in addition to cancer (Galis, Z. S., and Khatri, J. J., Circ. Res. 90, 251-262, 2002; Martel-Pelletier, J. et al., Best Pract. Res. Clin. Rheumatol. 15, 805-829, 2001).

To demonstrate the applicability of F-modified M-deleted SeV vectors to these diseases, MMP-selective infection of the vectors to human aortic smooth muscle cells was directed. Human smooth muscle cells (TAKARA) were cultured in a 96-well plate until confluence ($5 \times 10^5$ cells/well). After washing twice with MEM, 50 μL MEM containing SeV (F-uncleaved form: 1 HAU/mL ($1 \times 10^6$ particles/mL)) was added to the cells for infection. The equal amount (50 μL) of protease-containing MEM was added thereto and cultured for four days at 37° C. The number of cells expressing GFP per cells in 1 mm² was counted (FIG. 40). Infection of SeV/ΔM-GFP was enhanced only by the addition of trypsin, whereas infection of SeV/F(MMP#2)ΔM-GFP was enhanced by the addition of collagenase, MMP-2, MMP-3, and MMP-9.

Example 28

Protease-Dependent Cleavage of the F Protein in F-Modified M-Deficient SeV Vectors As shown in Example 20, by incorporating each of the protease degradation sequences into the F protein, F-modified M-deficient SeV vector showed cell fusogenic infection dependent on those degradation sequences. Furthermore, whether cleavage of F0 occurs in a protease-dependent manner after modification was confirmed by Western blotting. Sampling of viruses was performed by the following method. Three types of viral particles, SeV/ΔM, SeV/F(MMP#2)ΔM, and SeV/F(uPA)ΔM, were infected at MOI=3 to M protein-induced helper cells. Two days after infection, the supernatants were collected and centrifuged at 18,500×g for three hours, and the precipitates were resuspended in PBS. To each of the virus suspensions, proteases were added at final concentrations of 7.5 μg/mL for trypsin, 0.1 ng/mL for MMP-9, and 0.1 ng/mL for uPA and incubated at 37° C. for 30 minutes. Sample buffer was added to each mixture to prepare SDS-PAGE samples. SDS-PAGE and Western blotting were performed according to standard methods (Kido, H. et al. "Isolation and characterization of a novel trypsin-like protease found in rat bronchiolar epithelial Clara cells. A possible activator of the viral fusion glycoprotein." *J Biol Chem* 267, 13573-13579, 1992). Rabbit anti-F1 antibody was obtained as antiserum by immunization of a mixture of three synthetic peptides (FFGAVIGT+Cys: 117-124, EAREAKRDIALIK: 143-155, and CGTGRRPISQDRS: 401-413; which are SEQ ID NOs: 46, 47, and 48, respectively). HRP-labeled anti-rabbit IgG antibody (ICN, Aurola, Ohio) was used as the secondary antibody, and chemical fluorescence method (ECL Western blotting detection reagents; Amersham Biosciences, Uppsala, Sweden) was used for detecting developed colors. FIG. 41 shows the results of treatment with an M-deficient SeV vector comprising unmodified F (1, 4, 7, and 10), an M-deficient SeV vector inserted with MMP#2 sequence into F (2, 5, 8, and 11), and an M-deficient SeV vector inserted with uPA sequence into F (3, 6, 9, and 12) with the above-mentioned proteases at 37° C. for 30 minutes.

As shown in FIG. 41, cleavage of F1 occurred, according to the respective inserted protease substrates, i.e., in the presence of trypsin for the M-deficient SeV vector with unmodified F, in the presence of MMP for the M-deficient SeV vector inserted with MMP#2 sequence into F, and in the presence of uPA for the M-deficient SeV vector inserted with uPA into F. Although not shown herein, for the M-deficient SeV vector into which uPA sequence is inserted, cleavage of F1 was observed in the presence of trypsin when the degradation time was prolonged to four hours. This agrees well with the results of Example 20, and indicates that syncytium formation occurs in an F cleavage-dependent manner.

Example 29

Increase of Fusibility by Cytoplasmic Domain-Deletion of the F Protein

Infiltration of the paramyxovirus to the host is accomplished by the fusion of the viral membrane and the host cell membrane. In this infiltration mechanism, the HN protein of the Sendai virus binds to the sialic acid of the host, and the F protein causes cell membrane fusion. During this step, the conformational change of the F protein resulting from the binding of HN has been suggested to be important (Russell, C. J., Jardetzky, T. S. and Lamb, R. A., "Membrane fusion machines of paramyxoviruses: capture of intermediates of fusion." EMBO J. 20, 4024-34, 2001). Therefore, most of the F proteins of paramyxoviruses do not show fusogenicity of cells when they are expressed alone on cells. Only cells that simultaneously express the HN protein have fusiogenicity. The deletion of cytoplasmic domains within the F and HN proteins in a paramyxovirus is known to increase its fusiogenicity (Cathomen, T., Naim, H. Y. and Cattaneo, R., "Measles viruses with altered envelope protein cytoplasmic tails gain cell fusion competence." J. Virol. 72, 1224-34, 1998). To determine which deletion mutant of the cytoplasmic domain of the F protein in Sendai virus causes the largest increase in fusogenicity, deletion mutants were prepared and inserted into pCAGGS expression vector (Niwa, H. et al., Gene 108, 193-199, 1991). An HN-carrying pCAGGS was co-transfected and the resulting fusogenicity was confirmed from the number of formed syncytia.

PCR was performed on each of the mutant genes, in which the cytoplasmic domain of F had been deleted, using the primers as shown below, the resulting fragments were treated with XhoI and NotI, and then ligated to the pCAGGS vector. Primers used for PCR were as follows:

```
Fct27 primers
(5'-CCGCTCGAGCATGACAGCATATATCCAGAGA-3'/SEQ ID NO: 49,
and

5'-ATAGTTTAGCGGCCGCTCATCTGATCTTCGGCTCTAATGT-3'/SEQ ID NO: 50);

Fct14 primers
(5'-CCGCTCGAGCATGACAGCATATATCCAGAGA-3'/SEQ ID NO: 51,
and

5'-ATAGTTTAGCGGCCGCTCACCTTCTGAGTCTATAAAGCAC-3'/SEQ ID NO: 52);

Fct4 primers
(5'-CCGCTCGAGCATGACAGCATATATCCAGAGA-3'/SEQ ID NO: 53,
and

5'-ATAGTTTAGCGGCCGCTCACCTTCTGAGTCTATAAAGCAC-3'/SEQ ID NO: 54)
```

(Kobayashi M. et al., J. Viol., 77, 2607, 2003).

To measure cell fusogenicity, LLC-MK2 or HT1080 cells were plated onto a 24-well plate to reach confluence. 3 μL Fugene 6 was mixed with 50 μL Opti-MEM. 2 μg of each pCAGGS expression plasmid was mixed with an equal amount of pCAGGS/EGFP, and then added to the mixture of Opti-MEM and Fugene 6. After standing at room temperature for 15 minutes, this mixture was added to the 24-well plate in which the media was replaced with 500 μL MEM medium. After culturing at 37° C. under 5% $CO_2$ for three hours, the medium was replaced with MEM containing 1% FBS for HT1080, and MEM containing 7.5 μg/mL trypsin or a predetermined concentration of type IV collagenase (*Clostridium*) for LLC-MK2. After culturing for 48 hours, the number of fused syncytia per ×100 visual field (0.3 $cm^2$) of an inverted microscope was counted. Alternatively, the cultured cells were fixed in 4% paraformaldehyde for two hours, transferred to 70% ethanol and then to distilled water, stained for five minutes with hematoxylin, and washed with water to count the number of syncytium-forming nuclei in every 0.3 $cm^2$.

Three kinds of amino acid sequences of the F protein in which the cytoplasmic domain has been deleted are shown in FIG. 42 (A), and their fusion activities are shown in FIG. 42 (B). As indicated in FIG. 42(B), cells in which only the F protein were expressed did not fuse, but co-transfection of HN induced fusogenicity. Furthermore, the F protein (Fct14) having a sequence in which 28 amino acids were deleted so that the cytoplasmic domain becomes 14 amino acids was found to show the highest fusogenicity.

Example 30

Drastic Increases in Fusogenicity Caused by the F/HN Chimeric Protein

The envelope proteins of the paramyxovirus, the F and HN proteins form a trimer and a tetramer, respectively, on the cell membrane, and are known to interact with each other through their ectodomains and M protein (Plemper, R. K., Hammond, A. L. and Cattaneo, R., "Measles virus envelope glycoproteins hetero-oligomerize in the endoplasmic reticulum." J. Biol. Chem. 276, 44239-22346, 2001). As shown in FIG. 42, the F protein alone does not show fusogenicity, and the HN protein is essential for its fusogenicity. Therefore, a chimeric protein comprising the F and HN proteins was produced to produce vectors having enhanced fusogenicity by simultaneously expressing the F and HN proteins as a fusion protein on the same cell membrane. The F protein is a type II membrane protein and HN is a type I membrane protein. Therefore, as shown in FIG. 43(A), the chimeric protein (Fct14/HN) was prepared to form a U-shape on the cell membrane and comprise two transmembrane domains. Fct14 showing high fusogenicity was used as the F protein. A linker sequence consisting of 50 amino acids was inserted between the two proteins (Fct 14/Linker/HN). According to database searches at present, this linker sequence does not show homology to any protein. (A non-sense sequence synthesized by inverting from the N-terminus to C-terminus of the amino acid sequence of the cytoplasmic domain of env of simian immunodeficiency virus (SIVagm) was used.)

The method for producing the expression plasmid of the F/HN chimeric protein gene is specifically described below. The F/HN chimeric protein gene was inserted into the pCAGGS vector. PCRs were performed on the F gene and the HN gene, respectively, and the obtained two fragments were ligated to pCAGGS. During this step, a 150-bp linker gene (50 amino acids) was inserted or nothing was inserted between the F/HN genes. The sequences of the primers utilized are shown below:

```
F gene primers (F-F:
5'-ATCCGAATTCAGTTCAATGACAGCATATATCCAGAG-3'/SEQ ID NO: 55
and Fct14-R:
5'-ATCCGCGGCCGCCGGTCATCTGGATTACCCATTAGC-3'/SEQ ID NO: 56);

Linker/HN gene primers (Linker-HN-F:
5'-ATCCGCGGCCGCAATCGAGGGAAGGTGGTCTGAGTTAAAAATCAGGAGCAACGACGG

AGGTGAAGGACCAGAGGACGCCAACGACCCACGGGGAAAGGGGTGAACACATCCATATCC

AGCCATCTCTACCTGTTTATGGACAGAGGGTTAGG-3'/SEQ ID NO: 57)
and

HN-R:
5'-ATCCGCGGCCGCTTAAGACTCGGCCTTGCATAA-3'/SEQ ID NO: 58);
and

HN gene primers
(5'-ATCCGCGGCCGCAATGGATGGTGATAGGGGCA-3'/SEQ ID NO: 59
and

5'-ATCCGCGGCCGCTTAAGACTCGGCCTTGCA-3'/SEQ ID NO: 60).
```

As shown in FIG. 43(B), although a chimeric protein without the linker sequence shows low fusogenicity, insertion of a linker drastically increases the fusion activity to approximately five times to that obtained by co-transfection of the F and HN proteins.

Example 31

Maintenance of the Function of Fusogenicity and Substrate Specificity

In order to acquire fusogenicity, the F protein not only has to be expressed simultaneously with the HN protein, but also has to be cleaved into two subunits (F1 and F2) by a protease. In FIGS. 42 and 43, the fusogenicity is measured in the presence of trypsin, and the fusogenicity is completely absent under conditions without trypsin. The cleavage sequence of the F protein was modified in the Fct14/Linker/HN chimeric protein shown in FIG. 43 so that it acquires fusogenicity in an MMP-dependent manner. Many degradation substrate sequences of MMP have been reported. Among them, eight kinds of sequences were modified. The amino acid sequence of the cleavage site was modified as shown in FIG. 44(A) using QuickChange™ Site-Directed Mutagenesis Kit (Stratagene, La Jolla, Calif.). The sequence of the fusion peptide after cleavage by a protease was considered in the modification. The N-terminal region of F1 of the paramyxoviral F protein, which is called the fusion peptide, is reported to be important for its fusion activity, and fusogenicity of the F protein is sometimes lost by the mutation of amino acids in that region (Bagai, S. and Lamb, R. A., "A glycine to alanine substitution in the paramyxoviral SV5 fusion peptide increases the initial rate of fusion." Virology 238, 283-90, 1997). Therefore, the sequence of the N-terminal region of F1 whose importance has been indicated was left untouched. In that case as well, when inserting the general six-residue sequence known as a degradation substrate of MMP, the design of F1 after degradation by MMP involved addition of three residues to the N-terminus. This indicates that the addition may allow degradation by MMP, but may affect the fusogenicity of the F protein. Thus, in designing an F protein that undergoes MMP-dependent cleavage for activation, following two points must be taken into account: (1) substrate specificity by MMP; and (2) maintenance of fusogenicity of the F protein after cleavage.

MMP#1 is most well-known sequence as a synthetic substrate of MPP. This sequence is also used for targeting other MMPs. MMP#3 and MMP#8 are also commercially available sequences as synthetic substrates. The sequence of the degradation substrate, PLGMWS, of MMP-2 and MMP-9 were modified to PLGMTS and PQGMTS (SEQ ID NOs: 61 and 62, respectively) as MMP#2 and MMP#6, respectively, according to the consensus sequence, Pro-X-X-Hy-(Ser/Thr) for MMP-9 which was revealed by phage display. MMP#5 was constructed as PQGLYA (SEQ ID NO: 63) according to the report by Shneider et al. (American Society of Gene therapy, Annual meeting No. 1163, 2002, Boston). In MMP#4, the sequence of the fusion peptide after degradation is not modified. The sequence of MMP#7 was found by a phage display method for MMP-2.

The details of the preparation of expression plasmids that have a modified F activation site in the F/HN fusion gene are shown below. After constructing the F/HN fusion gene, mutagenesis of the activation site of the F protein was performed on pBluescript F/HN. To introduce mutation, QuikChange™ Site-Directed Mutagenesis Kit (Stratagene, La Jolla, Calif.) was used according to the method described in the kit. The sequences of synthetic oligos used for the mutagenesis were as follows:

F (MMP#1)
(5'-CTGTCACCAATGATACGACACAAAATGCCccTctTggCCtGggGttATTCTTCGGTGCTGTG

ATTGGTACTATCG-3'/SEQ ID NO: 64,
and

5'-CGATAGTACCAATCACAGCACCGAAGAATaaCccCaGGccAagAggGGCATTTTGTGTCGTAT

CATTGGTGACAG-3'/SEQ ID NO: 65);

F (MMP#2):
(5'-CTGTCACCAATGATACGACACAAAATGCCccTctTggCatGaCGAGtTTCTTCGGTGCTGTG

ATTGGTACTATC-3'/SEQ ID NO: 32,
and

5'-GATAGTACCAATCACAGCACCGAAGAAaCTCGtCatGccAagAggGGCATTTTGTGTCGTATC

ATTGGTGACAG-3'/SEQ ID NO: 33);

F (MMP#3):
(5'-CTGTCACCAATGATACGACACAAAATGCCccTctTggCCtGggGttATTCTTCGGTGCTGTG

ATTGGTACTATCG-3'/SEQ ID NO: 34,
and

5'-CGATAGTACCAATCACAGCACCGAAGAATaaCccCaGGccAagAggGGCATTTTGTGTCGTAT

CATTGGTGACAG-3'/SEQ ID NO: 35);

F (MMP#4):
5'-CAAAATGCCGGTGCTCCCCcGTtGgGATTCTTCGGTGCTGTGATT-33'/SEQ ID NO: 36,
and 5'-AATCACAGCACCGAAGAATCcCaACgGGGGAGCACCGGCATTTTG-3'/SEQ ID NO: 37);

F (MMP#5):
(5'-CTGTCACCAATGATACGACACAAAATGCCccTcagggCttGtatgctTTCTTCGGTGCTGTG

ATTGGTACTATC-3'/SEQ ID NO: 66,
and

5'-GATAGTACCAATCACAGCACCGAAGAAagcataCaaGccctgAggGGCATTTTGTGTCGTATC

ATTGGTGACAG-3'/SEQ ID NO: 67);

F (MMP#6):
(5'-CTGTCACCAATGATACGACACAAAATGCCccTcaaggCatGaCGAGtTTCTTCGGTGCTGTG

ATTGGTACTATC-33'/SEQ ID NO: 68,
and

5'-GATAGTACCAATCACAGCACCGAAGAAaCTCGtCatGccttgAggGGCATTTTGTGTCGTATC

ATTGGTGACAG-3'/SEQ ID NO: 69);

F (MMP#7):
(5'-CTGTCACCAATGATACGACACAAAATGCCctTgcTtaCtataCGgctTTCTTCGGTGCTGTG

ATTGGTACTATC-3'/SEQ ID NO: 70,
and

5'-GATAGTACCAATCACAGCACCGAAGAAagcCGtataGtaAgcAagGGCATTTTGTGTCGTATC

ATTGGTGACAG-3'/SEQ ID NO: 71);
and

F (MMP#8):
(5'-CTGTCACCAATGATACGACACAAAATGCCccTctTggCttGgCGAGaTTCTTCGGTGCTGTG

ATTGGTACTATC-3'/SEQ ID NO: 72,
and

5'-GATAGTACCAATCACAGCACCGAAGAAtCTCGcCaaGccAagAggGGCATTTTGTGTCGTATC

ATTGGTGACAG-3'/SEQ ID NO: 73).

The lower case letters indicates the mutated nucleotides. After modification, the sequences were cut out with EcoRI and ligated to pCAGGS.

Each of the vectors comprising the respective sequences and a vector comprising the EGFP gene (pCAGGS/EGFP) were mixed at equal amounts, and the mixture was transfected to HT1080 that highly express MMP. As a result, only when the genes of the sequences of MMP#2 and MMP#6 had been introduced, cell fusion occurred, and syncytia were formed (FIG. 44(B)). These sequences are in common that an Hy-S/T-S/T sequence (MTS) is added to the N-terminus of the F1 protein after cleavage with the protease. Therefore, the addition of the Hy-S/T-S/T sequence (particularly MTS sequence) was considered to very likely fulfill the requirements (1) cleavage of the F protein by HT1080-derived MMP, and (2) maintenance of fusogenicity of the F protein after cleavage. On the other hand, no cell fusion was observed for MMP#1, MMP#3, MMP#4, MMP#5, MMP#7, and MMP#8 at all. Since all the sequences, with the exception of MMP#4, are derived from synthetic substrates of MMP and are expected to be cleaved by proteases, the peptide of three amino acids added to F1 was suggested to limit the activity of the cleaved F protein. Regarding MMP#4, under this condition, it is highly unlikely that the cleavage itself does not take place. While the data is not shown, this is obvious from the fact that syncytium formation is observed with MMP#4 due to induction of MMP by the phorbol ester in HT1080.

Furthermore, in addition to the comparison of the fusogenicity of the sequences of MMP#2 and MMP#6, the MMP concentration-dependent cell fusogenicity of a sequence in which the 7th and 12th residues from the N-terminus of the fusion peptide sequence of #6 were modified from G to A was measured (FIG. 45). The sequences of synthetic oligos used for mutagenesis of this F/HN fusion gene were as follows: 5'-CTTCGGTGCTGTGATTGcTACTATCG-CACTTGcAGTGGCGACATCAGCAC-3' (SEQ ID NO: 74) and 5'-GTGCTGATGTCGCCACTgCAAGTGCGAT-AGTAgCAAATCACAGCACCGAAG-3' (SEQ ID NO: 75). The lower case letters indicate the mutated nucleotides. Preparation of Expression Plasmids was Performed Similarly as described above by, after mutagenesis, cutting out the sequence with EcoRI and then ligating to pCAGGS.

As a result, MMP#6 was found to have two to three times higher fusogenicity compared to MMP#2. Importantly, MMP#6 induces cell fusion even under low protease concentration conditions. Namely, accomplishes activation of the F protein at low concentrations. However, when a mutation from G to A, which has been reported as a mutation increasing the fusogenicity of the F protein (Peisajovich, S. G., Epand, R. F., Epand, R. M. and Shai, Y., "Sendai viral N-terminal fusion peptide consists of two similar repeats, both of which contribute to membrane fusion." Eur. J. Biochem. 269, 4342-50, 2002) was further introduced (#6G12A), the fusogenicity decreased to 1/10 or less. These results revealed that, by simply inserting a protease cleavage sequence to modify the tropism by a protease, the activity of the F protein cannot be maintained and causes loss of fusogenicity in most cases. When constructing a virus by introducing an objective degradation sequence, the fusogenicity can be confirmed using this system. In addition, since a significant fusion activity is exhibited by the Fct14/Linker/HN alone carried on pCAGGS, transfection of this plasmid is predicted to have antitumor effects.

Moreover, by introducing this chimeric protein into the M-deficient Sendai virus, further increase of antitumor effects is expected.

Example 32

Construction of an Improved F-Modified M-Deficient SeV Genomic cDNA with Increased Fusogenicity Examples 29 and 30 showed increases in fusogenicity through the modification of the F protein carried on the pCAGGS vector. Through similar modification of the M-deficient Sendai viral vector, preparation of an improved F-modified ΔM SeV, in which fusogenicity is increased, was expected. Gene construction of the improved F-modified M-deficient SeV genomic cDNA was performed by the method as described below. SeV/F(MMP#6)ΔM-GFP was constructed according to the same method as in Example 16. Mutation of the F gene was performed on LITMUSSalI/NheIfrgΔM-GFP using the oligonucleotide of SEQ ID NO: 69, and QuikChange™ Site-Directed Mutagenesis Kit (Stratagene, La Jolla, Calif.) according to the method described in the kit. The cDNA of SeV/F(MMP#6)ΔM-GFP was constructed by ligating a SalI and NheI-digested fragment of the mutated LITMUSSalI/NheIfrgΔM-GFP and a fragment comprising the NP gene (obtained by SalI and NheI digestion of the F-deficient Sendai viral full-length genomic cDNA carrying the EGFP gene at the F-deleted site (pSeV+18/F-GFP; Li, H et al., J. Viol. 74, 6564-6569, 2000; WO00/70070)) (FIG. 46). Multicloning site Sendai viral cDNA (referred to as pSeV(TDK)) (JP-A 2002-272465) was used as the basic framework for the construction of M-deficient Sendai virus in which 28 amino acids of the cytoplasmic domain of the F protein were deleted (SeV(TDK)/Fct14(MMP#6)ΔM-GFP) and M-deficient Sendai virus carrying the F/HN chimeric protein (SeV(TDK)/Fct14(MMP#6)/Linker/HNΔM-GFP). The M-deficient Sendai virus, SeV(TDK)/Fct14(MMP#6) ΔM-GFP, in which the cytoplasmic domain of the F protein has been truncated, was constructed as follows. Since TDK was used as the framework, firstly, pSeV(TDK)/ΔM-GFP was constructed. GFP/EIS (GFP added with the EIS sequence encoding transcription initiation and termination signals) was amplified by PCR using synthetic primers (Nhe-GFP-F: ATCCGCTAGCCCGTACGGCCATGGTGAGCAAG (SEQ ID NO: 94), and GFP-EIS-BssHII: ATCCGCGCGCCCG-TACGATGAACTTTCAC-CCTAAGTTTTTCTTACTACGGAGCTTTACTTGTAC AGCTCGTC (SEQ ID NO: 95)) with LITMUSSalI/NheIfrgΔM-GFP as a template. NheI and BssHII treatments were performed on the multicloning site of Sendai viral cDNA and the amplified GFP/EIS, and the resulting fragments were ligated to substitute the M protein with GFP in order to prepare pSeV(TDK)/ΔM-GFP.

Fct14(MMP#6) was amplified by PCR with pCAGGS/Fct14(MMP#6)/Linker/HN prepared in Example 31 as a template, using synthetic primers, Mlv-F: ATCCACGCGTCAT-GACAGCATATATCCAGAG (SEQ ID NO: 96) and Fct14-EIS-SalI: ATCCGTCGACACGATGAACTTTCAC-CCTAAGTTTTTCTTACTACTTTAACGGTCATCT GGATTACC (SEQ ID NO: 97). The Fct14(MMP#6) was inserted into the position of F to replace the F gene, resulting in the construction of pSeV(TDK)/Fct14(MMP#6)ΔM-GFP (FIG. 46). Next, an M-deficient Sendai virus carrying an F/HN chimeric protein (pSeV(TDK)/Fct14(MMP#6)/Linker/HNΔM-GFP) was constructed. GFP/EIS was amplified by PCR with GFP as a template, using synthetic primers (Nhe-GFP-F: ATCCGCTAGCCCGTACGGCCATGGTGAGCAAG (SEQ ID NO: 98) and GFP-EIS-SalI: ATCCGCTAGCCCGTACGATGAACTTTCAC-CCTAAGTTTTTCTTACTACGGAGCTTTACTTGTAC AGCTCGTC (SEQ ID NO: 99)). The GFP/EIS and multicloning site Sendai viral cDNA were treated with NheI and SalI. The resulting fragments were ligated to delete the M and F genes, and substitute with GFP to produce pSeV(TDK)/ΔMΔF-GFP. Fct14(MMP#6)/Linker/HN was amplified by PCR with Fct14(MMP#6)/Linker/HN prepared in Example 31 as template, using synthetic primers (F/HN5'Nhe-F: ATCCGCTAGCAGTTCAATGACAGCATATATCCAGAG (SEQ ID NO: 100), and F/HN3'Nhe-EIS-R: ATCCGCTAGCACGATGAACTTTCAC-CCTAAGTTTTTCTTACTACTTTTAA-GACTCGGCCTTGCA TAA (SEQ ID NO: 101)). pSeV (TDK)/Fct14(MMP#6)/Linker/HNΔM-GFP was constructed by ligating Fct14(MMP#6)/Linker/HN to the NheI site of the above-mentioned pSeV(TDK)/ΔMΔF-GFP.

Example 33

Reconstitution and Amplification of the Improved F-Modified M-Deficient Sendai Virus Reconstitution of a virus from the cDNA constructed in Example 32 was performed according to procedure reported by Li et al. (Li, H.-O. et al., J. Virology 74, 6564-6569, 2000; WO 00/70070). However, since the cDNA was of the M-deficient form as in Example 17, helper cells that provide the M protein in trans (Example 11) were used. Cre/loxP expression induction system was used for the production of helper cells. This system uses a plasmid, pCALNdLw, that is designed to inducibly express gene products by Cre DNA recombinase (Arai, T. et al., J. Virol. 72, 1115-1121, 1988). The inserted gene was expressed by infecting a recombinant adenovirus (AxCANCre), which expresses Cre DNA recombinase, to the transformant of this plasmid by the method of Saito et al. (Saito, I. et al., Nucleic Acids Res. 23, 3816-3821, 1995); Arai, T. et al., J. Virol. 72, 1115-1121, 1998). The M-deficient SeV in which the activation site of the F protein is substituted was reconstituted as described below. LLC-MK2 cells were plated onto a 100-mm dish at $5 \times 10^6$ cells/dish, cultured for 24 hours, and then infected at room temperature for one hour with recombinant vaccinia virus (at MOI=2) expressing T7 polymerase (PLWUV-VacT7: Fuerst, T. R. et al., Proc. Natl. Acad. Sci. USA 83, 8122-8126, 1986), which had been treated with psoralen under ultraviolet A (365 nm) for 20 minutes. The cells were washed with serum-free MEM. pSeV/F(MMP#6)ΔM-GFP (alternatively, pSeV(TDK)/Fct14 (MMP#6)ΔM-GFP or pSeV(TDK)/Fct14(MMP#6)/Linker/HNΔM-GFP), pGEM/NP, pGEM/P, pGEM/L (Kato, A. et al., Genes Cells 1, 569-579, 1996), pGEM/M, and pGEM/F-HN (Li, H.-O. et al., J. Virology 74, 6564-6569, 2000; WO 00/70070) plasmids were suspended in Opti-MEM (Gibco-BRL, Rockville, Md.) at densities of 12 μg, 4 μg, 2 μg, 4 μg, 4 μg, and 4 μg/dish, respectively. SuperFect transfection reagent (Qiagen, Bothell, Wash.) corresponding to 5 μL per 1 μg DNA was added to the mixture and mixed. After leaving standing at room temperature for 15 minutes, the mixture was ultimately mixed to 3 mL of Opti-MEM comprising 3% FBS, added to the cells, and then cultured. After culturing for five hours, the cells were washed twice with serum-free MEM, and then cultured in MEM containing 40 μg/mL cytosine 1-D-arabinofuranoside (AraC: Sigma, St. Louis, Mo.) and 7.5 μg/mL trypsin (Gibco-BRL, Rockville, Md.). After culturing for 24 hours, cells continuously expressing the F protein (LLC-MK2/F7/M62/A: Example 12) were layered at $8.5 \times 10^6$ cells/dish, and cultured for another two days at 37° C. in MEM containing 40 μg/mL AraC and 7.5 μg/mL trypsin (P0). These cells were collected, and the pellets were suspended in Opti-MEM at 2 mL/dish. After repeating the cycle of freezing and thawing for three times, the lysate was directly transfected to LLC-MK2/F7/M62/A, and the cells were cultured at 32° C. in serum-free MEM containing 40 μg/mL AraC, 7.5 μg/mL trypsin, and 50 U/mL type IV collagenase (ICN, Aurola, Ohio) (only trypsin for pSeV(TDK)/Fct14 (MMP#6)/Linker/HNΔM-GFP) (P1). Three to 14 days later, a portion of the culture supernatant was collected, infected to freshly prepared LLC-MK2/F7/M62/A, and the cells were cultured at 32° C. in serum-free MEM containing 40 μg/mL AraC, 7.5 μg/mL trypsin, and 50 U/mL type IV collagenase (only trypsin for pSeV(TDK)/Fct14(MMP#6)/Linker/HNΔM-GFP) (P2). Three to 14 days later, of the culture was infected to freshly prepared LLC-MK2/F7/M62/A and the cells were cultured for three to seven days at 32° C. in serum-free MEM containing 7.5 μg/mL trypsin and 50 U/mL type IV collagenase (only trypsin for pSeV(TDK)/Fct14(MMP#6)/Linker/HNΔM-GFP) (P3). The culture supernatant was collected, BSA was added thereto at a final concentration of 1%, and stored at −80° C. The stock virus solution was thawed, and used for later production and in vitro experiments.

As described above, SeV/F(MMP#6)ΔM-GFP in which the F protein cleavage site was modified from PLGMTS (SEQ ID NO: 61) to PQGMTS (SEQ ID NO: 62), SeV(TDK)/Fct14(MMP#6)ΔM-GFP in which 28 amino acids were deleted from the cytoplasmic domain, and SeV(TDK)/Fct14 (MMP#6)/Linker/HNΔM-GFP carrying the F/HN chimeric protein were successfully produced.

Example 34

Increase of Fusogenic Activity in the Improved F-Modified M-Deficient Sendai Viral Vectors In order to investigate the performance of the viruses produced in Example 33, various cancer cell lines having different expression levels of MMP-2 and MMP-9, and LLC-MK2, in which MMP expression is not detected, were infected as described below, and the cell fusiogenicities of the vectors were measured (FIG. 47). Each of the cancer cells (HT1080, U87MG, A172, U251, SW480, and LLC-MK2) was plated onto a 24-well plate with a media indicated by the supplier to be confluent. U87MG (ATCC No. HTB-14) and A172 (ATCC No. CRL-1620) were purchased from ATCC. U251 (IFO50288) was purchased from JCRB cell bank. After washing twice with MEM medium, each of the M-deficient Sendai viral vectors (SeV/ΔM-GFP) was infected at MOI=0.1. The cells were left standing at room temperature for one hour and washed with MEM medium, and then 0.5 mL of MEM containing 1% FBS was added to the 24-well plate. After culturing for 48 hours, the number of fused syncytia per X100 visual field (0.3 cm$^2$) of an inverted microscope was counted. Alternatively, the cultured cells were fixed in 4% paraformaldehyde for two hours, transferred to 70% ethanol and then to distilled water, stained for five minutes with hematoxylin, and washed with water to count the number of syncytium-forming nuclei in every 0.3 cm$^2$. The results are shown in FIG. 49.

The expression of MMP-2 and MMP-9 was confirmed by gelatin zymography performed in Example 22 (FIG. 48). As a result, expression of MMP-2 in HT1080, U87MG, and A172 was confirmed. Furthermore, low level of MMP-9 expression was confirmed in U251 and SW480. The apparent expression of MMP-2 in LLC-MK2 is due to the activity of MMP-2 in the 1% serum contained in the medium. Two days after infection of each of the cancer cell lines, the spread of GFP was observed. As a result, fusogenic activity was observed in U251 and SW480, which did not show the spread of infection with the conventional SeV/F(MMP#2)ΔM-GFP, infected with the improved F-modified M-deficient Sendai viral vector. In particular, those infected with the M-deficient Sendai viral vector carrying the F/HN chimeric protein (SeV (TDK)/Fct14(MMP#6)/Linker/HNΔM-GFP) showed fusogenic activity. Although data is not shown, murine Lewis lung carcinoma and murine colon-26 carcinoma as well showed fusogenic activity due to infection with improved M-deficient Sendai viral vectors. The improvement of vector is expected to effect to further enhance the effect and exhibit effect on cancers with low concentration of MMP.

INDUSTRIAL APPLICABILITY

The present invention provides vectors that specifically spread infection in the presence of an objective protease. The vectors of the present invention do not show significant production of virus-like particles, and are transferred to neighboring surrounding cells only by cell fusion. Therefore, the vectors of the present invention are useful for infecting vectors locally to a limited area of the tissue of interest. In particular, the present invention provides vectors that specifically spread their infection to cancer. These vectors have strong inhibitory effects on tumor proliferation. Gene therapy for cancer using the vectors of this invention is very likely to become a novel cancer treatment with little side-effects.

The invention claimed is:

1. A nucleic acid encoding a fusion protein having cell fusogenic activity and comprising the transmembrane regions of the paramyxoviral F and HN proteins, wherein the F and HN proteins are bound to each other on the cytoplasmic side.

2. A vector comprising the nucleic acid of claim 1.

3. A viral particle comprising a fusion protein having cell fusogenic activity and comprising the transmembrane regions of the paramyxoviral F and HN proteins, wherein the F and HN proteins are bound to each other on the cytoplasmic side or a nucleic acid encoding the fusion protein.

* * * * *